US011702667B2

(12) United States Patent
Yang et al.

(10) Patent No.: US 11,702,667 B2
(45) Date of Patent: *Jul. 18, 2023

(54) METHODS AND COMPOSITIONS FOR MULTIPLEX RNA GUIDED GENOME EDITING AND OTHER RNA TECHNOLOGIES

(71) Applicant: The Penn State Research Foundation, University Park, PA (US)

(72) Inventors: Yinong Yang, State College, PA (US); Kabin Xie, Wuhan (CN)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 929 days.

This patent is subject to a terminal disclaimer.

(21) Appl. No.: 16/386,903

(22) Filed: Apr. 17, 2019

(65) Prior Publication Data
US 2019/0330647 A1    Oct. 31, 2019

Related U.S. Application Data

(63) Continuation of application No. 14/885,140, filed on Oct. 16, 2015, now Pat. No. 10,308,947.

(60) Provisional application No. 62/065,093, filed on Oct. 17, 2014.

(51) Int. Cl.
| | | |
|---|---|---|
| C12N 15/11 | (2006.01) | |
| C12N 15/113 | (2010.01) | |
| C12N 15/85 | (2006.01) | |
| C12N 15/82 | (2006.01) | |

(52) U.S. Cl.
CPC ........ *C12N 15/8213* (2013.01); *C12N 15/111* (2013.01); *C12N 15/113* (2013.01); *C12N 15/8216* (2013.01); *C12N 15/8218* (2013.01); *C12N 15/85* (2013.01); *C12N 2310/10* (2013.01); *C12N 2310/20* (2017.05); *C12N 2310/51* (2013.01); *C12N 2330/31* (2013.01); *C12N 2330/51* (2013.01)

(58) Field of Classification Search
None
See application file for complete search history.

(56) References Cited

U.S. PATENT DOCUMENTS

2005/0203047 A1    9/2005   Thomann et al.

FOREIGN PATENT DOCUMENTS

| CN | 104955951 A | 9/2015 |
| WO | 2012164565 A8 | 12/2012 |
| WO | 2014022702 A2 | 2/2014 |

OTHER PUBLICATIONS

Scherer et al., Optimization and characterization of tRNA-shRNA expression constructs. Nucleic Acids Research (2007), 35(8): 2620-2628 (Year: 2007).*
Phizicky et al., tRNA biology charges to the front. Genes and Development (2010), 24: 1832-1860 (Year: 2010).*
Acker et al., Dicistronic tRNA-5S rRNA genes in Yarrowialipolytica: an alternative TFIIIA-independent way for expression of 5S rRNA genes. Nucleic Acids Research (2008), 36(18): 5832-5844 (Year: 2008).*
Feng et al., Multigeneration analysis reveals the inheritance, specificity, and patterns of CRISPR/Cas-induced gene modifications in Arabidopsis. PNAS (2014), 111(12): 4632-4637; published Mar. 25, 2014 (Year: 2014).*
Cong et al., Multiplex Genome Engineering Using CRISPR/Cas Systems. Science (2013), 339: 819-823 (Year: 2013).*
DiCarlo et al., Genome engineering in *Saccharomyces cerevisiae* using CRISPR-Cas systems. Nucleic Acids Research (2013), 41(7): 4336-4343 (Year: 2013).*
Crary et al., The Protein Component of Bacillus subtilis Ribonuclease P Increases Catalytic Efficiency by Enhancing Interactions with the 5' Leader Sequence of Pre-tRNAAsp, Biochemistry (1998), 37: 9409-9416 (Year: 1998).*
Li et al., "CRISPR/Cas: a novel way of RNA-guided genome editing", Hereditas, vol. 35, No. 11, 9 pages, Nov. 2013.
Xie et al., "Boosting CRISPR/Cas9 multiplex editing capability with the endogenous tRNA-processing system", PNAS, vol. 112, No. 11, pp. 3570-3575, Mar. 17, 2015.
Xie, Kabin, et al., "RNA-Guided Genome Editing in Plants Using a CRISPR-Cas System", Molecular Plant, vol. 3, No. 6, pp. 1975-1983. Nov. 1, 2013.
Cho, Seung Woo, et al., "Targeted genome engineering in human cells with the Cas9 RNA-guided endonuclease", Nature Biotechnology, vol. 31, No. 3, pp. 230-232. Mar. 1, 2013.
Hwang, Woong Y., et al., "Efficient genome editing in zebrafish using a CRISPR-Cas system", Nature Biotechnology, vol. 31, No. 3, pp. 227-229, Jan. 10, 2013.
DiCarlo, James, et al., "Genome engineering in *Saccharomyces cerevisiae* using CRISPR-Cas systems", Nucleic Acids Research, pp. 1-8. Feb. 11, 2013.

(Continued)

*Primary Examiner* — Lora E Barnhart Driscoll
*Assistant Examiner* — Catherine Konopka
(74) *Attorney, Agent, or Firm* — McKee, Voorhees & Sease, PLC

(57) ABSTRACT

The invention includes materials and methods to generate numerous small RNAs from one polynucleotide construct (synthetic gene) to facilitate RNA-guided multiplex genome editing, modification, inhibition of expression and other RNA-based technologies. The synthetic gene/polynucleotide construct encodes polycistronic RNA components separated by tRNAs, and preferably also includes regulatory components such as a promoter or terminator to form an expression cassette. Once transcribed in a cell, the transcript is processed by the cell to multiple RNA molecules by the endogenous tRNA processing system. The system can be sued for any RNA based gene manipulation method including RNA-mediated genome editing, artificial microRNA mediated gene silencing, small RNA mediated genetic manipulation, double-stranded RNA mediated gene silencing, antisense mechanisms and the like.

46 Claims, 50 Drawing Sheets

Figure 1A:
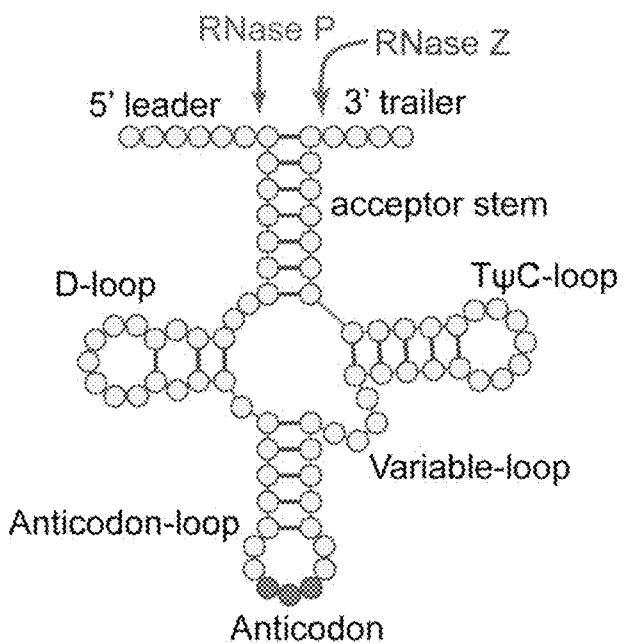

Specification includes a Sequence Listing.

(56) References Cited

OTHER PUBLICATIONS

Mali, Prashant, et al., "RNA-Guided Human Genome Engineering via Cas9", Science, vol. 339, pp. 823-826, Feb. 15, 2013.

Kruszka, Katarzyna, et al., "Plant dicistronic tRNA-snoRNA genes: a new mode of expression of the small nucleolar RNAs processed by RNase Z", The EMBO Journal, vol. 22, No. 3, pp. 621-632, Nov. 26, 2002.

Cong, Le, et al., "Multiplex Genome Engineering Using CRISPR/Cas Systems", Science, vol. 339, pp. 819-823. Feb. 15, 2013.

Van der Oost, John, "New Tool for Genome Surgery", Science, vol. 339, pp. 768-770, Feb. 15, 2013.

Mali, Prashant, et al., "RNA-Guided Human Genome Engineering via Cas9", Science, vol. 339, pp. 108, Feb. 15, 2013.

Mussolino, Claudio, et al., "RNA guides genome engineering", Nature Biotechnology, vol. 31, No. 3, pp. 208-209, Mar. 1, 2013.

Segal, David J., "Bacteria herald a new era of gene editing", eLIFE, Genome Engineering, 3 pages, Jan. 1, 2013.

Jinek, Martin, et al., "RNA-promgrammed genome editing in human cells", eLIFE, Genomics and evolutionary biology, pp. 1-9. Jan. 1, 2013.

Gao, Yangbin, et al., "Self-processing of ribozyme-flanked RNAs into guide RNAs invitro and in vivo for CRISPR-mediated genome editing", Journal of Integrative Plant Biology, vol. 56, Issue 4, pp. 343-349, Apr. 1, 2014.

The Penn State Research Foundation, "International Search Report and Written Opinion", Application No. PCT/US2015/055980, filed Oct. 16, 2015, dated Feb. 4, 2016, 13 pages.

Nissim, Lior, et al., "Multiplexed and Programmable Regulation of Gene Networks with an Integrated RNA and CRISPR/Cas Toolkit in Human Cells", Molecular Cell, Vo. 54, pp. 698-710, May 22, 2014.

Tsai, Shengdar Q., et al., "Dimeric CRISPR RNA-guided FokI nucleases for highly specific genome editing", Nature Biotechnology, vol. 32, No. 6, pp. 569-577, Jun. 1, 2014.

Thyme et al., "Internal guide RNA Interactions Interfere with Cas9-mediated cleavage", Nature Communications, 7 pages, Jun. 10, 2016.

\* cited by examiner

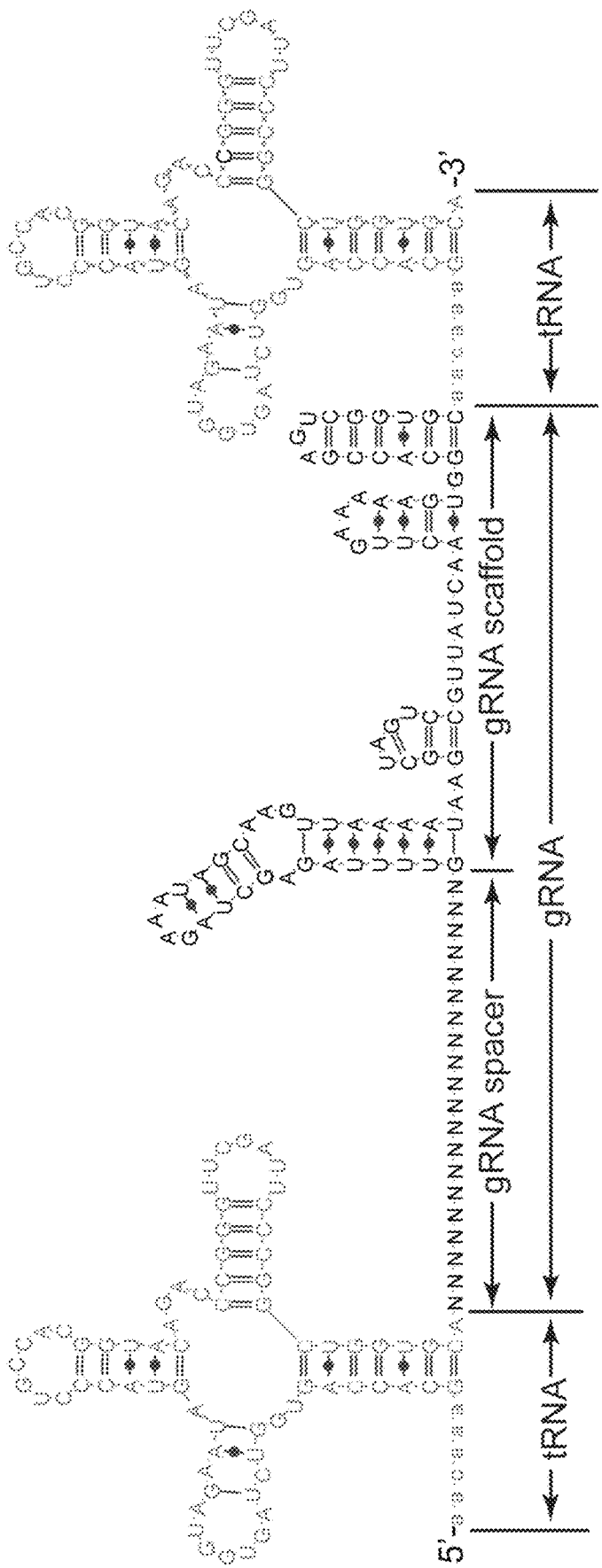

| Gene ID | # of gRNA | Targeted loci | Gene architecture |
|---|---|---|---|
| PTG3 | 2 | MPK1 | tRNA-gRNA3-tRNA-gRNA4 |
| PTG4 | 2 | MPK2 | tRNA-gRNA5-tRNA-gRNA6 |
| PTG5 | 2 | MPK6 | tRNA-gRNA7-tRNA-gRNA8 |
| PTG6 | 2 | MPK5 | tRNA-gRNA1-tRNA-gRNA2 |
| PTG7 | 4 | MPK5 and MPK1 | PTG6-PTG3 |
| PTG8 | 4 | MPK6 and MPK2 | PTG5-PTG4 |
| PTG9 | 8 | MPK5, MPK1, MPK6 and MPK2 | PTG7-PTG8 |

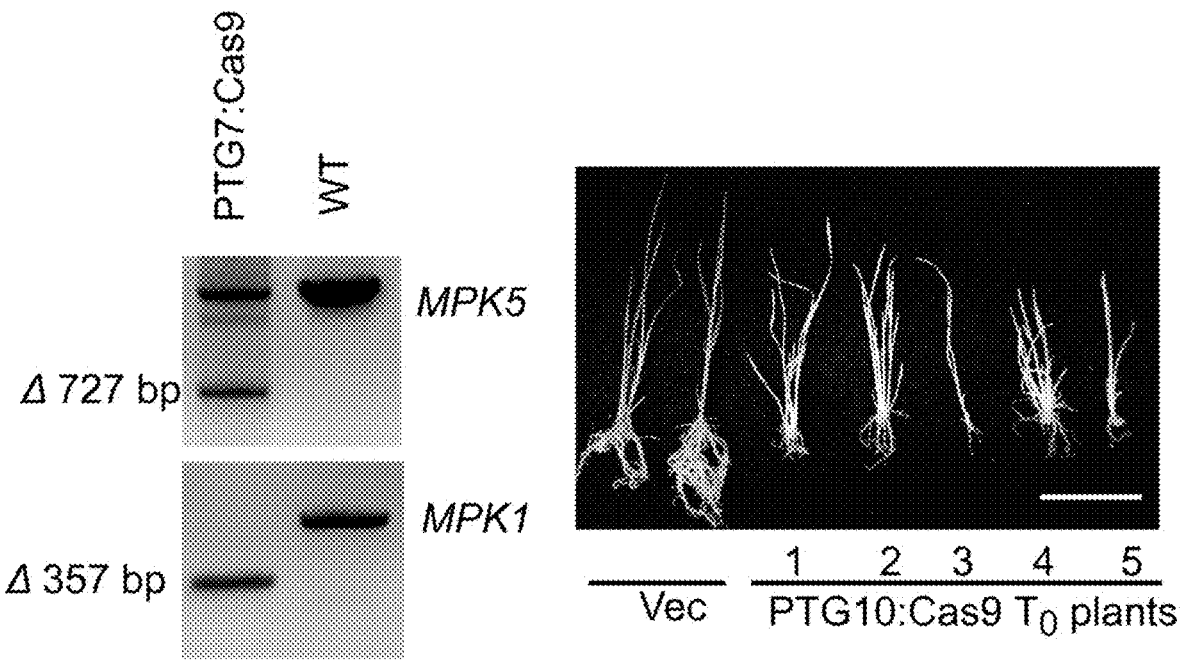
*FIG. 4A*
*FIG. 4B*
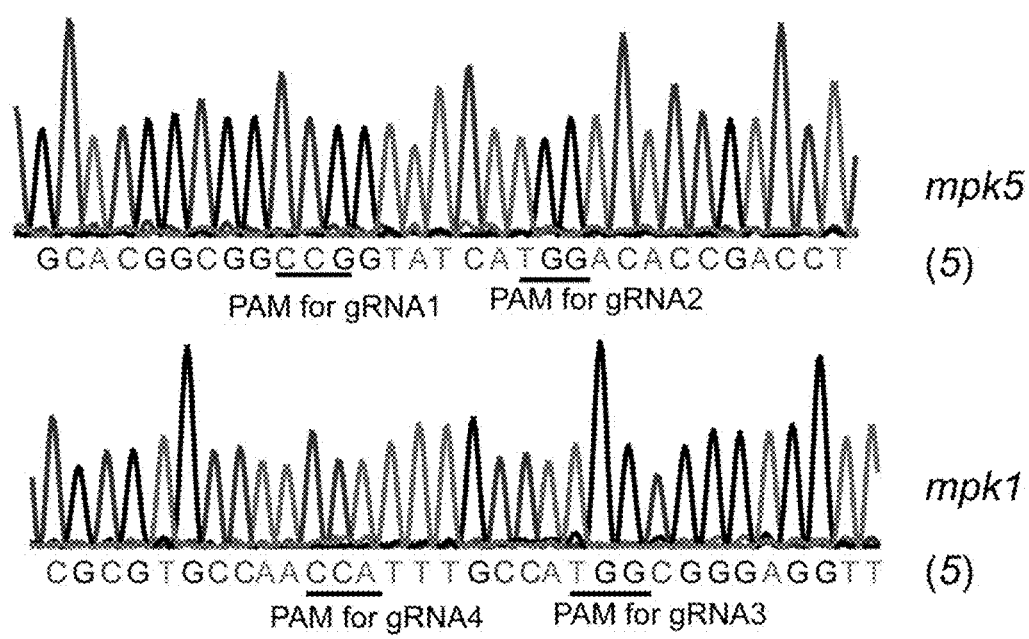
*FIG. 4C*

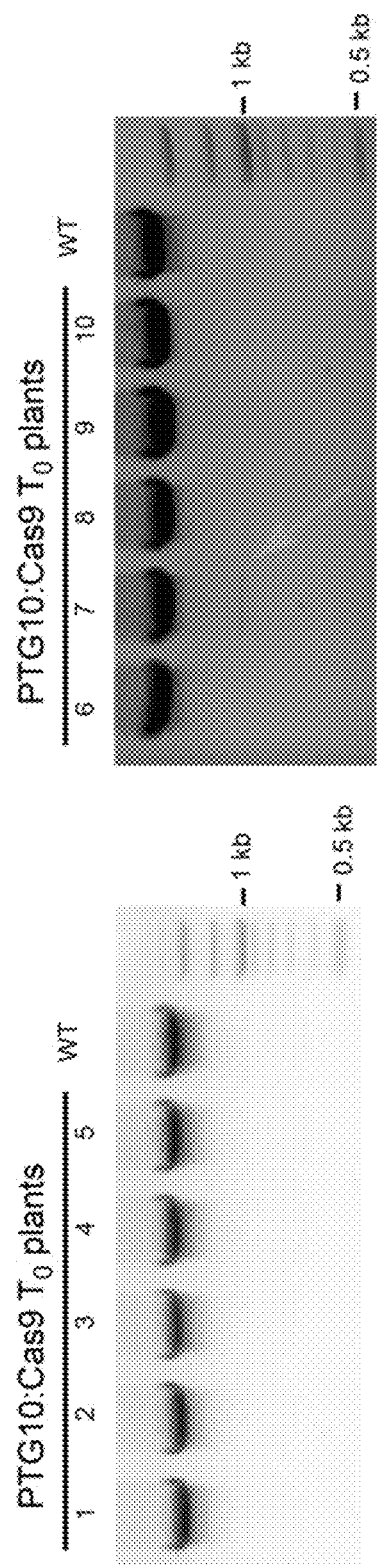

hPTG1

AACAAAGCACCAGTGGTCTAGTGGTAGAATAGTACCCTGCCAC
GGTACAGACCCGGGTTCGATTCCCGGCTGGTGCGTAAGACC
ACCGCACTAGGCgttttagagctagaaatagcaagttaaaataaggctagtccgtta
tcaacttgaaaaagtggcaccgagtcggtgcAACAAAGCACCAGTGGTCTAG
TGGTAGAATAGTACCCTGCCACGGTACAGACCCGGGTTCGATT
CCCGGCTGGTGCGCCCTGCAGCTATTACCATTgttttagagctagaa
atagcaagttaaaataaggctagtccgttatcaacttgaaaaagtggcaccgagtcggtgcT
TTTTTTTT
↑
Transcription end hPTG2

AACAAAGCACCAGTGGTCTAGTGGTAGAATAGTACCCTGCCAC
GGTACAGACCCGGGTTCGATTCCCGGCTGGTGCGTATTTAG
GATATTGGTGCgttttagagctagaaatagcaagttaaaataaggctagtccgtta
tcaacttgaaaaagtggcaccgagtcggtgcAACAAAGCACCAGTGGTCTAG
TGGTAGAATAGTACCCTGCCACGGTACAGACCCGGGTTCGATT
CCCGGCTGGTGCTGTTTCAATCTAACAGTCAAgttttagagctagaa
atagcaagttaaaataaggctagtccgttatcaacttgaaaaagtggcaccgagtcggtgcT
TTTTTTTT
↑
Transcription end

*FIG. 19C*

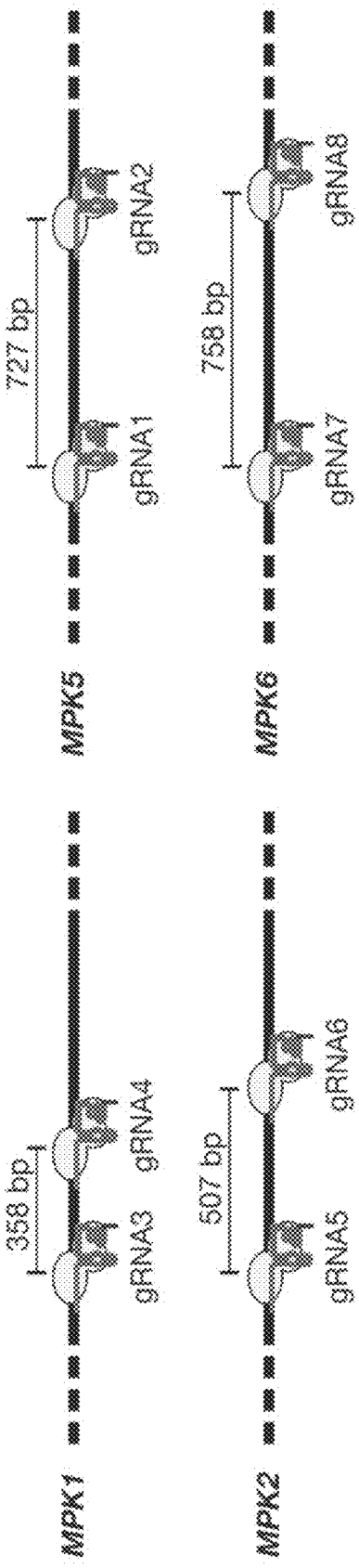

FIG. 23B

| | | |
|---|---|---|
| MPK1 | MDAGAQPPDTEMAEAGGGGQPPAAAAAGAGAGAGMMENIQATLSHGGRFIQYNIFGNVF | 60 |
| mpk1 1-2a | MDAGAQPPDTEMAEAGGGGQPPAAAAAGAGAGAGMMENIQAT------HGGRFIQYNIFGNVF | 55 |
| mpk1 2-1/3-2/4-2 | MDAGAQPPDTEMAEAGGGGQPPAAAAAGAGAGAGMMENIQAT-LHGGRFIQYNIFGNVF | 59 |
| mpk1 1-2b | MDAGAQPPDTEMAEAGGGGQPPAAAAAGAGAGAGMMENIQAT-LNGGRFIQYNIFGNVF | 59 |
| | ******************************************* :************ | |

FIG. 26C

| | | |
|---|---|---|
| mpk5 1-2 | MDGAPVAEFRPTMTHGGRYPA------------------------------------------ | 21 |
| mpk5 4-2 | MDGAPVAEFRPTMTHGGRY-------------------------------------------- | 19 |
| mpk5 3-2 | MDGAPVAEFRPTMTHGGRY-------------------------------------------- | 19 |
| mpk5 2-1 | MDGAPVAEFRPTMTHGGRF-------------------------------------------- | 19 |
| MPK5 | MDGAPVAEFRPTMTHGGRYLLYDIFGNKFEVTNKYQPPIMPIGRGAYGIVCSVMNFETRE | 60 |
| | *******************: | |

FIG. 26D

METHODS AND COMPOSITIONS FOR MULTIPLEX RNA GUIDED GENOME EDITING AND OTHER RNA TECHNOLOGIES

CROSS REFERENCE TO RELATED APPLICATION

This is a Continuation Application of U.S. Ser. No. 14/885,140, filed Oct. 16, 2015, which claims priority under 35 U.S.C. § 119 to provisional application Ser. No. 62/065,093, filed Oct. 17, 2014, all of which are herein incorporated by reference in their entirety.

GRANT REFERENCE

This invention was made with government support under Hatch Act Project Nos. PEN04256 and PEN04527 awarded by the United States Department of Agriculture and under Grant No. DBI0922747 awarded by the National Science Foundation. The Government has certain rights in the invention.

SEQUENCE LISTING

The instant application contains a Sequence Listing which has been submitted in ASCII format via Electronic Submission and is hereby incorporated by reference in its entirety. Said ASCII copy, created on Apr. 17, 2019, is named 2019-04-17_YANG_P11233US02_Seq_Listing.txt and is 69,559 bytes in size.

FIELD OF THE INVENTION

This invention relates to methods for gene targeting and genome editing in the field of molecular biology and genetic engineering. More specifically, the invention describes the use of the tRNA processing system to enable multiplex RNA based or guided genome engineering, gene inhibition etc.

BACKGROUND OF THE INVENTION

Methodologies for specific gene targeting or precise genome editing are of great importance to functional characterization of plant or animal genes. In recent years, sequence-specific nucleases have been developed to increase the efficiency of gene targeting or genome editing in plant, animal, or microbial systems.

Recently, a new genome editing tool has been developed in microbial and mammalian systems based on the cluster regularly interspaced short palindromic repeats (CRISPR)-associated nuclease system. The CRISPR-associated nuclease is part of adaptive immunity in bacteria and archaea. The Cas9 endonuclease, a component of Streptococcus pyogenes type II CRISPR/Cas system, forms a complex with two short RNA molecules called CRISPR RNA (crRNA) and trans-activating crRNA (transcrRNA), which guide the nuclease to cleave non-self DNA on both strands at a specific site. The crRNA-transcrRNA heteroduplex could be replaced by one chimeric RNA (so-called guide RNA (gRNA)), which can then be programmed to targeted specific sites. The minimal constrains to program gRNA-Cas9 is at least 15-base-pairing between engineered 5'-RNA and targeted DNA without mismatch, and an NGG motif (so-called protospacer adjacent motif or PAM) follows the base-pairing region in the targeted DNA sequence. Generally, 15-22 nt in the 5'-end of the gRNA region is used to direct Cas9 nuclease to generate DSBs at the specific site. The CRISPR/Cas system has been demonstrated for genome editing in human, mice, zebrafish, yeast and bacteria. Distinct from animal, yeast, or bacterial cells to which recombinant molecules (DNA, RNA or protein) could be directly transformed for Cas9-mediated genome editing, recombinant plasmid DNA is typically delivered into plant cells via the *Agrobacterium*-mediate transformation, biolistic bombardment, or protoplast transformation due to the presence of cell wall. Thus, specialized molecular tools and methods need to be created to facilitate the construction and delivery of plasmid DNAs as well as efficient expression of Cas9 and gRNAs for genome editing in, plant or animal cells. Compositions and methods for making and using CRISPR-Cas systems are described in U.S. Pat. No. 8,697,359, entitled "CRISPR-CAS SYSTEMS AND METHODS FOR ALTERING EXPRESSION OF GENE PRODUCTS," which is incorporated herein in its entirety.

In principle, multiplex genetic manipulation could be achieved by expressing multiple gRNAs with Cas9 (or Cas9 derived effectors) for corresponding target sites. Due to limitations in delivery method and capacity of current gRNA expressing devices, however, simultaneously producing numerous gRNAs in plant, animal, or microbial organisms is still a challenge.

It is an objective of the present invention to provide a strategy to use a cell's endogenous tRNA processing system as an efficient and precise approach to produce numerous gRNAs from a single polynucleotide construct/synthetic gene, thereby boosting the multiplex editing capability of CRISPR/Cas9 or other RNA mediated genetic manipulation tools for genome engineering.

In another aspect, the present invention relates to a polynucleotide construct, expression cassette, vector or recipient modified cell comprising a nucleic acid as described, supra.

It is a further objective, feature or advantage of the present invention to provide compositions and methods for manipulating multiple target genes, or multiple positions within a single target gene with introduction of a single expression cassette that includes sequences to utilize the tRNA system in the recipient cell.

Additional objectives, features and advantages may become obvious based on the disclosure contained herein.

SUMMARY OF THE INVENTION

Applicants have produced materials and methods to generate numerous small RNAs from one polynucleotide construct (synthetic gene) to facilitate RNA-guided multiplex genome editing, inhibition of expression, genetic and epigenetic modification, and other RNA-based technologies. The synthetic gene/polynucleotide construct encodes polycistronic RNA components separated by tRNAs, and preferably also includes regulatory components such as a promoter or terminator to form an expression cassette. Once transcribed in a cell, the transcript is processed by the cell to multiple RNA molecules by the endogenous tRNA processing system.

Methods of the invention can be used to improve any RNA-based genome editing and modulation technology, allowing for multiplex RNA generation and separation via a single polynucleotide construct and the endogeneous tRNA processing system. Such methods can include but are not limited to Cas9-mediated genome editing, artificial microRNA mediated gene silencing, and other RNA-mediated mechanisms and the like.

According to the invention a method for producing multiplex RNA genetic manipulation in a recipient cell includes, providing a heterologous polynucleotide sequence with two or more RNA mediated genetic manipulation sequences in tandem with one or more tRNA cleavage sequences (pre-tRNA). The polynucleotide is introduced to the recipient cell by any of a number of standard techniques, and upon expression, said recipient cells tRNA processing system cleaves the heterologous polynucleotide at the tRNA sequences. In particular the invention provides tRNA cleavage sequences for RNA-nucleolytic activity such as in pre-tRNA splicing, 3' end pre-mRNA endonuclease activity, pre-tRNA cleavage activity, and/or the pre-ribosomal RNA cleavage activity. The RNA genetic manipulation sequences and the RNA cleavage sequence are operably linked to regulatory sequences for expression in a recipient cell, such as promoter and terminator sequences.

A tRNA cleavage sequence includes any sequence and/or structural motif that actively interacts with and is cleaved by a cell's endogenous tRNA system such as RNase P, RNase Z and RNase E (bacteria). This can include structural recognition elements such as the acceptor stem, D-loop arm, T Psi C loop as well as specific sequence motifs. There are numerous tRNA active sequences and motifs known and available to those of skill in the art through sources such as the tRNA-SE program available at world wide web lowelab.ucsc.edu/tRNAscan-SE/ or world wide web trna.bioinfuni-leipzig.de/DataOutput/Organisms (for all organisms), or world wide web at plantrna.ibmp.cnrs.fr/ (for plants). Numerous articles and Genbank resources are also available and are recited herein.

The invention also includes polynucleotide constructs for multiplex RNA genetic manipulation, expression constructs, vectors and recipient cells that have been manipulated. The constructs comprise a polynucleotide sequence which encodes two or more RNA mediated genetic manipulation sequences in tandem with a sequence which encodes a tRNA cleavage sequence. In one embodiment the RNA mediated genetic manipulation sequence includes a guide RNA for CAS9-mediated genome editing. The guide RNA, or gRNA is introduced along with an endonuclease, in this case the CRISPR associated (Cas) nuclease, Cas9. The guide RNA provides the scaffold and a spacer sequence complementary to the target site. In another embodiment the RNA genetic manipulation sequence is an interfering RNA such as an siRNA, or a microRNA sequence designed for gene silencing according to standard methods in the art. The construct also includes one or more tRNA cleavage sequences which may be actively processed by the endogenous tRNA cleavage system within the cell. The construct is preferably an expression construct or synthetic gene which includes promoter and terminator sequences. Surprisingly, the applicant have found that when used with a CRISPR system, the RNA cleavage components provide for up to 30 times higher expression likely due to internal tRNA promoter elements.

The invention also includes cells and progeny thereof which have been genetically manipulated, such cells may include genomic insertions or deletions or manipulation of gene expression by gene silencing. Progeny of such cells may be used to develop lines, and plant and animal breeding materials. In some embodiments the cells are human cells.

While multiple embodiments are disclosed, still other embodiments of the present invention will become apparent to those skilled in the art from the following detailed description, which shows and describes illustrative embodiments of the invention.

Accordingly, the drawings and detailed description are to be regarded as illustrative in nature and not restrictive.

DETAILED DESCRIPTION OF THE FIGURES

Figure 1B:
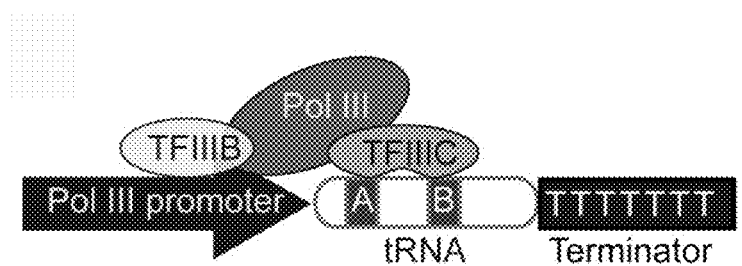
Figure 1C:
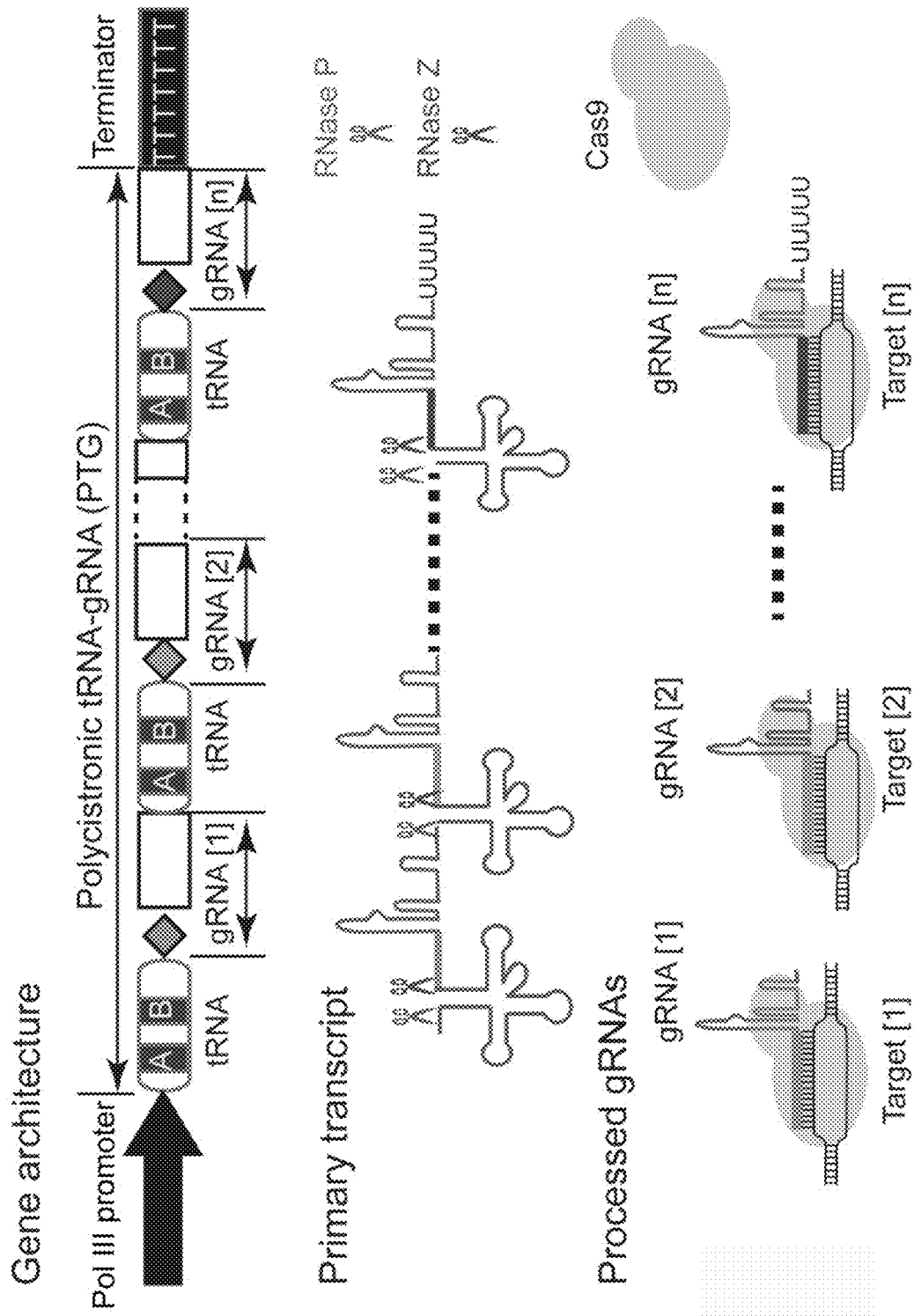

FIGS. 1A-C show engineering the endogenous tRNA system for multiplex genome editing with CRISPR/Cas9. FIG. 1A shows the eukaryotic pre-tRNA with 5' leader and 3' trailer is cleaved by RNase P and RNase Z at specific sites. FIG. 1B shows transcription of tRNA gene with RNA polymerase III (Pol III). The box A and box B elements in the tRNA gene function as internal transcriptional elements and are bound by transcription factor IIIC (TFIII C), which recruits TFIIIB and Pol III to start transcription. FIG. 1C shows a schematic depiction of PTG/Cas9 method for simultaneously targeting multiple sites. The synthetic PTG consists of tandemly arrayed tRNA-gRNA units with each gRNA containing target-specific spacer (labeled as diamond with different color) and conserved gRNA scaffold (rectangle). The tRNA containing box A and B elements is shown as round rectangles. The primary transcript of PTG is cleaved by endogenous RNase P and RNase Z (labeled as scissors) to release mature gRNAs and tRNA (red lines of cloverleaf structure). The excised mature gRNAs direct Cas9 to multiple targets.

Figure 2C:
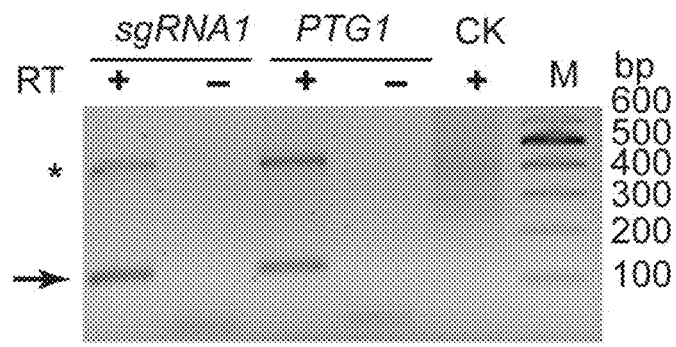
Figure 2D:
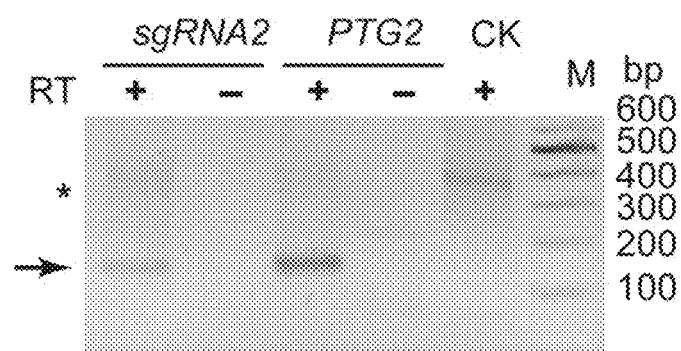
Figure 2E:
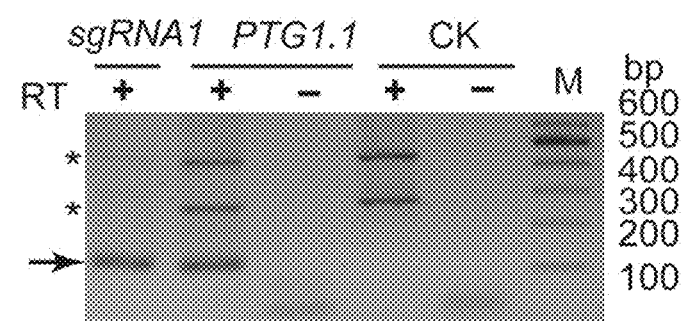
Figure 2F:
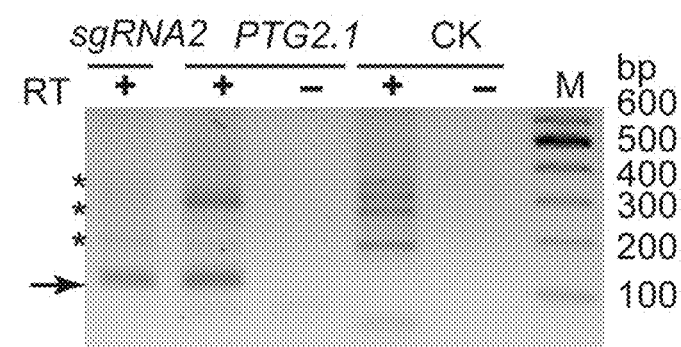
Figure 2G:
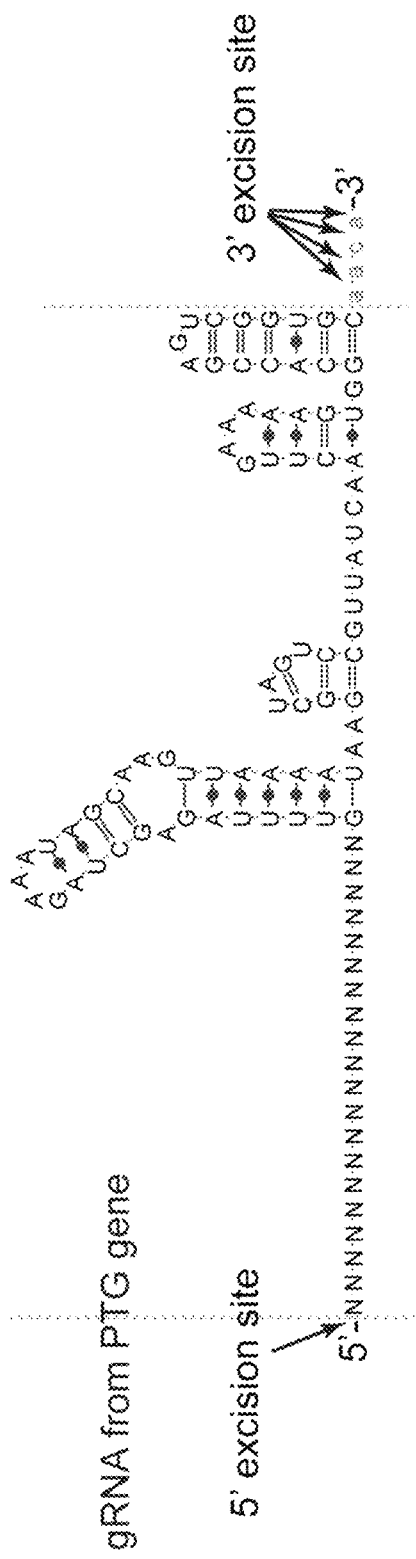
Figure 2H:
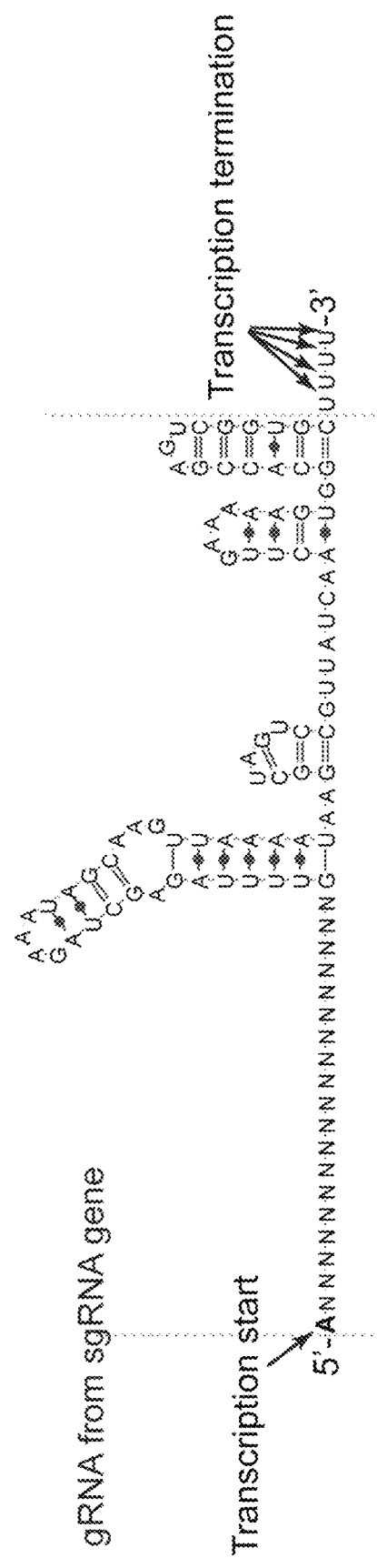
Figure 2I:
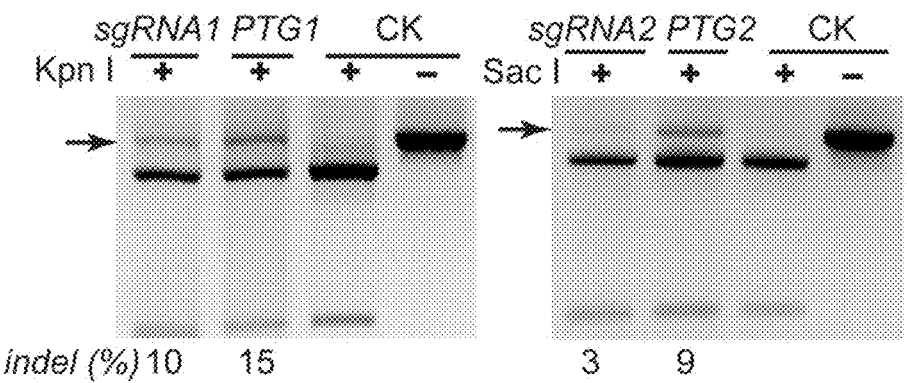
Figure 2J:
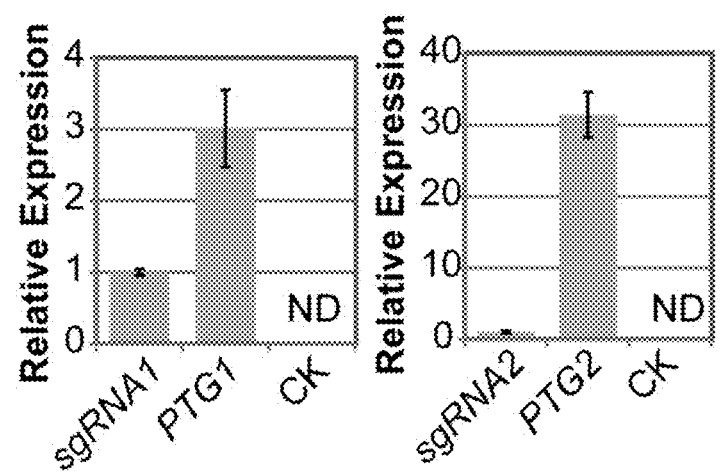

FIGS. 2A-J show precise excision of functional gRNAs in vivo from synthetic PTG genes. FIG. 2A shows the architecture of two sgRNA genes and four PTGs to produce one gRNA. FIG. 2B shows the sequence and predicted 2nd RNA structure of tRNA-gRNA-tRNA fusion of PTG gene (SEQ ID NO: 87). The bases of tRNA region are indicated with red color and the tRNA 5'-leader is shown in lowercase. The gRNA is indicated in black and the gRNA spacer sequence is shown as N. FIGS. 2C-F show the examination of mature gRNAs produced from sgRNA or PTGs with cRT-PCR. Total RNAs from the protoplasts expressing empty vector were used as control (CK). Arrows indicate mature gRNAs amplified by cRT-PCR, and asterisks indicate the nonspecifically amplified rRNA. FIG. 2G is a summary of excision sites in PTG (SEQ ID NO:88) according to mapped gRNA ends from cRT-PCR. Arrows indicate the cleavage sites in PTG to release gRNA. The mature gRNA 5'-ends were excised from PTG exactly at the tRNA-gRNA fusion site in all cRT-PCR results whereas its 3'-ends shifted 1-4 nt within the tRNA 5' leader (lowercase). FIG. 2H shows gRNA produced from U3p:sgRNA (SEQ ID NO:89). All detected U3p:sgRNA produced gRNA started with ribonucleotide A and terminated with multiple Us. FIG. 2I shows the introduction of indels at the desired sites by PTG1:Cas9 or PTG2:Cas9 in rice protoplasts as shown by PCR/RE. Arrows indicate mutated fragments resistant to RE digestion. The indel frequency is indicated at the bottom. FIG. 2J shows the relative expression of sgRNA1/2 and PTG1/2 in rice protoplasts. Data represent mean±SD. ND, not detected. CK, empty vector control.

Figures 3A, 3B:
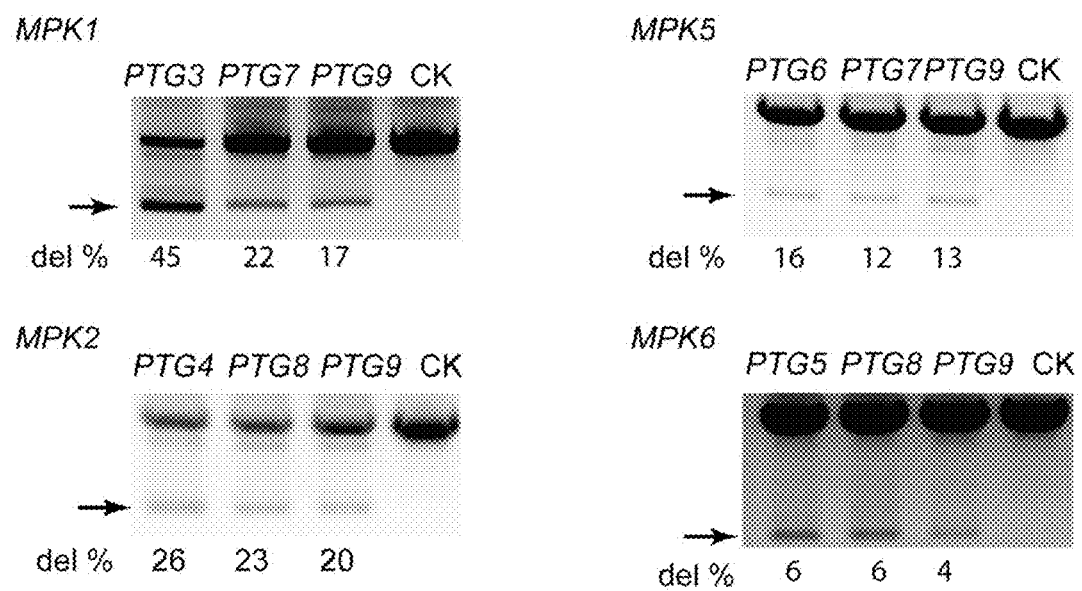
Figure 3C:
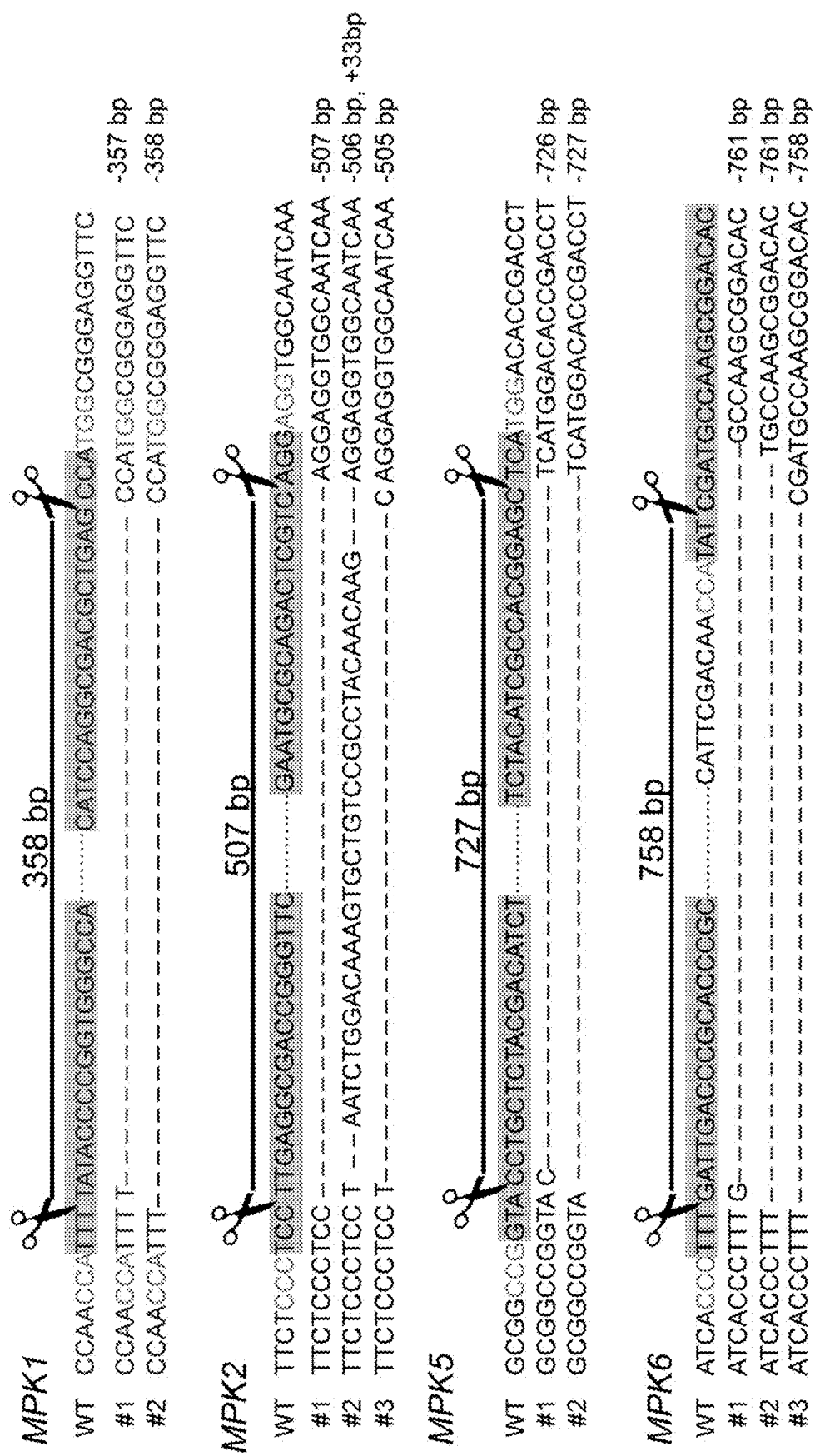

FIGS. 3A-C show the simultaneous editing of multiple genomic sites in rice protoplasts with the PTG:Cas9 system. FIG. 3A shows the architecture, gRNA components and targets of PTGs. FIG. 3B shows PCR detection of chromosomal fragment deletion at targeted loci in rice protoplasts expressing respective PTGs with Cas9. Successful deletion is shown as truncated PCR product (indicated with arrows). The chromosomal fragment deletion frequency (del %) is indicated at the bottom of each lane. The protoplast samples expressing an empty vector were used as control (CK). FIG. 3C shows representative sequences of chromosomal fragment deletion, including SEQ ID NOs 90-99, aligned with that of wild type (WT) (MPK1 WT, SEQ ID NO:79; MPK2 WT, SEQ ID NO:81; MPK5 WT, SEQ ID NO:82; MPK6 WT, SEQ ID NO:84). Dots in WT sequence indicate bases not shown and the total length between two Cas9 cut sites (labeled with scissor) is indicated on top. Short lines indicate gaps in alignment.

FIGS. 4A-C show highly efficient targeted mutagenesis in transgenic rice expressing PTG:Cas9. FIG. 4A shows chromosomal fragment deletion in PTG7:Cas9 plant at $T_0$ generation. Of note, only 5 mpk1 with 358 bp deletion (4358) was detected in genomic DNA. FIG. 4B shows albino seedlings were regenerated from calli transformed with PTG10:Cas9. All $T_0$ seedlings (n=12) exhibited a similar photo-bleach phenotype, suggesting a very high efficiency of knocking out PDS with PTG10:Cas9. Vec, control plants transformed with empty vector; Bar=5 cm. FIG. 4C shows sequence analysis of targeted deletions at MPK1 and MPK5 loci in PTG7:Cas9 plants. All sequenced PCR products (the number in parentheses) show identical deletion pattern (SEQ ID NOs 100-101).

Figures 5A, 5B:
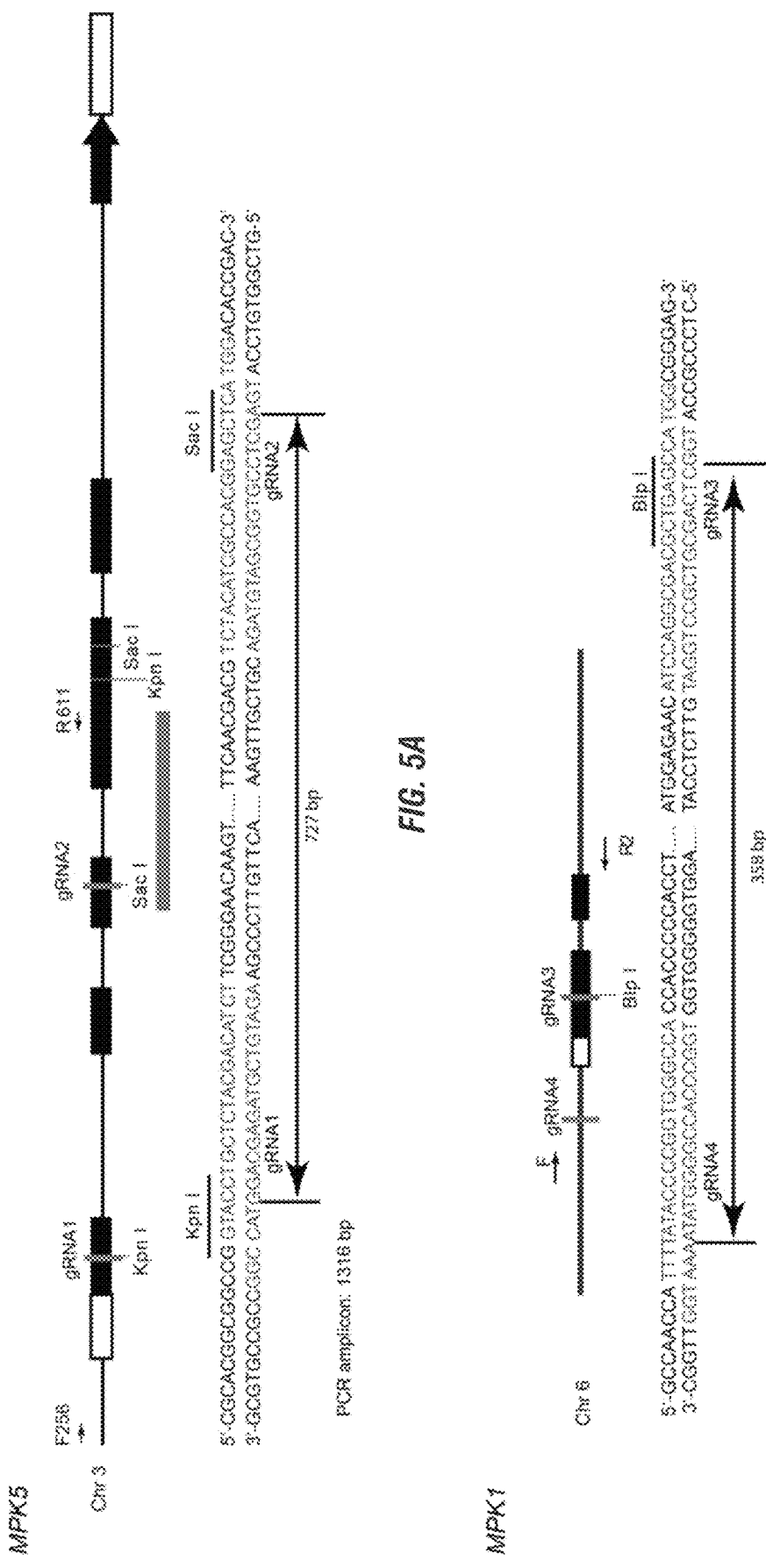
Figure 5C:
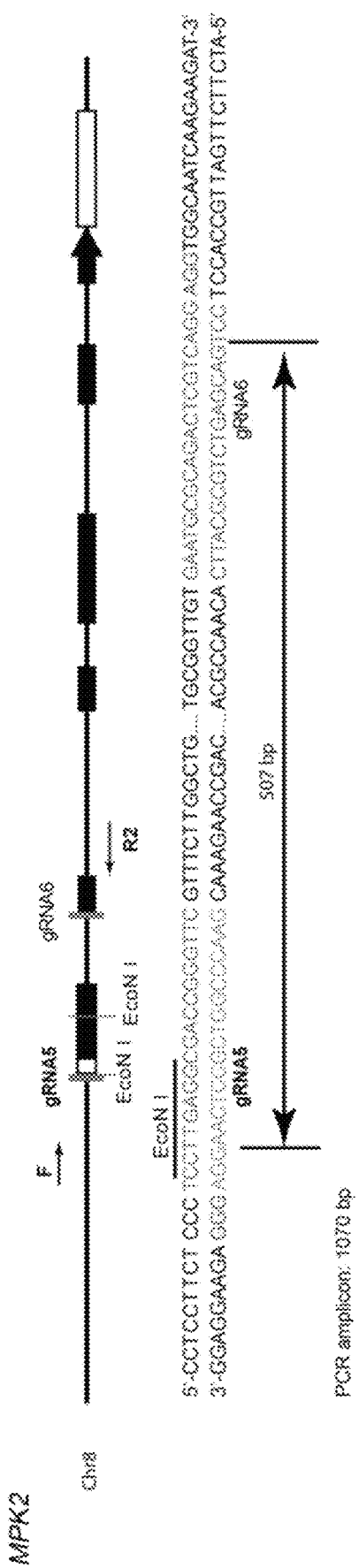
Figure 5D:
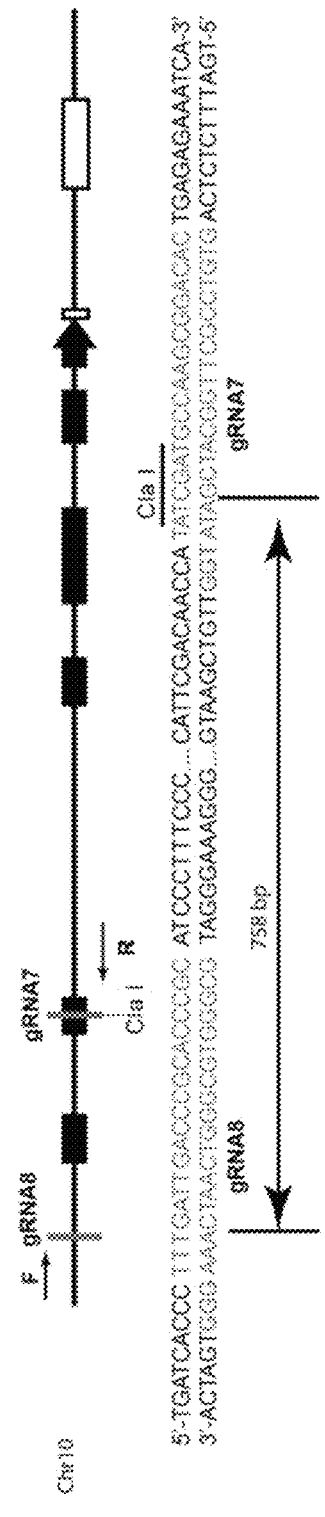

FIGS. 5A-D show a schematic diagram of rice MAPK genes (SEQ ID NOs 102-109) targeted by gRNA1-gRNA8 (SEQ ID NOs 3-10). FIG. 5A shows MPK5 target gene. FIG. 5B shows MPK1 target gene. FIG. 5C shows MPK2 target gene. FIG. 5D shows MPK6 target gene. The rectangles indicate exons while black rectangles indicate protein coding region. The relative location of gRNA targeting site is shown as green vertical line and PCR primers for genotyping are indicated with black arrow. The gRNA targeting regions (green letters), PAMs (red letters) and restriction enzyme sites for PCR/RE assay are also shown for each gene. The bar in FIG. 5A indicates the qPCR amplicon for deletion efficiency estimation. Only a partial region of MPK1 locus is shown here.

Figure 6A:
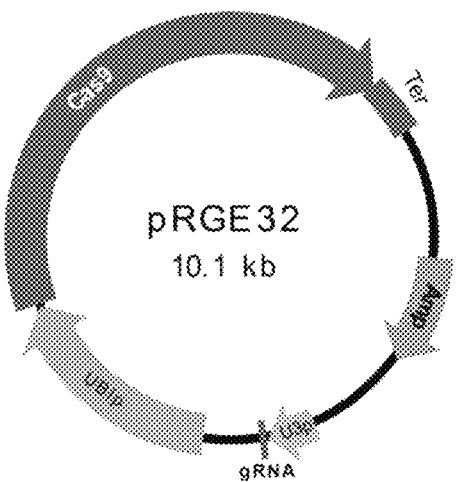
Figure 6B:
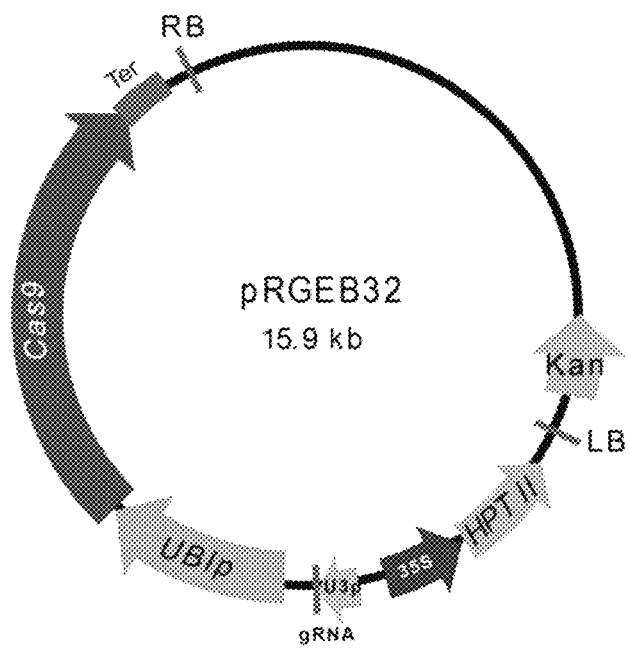
Figure 6C:
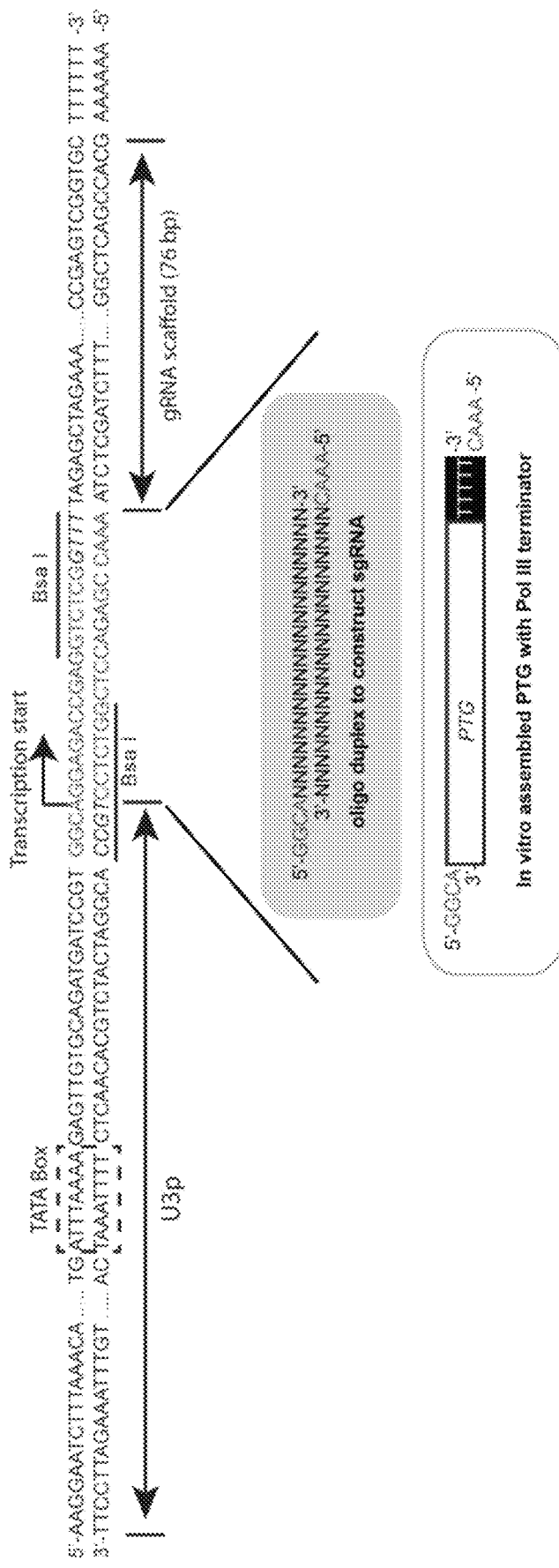

FIGS. 6A-C shows the illustration of pRGE32 and pRGEB32 plasmids used in this study. FIG. 6A and FIG. 6B show a schematic depiction of pRGE32 and pRGEB32 plasmid vectors. The pRGE32 vector was used for transient expression of sgRNAs and PTGs along with Cas9 in plant protoplasts, and pRGEB32 is a binary vector for the *Agrobacterium*-mediated transformation. FIG. 6C shows the cloning site (SEQ ID NOs 110-111) for insertion of gRNA spacer sequence or PTG genes into both vectors. The red letters in vector indicate the cut off fragment and italic letters indicates overhangs in linearized vectors after BsaI digestion. The appropriate overhangs of oligo-duplex or synthetic PTG genes are shown at the bottom. Amp, ampicillin resistance gene; Kan, kanamycin resistance gene; 35S, cauliflower mosaic virus 35S promoter; UBIp, rice ubiquitin promoter; U3p, rice U3 snoRNA promoter; HPT II, hygromycin phosphotransferase II; Ter, nopaline synthase terminator; LB, T-DNA left border; RB, T-DNA right border.

Figure 7:
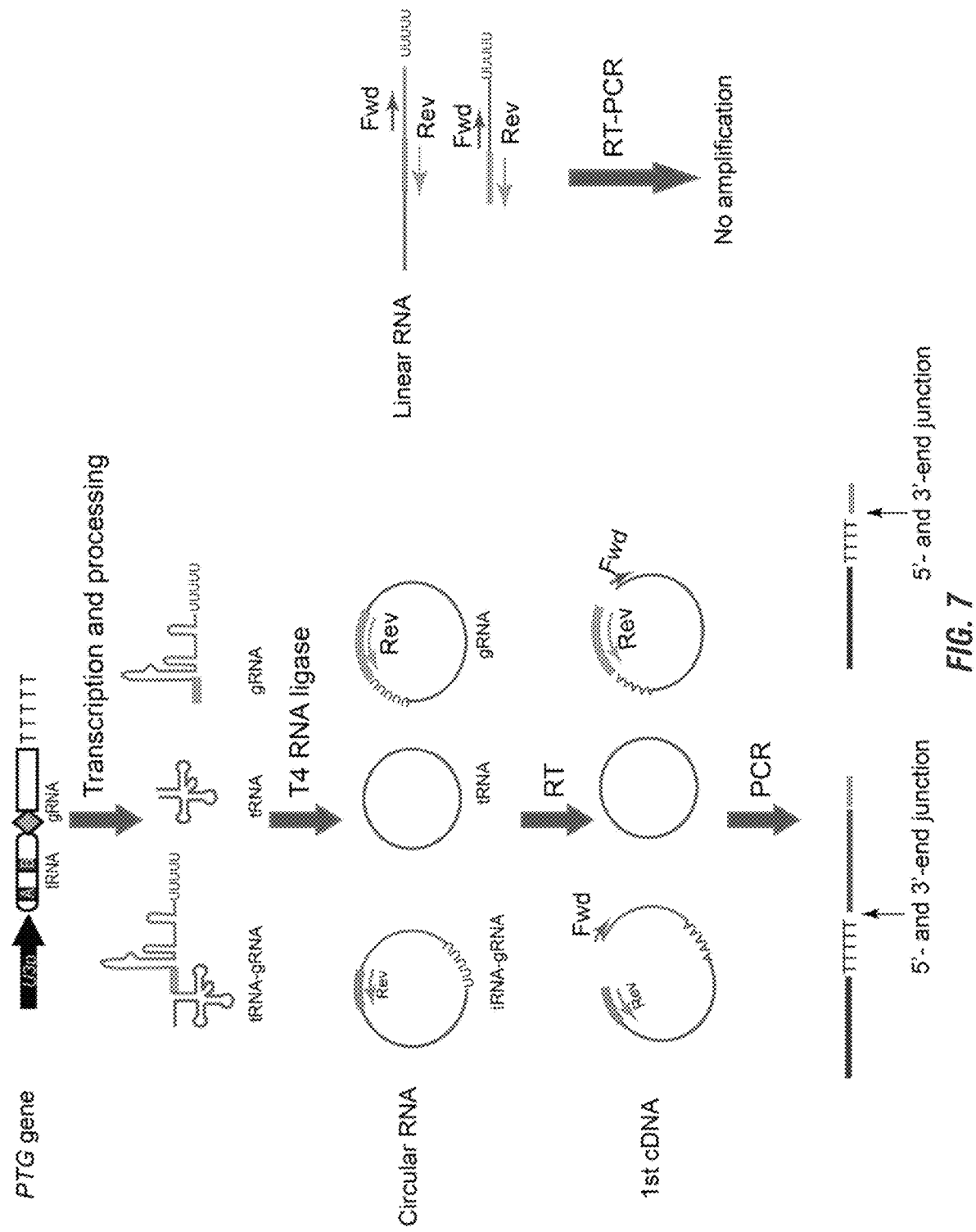

FIG. 7 shows a schematic depiction of cRT-PCR to map gRNA 5' and 3' ends. The primary PTG transcript or processed mature gRNA could be circularized by self-ligation with T4 RNA ligase. The circular RNA was reverse-transcribed to cDNA with gRNA spacer-specific primers (Rev). Then the fragment containing 5'- and 3'-end junction could be amplified with a pair of specific primers (Fwd and Rev) to obtain sequences with mature gRNA extremities. In the cRT-PCR, the linear RNA fraction could not be amplified (right panel) because the primers were not paired.

Figure 8:
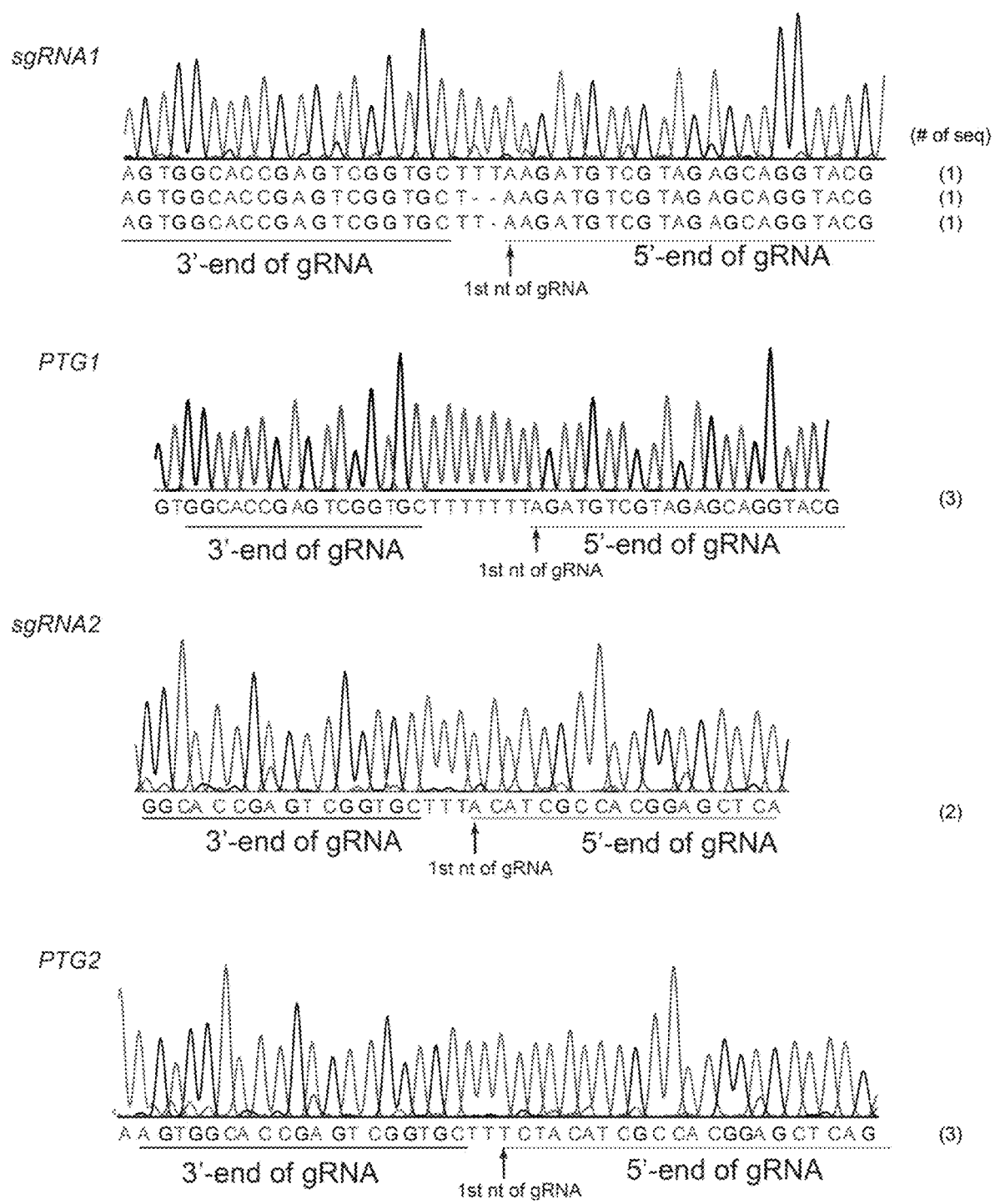

FIG. 8 shows the sequences of cRT-PCR products from sgRNA1 (SEQ ID NOs 112-114), sgRNA2 (SEQ ID NO:116), PTG1 (SEQ ID NO:115) and PTG2 (SEQ ID NO:117). An example of sequence chromatographs is shown for each cRT-PCR product. The number of individual colonies with the identical sequences is shown in parentheses. The sequencing results indicate that variable length of poly(U) tails were added to the 3'-end of gRNAs produced by these genes.

Figure 9A:
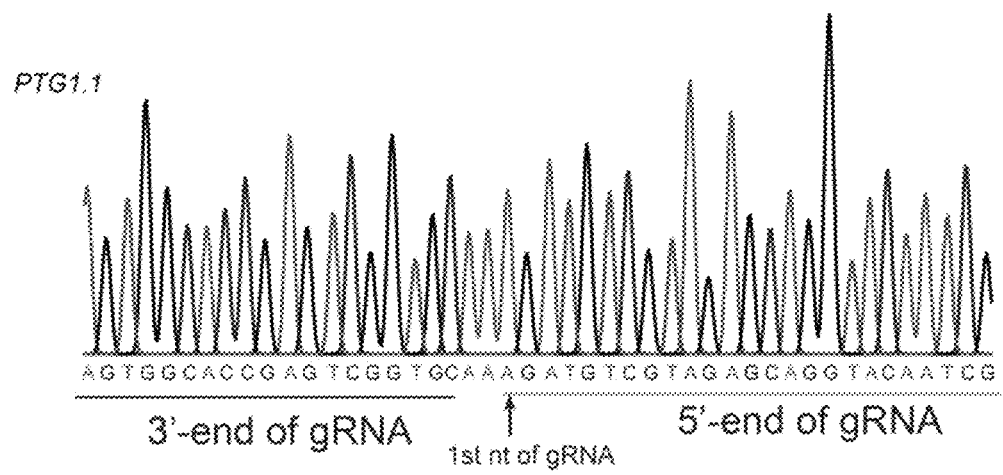
Figure 9B:
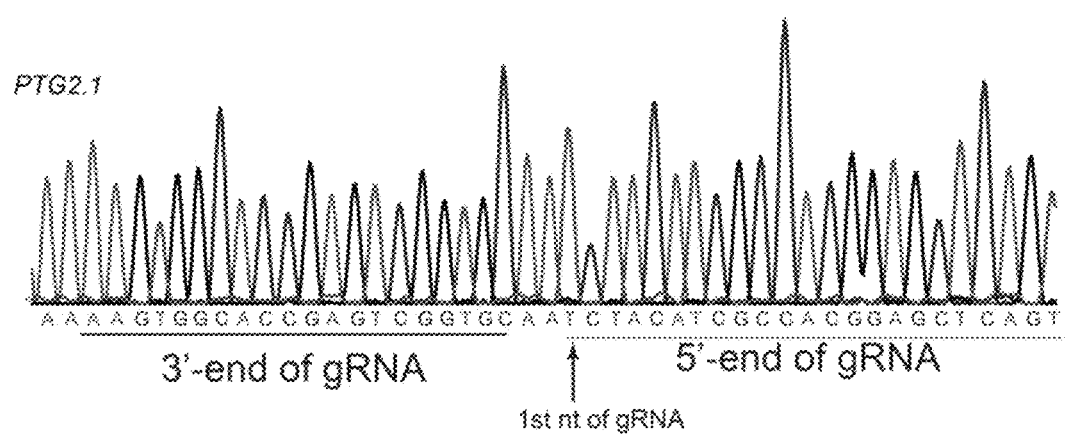
Figure 9C:
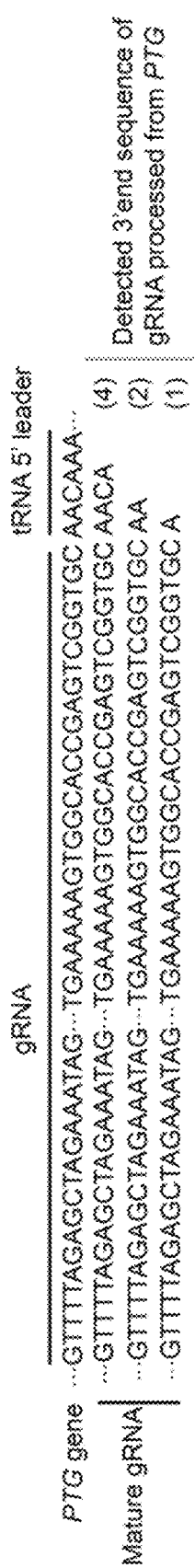

FIG. 9A-C show the sequences of cRT-PCR products from PTG1.1 (SEQ ID NO:118) and PTG2.1 (SEQ ID NO:119). FIG. 9A and FIG. 9B are representative sequencing chromatographs of cRT-PCR products. FIG. 9C shows a summary of the mapped 3'-end of mature gRNAs from PTG1.1 and PTG2.1. All sequences show identical Pt nt of gRNA 5'-end. The number of individually cloned PCR products with the identical sequences is shown in parentheses. Dots indicate bases not shown in the alignment (nucleotides 107-189 of SEQ ID NO:18 or SEQ ID NO:19).

Figure 10A:
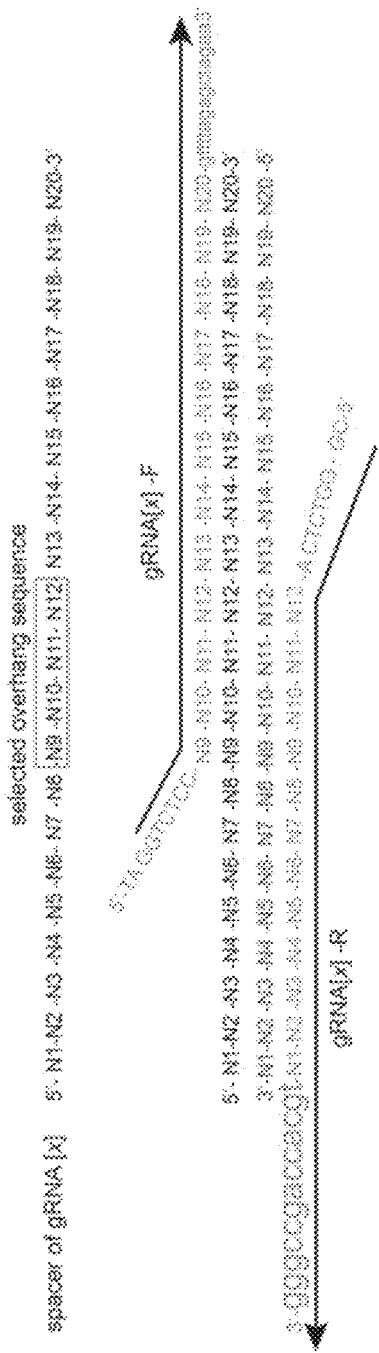
Figure 10B:
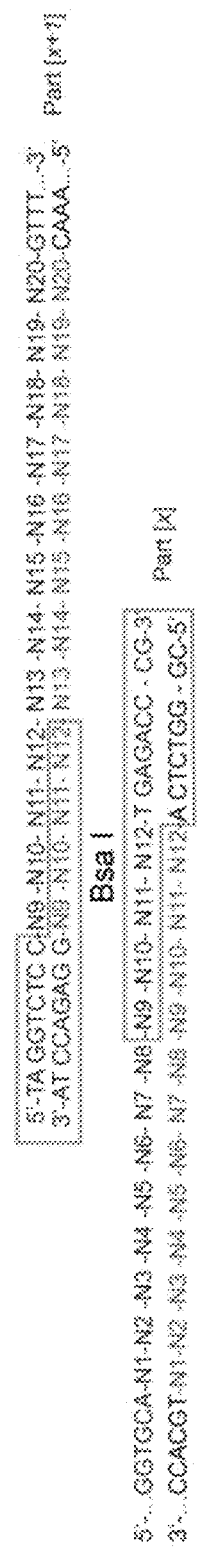
Figure 10C:
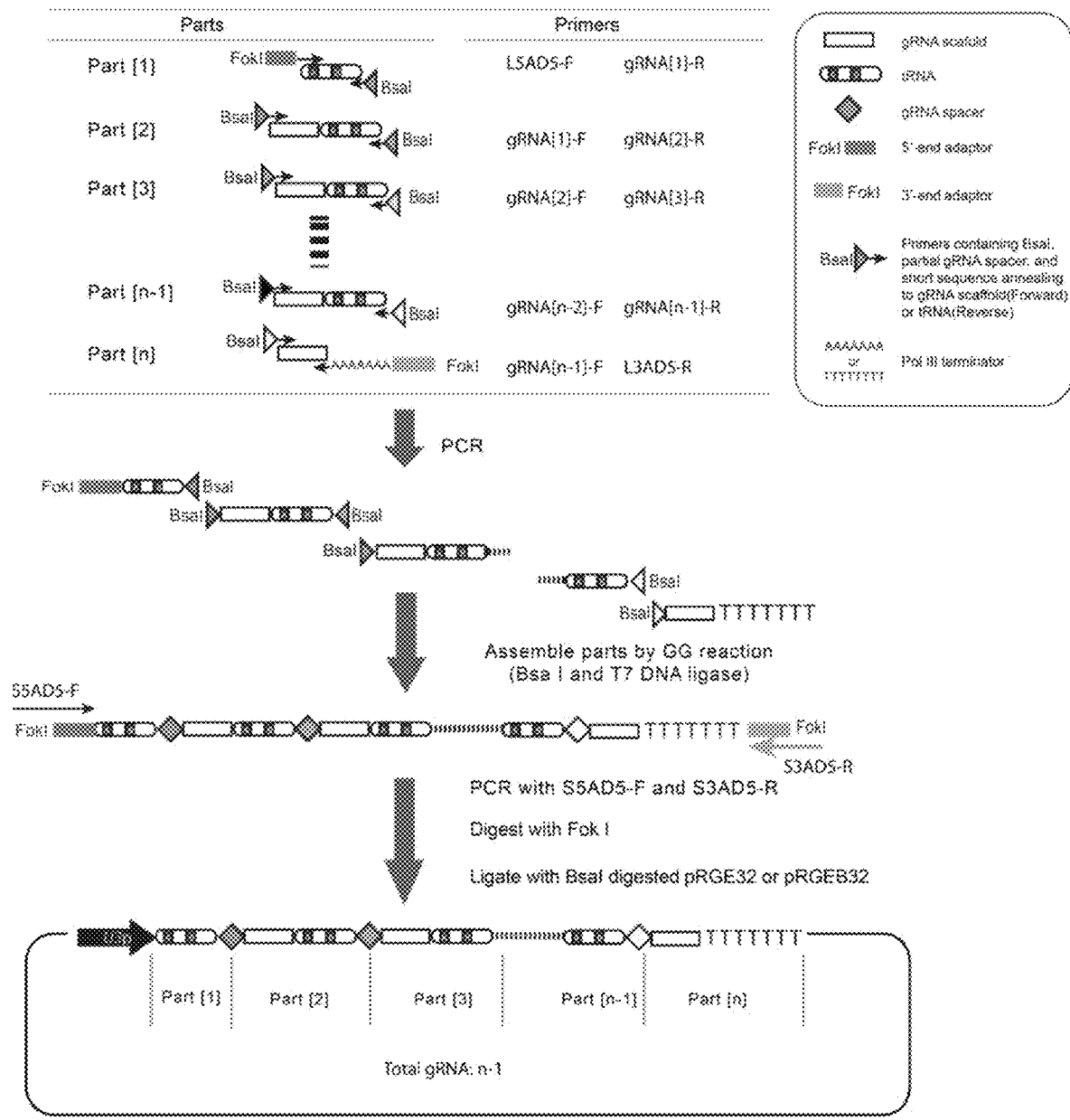

FIGS. 10A-C show the strategy to synthesize PTGs with one step (level 1) Golden Gate (GG) assembly. FIG. 10A shows a schematic guide to design gRNA spacer specific primers with 4 bp overlapping for Golden Gate assembly. The primers could be overlapped on any 4 consecutive nucleotides within the spacer. FIG. 10B shows the mechanism to generate a complete gRNA spacer during GG assembly. After PCR amplification and BsaI digestion, the 4 bp overlapped sequence in the gRNA spacer was generated as overhangs to ligate two parts and the resulting ligation product would produce a complete gRNA without extra nucleotides. The DNA sequences in the box indicate BsaI cut site. FIG. 10C shows schematic diagrams for level 1 GG assembly to synthesize PTGs from PCR parts and clone them into plasmid vectors (pRGE32 or pRGEB32). A PTG with n−1 gRNAs are divided into n parts (Part[1]-Part[n], see the bottom). Each part was amplified with spacer-specific primers containing BsaI adaptor, except two terminal parts using gRNA spacer primer and terminal specific primers containing Fok I site (L5AD5-F and L3AD5-R). These PCR parts were ligated together using GG assembly to produce the PTG with complete gRNA spacers. The assembled product was amplified with short terminal specific primers (S5AD5-F and S3AD5-R). After Fok I digestion, the PTG fragment was inserted into the BsaI digested pRGE32 and pRGEB32.

Figure 11:
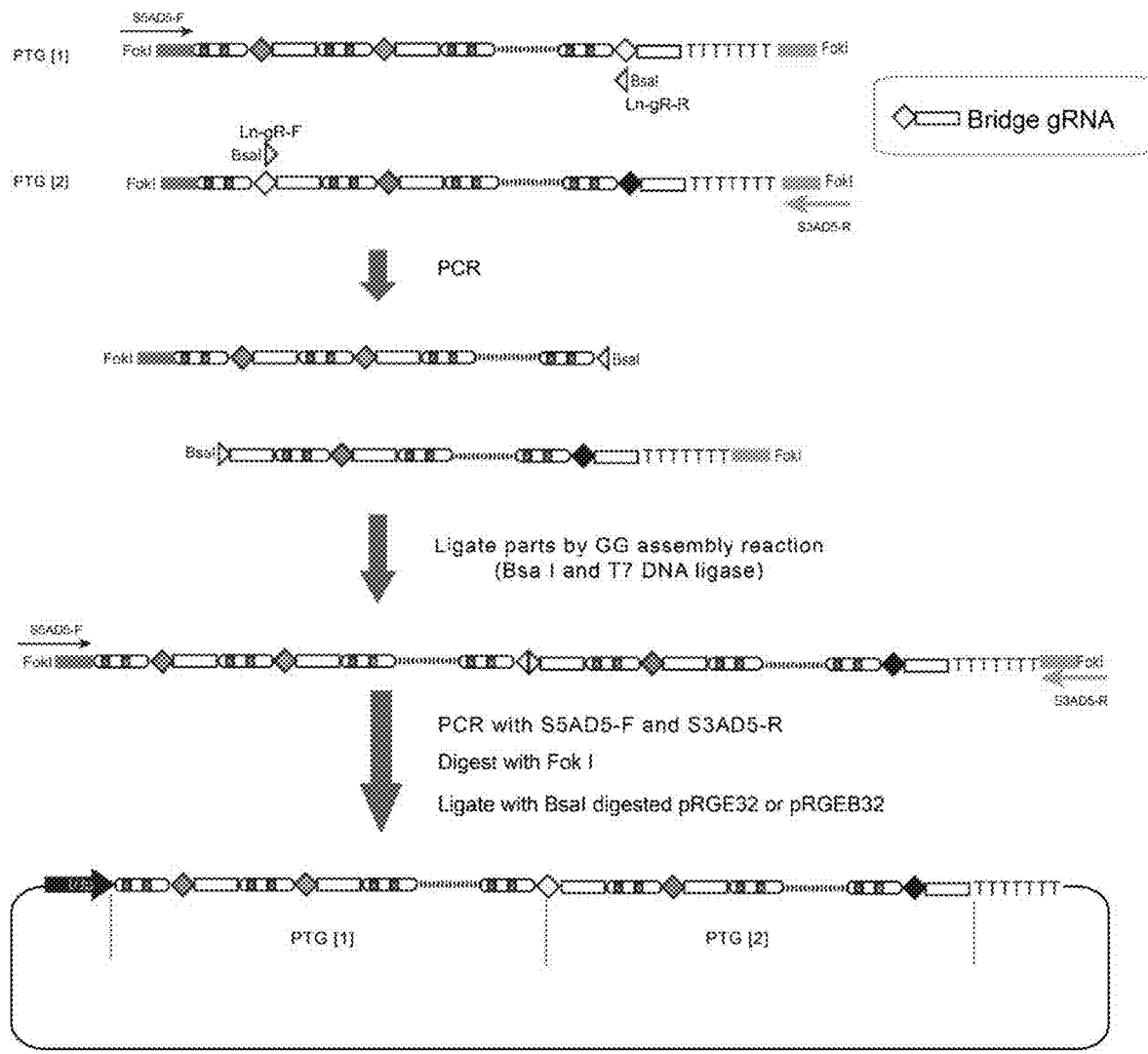

FIG. 11 shows a strategy to synthesize a large PTG from two PTG parts using level 2 Golden Gate (GG) assembly. Two PTG genes (PTG[1] and PTG[2]) containing different numbers (2-6) of gRNAs were synthesized by level 1 GG assembly. To concatenate PTG[1] with PTG[2], the last gRNA (bridge gRNA) in PTG[1] should contain the same spacers (show in yellow diamond) as the first gRNA in PTG[2]. Then level 2 GG parts were amplified from PTG[1] and PTG[2] with bridge gRNA spacer specific primers (Ln-gR-F and Ln-gR-R) containing BsaI site and terminal specific primers (S5AD5-F and S3AD5-R). After Fok I digestion, these two PTG parts were ligated together with GG assembly and inserted into BsaI digested pRGE32 or pRGEB32 vector.

Figure 12A:
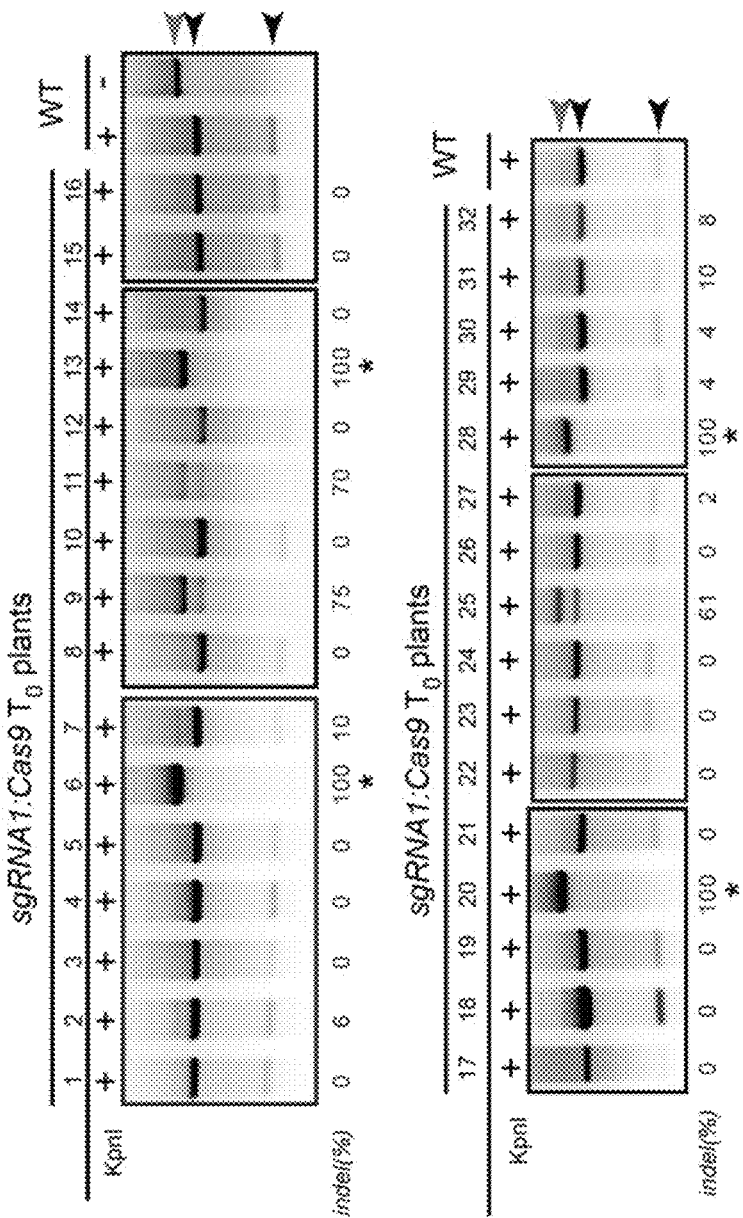
Figure 12B:
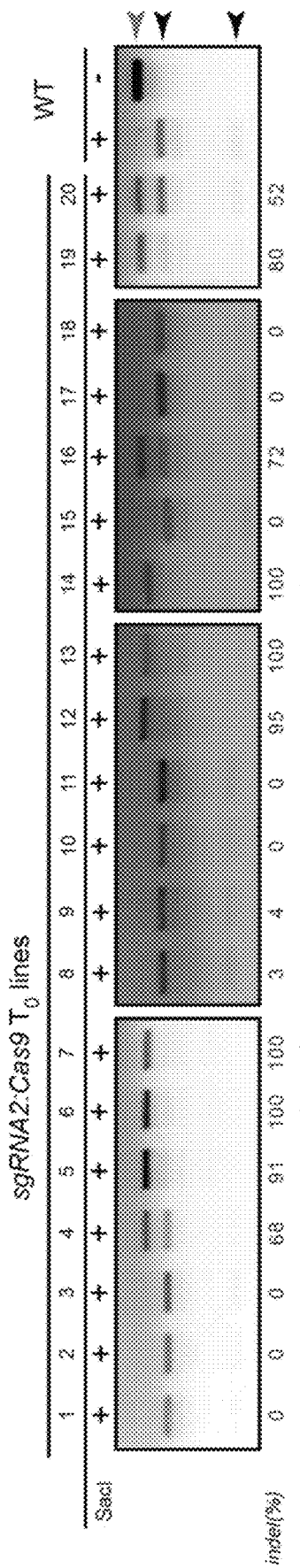

FIGS. 12A-B show targeted mutagenesis at MPK5 locus in transgenic plants expressing sgRNA:Cas9. Targeted DNA fragment was amplified from independent transgenic plants and analyzed with PCR/RE assays, and a wild type plant (WT) was included as control. Kpn I and SacI were used to examine mutation at sgRNA1/gRNA1 and sgRNA2/gRNA2 targets, respectively. On the agarose gels, mutated DNA fragments resistant to KpnI or SacI digestion are indicated with red arrow whereas digested WT DNA fragments are indicated with black arrow. The indel frequency, which was estimated based on the intensity of digested and undigested bands, is indicated at the bottom of each lane. The putative biallelic mutants are indicated by asterisk.

Figure 13:
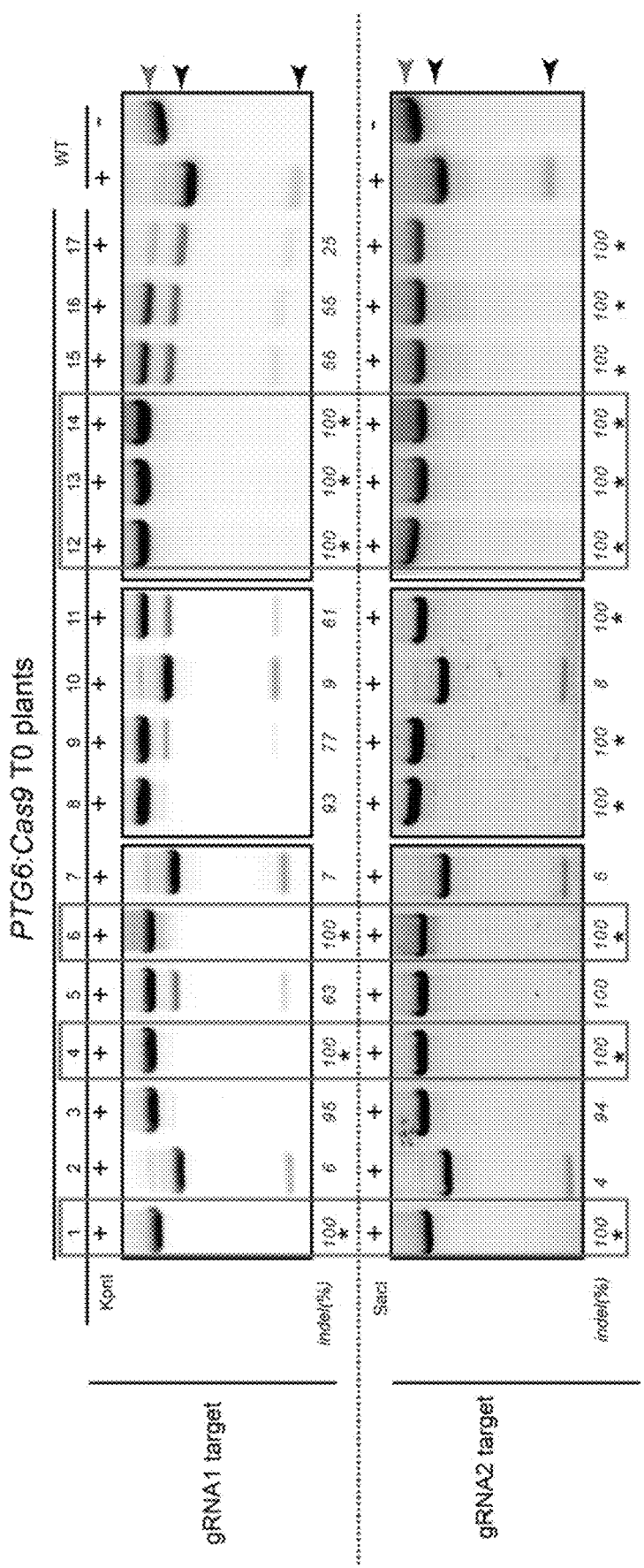

FIG. 13 shows targeted mutagenesis at MPK5 locus in transgenic plants expressing PTG6:Cas9. Mutations at MPK5 locus of PTG6:Cas9 plants were examined with PCR/RE assay. The putative biallelic mutants at gRNA1 or gRNA2 site are indicated with asterisk, and biallelic mutations at both sites are indicated with red rectangle. In the gel, mutated DNA fragments resistant to restriction enzyme (KpnI or SacI) digestion are indicated with red arrow whereas digested WT DNA fragments are indicated with black arrow. The indel frequency, which was estimated based on the intensity of digested and undigested bands, is indicated at the bottom of each lane.

Figure 14:
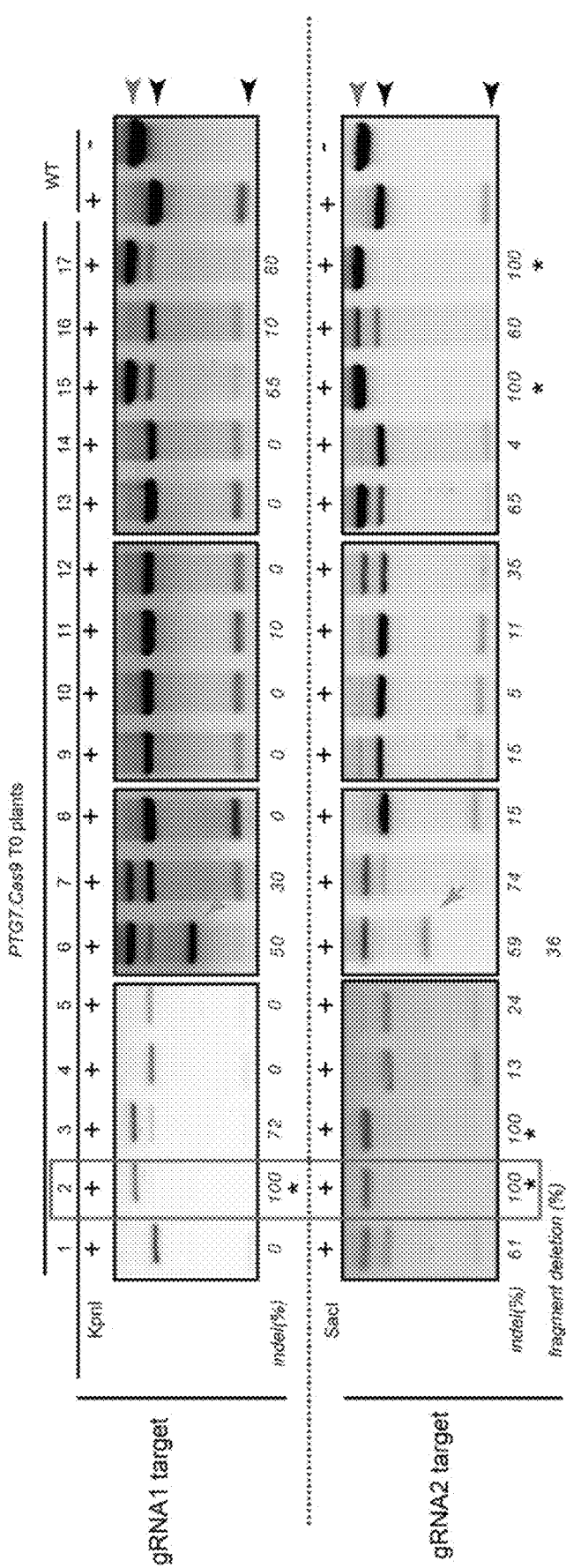

FIG. 14 shows targeted mutagenesis at MPK5 locus in transgenic plants expressing PTG7:Cas9. The mutations at gRNA1 and gRNA2 targets within MPK5 were examined by PCR/RE assays. The putative biallelic mutations at gRNA1 or gRNA2 site are indicated with asterisk, and biallelic mutations at both sites are marked with red rectangle. The deletion of a chromosomal fragment between gRNA1 and gRNA2 is shown with blue arrow. Mutated DNA fragments resistant to restriction enzyme digestion are indicated with red arrow whereas digested WT DNA fragments are indicated with black arrow. The indel frequency is indicated at the bottom of each lane.

Figure 15:
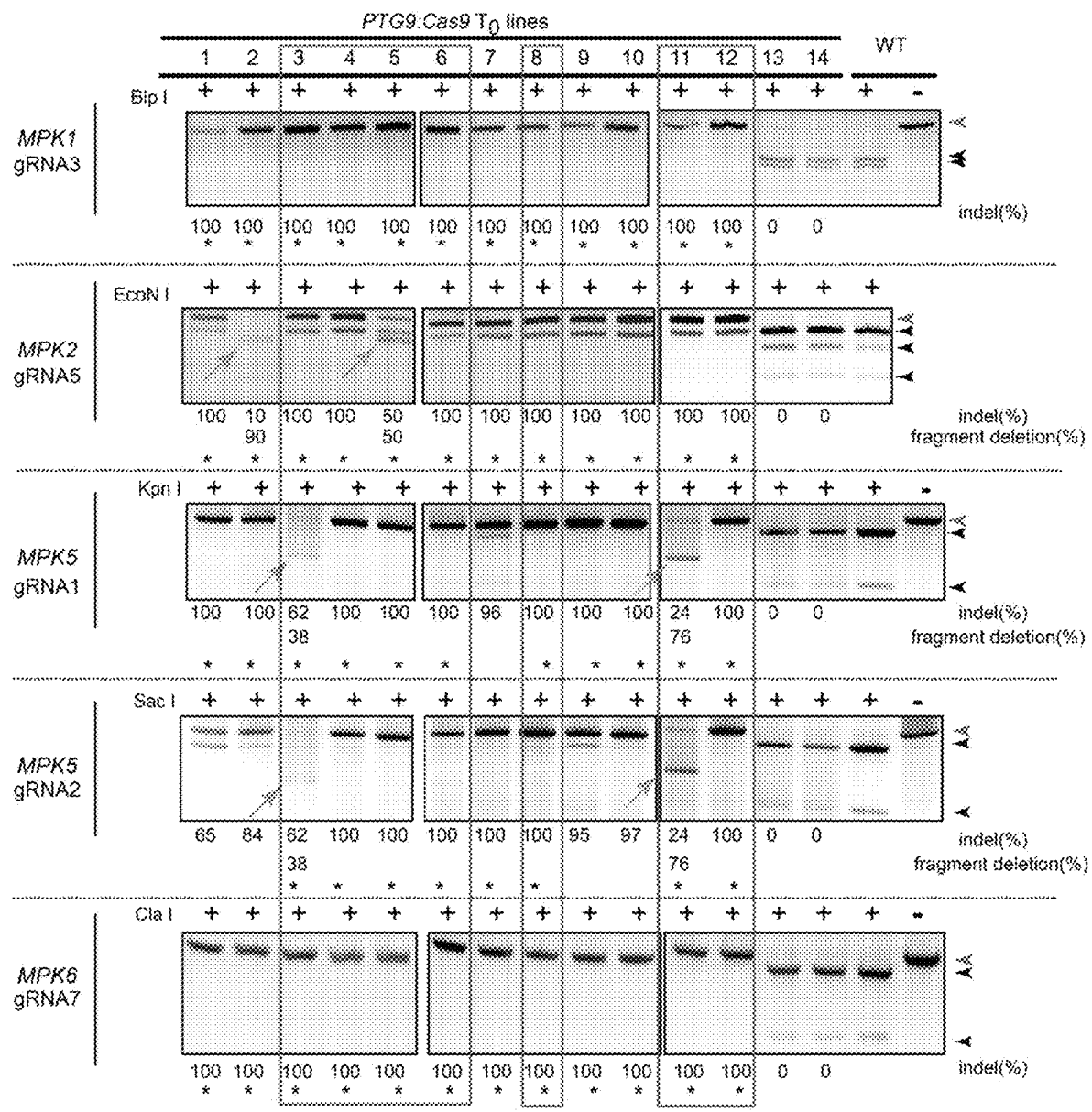

FIG. 15 shows targeted mutagenesis at five genomic sites in transgenic plants expressing PTG9:Cas9. The mutations at the targeting sites of gRNA1/2/3/5/7 were examined by PCR/RE assays. The transgenic lines carrying potential biallelic mutations at each target are indicated with asterisk, and biallelic mutations at all five sites are marked with red rectangle. The deletion of chromosomal fragments between paired gRNAs is indicated with blue arrow. Mutated DNA fragments resistant to restriction enzyme digestion are indicated with red arrows whereas digested WT DNA fragments are indicated with black arrow. The indel frequency and fragment deletion frequency in each line are indicated at the bottom. Of note, there are two EcoN I sites within the MPK2 amplicon and therefore the digestion of WT DNA fragment yielded three bands.

Figure 16:
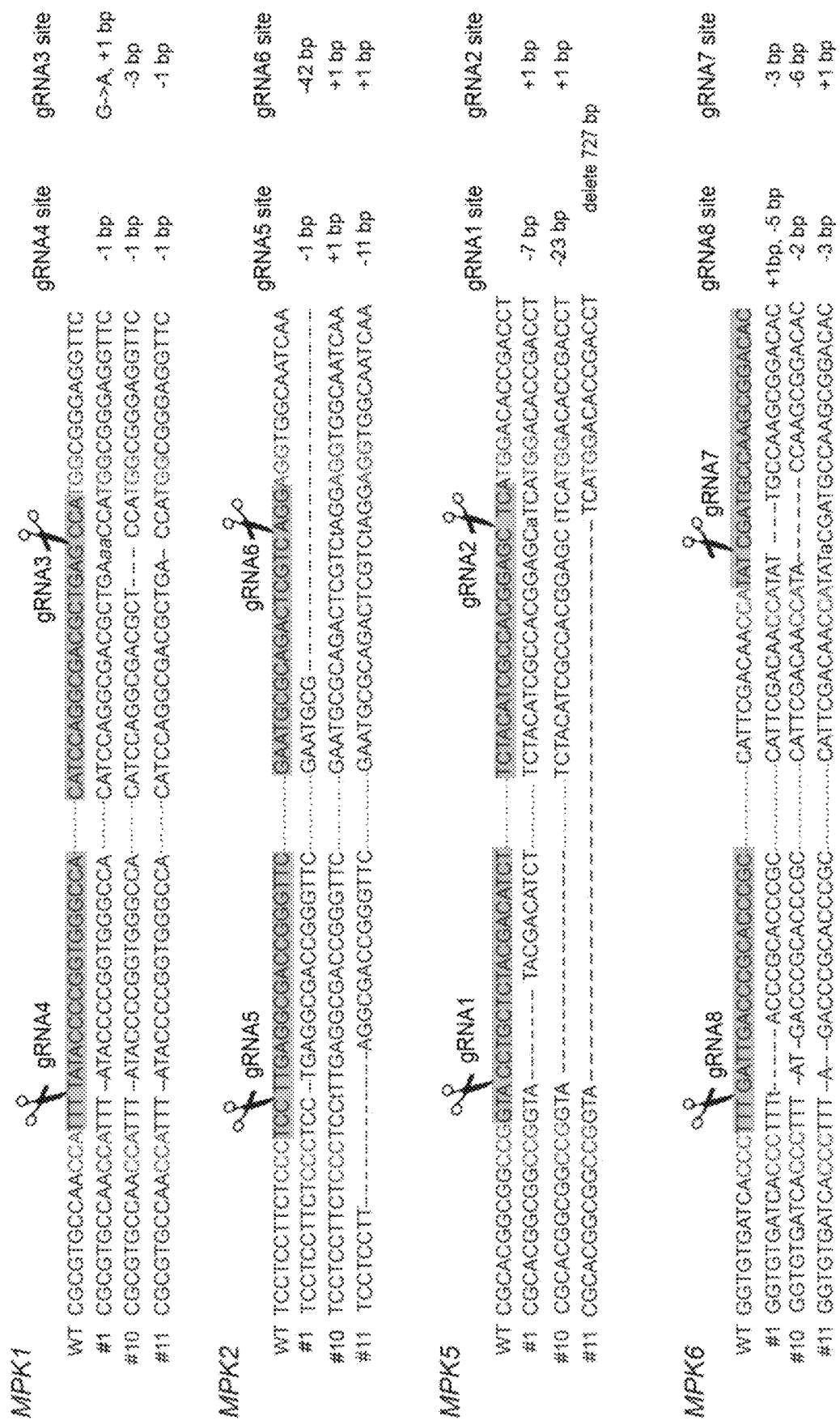

FIG. 16 shows targeted mutation at eight genomic sites in four MPK loci in PTG9:Cas9 lines. The mutated sequences from three transgenic lines (#1, #10 and #11) expressing PTG9:Cas9 were aligned with wild type sequences. Insertion or substitution is shown in lowercase. Short line (-) indicates base pair deletion and dot (.) indicates sequences not shown in the alignments. The Cas9/gRNA cut sites are indicated with scissor. MPK1 WT (SEQ ID NO:79); MPK1 #1 (SEQ ID NO:120); MPK1 #10 (SEQ ID NO:121); MPK1 #11 (SEQ ID NO:122); MPK2 WT (SEQ ID NO:81); MPK2 #1 (SEQ ID NO:123); MPK2 #10 (SEQID NO:124); MPK2 #11 (SEQ ID NO:125); MPK5 WT (SEQ ID NO:82); MPK5 #1 (SEQ ID NO:126); MPK5 #10 (SEQ ID NO:127); MPK5 #11 (SEQ ID NO:128); MPK6 WT (SEQ ID NO:84); MPK6 #1 (SEQ ID NO:129); MPK6 #10 (SEQ ID NO:130); and MPK6 #11 (SEQ ID NO:131).

Figure 17A:
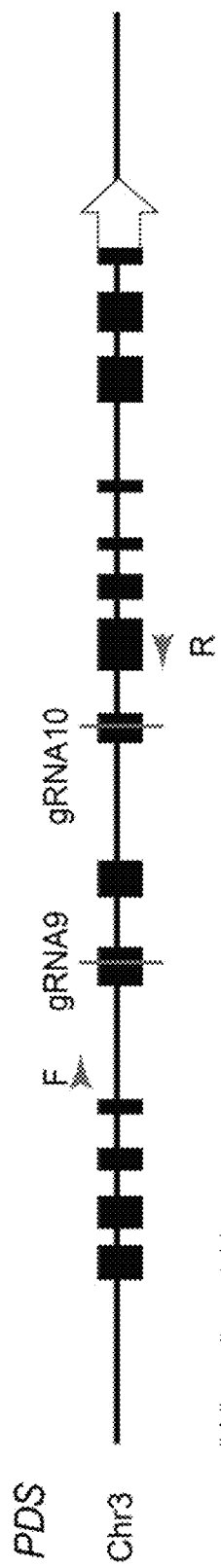
Figure 17B:
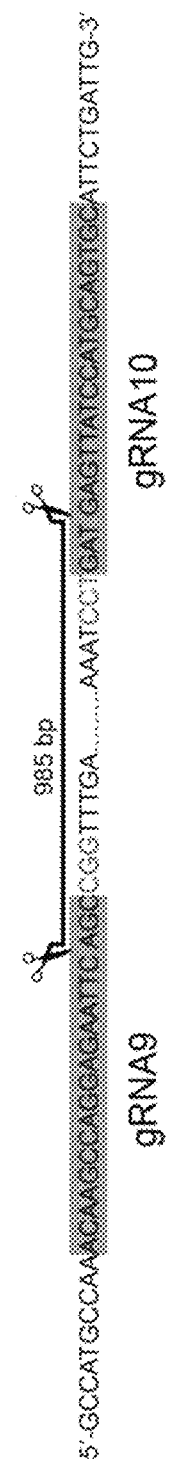
Figure 17E:
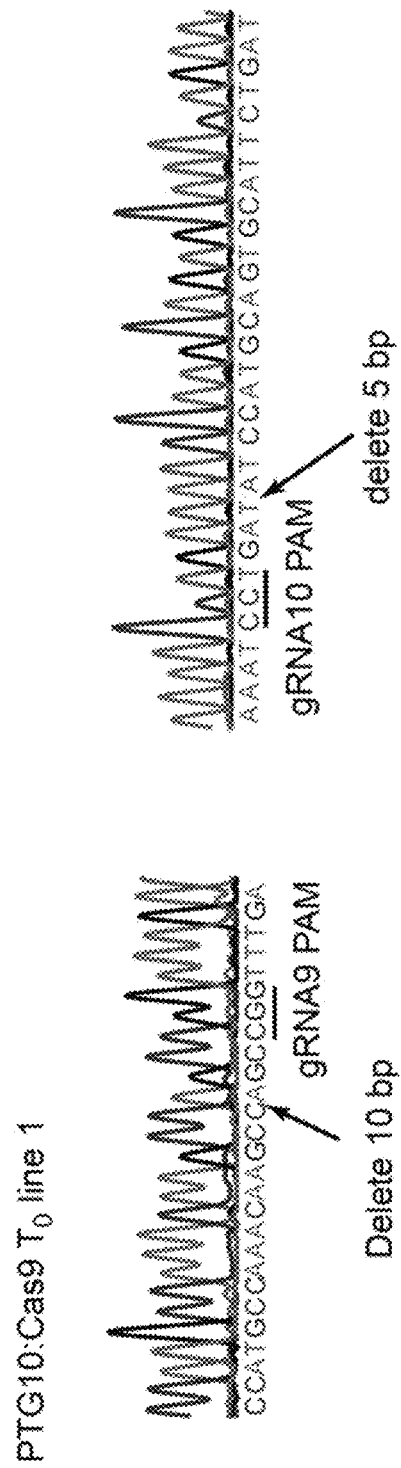

FIGS. 17A-E show targeted mutation of rice PDS gene in transgenic plants with PTG10:Cas9. FIG. 17A shows a schematic depiction of rice PDS locus. Rectangles represent exons, of which the black ones indicate coding regions. The targeting sites of gRNA9 and gRNA10 and the location of primers (F and R) for genotyping are indicated with blue line and arrow, respectively. FIG. 17B shows targeting sequences of gRNA9 and gRNA10 are highlighted in green color, and the relevant PAM sites are indicated with red letters (SEQ ID NO:132). FIG. 17C shows gene architecture of PTG10. (D) PCR amplification of targeted DNA sites from transgenic plants expressing PTG10:Cas9. The deletion of chromosomal fragment between gRNA1 and gRNA2 is indicated with blue arrow. FIG. 17E are examples of mutation at the PDS target sites (SEQ ID NO: 133 & 134).

Figure 18:
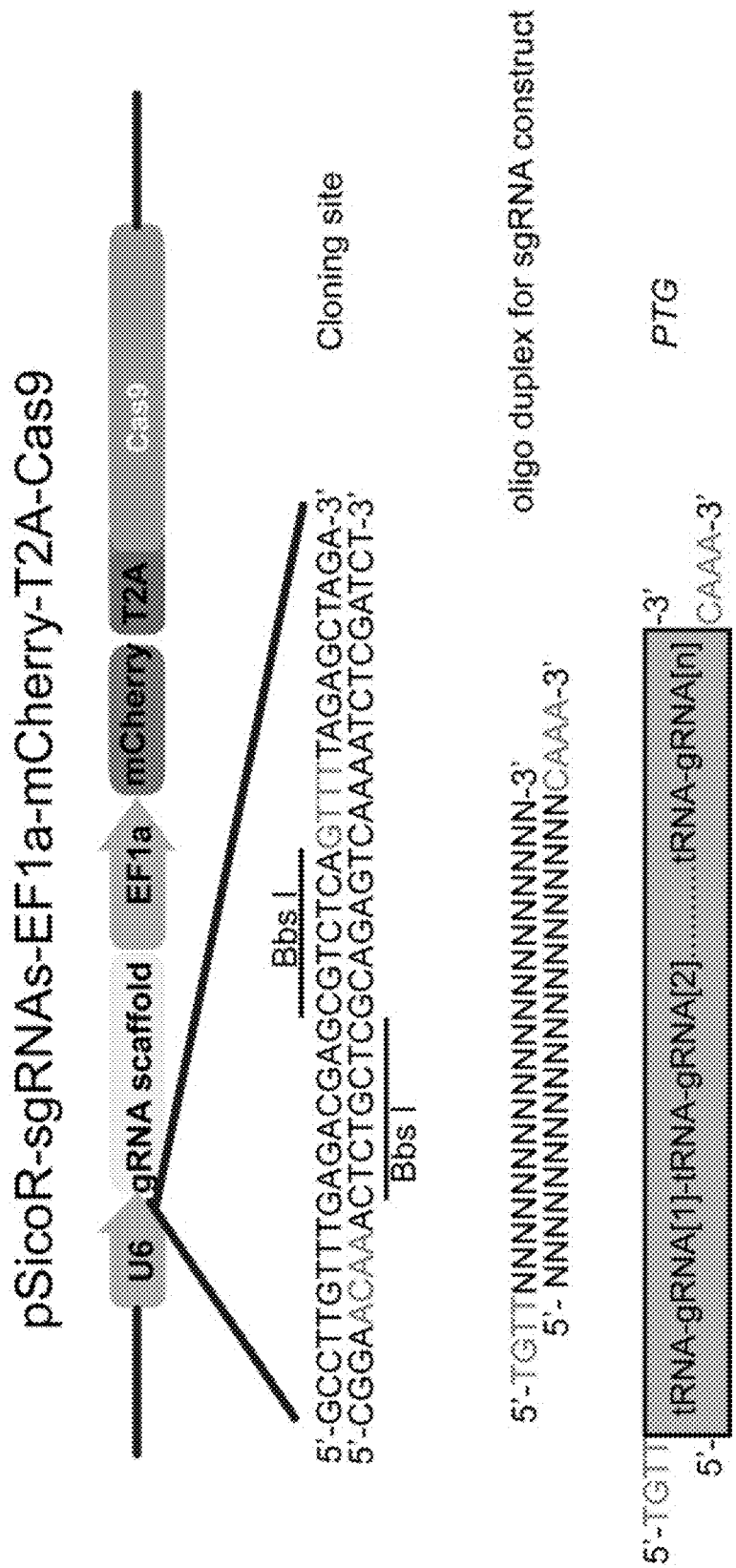

FIG. 18 shows a schematic map of the pSico-sgRNAs-EF1a-mCherry-T2A-Cas9 vector. The guide sequence or PTG genes could be expressed after inserting into the BbsI sites of this vector (SEQ ID NOs 190-191). The red letters indicated the overhangs in the cloning site.

Figure 19A:
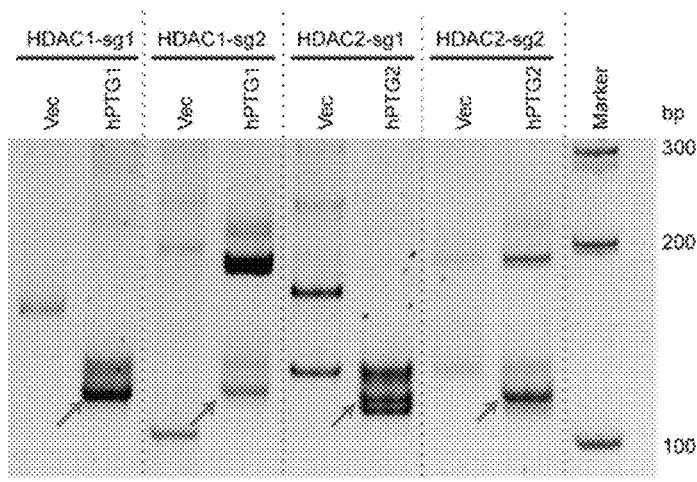
Figure 19B:
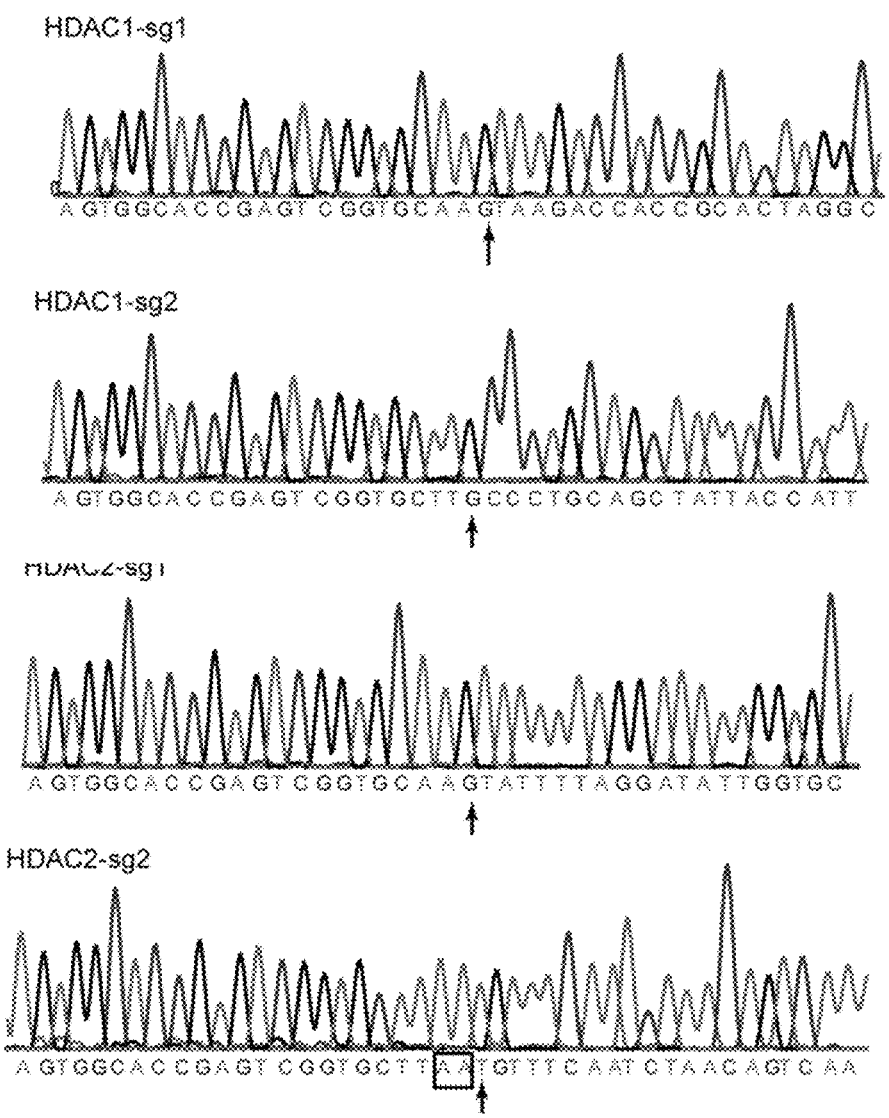

FIGS. 19A-C show mature gRNAs with desired guide sequences were precisely produced from hPTG genes. FIG. 19A shows electrophoresis of cRT-PCR products in an acrylamide gel. Red arrow indicates the mature gRNAs produced from hPTG1 and hPTG2. Vec, empty vector control. FIG. 19B shows chromatography of mature gRNA sequences as revealed by cRT-PCR and DNA sequencing (SEQ ID NOs 192-195). The arrow indicates the first nucleotide at the 5'-end of mature gRNAs. FIG. 19C shows the mapped cleavage site in hPTG1 (SEQ ID NO: 196) and hPTG2 (SEQ ID NO: 197) according to cRT-PCR results. The scissor indicates the cleaved site of the tRNA processing system. Blue letter, tRNA; red letter, gRNA guide sequence; lowercase letter, gRNA scaffold sequence; underlined letter, Pol III terminator.

Figure 20A:
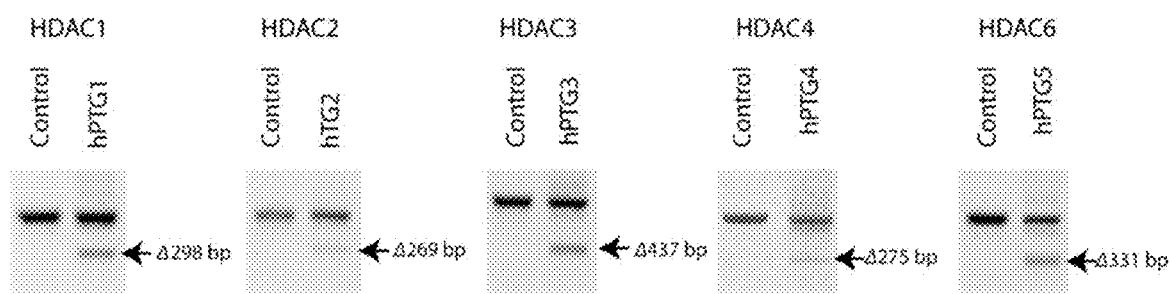
Figure 20B:
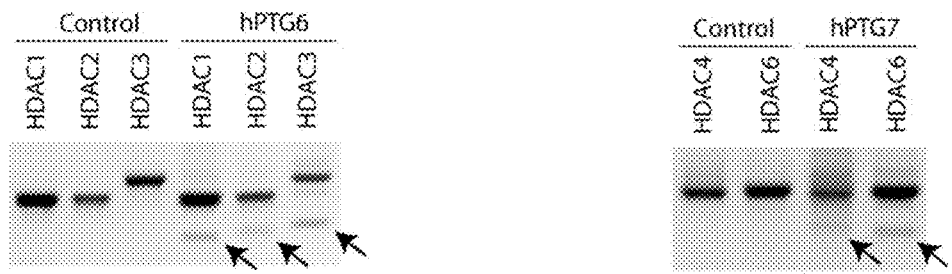
Figure 20C:
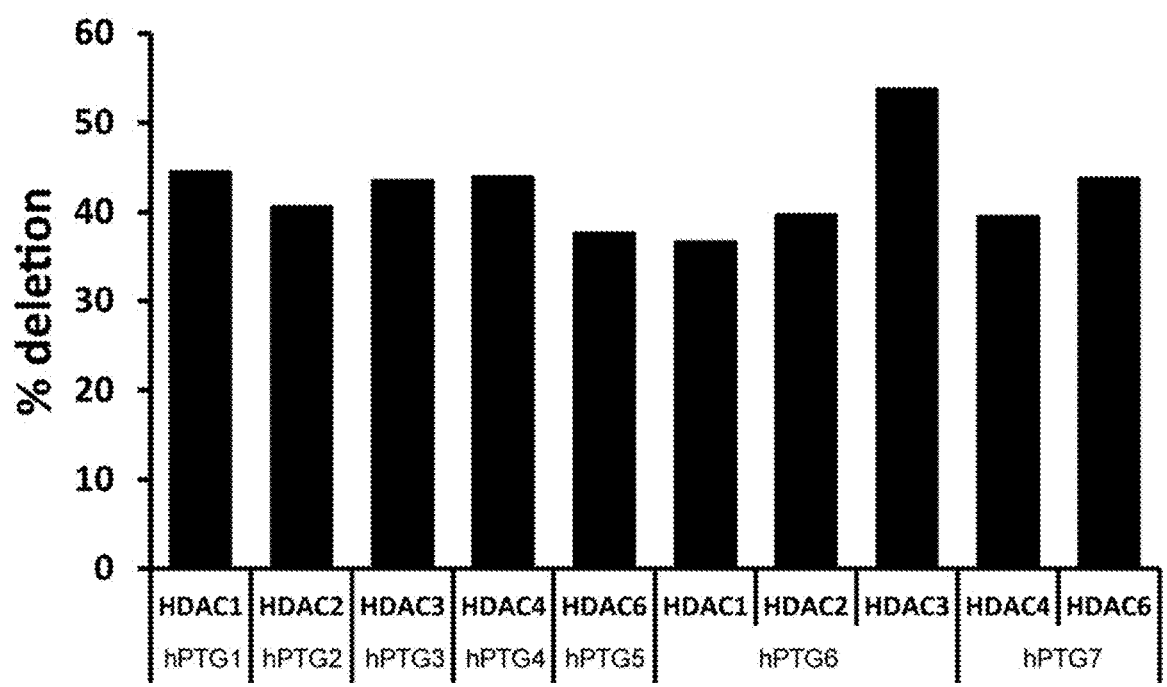

FIGS. 20A-C show targeted deletion of chromosomal fragment at HDAC loci. FIG. 20A and FIG. 20B show chromosomal fragment deletion were revealed by truncated PCR products (indicated by arrows) at respective HDAC loci in human cells expressing the Cas9-hPTG constructs. FIG. 20C shows deletion efficiency of hPTG constructs expressing different number of gRNAs.

Figure 21:
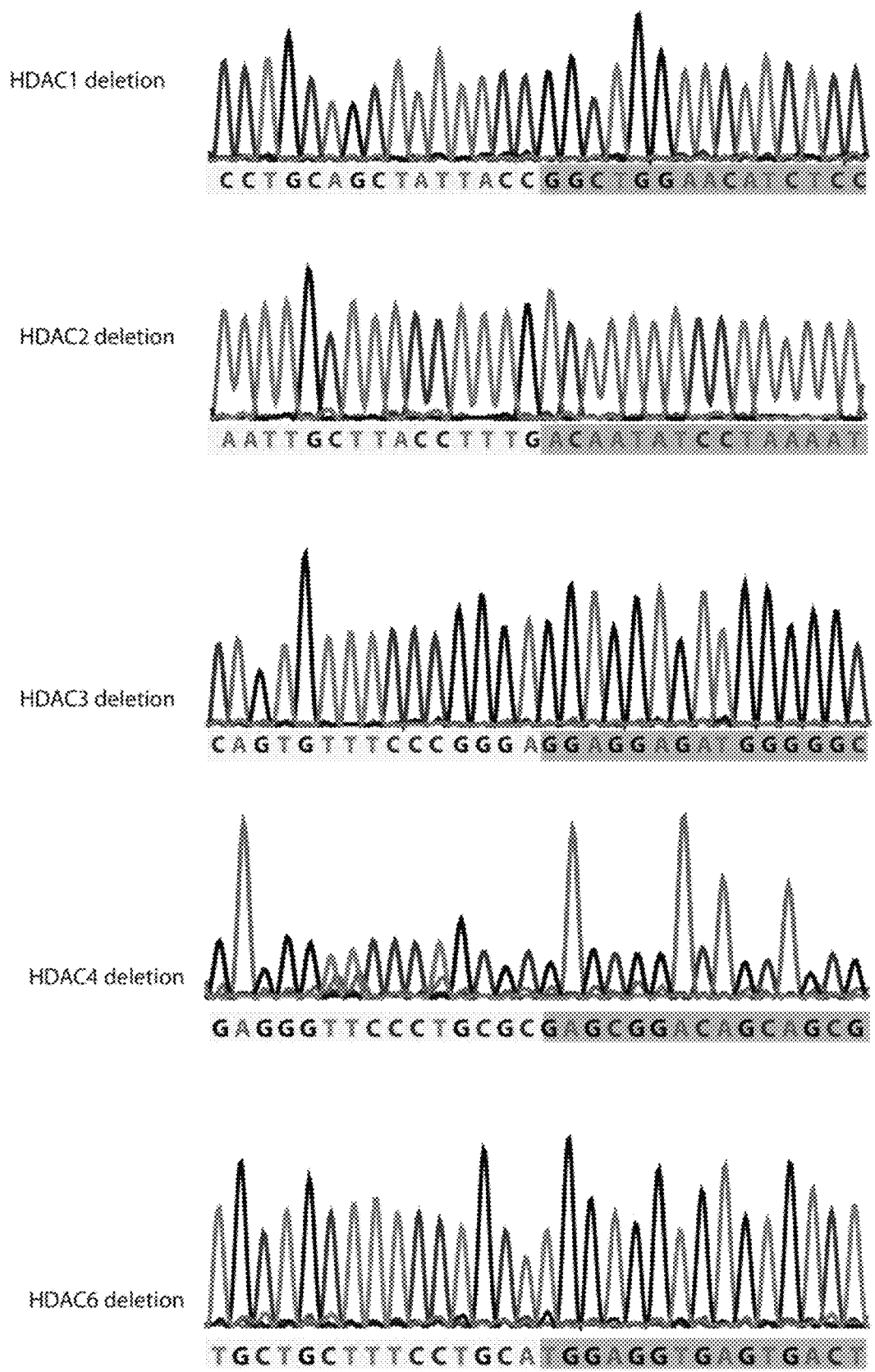

FIG. 21 shows DNA sequences of the amplicons with the chromosomal deletions at HDAC gene loci (SEQ ID NOs 198-202).

Figure 22A:
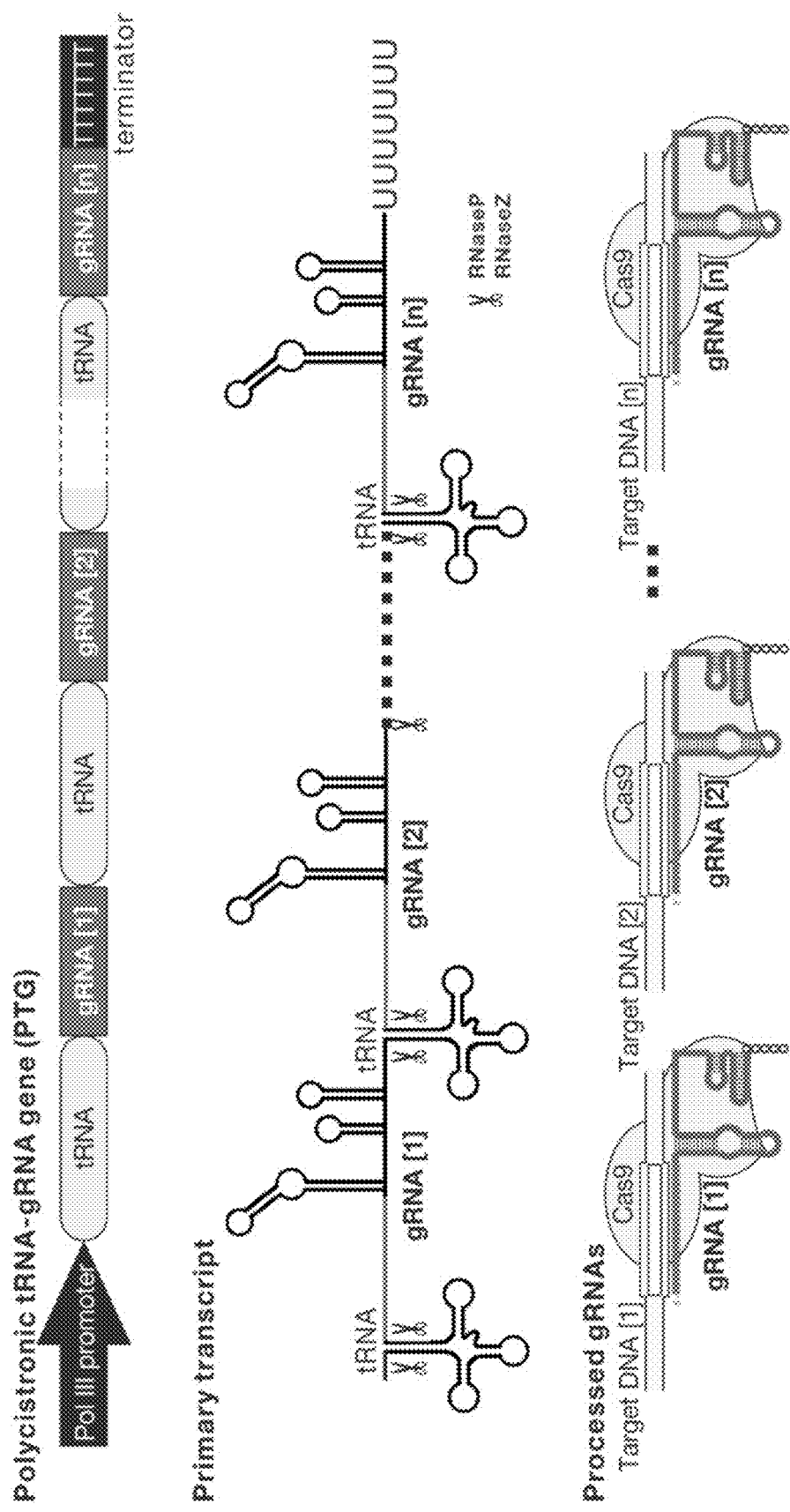

FIGS. 22A-C show a schematic diagram of a polycistronic tRNA-gRNA gene (PTG) processing system and design of PTGs to target four rice MPKs. FIG. 22A shows a polycistronic tRNA-gRNA gene (PTG) consists of tandemly arrayed tRNA-gRNA repeats with a Pol III promoter to initiate transcription that is stopped by a Pol III terminator. The cell's endogenous RNaseP and RNaseZ can recognize the secondary structure of the tRNAs within the primary transcript and splice multiple functional gRNAs from the transcript. The processed gRNAs can complex with the Cas9 endonuclease to simultaneously target multiple independent genomic sites. FIG. 22B shows eight gRNAs were designed to target four closely-related rice MPK genes for gene knock-out. Chromosomal deletion could occur on each gene in addition to small insertion and deletion of nucleotides by non-homologous end-joining because each gene is targeted by two gRNAs. FIG. 22C shows a total of eight PTG co-expressing one to eight gRNAs were used in this study. PTG2 and PTG6 target MPK5. PTG3, PTG4, and PTG5 target MPK1, MPK2, and MPK6, respectively. PTG7 and PTG8 target MPK1/MPK5 and MPK2/MPK6 to create double mutants. PTG9 co-expressed eight gRNAs to simultaneously target all four MPK genes.

Figure 23A:
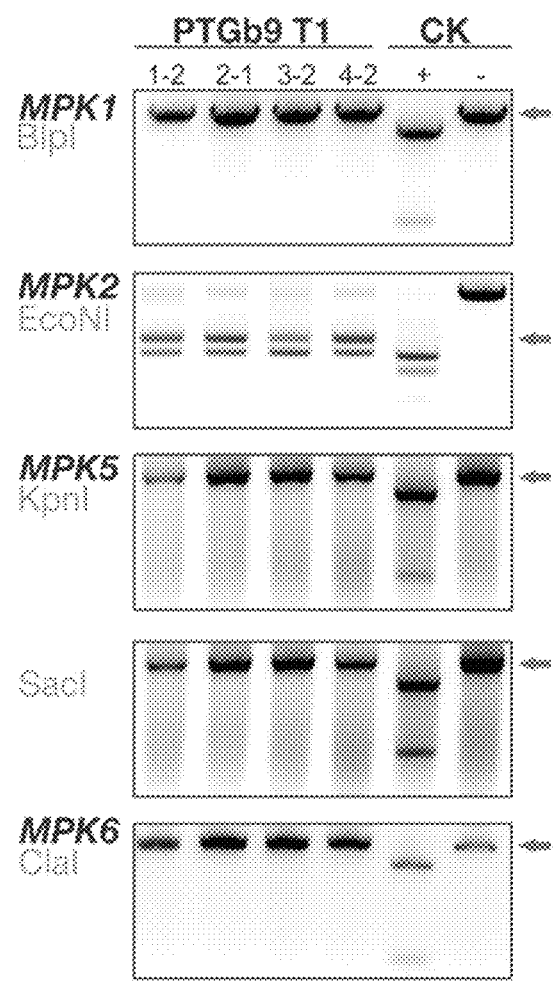
Figure 23B:
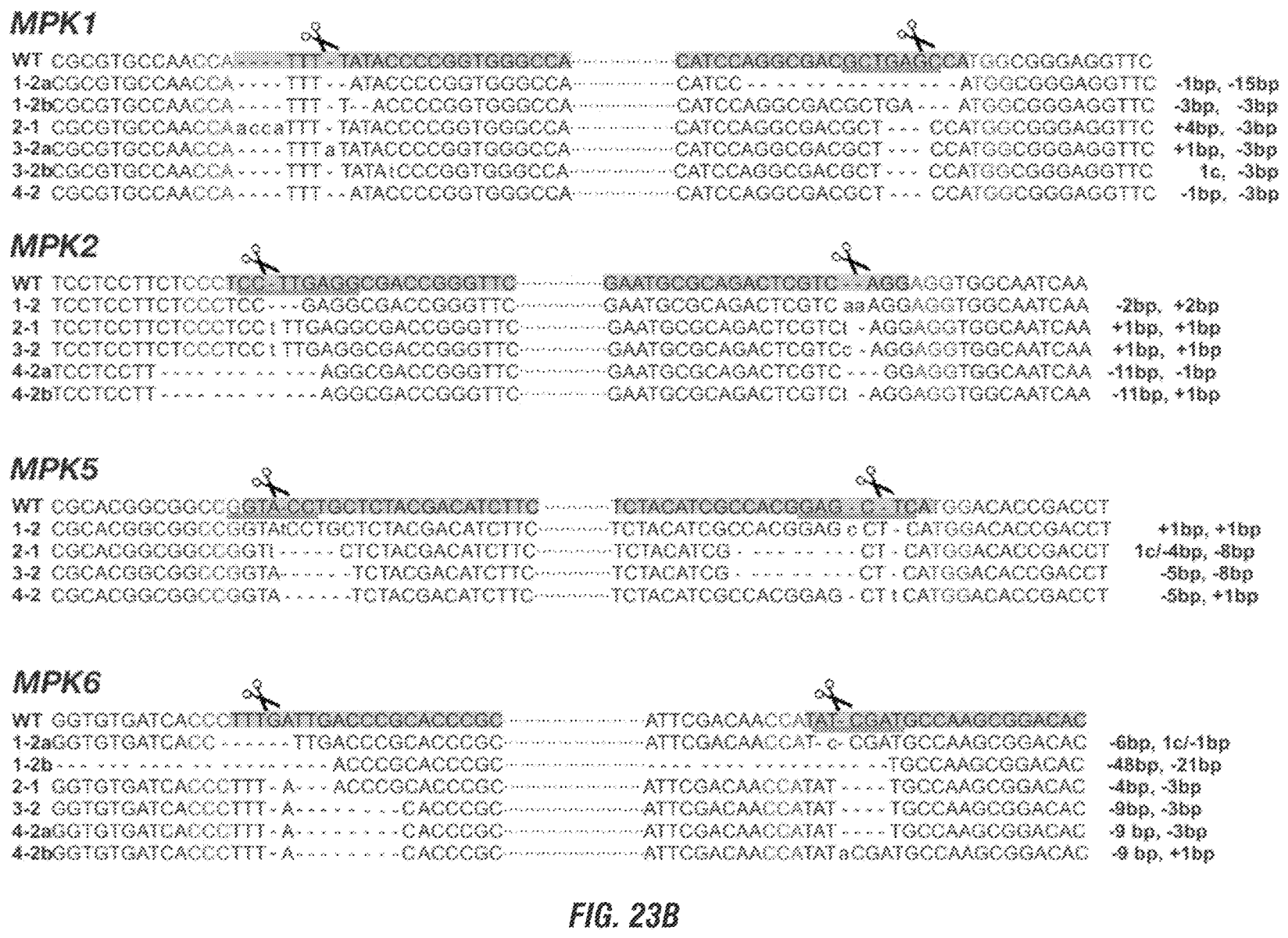

FIGS. 23A-B show $T_1$ generation rice plants of four PTGb9 lines carry eight biallalic mutations in four genes. FIG. 23A shows detection of mutations on five sites via PCR-RE assay. The PCR product of mutated DNA cannot be digested by the appropriate restriction enzyme (RE; blue name and underlined in FIG. 23B). PCR products of the corresponding genes in all four $T_1$ plants are resistant to digestion (red arrow) and scissors indicate indel mutations at these sites. Note that MPK2 possesses two EcoNI sites and digestion of PCR product from mutated DNA yields two bands instead of three bands in wildtype DNA control. CK:

wildtype DNA control. FIG. 23B shows the exact indel mutations at all eight targeted sites in the $T_1$ plants of four PTGb9 lines. Sequences were obtained by direct sequencing of the PCR product or TA clones in case of mpk6 sequences to plant 1-2. Smaller case letters a and b behind the plant number indicate different alleles. The sequences show that the RE sites (blue underline) and all remaining target sites are mutated. The scissors indicate the predicted DSB site 3 bp downstream the PAM (marked in red letters). The protospacer sequences used for targeting are highlighted in green. Dashes indicate deleted nucleotides when compared to wildtype and lower case letters indicate inserted or substituted nucleotides. MPK1 WT (SEQ ID NO:79); MPK1 1-2a (SEQ ID NO:135); MPK1 1-2b (SEQ ID NO:136); MPK1 2-1 (SEQ ID NO:137); MPK1 3-2a (SEQ ID NO:138); MPK1 3-2b (SEQ ID NO:139); MPK1 4-2 (SEQ ID NO:140); MPK2 WT (SEQ ID NO:81); MPK2 1-2 (SEQ ID NO:141); MPK2 2-1 (SEQ ID NO:142); MPK2 3-1 (SEQ ID NO:143); MPK2 4-2 (SEQ ID NO:144); MPK2 4-2b (SEQ ID NO:145); MPK5 WT (SEQ ID NO: 82); MPK5 1-2 (SEQ ID NO:146); MPK5 2-1 (SEQ ID NO:147); MPK5 3-2 (SEQ ID NO:148); MPK5 4-2 (SEQ ID NO:149); MPK6 WT (SEQ ID NO:84); MPK6 1-2a (SEQ ID NO:150); MPK6 1-2b (SEQ ID NO:151); MPK6 2-1 (SEQ ID NO:152); MPK6 3-2 (SEQ ID NO:153); MPK6 4-2a (SEQ ID NO:154); MPK6 4-2b (SEQ ID NO:155).

Figure 24:
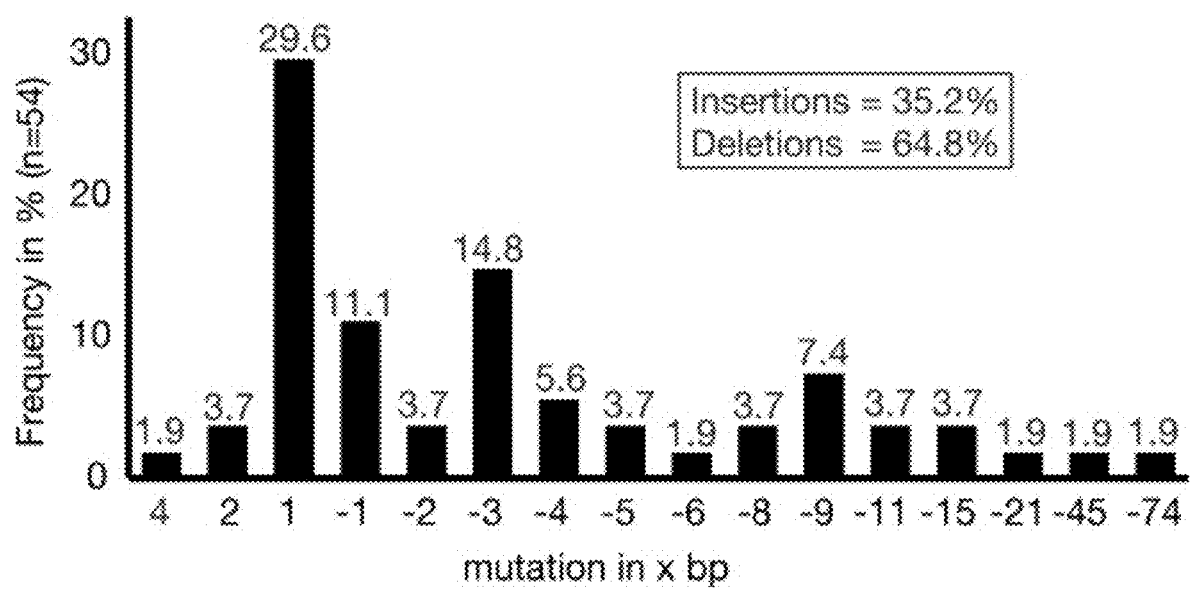

FIG. 24 shows PTG/Cas9 induced insertions and deletions and their frequency. Shown is a summary of the detected indel mutations and how frequent they were observed in a sample of 54 sequences from independent mutational events. The inserted box shows the calculated frequencies of all insertions versus all deletions.

Figure 25A:
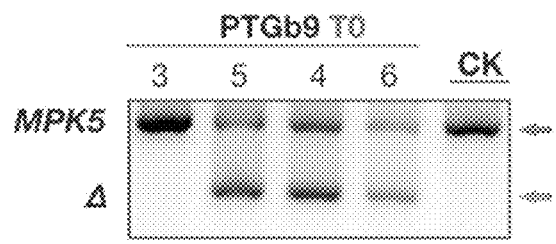
Figure 25B:
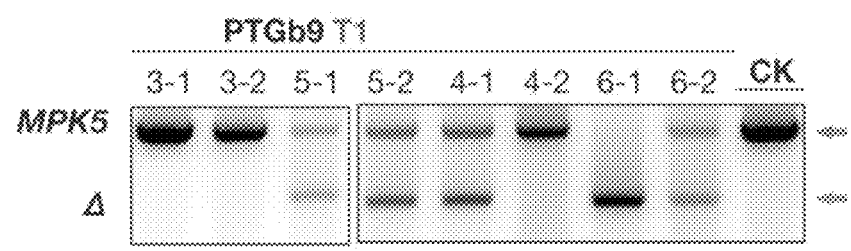
Figure 25C:
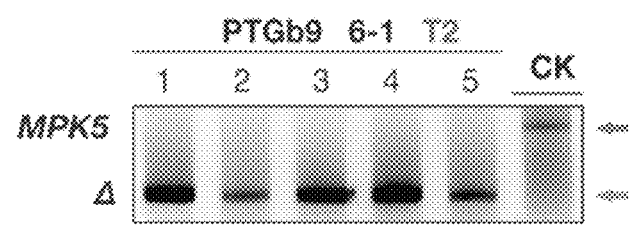

FIGS. 25A-C show the inheritance of chromosomal deletion in $T_1$ and $T_2$ generation plants. FIG. 25A shows detection of full length (MPK5) and chromosomal deletion (Δ) alleles on $T_0$ generation mutant plants. A chromosomal deletion at the targeted MPK5 locus is shown by a truncated PCR product (blue arrow) compared to a full length PCR product (green arrow). Lines 5, 4, and 6 are heterozygous for the deletion as indicated by amplification of full and truncated PCR product. FIG. 25B shows inheritance of chromosomal deletion into the $T_1$ generation. Note that plant 4-2 and 6-1 each only inherited one of the both alleles and became homozygous. FIG. 25C shows inheritance of the fixed deletion into the $T_2$ generation. Only the truncated PCR product indicating deletion was detected in the progeny of plant 6-1. CK: wildtype DNA control.

Figure 26A:
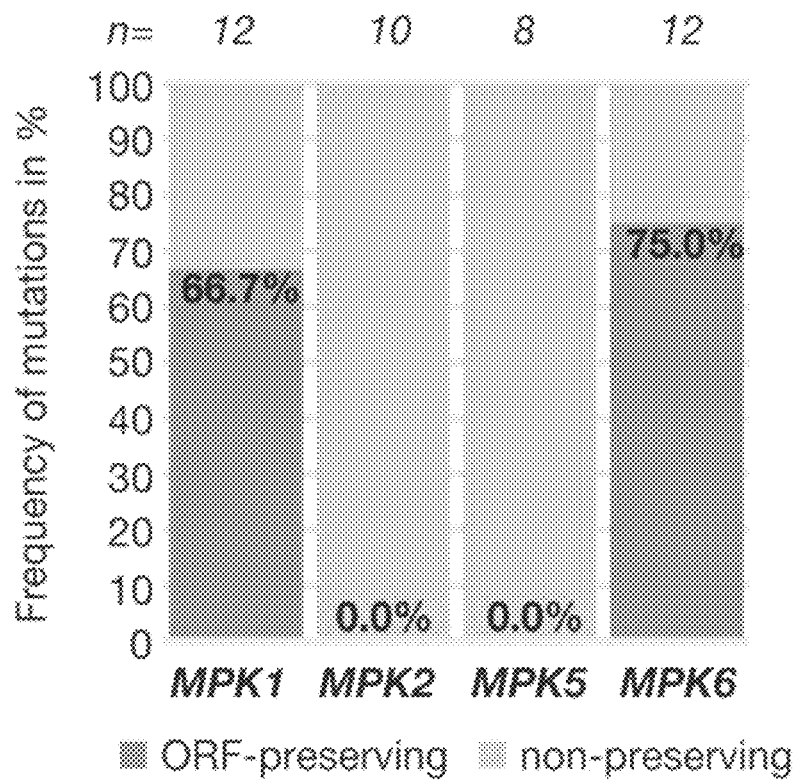
Figure 26B:
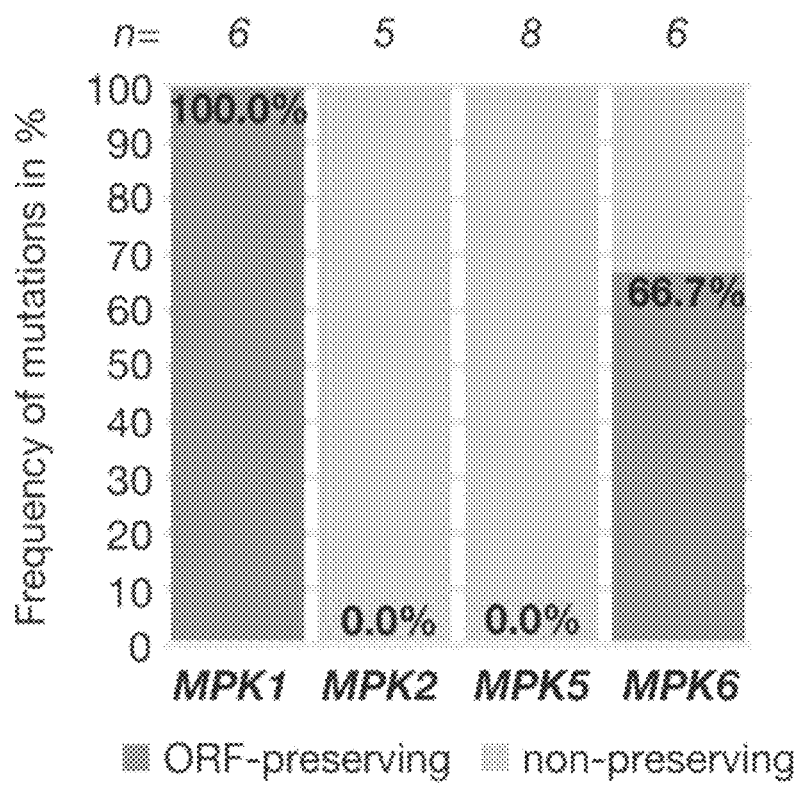
Figure 26E:
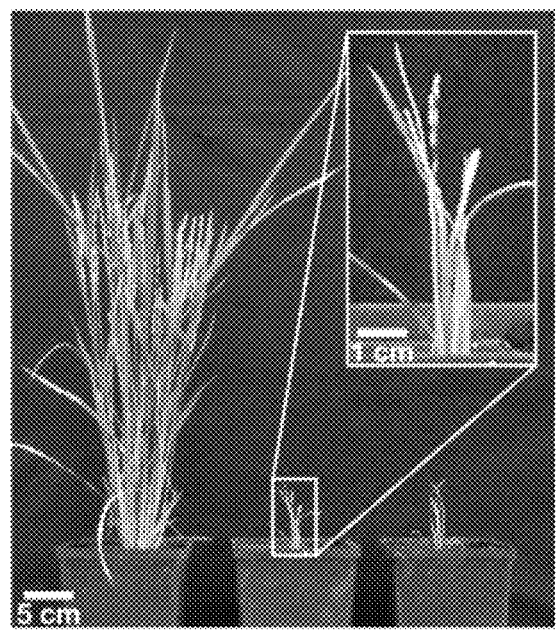

FIGS. 26A-E show that mutations in the MPK1 and MPK6 locus tend to preserve the open reading frame (ORF) of the sequence. FIG. 26A shows the frequency of ORF-preserving mutations versus non-preserving mutations on eight targeted sites in four genes of PTGb9 $T_1$ plants. FIG. 26B shows the frequency of ORF-preserving mutations when only considering target sites in exons. FIG. 26C shows predicted MPK1 protein sequence of the mutant alleles (lower case) (SEQ ID NOs 156-158) compared to the wildtype sequence (upper case) (SEQ ID NO:80). The mutations in MPK1 delete one to five amino acids in the MPK1 protein but keep the predicted protein kinase domains intact, which start at amino acid 67 in the wildtype protein. FIG. 26D shows predicted MPK5 protein sequence of the mutant alleles (SEQ ID NOs 159-162) compared to the wildtype sequence (SEQ ID NO:83). Mutations in all alleles produce a premature stop of the protein sequence before the predicted protein kinase domains of the wildtype protein starting from amino acid 35. FIG. 26E shows PTGb3 $T_0$ generation plants from the callus homozygous for chromosomal deletion on MPK1 compared to an empty vector control. Mature plants 4-A and 4-B stayed severely dwarfed and sterile compared to the control. Scale bar is 5 cm in the main photo and 1 cm in magnified insert.

Figure 27:
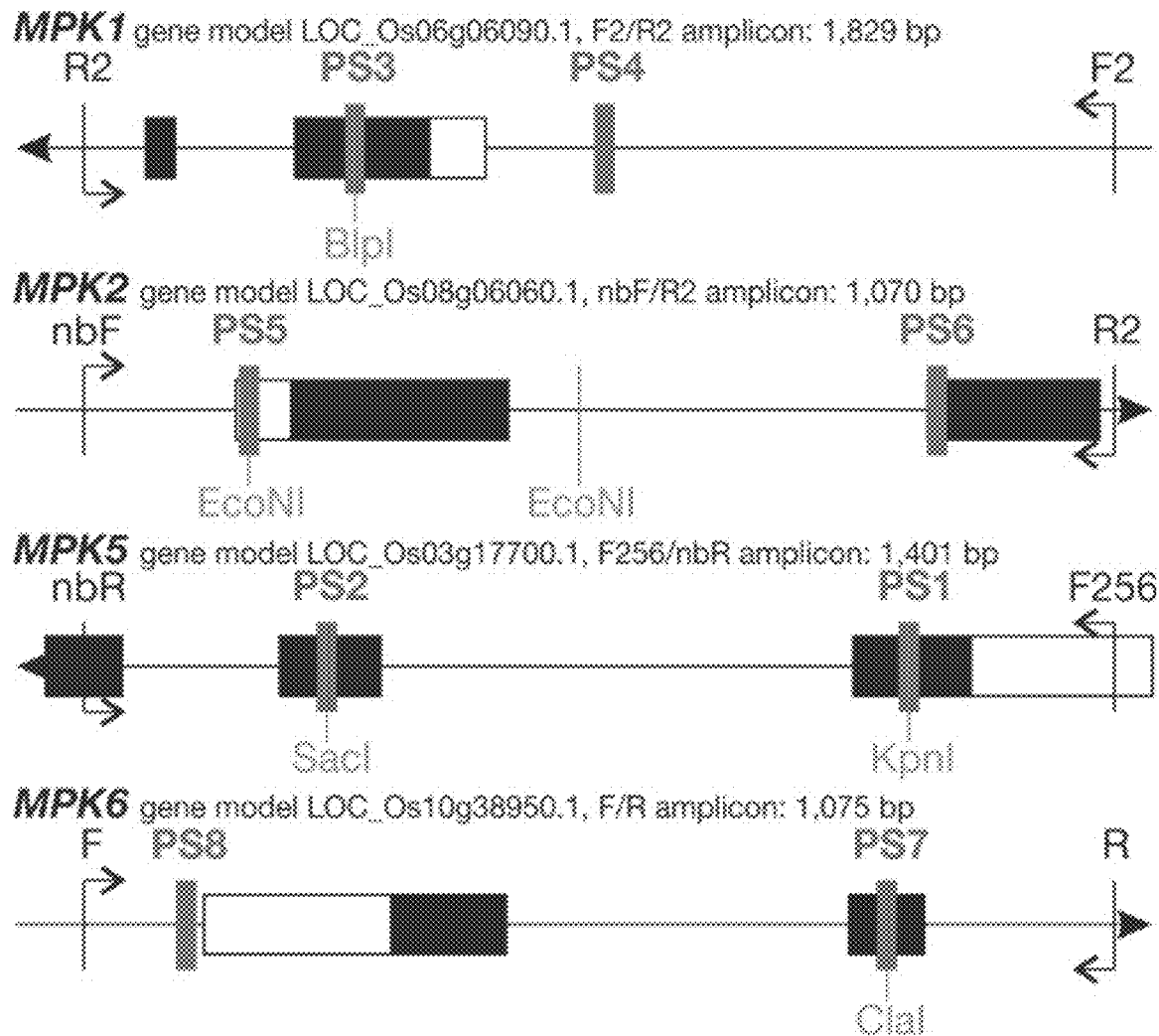

FIG. 27 is a schematic diagram showing that targeted sites of four MPK genes. The blank rectangles indicate the 5' untranslated regions of the first exon and the black-filled rectangles indicate the protein coding exons. The protospacer regions used as target sites for the gRNAs are marked with red bars. The restriction enzyme sites used for detection of mutation events in PCR-RE assays are marked with blue bars. Note that MPK2 possesses two EcoNI sites and digestion of PCR product from mutated DNA yields two bandsinstead of three bands. The primers used for amplification of the target regions are marked with black arrows.

Figure 28A:
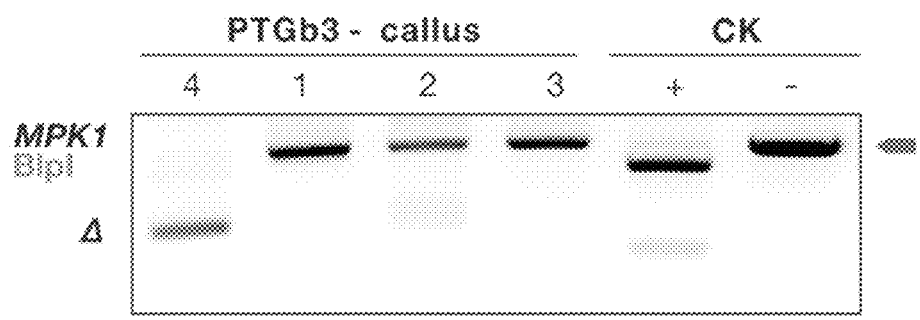
Figure 28B:
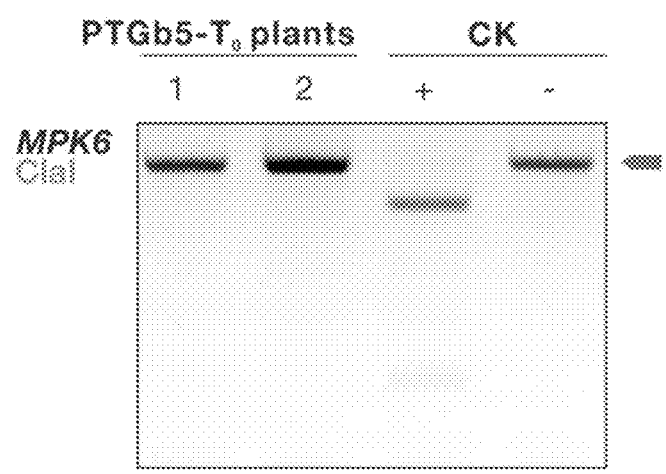

FIGS. 28A-B show the detection of mutagenesis in PTGb3 callus and PTGb5 plant lines. FIG. 28A shows successful and complete editing of MPK1 in four independent transgenic callus pieces was confirmed by PCR-RE assay (red arrow). Line 4 callus carries a chromosomal deletion on MPK1 as shown by the truncated PCR product (Δ). FIG. 28B shows the PCR-RE assay confirmed successful and complete editing of MPK6 in PTGb5 $T_0$ generation plants as the PCR product is indigestible (red arrow). CK: wildtype DNA control.

Figure 29A:
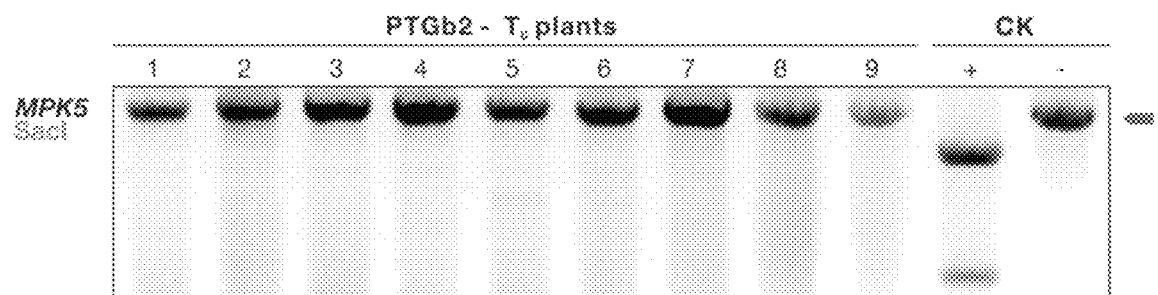
Figure 29B:
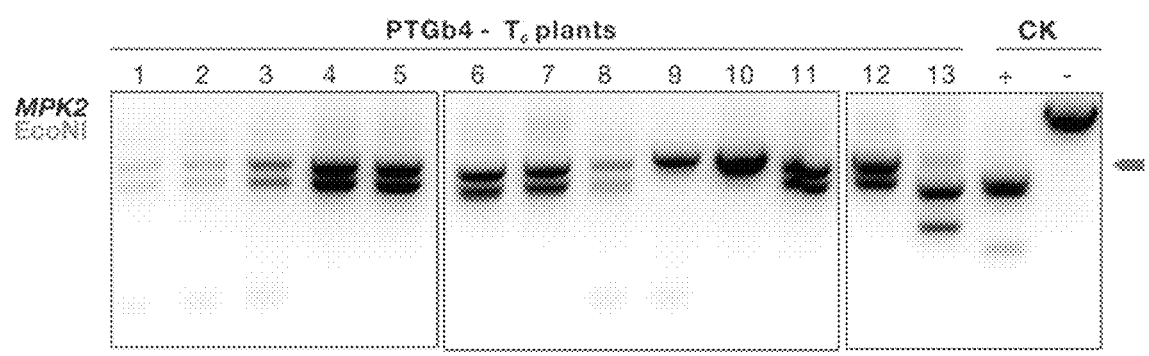
Figure 29C:
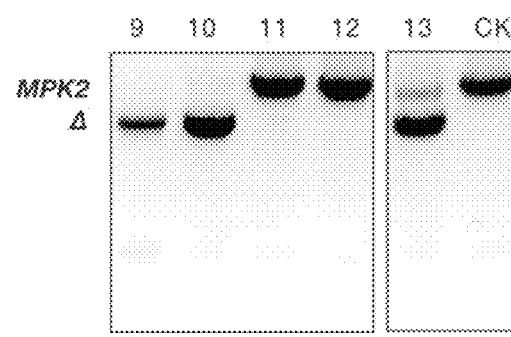

FIGS. 29A-C show the detection of mutagenesis PTGb2 and PTGb4 plant lines. FIG. 29A shows the PCR-RE assay confirmed successful and complete editing on the MPK5 locus of PTGb2 transformed plants as PCR product from all nine independent lines was resistant to digestion with the appropriate enzyme (red arrow). FIG. 29B shows the PCR-RE assays confirmed complete editing of MPK2 of all thirteen examined lines of PTGb4. Note that MPK2 possesses two EcoNI sites and digestion of PCR product from mutated DNA yields two bands and that the unusual band pattern of lines 9,10, and 13 are result of longer deletions on the MPK2 locus. FIG. 29C shows undigested PCR product from lines 9 to 13. The truncated PCR product (Δ) detected in lines 9, 10, and 13 indicate chromosomal deletions. CK: wildtype DNA control.

Figure 30:
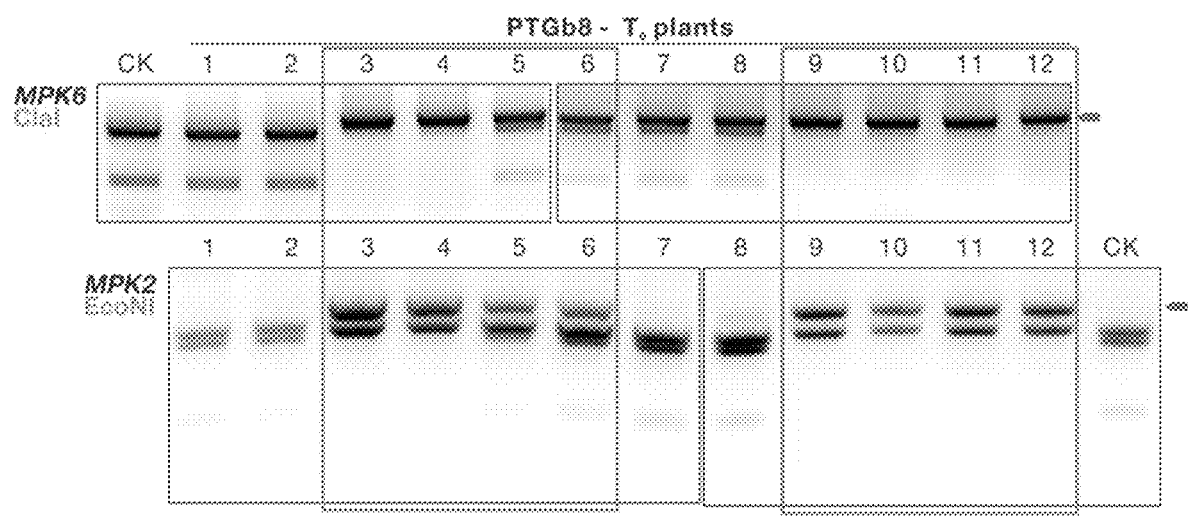

FIG. 30 shows the detection of mutagenesis in PTGb8 lines. The digestion resistant band (red arrows) on the MPK6 and MPK2 locus indicate lines with successful genome-editing. Note that the total number of lines with successful editing could theoretically be higher as only two out of four gRNA target sites could be examined by PCR-RE assay, and that MPK2 possesses two EcoNI sites and digestion of PCR product from mutated DNA yields two bands. The green boxes indicate transgenic lines that possess simultaneous mutations at both sites and are putative MPK6/MPK2 double knock-out lines. CK: wildtype DNA control.

Figure 31:
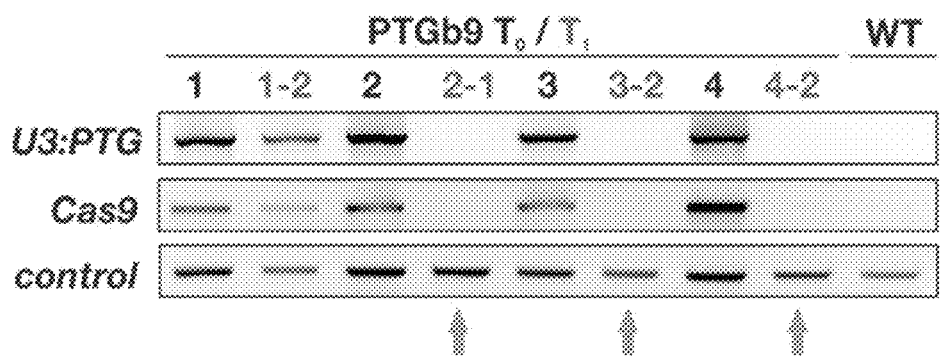

FIG. 31 shows the transgene-free $T_1$ plants of PTGb9 lines. The presence of the genome-editing device (U3:PTG and a 1 kb fragment of Cas9) was screened in $T_0$ and $T_1$ plants of PTGb9 lines. While $T_0$ lines contain a copy of genome-editing device in their genome, self-pollination of $T_0$ lines allows the removal of the genome-editing device from the $T_1$ generation plants. Genomic DNAs from plants 2-1, 3-2, and 4-2 (blue arrows) do not contain any detectable fragment of U3:PTG or Cas9. The control PCR product was readily amplified from the endogenous rice gene LOC_Os05g49730, indicating that the DNAs used have sufficient quality for PCR. WT: wildtype DNA control.

Figure 32:
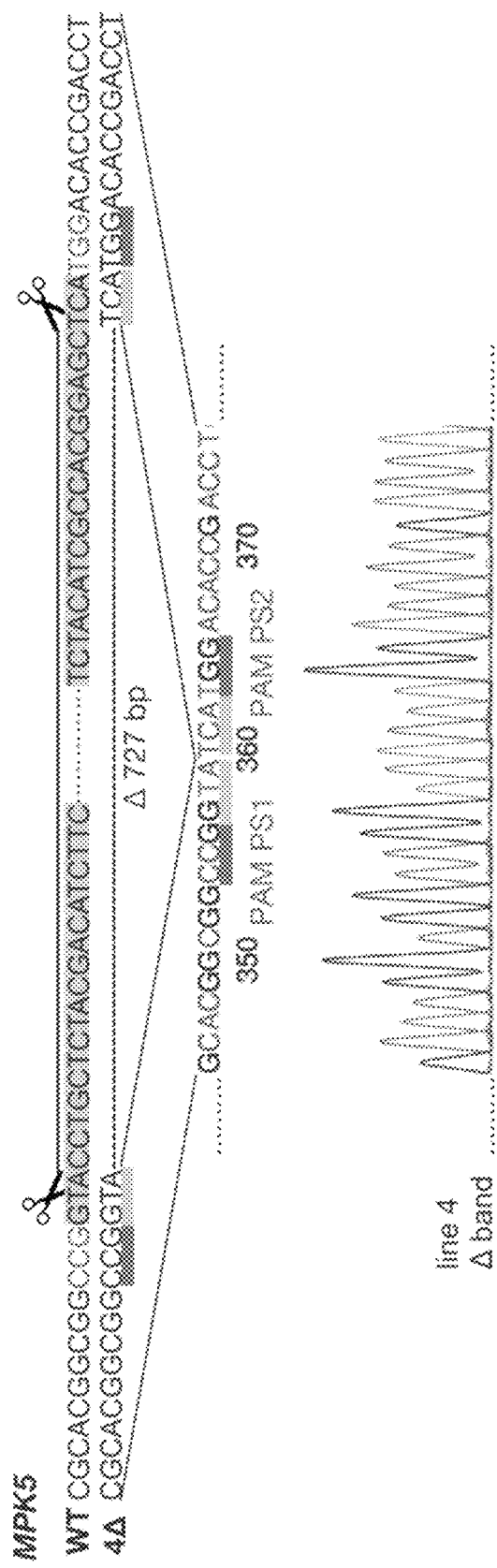

FIG. 32 shows the sequence of chromosomal deletion on MPK5. Shown is the sequencing result of the truncated fragment (Δ) from PTGb9 line 4 (SEQ ID NO:163). The DNA was precisely joined at the two predicted double strand break sites of the protospacers target sites (green highlight, green underlined) 3 bp downstream of the PAM (red letters, red underlined) producing a chromosomal deletion of 727 bp on the MPK5 locus.

Figure 33:
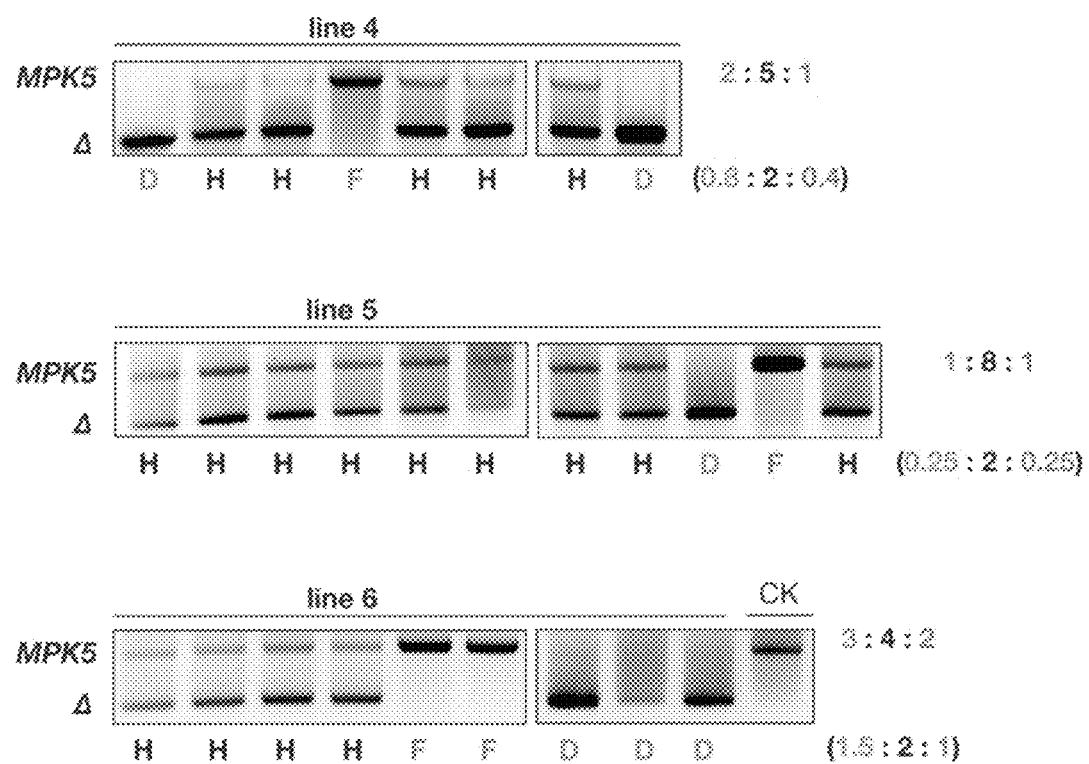

FIG. 33 shows the inheritance pattern of the full-length and truncated alleles of MPK5. Eight T1 plants from line 4, ten T1 plants from line 5, and nine T1 plants from lines 6 were screened for inheritance of the full-length (MPK5) or truncated mpk5 (Δ) allele. The plants were categorized into heterozygous (H) when containing both alleles, homozygous for full-length (F) if only the longer PCR product was detected, or homozygous for deletion (D) if only the truncated PCR product was detected. CK: wildtype DNA control.

DETAILED DESCRIPTION OF THE INVENTION

The technology provides a method to simultaneously manipulate multiple genes or DNA sequences based on RNA-guided genome editing or gene silencing through a single polynucleotide expression cassette. Generally, conventional genome editing or gene silencing technology is capable of manipulating only one gene target. Current methods for multiplex genome editing involve multiple promoters/terminators and cumbersome cloning steps.

Applicant's invention provides a simple, precise and effective approach to produce multiple small RNAs (e.g., gRNA of Cas9, siRNA or miRNA) in vivo from one polynucleotide construct (synthetic gene), and thus equips the current tools (like CRISPR/Cas9 system, RNAi) with the ability to manipulate multiple targets. As an general platform, this method also simplifies and improves the capability and fidelity of gRNA:Cas9/Cas9-nickase mediated genome editing, gRNA:deactive-Cas9 mediated gene activationrepression/labeling/epigenome editing, dsRNA-mediated gene silencing, artificial microRNA and other small RNA mediated gene silencing.

In plants this technology can be used to improve crop yield, quality, stress tolerance, insect and disease resistance, and/or herbicide resistance by simultaneously manipulating multiple essential genes or quantitative trait loci (QTLs). In animals this technology can be used to increase fertility, health and well-being of animals and help in the development of founder lines with improved traits such as weight gain, feed efficiency etc. In humans this technology can facilitate the virus-mediated multiple gRNA delivery because of its compact size and can be used to treat or ameliorate various disease states. Because this technology is based on the tRNA processing system that exists in all organisms, its applications in genome engineering extends to microbes, animals and humans for industrial and medical biotechnology.

Definitions

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, e.g., Sambrook et al. MOLECULAR CLONING: A LABORATORY MANUAL, 2d ed., Cold Spring Harbor Laboratory Press, 1989; 3d ed., 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolfe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value there between or thereabove), preferably between about 100 and 1,000 nucleotides in length (or any integer there between), more preferably between about 200 and 500 nucleotides in length.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively.

Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+Swiss protein+Spupdate+PIR. Details of these programs can be found at the following internet address: http://www.ncbi.nlm.gov/cgi-bin/BLAST. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; Nucleic Acid Hybridization: A Practical Approach, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., Molecular Cloning: A Laboratory Manual, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, Nucleic Acid Hybridization: A Practical Approach, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., Molecular Cloning: A Laboratory Manual, Second Edition, (1989) Cold Spring Harbor, N.Y.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" or "heterologous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

As used herein, the terms "coding region" and "coding sequence" are used interchangeably and refer to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators.

A polynucleotide that includes a coding region may include heterologous nucleotides that flank one or both sides of the coding region. As used herein, "heterologous nucleotides" refer to nucleotides that are not normally present flanking a coding region that is present in a wild-type cell. For instance, a coding region present in a wild-type microbe and encoding a Cas9 polypeptide is flanked by homologous sequences, and any other nucleotide sequence flanking the coding region is considered to be heterologous. Examples of heterologous nucleotides include, but are not limited to regulatory sequences. Typically, heterologous nucleotides are present in a polynucleotide disclosed herein through the use of standard genetic and/or recombinant methodologies well known to one skilled in the art. A polynucleotide disclosed herein may be included in a suitable vector.

As used herein, "genetically modified cell" refers to a cell, which has been altered "by the hand of man." A genetically modified cell, includes a cell, callus, tissue, plant, or animal into which has been introduced an exogenous polynucleotide. Genetically modified cell, also refers to a cell that has been genetically manipulated such that endogenous nucleotides have been altered to include a mutation, such as a deletion, an insertion, a transition, a transversion, or a combination thereof. For instance, an endogenous coding region could be deleted. Such mutations may result in a polypeptide having a different amino acid sequence than was encoded by the endogenous polynucleotide. Another example of a genetically modified cell, callus, tissue, plant, or animal is one having an altered regulatory sequence, such as a promoter, to result in increased or decreased expression of an operably linked endogenous coding region.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

As used herein, the term "tRNA cleavage sequence" refers to any nucleotide sequence recognized and excised by a tRNA splicing endonuclease, such as RNase P, RNase Z or RNAse E.

As used herein, the term "tRNA splicing endonuclease" refers to the enzyme that is responsible for the recognition of the splice sites contained in precursor tRNA and the cleavage of the introns present in precursor tRNA. The archaeal tRNA splicing endonuclease recognizes the bulge-helix-bulge motif in archaeal precursor tRNA. The eukaryotic tRNA splicing endonuclease recognizes the splice sites contained in precursor tRNA by measuring the distance from the mature domain to the splice sites.

The expression "antisense RNA" denotes a RNA that is capable of binding to a target nucleic sequence (DNA or RNA) so as to limit or prevent its functioning; in particular, antisense RNAs are able to bind to a target messenger RNA in order to prevent its translation (see, for example, Tafech et al. (2006) Curr. Med. Chem. 13: 863-881).

The expression "interfering RNA" denotes an RNA capable of preventing or limiting the expression of a target gene by the phenomenon of interference (see, for example, Tafech et al. (2006) Curr. Med. Chem. 13: 863-881).

Methods and Compositions of the Invention
tRNA

The general characteristics of a tRNA are well-known to the person skilled in the art. Preferably, a tRNA is formed of a single ribonucleotide chain which is capable of folding to adopt a characteristic, so-called cloverleaf secondary structure. This characteristic secondary structure comprises:

(i) an acceptor stem composed of the first 7 ribonucleotides of the 5' end of the ribonucleotide chain and the 7 ribonucleotides that precede the last 4 ribonucleotides of the 3' end of the ribonucleotide chain, thus forming a double-stranded structure comprising 6 or 7 pairs of ribonucleotides, it being possible for the ribonucleotides constituted by the first ribonucleotide of the 5' end of the ribonucleotide chain and the ribonucleotide that precedes the last 4 ribonucleotides of the 3' end of the ribonucleotide chain not to be paired;

ii) a D arm constituted by 4 pairs of ribonucleotides and a D loop constituted by 8 to 10 ribonucleotides, formed by the folding of a part of the ribonucleotide chain that follows the first 7 ribonucleotides of the 5' end of the ribonucleotide chain;

(iii) a stem of the anticodon constituted by 5 pairs of ribonucleotides, and a loop of the anticodon constituted by 7 ribonucleotides (stem-loop of the anticodon), formed by the folding of a part of the ribonucleotide chain that follows the D arm and the D loop;

(iv) a variable loop constituted by from 4 to 21 ribonucleotides and formed by a part of the ribonucleotide chain that follows the stem of the anticodon and the loop of the anticodon;

(v) a T arm constituted by 5 pairs of ribonucleotides, and a T loop constituted by 8 ribonucleotides, formed by the folding of a part of the ribonucleotide chain that follows the variable loop and precedes the ribonucleotides of the 3' end of the ribonucleotide chain which are involved in the constitution of the acceptor stem.

Likewise preferably, from the 5' end in the direction towards the 3' end, 2 ribonucleotides are present between the first 7 ribonucleotides of the 5' end of the ribonucleotide chain and the D arm and loop, 1 ribonucleotide is present between the D arm and loop, on the one hand, and the stem and the loop of the anticodon, on the other hand, and 1 ribonucleotide is present between the stem and the loop of the anticodon, on the one hand, and the variable loop, on the other hand.

Still preferably, and according to the numbering well-known to the person skilled in the art and defined by Sprinzl et al. (1998) "Compilation of tRNA sequences and sequences of tRNA genes". Nucleic Acids Res. 26: 148-153, the tRNA comprises 17 ribonucleotides, ensuring the three-dimensional structure of the tRNA and recognition by the cell enzymes, namely: $U_8$, $A_{14}$, (A or G)$_{15}$, $G_{18}$, $G_{19}$, $A_{21}$, $G_{53}$, $U_{54}$, $U_{55}$, $C_{56}$, (A or G)$_{57}$, $A_{58}$, (C or U)$_{60}$, $C_{61}$, $C_{74}$, $C_{75}$, $A_{76}$. The indicated ribonucleotides correspond to the sequence of the tRNA as transcribed before any post-transcriptional modifications of certain ribonucleotides by the cell machinery.

In particular, the tRNA defined above may be selected from the group constituted by Archean, bacterial, viral, protozoan, fungal, algal, plant or animal tRNAs.

The tRNAs which can be used according to the invention also include all the tRNAs described by Sprinzl et al. (1998) "Compilation of tRNA sequences and sequences of tRNA genes". Nucleic Acids Res. 26: 148-153 or those available on the site: http://www.uni-bayreuth.de/departments/biochemie/trna/.

In the context of the invention, the term "tRNA" also includes structures obtained by modifying a tRNA as defined above or natural variants of a tRNA as defined above, provided that those modified structures or those variants retain the functionalities of the unmodified tRNA, namely especially the interaction with proteins such as EF-Tu factor (see, for example, Rodnina et al. (2005) FEBS. Lett. 579: 938-942) or CCAse (see, for example, Augustin et al. (2003) J. Mol. Biol. 328: 985-994). There are numerous tRNA active sequences and motifs known and available to those of skill in the art through sources such as the tRNA-SE program available at world wide web lowelab.ucsc.edu/tRNAscan-SE/ or world wide web trna.bioinfuni-leipzig.de/DataOutput/Organisms (for all organisms), or world wide web at plantrna.ibmp.cnrs.fr/ (for plants). Numerous articles and Genbank resources are also available and are recited herein.

A substrate for a tRNA endonuclease of RNAse may be produced by any method well-known to one of skill in the art. For example, the substrate may be chemically synthesized using phosphoramidite or other solution or solid-phase methods. Detailed descriptions of the chemistry used to form polynucleotides by the phosphoramidite method are well known (see, e.g., Caruthers et al., U.S. Pat. Nos. 4,458,066 and 4,415,732; Caruthers et al., 1982, Genetic Engineering 4:1-17; User's Manual Model 392 and 394 Polynucleotide Synthesizers, 1990, pages 6-1 through 6-22, Applied Biosystems, Part No. 901237; Ojwang, et al., 1997, Biochemistry, 36:6033-6045). After synthesis, the substrate can be purified using standard techniques known to those skilled in the art (see Hwang et al., 1999, Proc. Natl. Acad. Sci. USA 96(23):12997-13002 and references cited therein). Depending on the length of the substrate and the method of its synthesis, such purification techniques include, but are not limited to, reverse-phase high-performance liquid chromatography ("reverse-phase HPLC"), fast performance liquid chromatography ("FPLC"), and gel purification.

There are numerous RNase resources available to those of skill in the art including the following:

RNase E
1. Soderbom F, Svard S G, Kirsebom L A. 2005. RNase E cleavage in the 5' leader of a tRNA precursor. J Mol Biol 352(1): 22-27.
2. Nakajima N, Ozeki H, Shimura Y. 1981. Organization and structure of an *E. coli* tRNA operon containing seven tRNA genes. Cell 23(1): 239-249.
3. Li Z, Deutscher M P. 2002. RNase E plays an essential role in the maturation of *Escherichia coli* tRNA precursors. RNA 8(1): 97-109.

RNase P
1. Kirsebom L A. 2007. RNase P RNA mediated cleavage: substrate recognition and catalysis. Biochimie 89(10): 1183-1194.
2. Gutmann B, Gobert A, Giege P. 2012. PRORP proteins support RNase P activity in both organelles and the nucleus in *Arabidopsis*. Genes Dev. 26(10): 1022-1027.
3. Forster A C, Altman S. 1990. External guide sequences for an RNA enzyme. Science 249(4970): 783-786.
4. Yuan Y, Altman S. 1995. Substrate recognition by human RNase P: identification of small, model substrates for the enzyme. EMBO J 14(1): 159-168.

RNase Z
1. Kruszka K, Barneche F, Guyot R, Ailhas J, Meneau I, Schiffer S, Marchfelder A, Echeverria M. 2003. Plant dicistronic tRNA-snoRNA genes: a new mode of expression of the small nucleolar RNAs processed by RNase Z. EMBO J 22(3): 621-632.
2. Schiffer S, Rosch S, Marchfelder A. 2002. Assigning a function to a conserved group of proteins: the tRNA 3'-processing enzymes. EMBO J 21(11): 2769-2777.
3. Barbezier N, Canino G, Rodor J, Jobet E, Saez-Vasquez J, Marchfelder A, Echeverria M. 2009. Processing of a dicistronic tRNA-snoRNA precursor: combined analysis in vitro and in vivo reveals alternate pathways and coupling to assembly of snoRNP. Plant Physiol 150(3): 1598-1610.
4. Canino G, Bocian E, Barbezier N, Echeverria M, Forner J, Binder S, Marchfelder A. 2009. *Arabidopsis* encodes four tRNase Z enzymes. Plant Physiol 150(3): 1494-1502.

As used herein, the phrase "a substrate for a 3' end pre-mRNA endonuclease" refers to any nucleotide sequence recognized and excised by a 3' end pre-mRNA endonuclease. For example, a nucleotide sequence comprising a hexanucleotide with the sequence AAUAAA upstream and a G/U-rich sequence element downstream of the cleavage site may be utilized as a substrate for 3' end pre-mRNA endonuclease in an assay described herein. A nucleotide sequence recognized and excised by a 3' end pre-mRNA endonuclease may comprise 10 nucleotides, 15 nucleotides, 20 nucleotides, 25 nucleotides, 25 nucleotides, 30 nucleotides, 40 nucleotides. 45 nucleotides, 50 nucleotides, 55 nucleotides, 60 nucleotides, 65 nucleotides, 75 nucleotides. 100 nucleotides, 125 nucleotides, 150 nucleotides, or more. In a specific embodiment, the substrates for 3' end pre-mRNA endonuclease utilized in the assays described herein comprise a cleavage and polyadenylation site.

Vectors and Nucleic Acids

A variety of nucleic acids may be introduced into cells for purposes of the invention. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) Antisense Nucleic Acid Drug Dev. 7(3):187; and Hyrup et al. (1996) Bioorgan. Med. Chem. 4:5. In addition, the deoxyphosphate backbone can be replaced with, for example, a phosphorothioate or phosphorodithioate backbone, a phosphoroamidite, or an alkyl phosphotriester backbone.

The nucleic acid sequence can be operably linked to a regulatory region such as a promoter. Regulatory regions can be porcine regulatory regions or can be from other species. As used herein, operably linked refers to positioning of a regulatory region relative to a nucleic acid sequence in such a way as to permit or facilitate transcription of the target nucleic acid.

Any type of promoter can be operably linked to a target nucleic acid sequence. Examples of promoters include, without limitation, tissue-specific promoters, constitutive promoters, inducible promoters, and promoters responsive or unresponsive to a particular stimulus. Suitable tissue specific promoters can result in preferential expression of a nucleic acid transcript in beta cells and include, for example, the human insulin promoter. Other tissue specific promoters can result in preferential expression in, for example, hepatocytes or heart tissue and can include the albumin or alpha-myosin heavy chain promoters, respectively. In other embodiments, a promoter that facilitates the expression of a nucleic acid molecule without significant tissue or temporal-specificity can be used (i.e., a constitutive promoter). For example, a beta-actin promoter such as the chicken beta-actin gene promoter, ubiquitin promoter, miniCAGs promoter, glyceraldehyde-3-phosphate dehydrogenase (GAPDH) promoter, or 3-phosphoglycerate kinase (PGK) promoter can be used, as well as viral promoters such as the herpes simplex virus thymidine kinase (HSV-TK) promoter, the SV40 promoter, or a cytomegalovirus (CMV) promoter. In some embodiments, a fusion of the chicken beta actin gene promoter and the CMV enhancer is used as a promoter. See, for example, Xu et al. (2001) Hum. Gene Ther. 12:563; and Kiwaki et al. (1996) Hum. Gene Ther. 7:821.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

A nucleic acid construct may be used that encodes signal peptides or selectable markers. Signal peptides can be used such that an encoded polypeptide is directed to a particular cellular location (e.g., the cell surface). Non-limiting examples of selectable markers include puromycin, ganciclovir, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known.

Polynucleotide constructs may be introduced into the genome of a desired host or recipient cell by a variety of conventional techniques. For reviews of such techniques see, for example, Weissbach & Weissbach Methods for Cell, Molecular Biology (1988, Academic Press, N.Y.) Section VIII, pp. 421-463; and Grierson & Corey, Cell Molecular Biology (1988, 2d Ed.), Blackie, London, Ch. 7-9. For example, the DNA construct may be introduced directly into the genomic DNA of the cell using techniques such as electroporation and microinjection, or the DNA constructs can be introduced directly to plant or animal tissue using biolistic methods, such as DNA particle bombardment (see, e.g., Klein et al (1987) Nature 327:70-73).

Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) Science 233:496-498, and Fraley et al (1983) Proc. Nat'l. Acad. Sci. USA 80:4803. The virulence functions of the *Agrobacterium tumefaciens* host will direct the insertion of the construct and adjacent marker into the cellular DNA when the cell is infected by the bacteria using binary T DNA vector (Bevan (1984) Nuc. Acid Res. 12:8711-8721) or the co-cultivation procedure (Horsch et al (1985) Science 227:1229-1231). See Hernalsteen et al (1984) EMBO J 3:3039-3041; Hooykass-Van Slogteren et al (1984) Nature 311:763-764; Grimsley et al (1987) Nature 325:1677-179; Boulton et al (1989) Cell Mol. Biol. 12:31-40; and Gould et al (1991) Cell Physiol. 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) EMBO J3:2717-2722, Potrykus et al. (1985) Molec. Gen. Genet. 199:169-177; Fromm et al. (1985) Proc. Nat. Acad. Sci. USA 82:5824-5828; and Shimamoto (1989) Nature 338:274-276) and electroporation of cell, plant or animal tissues (D'Halluin et al. (1992) Cell, 4:1495-1505). Additional methods for cell transformation include microinjection, silicon carbide mediated DNA uptake (Kaeppler et al. (1990) Cell Reporter 9:415-418), and microprojectile bombardment (see Klein et al. (1988) Proc. Nat. Acad. Sci. USA 85:4305-4309; and Gordon-Kamm et al. (1990) Cell 2:603-618).

A transformed cell, callus, tissue plant or animal may be identified and isolated by selecting or screening the engineered cell, plant or animal material for traits encoded by the marker genes present on the transforming DNA. For instance, selection may be performed by growing the engineered cell, on media containing an inhibitory amount of the antibiotic or herbicide to which the transforming gene construct confers resistance. Further, transformed cells may also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify transformants containing inserted gene constructs. These methods include but are not limited to: 1) Southern analysis or PCR amplification for detecting and determining the structure of the recombinant DNA insert; 2) Northern blot, 51 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific cell, plant or animal organs and tissues. The methods for doing all these assays are well known to those skilled in the art.

Genomic changes including exogenous polynucleotides that are stably incorporated into cells, or indels created by gene editing can be introduced into other cells, tissues, plants or animals using, for example, standard breeding techniques.

Genetically modified cells which are produced by any of the above transformation techniques can be cultured to regenerate a whole plant or animal tissues which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. plant or animal regeneration from cultured protoplasts is described in Evans, et al., "Protoplasts Isolation and Culture" in Handbook of Cell, plant or animal Cell Culture, pp. 124-176, Macmillian Publishing Company, New York, 1983; and Binding, Regeneration of Protoplasts, pp. 21-73, CRC Press, Boca Raton, 1985. Regeneration can also be obtained from callus, excell, organs, pollens, embryos or parts thereof. Such regeneration techniques are described generally in Klee et al (1987) Ann. Rev. of Cell, plant or animal Phys. 38:467-486.

Nucleic acids introduced into a cell, can be used to confer desired traits on essentially any cell, plant or animal. A wide variety of cell, plant or animal systems may be engineered for the desired physiological and agronomic characteristics described herein using the nucleic acid constructs of the present disclosure and the various transformation methods mentioned above. In preferred embodiments, target cells, for engineering in plants can include, but are not limited to, those monocotyledonous and dicotyledonous cell, plant or animals, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering cell, plant or animals (e.g., petunia, rose, chrysanthemum), conifers and pine trees (e.g., pine fir, spruce); cell, plant or animals used in phytoremediation (e.g., heavy metal accumulating cell, plant or animals); oil crops (e.g., sunflower, rape seed) and cell, plant or animals used for experimental purposes (e.g., *Arabidopsis*). Thus, the disclosed methods and compositions have use over a broad range of cell, plant or animals, including, but not limited to, species from the genera Asparagus, *Avena, Brassica, Citrus, Citrullus, Capsicum, Cucurbita, Daucus, Glycine, Hordeum, Lactuca, Lycopersicon, Malus, Manihot, Nicotiana, Oryza, Persea, Pisum, Pyrus, Prunus, Raphanus, Secale, Solanum, Sorghum, Triticum, Vitis, Vigna*, and *Zea*. One of skill in the art will recognize that after the expression cassette is stably incorporated in transgenic cell, plant or animals and confirmed to be operable, it can be introduced into other cell, plant or animals by sexual crossing. Any of a number of standard breeding techniques can be used, depending upon the species to be crossed.

Effects of gene manipulation using the methods disclosed herein can be observed by, for example, northern blots of the RNA (e.g., mRNA) isolated from the tissues of interest. Typically, if the amount of mRNA has increased, it can be assumed that the corresponding endogenous gene is being expressed at a greater rate than before. Other methods of measuring gene activity can be used. Different types of enzymatic assays can be used, depending on the substrate used and the method of detecting the increase or decrease of a reaction product or by-product. In addition, the levels of and/or protein expressed can be measured immunochemically, i.e., ELISA, RIA, EIA and other antibody based assays well known to those of skill in the art, such as by electrophoretic detection assays (either with staining or western blotting). The transgene may be selectively expressed in some tissues or at some developmental stages, or the transgene may be expressed in substantially all cells, substantially along its entire life cycle. However, any combinatorial expression mode is also applicable.

The present disclosure further encompasses the progeny, clones, cell lines or cells of the transgenic cell described above wherein said progeny, clone, cell line or cell has the transgene or gene construct or has been edited.

Plasmid Vectors for Gene Targeting and Genome Editing

According to one aspect of the invention, compositions are provided that allow gene targeting and genome editing in cells. In one aspect, specific RNA-guided Genome Editing vectors are provided. In a preferred embodiment, the vectors include a first regulatory element operable in a plant or animal cell operably linked to at least one nucleotide sequence encoding a CRISPR-Cas system guide RNA that hybridizes with the target sequence; and a second regulatory element operable in a plant or animal cell operably linked to a nucleotide sequence encoding a Type-II CRISPR-associated nuclease. The nucleotide sequence encoding a CRISPR-Cas system guide RNA and the nucleotide sequence encoding a Type-II CRISPR-associated nuclease may be on the same or different vectors of the system. The guide RNA targets the target sequence, and the CRISPR-associated nuclease cleaves the DNA molecule, whereby expression of at least one gene product is altered.

In a preferred embodiment, the vectors include a nucleotide sequence comprising a DNA-dependent RNA polymerase III promoter, wherein said promoter operably linked to a gRNA molecule and a Pol III terminator sequence, wherein said gRNA molecule includes a DNA target sequence; and a nucleotide sequence comprising a DNA-dependent RNA polymerase II promoter operably linked to a nucleic acid sequence encoding a type II CRISPR-associated nuclease. The CRISPR-associated nuclease is preferably a Cas9 protein.

In another embodiment, vectors are provided for the *Agrobacterium*-mediated transient expression or stable transformation in plant or animal tissues. In particular the plasmid vectors for transient expression in protoplasts, tissue cultures contain: (1) a DNA-dependent RNA polymerase III (Pol III) promoter (for example, rice snoRNA U3 or U6 promoter) to control the expression of engineered gRNA molecules in the cell, plant or animal cell, where the transcription was terminated by a Pol III terminator (Pol III Term), (2) a DNA-dependent RNA polymerase II (Pol II) promoter (e. g., 35S promoter) to control the expression of Cas9 protein; (3) a multiple cloning site (MCS) located between the Pol III promoter and gRNA scaffold, which is used to insert a 15-30 bp DNA sequence for producing an engineered gRNA. To facilitate the *Agrobacterium*-mediated transformation, binary vectors are provided (e.g., the pCAMBIA 1300 vector), wherein gRNA scaffold/Cas9 cassettes are inserted into the plant, animal and fungal cells via *Agrobacterium* transformation. To program gRNA, a 15-30 bp long synthetic DNA sequence complementary to the targeted genome sequence can be inserted into the MCS site of the vector.

Methods to Introduce Engineered gRNA-Cas9 Constructs into Cells for Genome Editing and Genetic Modification.

According to another aspect of the invention, gene constructs carrying gRNA-Cas9 nuclease can be introduced into cells by various methods, which include but are not limited to PEG- or electroporation-mediated protoplast transformation, tissue culture or cell, plant or animal tissue transformation by biolistic bombardment, or the *Agrobacterium*-mediated transient and stable transformation. The transformation can be transient or stable transformation.

Target gene sequences for genome editing and genetic modification can be selected using methods known in the art, and as described elsewhere in this application. In a preferred embodiment, target sequences are identified that include or are proximal to protospacer adjacent motif (PAM). Once identified, the specific sequence can be targeted by synthesizing a pair of target-specific DNA oligonucleotides with appropriate cloning linkers, and phosphorylating, annealing, and ligating the oligonucleotides into a digested plasmid vector, as described herein. The plasmid vector comprising the target-specific oligonucleotides can then be used for transformation of a cell, plant or animal.

Methods of Designing Specific gRNAs with Minimal Off-Target Risk

According to one aspect, the invention provides methods to design DNA/RNA sequences that guide Cas9 nuclease to target a desired site at a high specificity. The specificity of engineered gRNA could be calculated by sequence alignment of its spacer sequence with genomic sequence of targeting organism.

Approaches to Produce Non-Transgenic, Genetically Modified Plant or Animals

Using the aforementioned plasmid vectors and delivery methods, genetically engineered cells, plants or animals can be produced through specific gene targeting and genome editing. In many cases, the resulting genetically modified crops contain no foreign genes and basically are non-transgenic. A DNA sequence encoding gRNA can be designed to specifically target any genes or DNA sequences for targeted mutation via insertion or deletion or other modifications (e.g., transcriptional activation and repression, methylation and demethylation, labeling) through this technology. The ability to efficiently and specifically create targeted mutations or modifications in the cell, plant or animal genome greatly facilitates the development of many new progeny with improved or novel traits. Because the CRISPR/Cas gene constructs are only transiently expressed in protoplasts and are not integrated into the genome, genetically modified plants or animals regenerated from protoplasts contain no foreign DNAs and are basically non-transgenic. In addition, transgene-free plants or animals can be obtained through genetic segregation after the backcrossing or selfing of genome edited transgenic lines.

Other RNA-Based Genetic Manipulation Techniques

The invention is equally applicable to other RNA mediated genetic manipulation techniques such as RNA based inhibition of gene expression. Typically, an expression cassette capable of producing an RNA molecule that inhibits the transcription and/or translation of at least one polypeptide is included in the invention.

In some embodiments of the present invention, a cell is transformed with an expression cassette that is capable of expressing a polynucleotide that inhibits the expression of polypeptide. The term "expression" as used herein refers to the biosynthesis of a gene product, including the transcription and/or translation of said gene product. The "expression" or "production" of a protein or polypeptide from a DNA molecule refers to the transcription and translation of the coding sequence to produce the protein or polypeptide, while the "expression" or "production" of a protein or polypeptide from an RNA molecule refers to the translation of the RNA coding sequence to produce the protein or polypeptide.

Examples of polynucleotides that inhibit the expression of a polypeptide include sense Suppression/Cosuppression, where an expression cassette is designed to express an RNA molecule corresponding to all or part of a messenger RNA encoding the polypeptide in the "sense" orientation and over expression of the RNA molecule can result in reduced expression of the native gene; Antisense Suppression where the expression cassette is designed to express an RNA molecule complementary to all or part of a messenger RNA encoding the ACC synthase polypeptide and over expression of the antisense RNA molecule can result in reduced expression of the native gene; Double-Stranded RNA Interference, where a sense RNA molecule like that described above for cosuppression and an antisense RNA molecule that is fully or partially complementary to the sense RNA molecule are expressed in the same cell, resulting in inhibition of the expression of the corresponding endogenous messenger RNA, Hairpin RNA Interference and Intron-Containing Hairpin RNA Interference, where the expression cassette is designed to express an RNA molecule that hybridizes with itself to form a hairpin structure that comprises a single-stranded loop region and a base-paired stem, Small Interfering RNA or Micro RNA, where the expression cassette is designed to express an RNA molecule that is modeled on an endogenous miRNA gene.

In addition, the multiplex gRNA-mediated genome editing described in this invention can be used together with a deactive Cas protein for transcriptional activation and repression of multiple genes, epigenome editing (e.g., methylation and demethylation) of multiple sites or genes, labeling of genomic elements, and other multiplex genetic manipulations in the living organisms.

Example 1

The CRISPR/Cas9 system is being harnessed as a powerful tool for genome engineering in basic research, molecular therapy and crop improvement. This system utilizes a small guide RNA (gRNA) to direct Cas9 endonuclease to a specific DNA site, thus its targeting capability is largely constrained by the gRNA expressing device. Applicants developed a general strategy to produce numerous gRNAs from a single polycistronic gene. The endogenous tRNA processing system, which precisely cleaves both ends of the tRNA precursor, was engineered as a simple and robust platform to boost the targeting and multiplex editing capability of the CRISPR/Cas9 system. Applicants herein demonstrate that synthetic genes with tandemly arrayed tRNA-gRNA architecture were efficiently and precisely processed into gRNAs with desired 5' targeting sequences in vivo, which directed Cas9 to edit multiple chromosomal targets. Using this strategy, multiplex genome editing and chromosomal fragment deletion were readily achieved in stable transgenic rice plants with a high efficiency (up to 100%). Because tRNA and its processing system are virtually conserved in all living organisms, this method could be broadly utilized to boost targeting capability and editing efficiency of CRISPR/Cas9 toolkits.

Higher organisms often employ complicate genetic networks with functionally redundant genes to fine tune cellular processes. Therefore, molecular tools with the capability to simultaneously manipulate multiple genes are of great value in both basic research and practical applications of genetic engineering. Recently, the bacterial type II clustered regularly interspaced short palindromic repeats (CRISPR) and CRISPR-associated protein (Cas) system is emerging as a promising tool for this purpose. The Cas9 endonuclease from *Streptococcus pyogenes*, coupled with an artificial guide RNA (gRNA), is able to target DNA sequence of 5'-N20-NGG-3' (N indicates any base) in which N20 is the same as 20 bases of gRNA 5' sequence (referred as gRNA spacer hereafter) and NGG is the protospacer-adjacent-motif (PAM) (1-3). The simple RNA-guided programmable rule and high occurrence of PAM in genomes allowed Cas9-gRNA to readily target almost all genetic elements for genome editing. Owing to its simplicity and high efficiency, Cas9-based tools have been rapidly developed for genome/epigenome editing, transcriptional regulation and other applications in genetic engineering (4-6).

In principle, multiplex genome editing could be achieved by expressing Cas9 (or Cas9 derived effectors) along with multiple gRNAs for respective target sites. Conventional delivery methods involve either microinjection or expression of gene constructs containing multiple single gRNA (sgRNA) expressing cassettes for multiplex genome editing (2, 3, 7-11). Direct microinjection of in vitro synthesized gRNAs and Cas9 protein (or Cas9 mRNA) into the cell or embryo is only suitable for very few systems. As a result, the most common strategy is to stack multiple sgRNA expressing cassettes in one plasmid construct or to use multiple constructs. The typical size of one sgRNA expressing cassette is about 400-500 bp and consists of RNA Polymerase III (Pol III) promoter, gRNA and Pol III terminator. Due to the limitation of delivery method and plasmid vector capacity, simultaneous production of numerous gRNAs would be a challenge with such a gRNA expressing strategy for most organisms. Moreover, eukaryotic Pol III transcribed RNA is obligated to start with a specific ribonucleotide which may reduce the Cas9/gRNA targetable sites. An advanced strategy is to compact multiple gRNAs in one synthetic gene and engineered an RNA processing system to excise individual gRNAs from the primary transcript. The only proved method based on such a strategy is the expression of Csy4 endoribonuclease (endo-RNase) with Cas9 to processed a transcript containing gRNAs fused with Csy4-cleavable RNA (12, 13). Nevertheless, more robust and precise methods for simultaneous production of multiple gRNAs are needed to improve multiplex editing capability and facilitate more sophisticated Cas9 applications.

RNA is a fundamental cellular component and its production is guaranteed by the conserved and precise RNA processing systems in different organisms. This inspired us to engineer an endogenous RNA processing system to produce multiple gRNAs from a single transcript, rather than introducing any additional RNases along with Cas9/gRNA components. Applicants herein demonstrate that multiple gRNAs could be efficiently produced from a single synthetic gene with the tRNA-gRNA architecture after precise excision of transcripts in vivo by the endogenous RNases. This gRNA expressing strategy was shown to not only allow multiplex targeting but also improve editing efficiency of the CRISPR/Cas9 system in plants. Because the tRNA processing system exists virtually in all organisms, this strategy could be broadly utilized to boost the multiplex editing capability of CRISPR/Cas9 tools for genome engineering.

Results
Strategy to Engineer tRNA Processing System for Producing Numerous gRNAs In order to simultaneously produce multiple gRNAs from one primary transcript, we aimed to compact a cluster of gRNAs with different spacers in one polycistronic gene and hijack an endogenous RNA processing system for cleavage of this transcript into individual gRNAs in nucleus. In search of RNA and endo-RNases that potentially meet this requirement, tRNA attracted our attentions for its characteristics as follows. (I) In nucleoplasm, the tRNA precursor (pre-tRNA) are cleaved at specific sites in eukaryotes by RNase P and RNase Z (or RNase E in bacterium) to remove 5' and 3' extra sequences (FIG. 1A), respectively (14-18). (II) RNase P and RNase Z recognize the tRNA structure, regardless of the pre-tRNA sequence (17, 18). Previous studies revealed that only the acceptor stem, D-loop arm, and TψC-loop arm of tRNA are necessary for RNase P and RNase Z cleavage of pre-tRNA (16-19). (III) tRNA was found in polycistronic transcription unit in bacteria (20) and occasionally in eukaryotes (19, 21), suggesting that the tRNA processing system is likely utilized as an intrinsic mechanism to produce different small RNAs (e.g., snoRNA) with tRNA from a single polycistronic gene (19). (IV) Since tRNA is one of the most abundant cellular components, the endogenous tRNA processing system should be robust to process a large amount of substrates. (V) The tRNA genes contain internal promoter elements (box A and B) to recruit RNA polymerase III (Pol III) complex (FIG. 1B) (22, 23). Hence the tRNA sequence may also work as a potential transcriptional enhancer for Pol III. Based on these features, we hypothesized that the endogenous tRNA system could be engineered as a general platform for precise processing of gRNAs.

To utilize the endogenous tRNA system for multiplex genome editing with Cas9/gRNA, we designed polycistronic tRNA-gRNA (PTG) gene for simultaneous production of numerous gRNAs. As shown in FIG. 1C, this PTG gene consists of tandem repeats of tRNA-gRNA and would be transcribed as a normal snoRNA or sgRNA gene under the control of Pol III promoter. The endogenous tRNA processing RNases (e.g., RNase P and RNase Z in plants) would recognize the tRNA components and excise individual gRNAs from the PTG transcript. The resulting gRNAs would then direct Cas9 to multiple target sites for genome editing (FIG. 1C).

Precise Processing of PTG to Produce Functional gRNAs with Desired Targeting Sequences To explore whether the synthetic PTG gene would be transcribed, processed and function as we predicted (FIG. 1C), we synthesized four PTG genes with a structure of tRNA-gRNA (PTG1 and PTG2) or tRNA-gRNA-tRNA (PTG1.1 and PTG2.1, FIG. 2A). These four PTG genes were designed to produce gRNA1 (PTG1 and PTG1.1) and gRNA2 (PTG2 and PTG2.1) which have been tested previously (24) with sgRNA genes (sgRNA1 and sgRNA2) in the Cas9-mediated genome editing (Example 2, FIG. 5A and see gene sequence in Table 2.1). Both gRNAs targeted rice MPK5 gene which encodes a mitogen-activated protein kinase (MAPK) involved in biotic and abiotic signaling pathways. These PTGs were constructed with a 77-bp long pre-tRNA$^{Gly}$ gene which recognizes the GGC codon and is widely present among various genomes (25). The chosen pre-tRNA$^{Gly}$ sequence consists of 5' leader (5 '-AACAAA-3', 6 bp) and mature tRNA (71 bp) (FIG. 2B). Such tRNA-gRNA fusion in PTGs mimics the native tRNA-snoRNA43 dicistron in plants (19).

In this study, we used a plasmid vector (Example 2, FIG. 6) in which sgRNA or PTG is expressed with rice U3 snoRNA promoter (U3p) and Cas9 is expressed with a rice ubiquitin promoter plus the complete 5' untranslated region (UBIp). After transfecting rice protoplasts with plasmids containing U3p: sgRNA or U3p:PTG, circularized reverse transcription PCR (cRT-PCR)(26, 27) was performed to map both 5'- and 3'-ends of mature gRNAs (See SI Appendix and Table S2 for the principle of cRT-PCR). Mature gRNAs with the expected size were detected from the protoplasts expressing PTGs or sgRNAs (FIG. 2C-2F). However, the tRNA-gRNA fused transcript from PTGs was not detectable by cRT-PCR, probably due to the highly robust tRNA processing system that cleaved most (if not all) primary transcripts of PTGs. Sequence analysis of the cRT-PCR products revealed that all four PTG transcripts were precisely cleaved at the tRNA-gRNA junction and produced mature gRNAs carrying the desired 5' spacer sequences without extra nucleotides (FIG. 2G and Example 2, FIGS. 8 and 9). On the other hand, the 3'-end of mature gRNAs carried a 1-7 nt long poly (U) tail if it preceded the Pol III terminator (sgRNA,PTG1 and PTG2, see Example 2, FIG. 8), or 1-4 nt ribonucleotides from the tRNA-leader when it preceded the tRNA (PTG1.1 and PTG2.1, see Example 2, FIG. 9). The cRT-PCR data also confirmed that gRNAs transcribed from U3p:sgRNA were obligated to start with nucleotide A, whereas U3p:PTGs produced gRNAs without constraint of the first nucleotide (Example 2, FIGS. 8 and 9). In summary, the gRNAs produced from PTG are the same as the sgRNAs but are not obligated to start with a specific nucleotide (FIGS. 2G and 2H).

The functionality of PTG1 and PTG2 was confirmed by examining the insertion/deletion (indel) mutations introduced by non-homologous end joining (NHEJ) repairing at the predicted Cas9:gRNA cleavage site. Because gRNA1 and gRNA2 targets contain the KpnI and SacI restriction enzyme (RE) sites (Example 2, FIG. 5A), respectively, the mutations induced by PTG1/Cas9 and PTG2/Cas9 could be readily analyzed by the digestion of PCR products encompassing the targeted sites with corresponding RE (PCR/RE assay). In rice protoplasts transfected with PTG1/Cas9 and PTG2/Cas9, 15% and 9% of the target sites were found to carry indels, respectively (FIG. 2I), which are slightly higher than the mutation rate of sgRNA:Cas9 constructs we used previously (24). In consistence with our hypothesis that tRNA may function as a transcriptional enhancer for Pol III, the quantitative RT-PCR with gRNA specific primers revealed that the transcript levels of PTG1 and PTG2 were about 3 and 31 times higher than those of sgRNA1 and sgRNA2 in protoplasts (FIG. 2J), respectively. Taken together, our results demonstrated that the endogenous tRNA system could be utilized as a precise and robust tool to produce gRNAs from PTG for Cas9-mediated genome editing.

Efficient Multiplex Genome Editing in Rice Protoplasts Via PTG/Cas9

To test the targeting capacity and efficiency of the PTG system, up to eight gRNAs (gRNA1-gRNA8, Example 2, Table 2.3 and FIG. 5) have been tandemly arrayed to construct PTGs for targeting four homologous rice MAPKs (MPK1/2/5/6) which may function redundantly in diverse cellular signaling pathways. These gRNAs were divided into four pairs and each pair targeted two genomic sites within a gene locus with a distance of 350-750 bp between them (Example 2, FIG. 5). By combining different gRNA pairs, we designed PTG genes encoding 2 (PTG3/4/5/6), 4 (PTG7/8), and 8 (PTG9) gRNAs to simultaneously target 1, 2, and 4 MPK loci, correspondingly (FIG. 3A and Example 2, Table 2.1). We expected that such a design might result in a deletion of short chromosomal fragment between two Cas9 cut sites and allowed us to readily examine the efficacy of PTGs.

To synthesize PTG with repetitive tRNA-gRNA architecture, we designed a scalable and flexible approach to assemble PTGs from PCR components based on the principle of Golden Gate assembly strategy (28) (See Example 2, FIGS. 10 and 11 for details). Our gene assembly approach allowed fast synthesis of PTGs with different combination of gRNAs from common oligonucleotide primers. Using one- or two-steps assembly, we synthesized PTG3-PTG9 genes and cloned them into the CRISPR/Cas9 expressing vectors (Example 2, FIG. 6 and Table 2.1-2.3).

We then transfected rice protoplasts with these plasmids containing both U3p:PTG3-PTG9 and UBIp:Cas9. Chromosomal fragment deletions at four MAPK loci, which were revealed by amplification of truncated PCR products with target specific primers, were detected in protoplasts expressing respective PTGs with 4%-45% efficiency (FIG. 3B). Even though 8 gRNAs were simultaneously produced from PTG9, they still guided Cas9 to efficiently excise chromosomal fragments at all four targeted loci with 4%-20% frequency (FIG. 3B). The fragment deletion efficiency at MPK5 loci was further confirmed by quantitative PCR using primers encompassing the gRNA2 cut site (SI Appendix, Table S4). Sequencing of these truncated PCR products confirmed that fragments between two gRNA/Cas9 cut sites were excised from targeted loci with or without additional indels (FIG. 3C). In general, the fragment deletion efficiency was negatively correlated to the distance between two paired cut sites (correlated efficiency r=−0.95) despite different gRNAs may have variable efficiencies. We noticed that the total number of gRNAs in one PTG affected the deletion efficiency with variable extent at different targets in protoplasts (FIG. 3B). At three targeting loci (MPK2/5/6), the PTGs (PTG4/5/6) containing 2 gRNAs exhibited only slightly higher efficiency than the PTGs with 4 (PTG7/8) and 8 (PTG9) gRNAs. But at the MPK1 locus, PTG3 (2 gRNAs) showed ~2 times higher deletion frequency than PTG7 (4 gRNA) or PTG9 (8 gRNAs). Such a reduction of efficiency of PTGs with a higher number of gRNAs was likely due to the competition for Cas9 among gRNAs. Nevertheless, PTG with tandemly arrayed tRNA-gRNA architecture is capable of simultaneously producing numerous gRNAs and guiding Cas9 to multiple chromosomal targets with a high efficiency.

Improving Multiplex Genome Editing in Stable Transgenic Plants with PTG/Cas9

Because many plants, including important crops like rice, could not be readily regenerated from protoplasts, we used the conventional *Agrobacterium*-mediated transformation to produce stable transgenic lines and evaluated the efficacy of PTG/Cas9 system for multiplex genome editing in intact rice plants. Mutagenesis frequency at gRNA1 and gRNA2 targets in transgenic plants expressing sgRNA 1:Cas9, sgRNA2:Cas9, PTG6:Cas9 or PTG7:Cas9 were examined at $T_0$ generation. Among $T_0$ generation of sgRNA1:Cas9 (n=32) and sgRNA2:Cas9 plants (n=20), 44% and 60% of them carried indels while 13% and 20% of them had biallelic mutations, respectively (Table 1 and Example 2, FIG. 12). By contrast, indels at both targets were detected in all PTG6:Cas9 plants (100%, n=17) including 35% (gRNA1) and 76% (gRNA2) biallelic mutations (Table 1 and Example 2, FIG. 13). But the chromosomal fragment deletion between gRNA1 and gRNA2 target sites was not detected in PTG6:Cas9 plants with PCR, which may occur at a lower frequency in regenerated calli/plants than in protoplasts. Nevertheless, the results showed that PTG6 not only expressed two gRNAs simultaneously, but also enhanced the mutagenesis efficiency at individual targets than sgRNA did (student's t-test P<0.01, Table 1 and Example 2, FIGS. 12 and 13).

When total number of targets increased to four in PTG7:Cas9 plants, a comparable indel frequency to sgRNA1:Cas9 plants was observed at gRNA1 site, but a significantly higher frequency of indels than sgRNA2:Cas9 was found at gRNA2 site (Table 1 and Example 2, FIG. 14). Interestingly, we obtained one PTG7:Cas9 line (6%) carrying biallelic deletion of ~350 bp in MPK1 and monoallelic deletion of ~750 bp in MPK5 (FIGS. 4A and 4B). This prompted us to further examine the efficiency of all eight gRNAs in PTG9:Cas9 lines. At five gRNA targets (gRNA1/2/3/5/7) whose mutation would destroy RE sites, 50% (n=14) of PTG9:Cas9 $T_0$ lines carried biallelic mutations at all five targets (Example 2, FIG. 15). Interestingly, PCR/RE assays suggested that these five gRNAs exhibited comparable efficiency and all of them showed significantly higher mutagenesis activities than what we observed in sgRNA1/2:Cas9 lines (Table 1). Sanger sequencing of the fragments from four MPK loci of PTG9:Cas9 plants confirmed that mutations were introduced at all eight sites (Example 2, FIG. 16). However, the fragment deletion was only detected at MPK2 and MPK5 loci in two PTG9:Cas9 lines (Example 2, FIG. 15). In comparison with protoplasts, the efficiency of targeted chromosomal fragment deletion between paired gRNA/Cas9 cut sites is lower in transgenic plants, which might be due to a relatively lower expression of gRNAs and Cas9 in rice calli/regenerated plants (typically only a single copy of transgene is integrated into rice genome after the *Agrobacterium*-mediated transformation). Our data demonstrate that PTG method not only increase the gRNA number and targeting sites, but also likely enhance mutagenesis efficiency at individual sites, especially when multiple gRNAs are expressed using PTG. To further substantiate the high efficiency of mutagenesis with PTG/Cas9, we synthesized PTG10 with two gRNAs (gRNA9 and gRNA10) to target the rice phytoene desaturase (PDS) gene (Example 2, FIG. 13A). PDS is frequently used as a convenient gene target to examine knock-out efficiency because plants with null functional PDS would lead to visible photo-bleached phenotype. Strikingly, all PTG10:Cas9 transgenic seedlings ($T_0$ generation, n=15) regenerated from calli showed photo-bleaching phenotype, and 13 of them were completely albino, indicating these plants carried null functional PDS (FIG. 4C). Though we only identified one line carrying chromosomal deletions between two gRNA targeted sites, sequencing of the PDS targets from all the lines confirmed that indels were introduced at the target sites (Example 2, FIG. 13). By comparing these data with the previously reported efficiency of sgRNA/Cas9 system (9, 11, 29-32), to our knowledge, the PTG/Cas9 approach yielded the highest efficiency of targeted mutagenesis (up to 100%, FIG. 4 and Table 1) in plants. Our results also demonstrate that targeting one gene with two gRNAs using PTG will greatly increase the efficiency of complete gene knock-out.

DISCUSSION

We developed a general strategy and platform to produce multiple gRNAs from a single synthetic PTG gene by hijacking the endogenous tRNA processing system (FIG. 1). We also provided a framework to design, synthesize and utilize PTG for multiplex genome editing with Cas9. These PTGs were expressed with Pol III promoters (e.g. U3p) in the same manner as sgRNA genes but not obligated to start with a specific nucleotide (FIG. 2). As a result, current CRISPR/Cas9 vectors for expressing sgRNA could be directly used to express PTG for multiplex genome editing as we demonstrated in this study. By producing multiple gRNAs from a single polycistronic gene, the PTG technology could be employed to improve simultaneous mutagenesis of multiple genomic loci or deletion of short chromosomal fragments (FIGS. 3 and 4). Such a genome engineering approach may lead to simultaneous knock-out of multiple protein coding genes or deletion of no-coding RNA regions and other genetic elements. In addition to targeted mutagenesis/deletion, the PTG approach could facilitate other Cas9-based applications in which multiple gRNAs are required. For example, PTG could be utilized with Cas9 nickase to improve targeting fidelity (13, 33, 34), or with deactivated Cas9 transcriptional-activator or -repressor to manipulate multiple gene expression (35, 36). Given the high processing accuracy and capability of RNase P and RNase Z we observed (FIG. 2), the tRNA processing system also could be utilized as a general platform to produce other regulatory RNAs (e.g. short hairpin RNA or artificial microRNA) from a single synthetic gene. These different classes of regulatory RNAs, like gRNA and short hairpin RNA, also could be compacted into a single polycistronic gene to develop more sophisticated device for genetic engineering.

Recently, polycistronic transcripts that fused gRNA with a 28 nt RNA (referred as gRNA-28nt) was successfully utilized to guide Cas9 to target up to four targets in human cells (12, 13). The synthetic gene with gRNA-28nt architecture produced mature gRNAs with 28 nt extra 3' sequence and also required co-expressing the endonuclease Csy4 from *Pseudomonas aeruginosa* to cleave the transcript. In comparison with the gRNA-28nt strategy, our approach utilizes the robust endogenous tRNA processing system that enables precise production of gRNAs with only 1-4 nt extra sequence at the gRNA 3' end (FIGS. 1 and 2) and carries no additional risk of the endonuclease Csy4 toxicity to recipients. Given the extremely large number of tRNA genes with variable sequences and the fact that RNase P and RNase Z precisely recognize RNA substrates with tRNA-like structures (18, 37), there are many choices of tRNA sequence to be embedded in PTG. Furthermore, the tRNA processing system is universal in all living organisms, thus the PTG technology could be directly adapted to other organisms for Cas9-mediated genome engineering.

When multiple DSBs were generated by PTG/Cas9 in rice plants, indels resulting from the error-prone NHEJ repairing occurred more frequently than fragment deletions generated by directly joining two DSBs (Example 2, FIGS. 14 and 15). To date, the molecular mechanism by which two DSBs directly link together to generate chromosomal translocation or fragment deletion in vivo is largely unclear. We speculate that the process leading to such a chromosomal disorder may require two DSBs at the same time interval and is likely determined by the highly dynamic interaction between gRNA/Cas9 cutting and endogenous DNA repairing and also by the distance between DSBs. Due to the differences in the delivery, expression and activity of gRNAs and Cas9, it is not surprising to see some discrepancies in fragment deletion frequency between protoplasts (FIG. 3B) and stable transgenic plants and among different PTG transgenic lines (FIG. 4A and Example 2, FIG. 13-15). Because the PTG technology enables to generate many DSBs in genomic DNAs, it may provide an efficient tool to help dissect the molecular process of chromosomal deletion. More importantly, the PTG technology significantly improves multiplex editing capability and efficiency and is expected to facilitate more sophisticated Cas9 applications such as targeted mutagenesis and deletion of redundant genes or genetic elements, transcriptional modulation of multiple genes and pathways, modification and labeling of numerous genomic sites, site-specific integration and gene replacement.

Materials and Methods

Plant Materials

Rice (*Oryza sativa* L. ssp) cultivars Kitaake and Nipponbare were used in this study. Rice plants were grown in a green house or growth chamber at 28° C. day/23° C. night with 12 h of light.

Plasmid Vector Construction

The plasmid vectors pRGE32 was used to transiently express U3p:sgRNA or U3p:PTG along with UBIp:Cas9 in rice protoplasts and pRGEB32 was used for the *Agrobacterium*-mediated rice transformation (Example 2, FIG. 6). See Example 2, SI Methods for the details about plasmid vector construction.

sgRNA:Cas9 and PTG:Cas9 Expression Constructs

The U3p:sgRNA1 and U3p:sgRNA2 constructs were made as described previously (24). The specific spacer sequences for gRNA3-gRNA8 (Example 2, Table 2.3) were selected using the CRISPR-PLANT database at world wide web at genome.arizona.edu\crispr\ (38). The PTG genes and U3p:PTG constructs were generated as described in Example 2, SI Methods, FIG. 10-11 and Table 2.3. The synthesized PTGs were inserted into the Bsa I digested pRGE32 or pRGEB32 for transient protoplast expression or stable rice transformation, respectively. The sequences of sgRNA1, sgRNA2 and PTG genes used in this study were listed in Example 2, Table 2.1.

Rice Protoplast Transfection

The rice protoplast preparation and transfection were performed as we described previously (24). Briefly, 20 µg of plasmid DNA was used to transfected $2 \times 10^5$ protoplasts with a transfection efficiency of ~40%-50%. Total rice genomic DNAs were extracted from the protoplast samples at 36h after transfection and then used for PCR and sequence analysis.

Agrobacterium-Mediated Rice Transformation

Transgenic rice plants were generated by the *Agrobacterium tumefaciens*-mediated transformation using rice mature seed-derived calli according to a conventional protocol (39).

Genomic DNA Extraction and PCR/RE Assay

Rice genomic DNA was extracted as described previously with the CTAB method (24). To detect mutagenesis at desire sites, target regions were amplified with specific primers (See Example 2, Table 2.2 for primer sequences) using GoTaq DNA polymerase (Promega). The PCR product was separated in 1% agarose gel and stained with ethidium bromide to detect chromosomal fragment deletion. To detect indel at specific sites with PCR/RE, the PCR products encompassing the target sites were digested with appropriate restriction enzymes (RE) for 5 hours, and then were analyzed with 1% agarose gel electrophoresis and ethidium bromide staining. The stained gels were imaged using Gel Doc XRS system (Bio-Rad) and quantified with the Quantity One 4.6 program (Bio-Rad). Selected PCR products were cloned into pGEM T-easy vector (Promega) for DNA sequencing.

RNA extraction, cRT-PCR and quantitative PCR

See Example 2, SI Methods for details.

Gene accession number in Genebank

Genes and their Genebank RefSeq accession numbers are as follow: MPK1, Os06g0154500; MPK2, Os08g0157000; MPK5, Os03g0285800; MPK6, Os10g0533600; UBI, Os02g0161900; and PDS, Os03g0184000.

REFERENCES

1. Jinek M, et al. (2012) A programmable dual-RNA-guided DNA endonuclease in adaptive bacterial immunity. *Science* 337(6096):816-821.
2. Cong L, et al. (2013) Multiplex genome engineering using CRISPR/Cas systems. *Science* 339(6121):819-823.
3. Mali P, et al. (2013) RNA-guided human genome engineering via Cas9. *Science* 339(6121):823-826.
4. Mali P, Esvelt K M, Church G M (2013) Cas9 as a versatile tool for engineering biology. *Nat Methods* 10(10):957-963.
5. Sander J D, Joung J K (2014) CRISPR-Cas systems for editing, regulating and targeting genomes. *Nat Biotechnol* 32(4): 347-355.
6. Hsu P D, Lander E S, Zhang F (2014) Development and applications of CRISPR-Cas9 for genome engineering. *Cell* 157(6): 1262-1278.
7. Wang H, et al. (2013) One-Step generation of mice carrying mutations in multiple genes by CRISPR/Cas-mediated genome engineering. *Cell* 153(4):910-918.
8. Jinek M, et al. (2013) RNA-programmed genome editing in human cells. *eLife* 2: e00471.
9. Li J F, et al. (2013) Multiplex and homologous recombination-mediated genome editing in *Arabidopsis* and *Nicotiana benthamiana* using guide RNA and Cas9. *Nat Biotechnol* 31(8):688-691.
10. Zhou H, Liu B, Weeks D P, Spalding M H, Yang B (2014) Large chromosomal deletions and heritable small genetic changes induced by CRISPR/Cas9 in rice. *Nucleic acids research* 42(17): 10903-10914.
11. Shan Q, et al. (2013) Targeted genome modification of crop plants using a CRISPR-Cas system. *Nat Biotechnol* 31(8):686-688.
12. Nissim L, Perli S D, Fridkin A, Perez-Pinera P, Lu T K (2014) Multiplexed and programmable regulation of gene networks with an integrated RNA and CRISPR/Cas toolkit in human cells. *Mol Cell* 54(4):698-710.
13. Tsai S Q, et al. (2014) Dimeric CRISPR RNA-guided FokI nucleases for highly specific genome editing. *Nat Biotechnol* 32(6):569-576.
14. Phizicky E M, Hopper A K (2010) tRNA biology charges to the front. *Genes Dev* 24(17):1832-1860.
15. Schiffer S, Rosch S, Marchfelder A (2002) Assigning a function to a conserved group of proteins: the tRNA 3'-processing enzymes. *EMBO J* 21(11):2769-2777.
16. Gutmann B, Gobert A, Giege P (2012) PRORP proteins support RNase P activity in both organelles and the nucleus in *Arabidopsis*. *Genes Dev* 26(10):1022-1027.
17. Barbezier N, et al. (2009) Processing of a dicistronic tRNA-snoRNA precursor: combined analysis in vitro and in vivo reveals alternate pathways and coupling to assembly of snoRNP. *Plant Physiol* 150(3):1598-1610.
18. Canino G, et al. (2009) *Arabidopsis* encodes four tRNase Z enzymes. *Plant Physiol* 150(3): 1494-1502.
19. Kruszka K, et al. (2003) Plant dicistronic tRNA-snoRNA genes: a new mode of expression of the small nucleolar RNAs processed by RNase Z. *EMBO J* 22(3): 621-632.
20. Nakajima N, Ozeki H, Shimura Y (1981) Organization and structure of an *E. coli* tRNA operon containing seven tRNA genes. *Cell* 23(1):239-249.
21. Nakaar V, Dare A O, Hong D, Ullu E, Tschudi C (1994) Upstream tRNA genes are essential for expression of small nuclear and cytoplasmic RNA genes in trypanosomes. *Mol Cell Biol* 14(10):6736-6742.
22. White R J (2011) Transcription by RNA polymerase III: more complex than we thought. *Nat Rev Genet* 12(7): 459-463.
23. Dieci G, Fiorino G, Castelnuovo M, Teichmann M, Pagano A (2007) The expanding RNA polymerase III transcriptome. *Trends Genet* 23(12):614-622.
24. Xie K, Yang Y (2013) RNA-guided genome editing in plants using a CRISPR-Cas system. *Mol Plant* 6(6): 1975-1983.
25. Chan P P, Lowe T M (2009) GtRNAdb: a database of transfer RNA genes detected in genomic sequence. *Nucleic Acids Res* 37(Database issue):D93-97.
26. Kuhn J, Binder S (2002) RT-PCR analysis of 5' to 3'-end-ligated mRNAs identifies the extremities of cox2 transcripts in pea mitochondria. *Nucleic Acids Res* 30(2): 439-446.
27. Yokobori S, Paabo S (1995) Transfer RNA editing in land snail mitochondria. *Proc Natl Acad Sci USA* 92(22): 10432-10435.
28. Engler C, Kandzia R, Marillonnet S (2008) A one pot, one step, precision cloning method with high throughput capability. *PloS one* 3(11):e3647.
29. Nekrasov V, Staskawicz B, Weigel D, Jones J D, Kamoun S (2013) Targeted mutagenesis in the model plant *Nicotiana benthamiana* using Cas9 RNA-guided endonuclease. *Nat Biotechnol* 31(8): 691-693.
30. Feng Z, et al. (2014) Multigeneration analysis reveals the inheritance, specificity, and patterns of CRISPR/Cas-induced gene modifications in *Arabidopsis*. *Proc Natl Acad Sci USA* 111(12):4632-4637.
31. Wang Y, et al. (2014) Simultaneous editing of three homoeoalleles in hexaploid bread wheat confers heritable resistance to powdery mildew. *Nat Biotechnol* 32(9): 947-951.
32. Zhang H, et al. (2014) The CRISPR/Cas9 system produces specific and homozygous targeted gene editing in rice in one generation. *Plant Biotechnol J* 12(6):797-807.
33. Ran F A, et al. (2013) Double nicking by RNA-Guided CRISPR Cas9 for enhanced genome editing specificity. *Cell* 154(6):1380-1389.
34. Guilinger J P, Thompson D B, Liu D R (2014) Fusion of catalytically inactive Cas9 to FokI nuclease improves the specificity of genome modification. *Nat Biotechnol* 32(6): 577-582.
35. Gilbert L A, et al. (2013) CRISPR-mediated modular RNA-guided regulation of transcription in eukaryotes. *Cell* 154(2):442-451.
36. Mali P, et al. (2013) CAS9 transcriptional activators for target specificity screening and paired nickases for cooperative genome engineering. *Nat Biotechnol* 31(9):833-838.
37. Forster A C, Altman S (1990) External guide sequences for an RNA enzyme. *Science* 249(4970):783-786.
38. Xie K, Zhang J, Yang Y (2014) Genome-wide prediction of highly specific guide
RNA spacers for CRISPR-Cas9-mediated genome editing in model plants and major crops. *Mol Plant* 7(5):923-926.
39. Hiei Y, Komari T (2008) *Agrobacterium*-mediated transformation of rice using immature embryos or calli induced from mature seed. *Nat Protoc* 3(5):824-834.

Example 2

Supporting Information
Plasmid Vector Construction

To construct pRGE32, the rice UBIp fragment was amplified from genomic DNA of Nipponbare cultivar with a pair of specific primers (UBI-F and UBI-R, see Table S2 for primer sequences). After amplifying the U3p-gRNA fragment from pRGE31 (Addgene plasmid 50929) with primers UGW-U3-F and UGW-gRNA-R, the U3p-gRNA and UBIp fragments were linked together by overlapping extension PCR with primers UGW-U3-F and UBI-R. Then pRGE32 was constructed by Gibson Cloning (New England Biolabs) to replace the U3p-gRNA-35S fragment in pRGE31 with U3p-gRNA-UBIp. The pRGEB32 binary vector (see FIG. 6 for vector map) used for the *Agrobacterium*-mediated rice transformation was created by inserting the U3p-gRNA-UBIp-Cas9 fragment from pRGE32 into pCAMBIAI301-BsaI with Gibson Cloning (New England Biolabs). The pCAMBIAI300-BsaI is derived from pCAMBIAI300 after removing all of BsaI sites through site-directed mutagenesis. The primers used in plasmid construction are listed in Table 2.2.

The pGTR plasmid, which contains a gRNA-tRNA fused fragment, was used as a template to synthesize PTGs in this study. To construct pGTR, the gRNA scaffold fragment was amplified by PCR using a pair of specific primers (Bsa-gRNA-F and gRNA-R) whereas the tRNA$^{Gly}$ fragment was amplified as a primer dimer of g-tRNA-F and tRNA-R. Then these two fragments were fused as gRNA-tRNA by overlapping extension PCR using primers Bsa-gRNA-F and tRNA-R. The overlapping PCR product was separated and purified from an agarose gel, and then inserted into pGEM-T easy (Promega) to generate pGTR plasmid. The sequence of gRNA-tRNA fusion in pGTR is shown in Table S1. The primers used in plasmid construction are listed in Table 2.2.

RNA Extraction, cRT-PCR and Quantitative PCR

Total RNAs were extracted from protoplasts using the TRIzol Reagent (Life Technologies) according to the manufacturer's instruction. The cRT-PCR was schematically depicted in FIG. 7 and performed as follow. To circularize RNA, 1 µg of total RNA was incubated in a 20 µl reaction containing 1×T4 RNA ligase buffer (New England Biolabs), 50 µM of ATP, 10% PEG8000, 20 U of RNase inhibitor (New England Biolabs) and 10 U of T4 RNA ligase (New England Biolabs). The ligation was carried out at 25° C. for 4 h. Then 10 U of DNase I (New England Biolabs) was added into ligation reaction to remove genomic DNA contamination at 25° C. for 20 min. Then circularized RNA was purified with TRIzol Reagent (Life Technologies) and dissolved in nuclease free water. A total of 200 ng circularized RNA was mixed with 0.5 mM dNTP and 1 µM of oligos specific to gRNA spacer (gRNA1-R and gRNA2-R, see Table S2) and denatured at 70° C. for 5 min. After chilling on ice, 1× MuMLV Reverse Transcriptase buffer, 20 U of RNase inhibitor (New England Biolabs), and 10 U of MuMLV reverse transcriptase (New England Biolabs) were added to synthesize 1$^{st}$ cDNA at 42° C. for 1 hour. The negative controls without adding MuMLV reverse transcriptase (−RT) were also performed for all samples. After

TABLE 1

Targeted mutation efficiency in PTG:Cas9 vs. sgRNA:Cas9 plants.

| Gene ID | # of T$_0$ Lines | Editing at gRNA1 target | | Editing at gRNA2 target | | Editing at gRNA3/5/7 targets | |
|---|---|---|---|---|---|---|---|
| | | Mut. | Bi-Mut | Mut. | Bi-mut. | Mut. | Bi-mut. |
| sgRNA1 | 32 | 44% | 13% | n.a. | n.a. | n.a. | n.a. |
| sgRNA2 | 20 | n.a. | n.a. | 60% | 20% | n.a. | n.a. |
| PTG6 | 17 | 100%** | 35%** | 100%** | 76%** | n.a. | n.a. |
| PTG7 | 17 | 47% | 6% | 100%* | 24% | n.a. | n.a. |
| PTG9 | 14 | 86%** | 78%** | 86%** | 57%** | 86% | 86% |

The frequency of mutation (Mut.) and biallelic mutation (Bi-Mut.) at the targeting sites in transgenic lines was examined and calculated based on PCR/RE assays (Example 2, FIG. S8-S11). The editing frequencies at gRNA1 and gRNA2 targets were compared between sgRNA and PTG plants.
**student's t-test P < 0.01;
*student's t-test P < 0.05;
n.a., not applied.

reverse transcription, MuMLV was inactivated at 70° C. for 10 min. Then PCR was performed with the following 50 µl reaction: one twentieth of 1$^{st}$ cDNA, 1× Phusion HF buffer, 0.2 mM dNTPs, 0.5 µM of forward primers, 0.5 µM reverse primers, and 1 U of Phusion DNA polymerase (Thermo Scientific). The resulting PCR products were analyzed with 2% agarose gel electrophoresis. The cRT-PCR products were then sequenced after cloning into pGEM-T easy vector (Promega). See Table 2.2 for primer sequences used in cRT-PCR.

For quantitative RT-PCR, the DNase I treated total RNAs were reverse-transcribed to produce cDNAs using a specific primer gRNA-R along with MuMLV (New England Biolabs) according to the manufacturer's instructions. The real-time PCR was performed using GoTaq qPCR Master Mix (Promega) in the StepOnePlus Realtime PCR system (Life technologies). The gRNA1-F and gRNA-R primers were used for sgRNA1 and PTG1, and gRNA2-F and gRNA-R primer were used for sgRNA2 and PTG2. The rice UBI gene was used as the internal reference for relative quantification. See Table S2 for primer sequences.

To quantify deletion efficiency, quantitative PCR was performed using 10 ng of the genomic DNA as a template to amplify the genomic fragments within MPK5 or UBI loci. A pair of specific primers (MPK5-qF and MPK5-R611, Table S2) which encompass the gRNA2 cut site were used to amplify MPK5 copies containing no fragment deletion. The relative quantity (RQ) of MPK5 fragment without deletion was calculated using UBI as a reference gene. Because only MPK5 fragments without deletion were amplified, the fragment deletion efficiency could be estimated as 100%-RQ (Table 2.4).

Synthesis of Polycistronic tRNA-gRNA (PTG) Genes by Golden Gate Assembly

The PTG genes were synthesized based on the principle of Golden Gate (GG) assembly which is broadly used to assemble DNA parts like customized transcription activator-like effector (TALE). Our assembly approach allows synthesizing PTGs with different combinations of gRNAs using the same components. For example, we made PTG3-PTG9 with the same set of oligo primers (Table S3). By hierarchical GG assembly reaction, two PTGs could be assembled together to create a longer PTG (like PTG9). PTGs with no more than 6 gRNAs (e.g. PTG1-PTG8) could be synthesized by one step GG assembly (Level 1, FIG. 10), whereas PTGs with more than 6 gRNAs (e.g., PTG9) require two or more steps of GG assembly (Level 2, FIG. 11). The schematic diagrams of PTG synthesis approach are shown in FIGS. 10 and 11, and details of primer design, GG assembly and plasmid construction are described as follow.

Step 1. Design Primers to Amplify gRNA-tRNA Parts

In order to ligate multiple DNA parts in a desired order, GG assembly requires distinct 4-bp overhangs to ligate two DNA parts after digestion with BsaI (or other type II endonucleases such as AarI, BbsI, BsmAI, BsmBI). The gRNA spacer is the only unique sequence in PTG (FIG. 1C), thus PTGs should be divided into DNA parts within the gRNA spacer region. As shown in FIGS. 10A and 10B, a gRNA spacer was split into two parts with 4 bp overlap and each half of the spacer was synthesized within oligo primers with a BsaI site. Details to design gRNA specific primers are described below:

1.1. Select a 4-bp long sequence within each gRNA spacer as BsaI overhangs in GG assembly. The overhang could be any 4 consecutive nucleotides of the gRNA spacer. Of note, DNA parts that assembled in the same GG reaction should have a distinct 4-bp overhang, and could not be 5'-GGCA-3' or 5'-AAAC-3' which are used in terminal adaptors for cloning to pRGE32 and pRGEB32 (FIG. 6).

1.2. Design the primer sequences as follow (also see FIG. 6):
In this example, the 9th to 12th nucleotides of a 20 nt long spacer of gRNA[x] is chosen as the BsaI overhang for GG cloning:

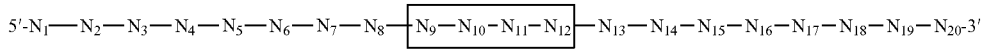

The primer should be:

gRNA[x]-F (Forward primer, anneal to 5'-end of gRNA scaffold):

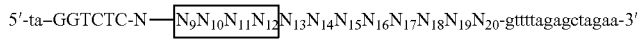

gRNA[x]-R (Reverse primer, anneal to 3'-end of pre-tRNA):

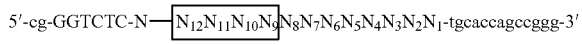

Note: Any 4 consecutive nucleotides in the spacer could be selected as overhangs for GG assembly. This allows the selection of a specific overhang for each DNA part in GG assembly. The two 5'-terminal bases (shown in lowercase) are randomly added nucleotides to enhance BsaI digestion of PCR products. The red color indicates the reverse complementary sequence to the spacer. The lowercase letters at the 3'-end indicate bases that anneal to gRNA (Forward primer) or tRNA (Reverse primer).

Step 2. Level 1 GG Assembly (Construction of PTG1-PTG8 Genes)
See Fig. S6C for the overall strategy of level 1 GG assembly of PTGs.
2.1. Set up 50 µL PCR reactions to amplify DNA parts for PTG construction.

| | |
|---|---|
| pGTR plasmid | 0.1 ng |
| 5X Phusion HF buffer | 10 µl |
| dNTPs (10 mM) | 1 µl |
| Forward primer (10 µM) | 2.5 µl |
| Reverse Primer (10 µM) | 2.5 µl |

| | | |
|---|---|---|
| Phusion (2 U/µl, NEB) | 0.5 µl | |
| H2O | x µl | |
| Total | 50 µl | |

To construct PTGs used in this study, the forward and reverse primers to amplify level 1 parts were added as follow:

| PCR ID | Forward primer | Reverse primer | Level 1 parts symbol |
|---|---|---|---|
| P1 | L5AD5-F | gR1-R | L5AD-gR1 |
| P2 | gR1-F | L3AD5-R | gR1-L3AD |
| P3 | L5AD5-F | gR2-R | L5AD-gR2 |
| P4 | gR2-F | L3AD5-R | gR2-L3AD |
| P5 | gR1-F | gR2-R | gR1-gR2 |
| P6 | L5AD5-F | gR3-R | L5AD-gR3 |
| P7 | gR3-F | gR4-R | gR3-gR4 |
| P8 | gR4-F | L3AD5-R | gR4-L3AD |
| P9 | L5AD5-F | gR5-R | L5AD-gR5 |
| P10 | gR5-F | gR6-R | gR5-gR6 |
| P11 | gR6-F | L3AD5-R | gR6-L3AD |
| P12 | L5AD5-F | gR7-R | L5AD-gR7 |
| P13 | gR7-F | gR8-R | gR7-gR8 |
| P14 | gR8-F | L3AD5-R | gR8-L3AD |
| P15 | gR2-F | gR3-R | gR2-gR3 |
| P16 | gR8-F | gR5-R | gR8-gR5 |
| P17 | gR4-F | gR7-R | gR4-gR7 |

PCRs were run with the following program:

| Temperature | Time | Cycles |
|---|---|---|
| 98° C. | 2 min | 1 |
| 98° C. | 10 sec | 35 |
| 50° C. | 20 sec | |
| 72° C. | 20 sec | |
| 72° C. | 2.5 min | 1 |
| 4° C. | Hold | 1 |

2.2. The PCR products were purified with Spin Column PCR Products Purification kit (BioBasic).

2.3. Individual parts were ligated together by GG assembly with the following reaction:

| | |
|---|---|
| Level 1 parts | 25-50 ng (add equal amount for each parts) |
| 2x T7 DNA ligase Buffer (NEB) | 10 µl |
| Bovine Serum Albumin (1 mg/ml) | 2 µl |
| Bsa I (10 U/µl, NEB) | 0.5 µl |
| T7 DNA Ligase (3000 U/µl, NEB) | 0.5 µl |
| Total Volume | 20 µl |

For GG assembly reactions to construct PTG1-PTG8, the level 1 parts were added as follow:

| Gene ID | Encoding gRNAs | Level 1 parts used |
|---|---|---|
| PTG1 | gRNA1 | L5AD-gR1 and gR1-L3AD |
| PTG2 | gRNA2 | L5AD-gR2 and gR2-L3AD |
| PTG3 | gRNA3-gRNA4 | L5AD-gR3, gR3-R4, and gR4-L3AD |
| PTG4 | gRNA5-gRNA6 | L5AD-gR5, gR5-gR6, and gR6-L3AD |
| PTG5 | gRNA7-gRNA8 | L5AD-gR7, gR7-gR8, and gR8-L3AD |
| PTG6 | gRNA1-gRNA2 | L5AD-gR1, gR1-gR2, and gR2-L3AD |
| PTG7 | gRNA1-gRNA2-gRNA3-gRNA4 | L5AD-gR1, gR1-gR2, gR2-gR3, gR3-gR4, and gR4-L3AD |
| PTG8 | gRNA7-gRNA8-gRNA5-gRNA6 | L5AD-gR7, gR7-gR8, gR8-gR5, gR5-gR6, and gR6-L3AD |

2.4. GG reactions were performed in a thermal cycler (Bio-Rad) by incubation at 37° C., 5 min and 20° C., 10 min for 30-50 cycles; and then held at 20° C. for 1 hour.

2.5. The GG reaction product was diluted with 180 µl of H2O.

2.6. The level 1 GG assembly products were amplified in the 50 µl PCR reaction:

| | |
|---|---|
| Ligation product (1:10 dilution) | 1 µl |
| 5X Go Green buffer (Promega) | 10 µl |
| dNTPs (10 mM) | 1 µl |
| S5AD5-F (10 µM) | 1 µl |
| S3AD5-R (10 µM) | 1 µl |
| GoTaq DNA polymerase (2 U/µl, Promega) | 1 µl |
| H2O | 35 µl |
| Total | 50 µl |

PCR was run in a thermal cycler (Bio-Rad) with the following program:

| Temperature | Time | Cycles |
|---|---|---|
| 95° C. | 2 min | 1 |
| 95° C. | 10 sec | 35 |
| 60° C. | 20 sec | |
| 72° C. | 1 min/kb | |
| 72° C. | 5 min | 1 |
| 4° C. | Hold | 1 |

2.7. Purify the PCR product with Spin Column PCR Products Purification kit (Bio Basic).

2.8. Digest the purified PCR product with Fok I (NEB).

2.9. Separate the Fok I digested products in 1% agarose gel; Excise the DNA bands with the expected size from the gel and then purify them with Spin Column DNA Gel Extraction Kit (Bio Basic).

2.10. Ligate the Fok I digested GG fragment into the BsaI digested pRGE32 or pRGEB32 vectors with T4 DNA ligase (NEB).

2.11. Transform the ligation product to *E. coli* DH5a, purify the recombinant plasmids and confirm the constructs by Sanger sequencing.

Step 3. Level 2 GG Assembly (Construct PTG9 by Two-Step GG Assembly)

The schematic diagram of level 2 GG assembly is shown in FIG. 11. Level 2 GG assembly is used to synthesize PTGs with more than six gRNAs. Such a large PTG is constructed by ligating two smaller PTGs (level 2 parts) together. These two small PTGs are synthesized by level 1 GG assembly and contain one overlapped gRNA as a bridge (bridge gRNA, FIG. 11) to ligate level 2 parts in a next GG assembly reaction. To amplify level 2 parts from level 1 assembled PTGs, a pair of specific primers annealing only to the bridge gRNA spacer are required for PCR with the terminal adaptor primers (S5AD5-F and S3AD5-R). In this study, the PTG9 was synthesized with this approach and gRNA7 was used as the bridge gRNA.

3.1. Design bridge gRNA spacer-specific primers to amplify level 2 parts.

Bridge gRNA spacer:

5'-$N_1$—$N_2$—$N_3$—$N_4$—$N_5$—$N_6$—$N_7$—$N_8$—$\boxed{N_9-N_{10}-N_{11}-N_{12}}$—$N_{13}$—$N_{14}$—$N_{15}$—$N_{16}$—$N_{17}$—$N_{18}$—$N_{19}$—$N_{20}$-3'

Any consecutive 4-bp could be selected as an overhang for GG assembly. In this example, $N_9$-$N_{10}$-$N_{11}$-$N_{12}$ was selected as an overhang.

Ln-gR[x]-F (Forward primer, only annealing to bridge gRNA spacer):

5'-ta-GGTCTC-N—$\boxed{N_9N_{10}N_{11}N_{12}}$$N_{13}N_{14}N_{15}N_{16}N_{17}N_{18}N_{19}N_{20}$-3'

Ln-gR[x]-R (Reverse primer, only annealing to bridge gRNA spacer):

5'-cg-GGTCTC-N—$\boxed{N_{12}N_{11}N_{10}N_9}$$N_8N_7N_6N_5N_4N_3N_2N_1$-3'

Note:
The two 5'-terminal bases (shown in lowercase) are randomly added nucleotides to enhance Bsa I digestion of PCR products. The red color indicates the reverse complementary sequence to the spacer.

3.2. Set up GG reactions with the following level 1 parts generated from 2.1-2.2.

| PTG ID | Encoding gRNAs | Level 1 Parts used in GG assembly reaction |
|---|---|---|
| PTG7-Ln | gRNA1-gRNA2-gRNA3-gRNA4-gRNA7 | L5AD-gR1, gR1-gR2, gR2-gR3, gR3-R4, gR4-gR7, and gR7-L3AD |

The level 1 GG assembly was carried out in the same manner as steps 2.4-2.5.

3.3. Amplify level 2 DNA parts with the following primers and templates:

| PCR ID | Forward primer | Reverse primer | Template (1:10 diluted Level 1 GG reaction) |
|---|---|---|---|
| L2-P1 | S5AD5-F | Ln-gR7-R | PTG7-Ln (step 3.2) |
| L2-P2 | Ln-gR7-F | S3AD5-R | PTG8 (step 2.5) |

The PCR condition is the same as step 2.6.

3.4. 
Separate the PCR products in 1% agarose gel. Excise the PCR bands with the expected size from the gel and purify them with Spin Column DNA Gel Extraction kit (Bio Basic).

3.5. Set up GG assembly reactions to ligate two DNA parts (L2-P1 and L2-P2) together.

| | |
|---|---|
| L2-P1 PCR product | 50 ng |
| L2-P2 PCR product | 50 ng |
| 2 x T7 DNA ligase Buffer (NEB) | 10 μl |
| Bovine Serum Albumin (1 mg/ml) | 2 μl |
| Bsa I (10 U/μl, NEB)TABEL OF SEQUENCES | 0.5 μl |
| T7 DNA Ligase (3000 U/μl, NEB) | 0.5 μl |
| Total Volume | 20 μl |

3.6 
Perform GG assembly reactions in a thermal cycler (Bio-Rad) using the following program: 37° C., 5 min; 20° C., 10 min for 25 cycles; and 20° C. for 1 hour.

3.7. 
Amplify Level 2 GG assembled product with S5AD5-F and S3AD5-R, then inserted the amplified product into pRGE32 or pRGEB32 using the same procedure as steps 2.6-2.11.

Example 2 Tables

TABLE 2.1

Sequence of synthetic genes used in this study

| Gene (Architecture) | Sequence (5'->3') |
|---|---|
| Sequence of gRNA-tRNA fusion in pGTR plasmid SEQ ID NO: 15 | GTTTTAGAGCTAGAAATAGCAAGTTAAAATAAGGCTAGTCCG<br>TTATCAACTTGAAAAAGTGGCACCGAGTCGGTGC$\boxed{\text{AACAAAGC}}$<br>$\boxed{\text{ACCAGTGGTCTAGTGGTAGAATAGTACCCTGCCACGGTACAGACC}}$<br>$\boxed{\text{CGGGTTCGATTCCCGGCTGGTGCA}}$ |
| sgRNA1 SEQ ID NO: 1 | GATCCGTGGCAAGATGTCGTAGAGCAGGTACGTTTTAGAGCTAGA<br>AATAGCAAGTTAAAATAAGGCTAGTCCGTTATCAACTTGAAAA<br>AGTGGCACCGAGTCGGTGCTTTTTT |
| sgRNA2 SEQ ID NO: 2 | GATCCGTGGCAGTCTACATCGCCACGGAGCTCAGTTTTAGAGCT<br>AGAAATAGCAAGTTAAAATAAGGCTAGTCCGTTATCAACTTGA<br>AAAAGTGGCACCGAGTCGGTGCTTTTTT |
| PTG1 (tRNA-gRNA1) | GATCCGTGGC$\boxed{\text{AACAAAGCACCAGTGGTCTAGTGGTAGAATAGTAC}}$<br>$\boxed{\text{CCTGCCACGGTACAGACCCGGGTTCGATTCCCGGCTGGTGCA}}$AGA |

TABLE 2.1-continued

Sequence of synthetic genes used in this study

| Gene (Architecture) | Sequence (5'->3') |
|---|---|
| SEQ ID NO: 16 | *TGTCGTAGAGCAGGTAC*GTTTTAGAGCTAGAAATAGCAAGTTAAAATAAGGCTAGTCCGTTATCAACTTGAAAAAGTGGCACCGAGTCGGTGCTTTTTTTTTT |
| PTG2 (tRNA-gRNA2) SEQ ID NO: 17 | GATCCGTGGC<u>AACAAAGCACCAGTGGTCTAGTGGTAGAATAGTAC</u><br><u>CCTGCCACGGTACAGACCCGGGTTCGATTCCCGGCTGGTGCA</u>TCT<br>*ACATCGCCACGGAGCTCA*GTTTTAGAGCTAGAAATAGCAAGTTAAAATAAGGCTAGTCCGTTATCAACTTGAAAAAGTGGCACCGAGTCGGTGCTTTTTTTTTT |
| PTG1.1 (tRNA-gRNA1-tRNA) SEQ ID NO: 18 | GATCCGTGGC<u>AACAAAGCACCAGTGGTCTAGTGGTAGAATAGTAC</u><br><u>CCTGCCACGGTACAGACCCGGGTTCGATTCCCGGCTGGTGC</u>AAGA<br>*TGTCGTAGAGCAGGTAC*GTTTTAGAGCTAGAAATAGCAAGTTAAAATAAGGCTAGTCCGTTATCAACTTGAAAAAGTGGCACCGAGTCGGTGC<u>AACAAAGCACCAGTGGTCTAGTGGTAGAATAGTACCCT</u><br><u>GCCACGGTACAGACCCGGGTTCGATTCCCGGCTGGTGCA</u>TTTTTTTTTT |
| PTG2.1 (tRNA-gRNA2-tRNA) SEQ ID NO: 19 | GATCCGTGGC<u>AACAAAGCACCAGTGGTCTAGTGGTAGAATAGTAC</u><br><u>CCTGCCACGGTACAGACCCGGGTTCGATTCCCGGCTGGTGCA</u>TCT<br>*ACATCGCCACGGAGCTCA*GTTTTAGAGCTAGAAATAGCAAGTTAAAATAAGGCTAGTCCGTTATCAACTTGAAAAAGTGGCACCGAGTCGGTGC<u>AACAAAGCACCAGTGGTCTAGTGGTAGAATAGTACC</u><br><u>CTGCCACGGTACAGACCCGGGTTCGATTCCCGGCTGGTGCA</u>TTTTTTTTT |
| PTG3 (tRNA-gRNA3-tRNA-gRNA4) SEQ ID NO: 20 | GATCCGTGGC<u>AACAAAGCACCAGTGGTCTAGTGGTAGAATAGTAC</u><br><u>CCTGCCACGGTACAGACCCGGGTTCGATTCCCGGCTGGTGCA</u>ATC<br>*CAGGCGACGCTGAGCCA*GTTTTAGAGCTAGAAATAGCAAGTTAAAATAAGGCTAGTCCGTTATCAACTTGAAAAAGTGGCACCGAGTCGGTGC<u>AACAAAGCACCAGTGGTCTAGTGGTAGAATAGTACC</u><br><u>CTGCCACGGTACAGACCCGGGTTCGATTCCCGGCTGGTGCA</u>TGGC<br>CCACCGGGTATAAAAGTTTTAGAGCTAGAAATAGCAAGTTAAAATAAGGCTAGTCCGTTATCAACTTGAAAAAGTGGCACCGAGTCGGTGCTTTTTTTTT |
| PTG4 (tRNA-gRNA5-tRNA-gRNA6) SEQ ID NO: 21 | GATCCGTGGC<u>AACAAAGCACCAGTGGTCTAGTGGTAGAATAGTAC</u><br><u>CCTGCCACGGTACAGACCCGGGTTCGATTCCCGGCTGGTGCA</u>GAA<br>*CCCGGTCGCCTCAAGGA*GTTTTAGAGCTAGAAATAGCAAGTTAAAATAAGGCTAGTCCGTTATCAACTTGAAAAAGTGGCACCGAGTCGGTGC<u>AACAAAGCACCAGTGGTCTAGTGGTAGAATAGTACCCT</u><br><u>GCCACGGTACAGACCCGGGTTCGATTCCCGGCTGGTGCA</u>GAATGC<br>*GCAGACTCGTCAGG*GTTTTAGAGCTAGAAATAGCAAGTTAAAATAAGGCTAGTCCGTTATCAACTTGAAAAAGTGGCACCGAGTCGGTGCTTTTTTTTTT |
| PTG5 (tRNA-gRNA7-tRNA-gRNA8) SEQ ID NO: 22 | GATGATCCGTGGC<u>AACAAAGCACCAGTGGTCTAGTGGTAGAATAG</u><br><u>TACCCTGCCACGGTACAGACCCGGGTTCGATTCCCGGCTGGTGCA</u><br>*GTGTCCGCTTGGCATCGATA*GTTTTAGAGCTAGAAATAGCAAGTTAAAATAAGGCTAGTCCGTTATCAACTTGAAAAAGTGGCACCGAGTCGGTGC<u>AACAAAGCACCAGTGGTCTAGTGGTAGAATAGTAC</u><br><u>CCTGCCACGGTACAGACCCGGGTTCGATTCCCGGCTGGTGCA</u>GC<br>*GGGTGCGGGTCAATCAAA*GTTTTAGAGCTAGAAATAGCAAGTTAAAATAAGGCTAGTCCGTTATCAACTTGAAAAAGTGGCACCGAGTCGGTGCTTTTTTTT |

TABLE 2.1-continued

Sequence of synthetic genes used in this study

| Gene (Architecture) | Sequence (5'->3') |
|---|---|
| PTG6 (tRNA-gRNA1-tRNA-gRNA2) SEQ ID NO: 23 | GATCCGTGGCAACAAAGCACCAGTGGTCTAGTGGTAGAATAGTAC CCTGCCACGGTACAGACCCGGGTTCGATTCCCGGCTGGTGCAAGA *TGTCGTAGAGCAGGTAC*GTTTTAGAGCTAGAAATAGCAAGTTAA AATAAGGCTAGTCCGTTATCAACTTGAAAAAGTGGCACCGAG TCGGTGCAACAAAGCACCAGTGGTCTAGTGGTAGAATAGTACCCT *GCCACGGTACAGACCCGGGTTCGATTCCCGGCTGGTGCA*TCTACA *TCGCCACGGAGCTCA*GTTTTAGAGCTAGAAATAGCAAGTTAAAA TAAGGCTAGTCCGTTATCAACTTGAAAAAGTGGCACCGAGTC GGTGCTTTTTTTTTT |
| PTG7 (tRNA-gRNA1-tRNA-gRNA2-tRNA-gRNA3-tRNA-gRNA4) SEQ ID NO: 24 | GATCCGTGGCAAtAAAGCACCAGTGGTCTAGTGGTAGAATAGTACC CTGCCACGGTACAGACCCGGGTTCGATTCCCGGCTGGTGCAAGAT *GTCGTAGAGCAGGTAC*GTTTTAGAGCTAGAAATAGCAAGTTAAA ATAAGGCTAGTCCGTTATCAACTTGAAAAAGTGGCACCGAGT CGGTGCAACAAAGCACCAGTGGTCTAGTGGTAGAATAGTACCCT *GCCACGGTACAGACCCGGGTTCGATTCCCGGCTGGTGCA*TCTACA *TCGCCACGGAGCTCA*GTTTTAGAGCTAGAAATAGCAAGTTAAAA TAAGGCTAGTCCGTTATCAACTTGAAAAAGTGGCACCGAGTC GGTGCAACAAAGCACCAGTGGTCTAGTGGTAGAATAGTACCCTGC *CACGGTACAGACCCGGGTTCGATTCCCGGCTGGTGCA*ATCCAGGC *GACGCTGAGCCA*GTTTTAGAGCTAGAAATAGCAAGTTAAAATA AGGCTAGTCCGTTATCAACTTGAAAAAGTGGCACCGAGTCGG TGCAACAAAGCACCAGTGGTCTAGTGGTAGAATAGTACCCTGCCA *CGGTACAGACCCGGGTTCGATTCCCGGCTGGTGCA*TGGCCCACCG *GGGTATAAAA*GTTTTAGAGCTAGAAATAGCAAGTTAAAATAAGG CTAGTCCGTTATCAACTTGAAAAAGTGGCACCGAGTCGGTGC TTTTTTTTTT |
| PTG8 (tRNA-gRNA7-tRNA-gRNA8-tRNA-gRNA5-tRNA-gRNA6) SEQ ID NO: 25 | GATCCGTGGCAACAAAGCACCAGTGGTCTAGTGGTAGAATAGTAC CCTGCCACGGTACAGACCCGGGTTCGATTCCCGGCTGGTGCAGTG *TCCGCTTGGCATCGATA*GTTTTAGAGCTAGAAATAGCAAGTTAA AATAAGGCTAGTCCGTTATCAACTTGAAAAAGTGGCACCGAG TCGGTGCAACAAAGCACCAGTGGTCTAGTGGTAGAATAGTACCCT *GCCACGGTACAGACCCGGGTTCGATTCCCGGCTGGTGCA*GCGGG *TGCGGGTCAATCAAAG*TTTTAGAGCTAGAAATAGCAAGTTAAAA TAAGGCTAGTCCGTTATCAACTTGAAAAAGTGGCACCGAGTC GGTGCAACAAAGCACCAGTGGTCTAGTGGTAGAATAGTACCCTGC *CACGGTACAGACCCGGGTTCGATTCCCGGCTGGTGCA*GAACCCGG *TCGCCTCAAGGA*GTTTTAGAGCTAGAAATAGCAAGTTAAAATAA GGCTAGTCCGTTATCAACTTGAAAAAGTGGCACCGAGTCGGT GCAACAAAGCACCAGTGGTCTAGTGGTAGAATAGTACCCTGCCAC *GGTACAGACCCGGGTTCGATTCCCGGCTGGTGCA*GAATGCGCAGA *CTCGTCAGG*GTTTTAGAGCTAGAAATAGCAAGTTAAAATAAGG CTAGTCCGTTATCAACTTGAAAAAGTGGCACCGAGTCGGTGC TTTTTTTTT |
| PTG9 (tRNA-gRNA1-tRNA-gRNA2tRNA-gRNA3-tRNA-gRNA4-tRNA-gRNA7ARNA-gRNA8-tRNA-gR | GATCCGTGGCAACAAAGCACCAGTGGTCTAGTGGTAGAATAGTAC CCTGCCACGGTACAGACCCGGGTTCGATTCCCGGCTGGTGCAGA *TGTCGTAGAGCAGGTAC*GTTTTAGAGCTAGAAATAGCAAGTTAA AATAAGGCTAGTCCGTTATCAACTTGAAAAAGTGGCACCGAG TCGGTGCAACAAAGCACCAGTGGTCTAGTGGTAGAATAGTACCCT *GCCACGGTACAGACCCGGGTTCGATTCCCGGCTGGTGCA*TCTACA |

TABLE 2.1-continued

Sequence of synthetic genes used in this study

| Gene (Architecture) | Sequence (5'->3') |
|---|---|
| NA5-tRNA-gRNA6) SEQ ID NO: 26 | TCGCCACGGAGCTCGTTTTAGAGCTAGAAATAGCAAGTTAAAA TAAGGCTAGTCCGTTATCAACTTGAAAAAGTGGCACCGAGTC GGTGC*AACAAAGCACCAGTGGTCTAGTGGTAGAATAGTACCCTGC* *CACGGTACAGACCCGGGTTCGATTCCCGGCTGGTGCA*ATCCAGGC GACGCTGAGCCAGTTTTAGAGCTAGAAATAGCAAGTTAAAATA AGGCTAGTCCGTTATCAACTTGAAAAAGTGGCACCGAGTCGG TGC*AACAAAGCACCAGTGGTCTAGTGGTAGAATAGTACCCTGCCA* *CGGTACAGACCCGGGTTCGATTCCCGGCTGGTGCA*TGGCCCACCG GGGTATAAAAGTTTTAGAGCTAGAAATAGCAAGTTAAAATAAGG CTAGTCCGTTATCAACTTGAAAAAGTGGCACCGAGTCGGTGC *AACAAAGCACCAGTGGTCTAGTGGTAGAATAGTACCCTGCCACGG* *TACAGACCCGGGTTCGATTCCCGGCTGGTGCA*GTGTCCGCTTGGC ATCGATAGTTTTAGAGCTAGAAATAGCAAGTTAAAATAAGGCTA GTCCGTTATCAACTTGAAAAAGTGGCACCGAGTCGGTGCAAC *AAAGCACCAGTGGTCTAGTGGTAGAATAGTACCCTGCCACGGTAC* *AGACCCGGGTTCGATTCCCGGCTGGTGCA*GCGGGTGCGGGTCAAT CAAAGTTTTAGAGCTAGAAATAGCAAGTTAAAATAAGGCTAGT CCGTTATCAACTTGAAAAAGCGGCACCGAGTCGGTGCAACAA *AGCACCAGTGGTCTAGTGGTAGAATAGTACCCTGCCACGGTACAG* *ACCCGGGTTCGATTCCCGGCTGGTGCA*GAACCGGTCGCCTCAAG GAGTTTTAGAGCTAGAAATAGCAAGTTAAAATAAGGCTAGTCC GTTATCAACTTGAAAAAGTGGCACCGAGTCGGTGCAACAAAG *CACCAGTGGTCTAGTGGTAGAATAGTACCCTGCCACGGTACAGAC* *CCGGGTTCGATTCCCGGCTGGTGCA*GAATGCGCAGACTCGTCAGG GTTTTAGAGCTAGAAATAGCAAGTTAAAATAAGGCTAGTCCG TTATCAACTTGAAAAAGTGGCACCGAGTCGGTGCTTTTTTTTT |
| PTG10 (tRNA-gRNA9-tRN A-gRNA10) SEQ ID NO: 27 | GATCCGTGGC*AACAAAGCACCAGTGGTCTAGTGGTGGAATAGTAC* *CCTGCCACGGTACAGACCCGGGTTCGATTCCCGGCTGGTGCA*ACA AGCAGGAGAATTCAGGTTTTAGAGCTAGAAATAGCAAGTTAA AATAAGGCTAGTCCGTTATCAACTTGAAAAAGTGGCACCGAG TCGGTGC*AACAAAGCACCAGTGGTCTAGTGGTAGAATAGTACCCT* *GCCACGGTACAGACCCGGGTCCGATTCCCGGCTGGTGCA*CACTGC ATGGATAACTCATCGTTTTAGAGCTAGAAATAGCAAGTTAAAATA AGGCTAGTCCGTTATCAACTTGAAAAAGTGGCACCGAGTCGG TGCTTTTTTTTTTT |

The sequences are annotated as follows:
Last 10 bp of U3p (SEQ ID NO: 14: underlined gRNA scaffold: bold pre-tRNA (SEQ ID NO: 13) boxed, bold italics gRNA spacer: italics

TABLE 2.2

Primers used for plasmid construction, cRT-PCR, and genotyping

| Oligo Name | Sequence (5'->3') | Purpose |
|---|---|---|
| gRNA1-R (SEQ ID NO: 28) | AAACGTACCTGCTCTACGAC | cRT-PCR of gRNA1 |
| gRNA2-R (SEQ ID NO: 29) | AAACTGAGCTCCGTGGCGAT | cRT-PCR of gRNA2 |
| Bsa-gRNA-F (SEQ ID NO: 30) | GGAGACCGAGGTCTCGGTTTTAGAGCTAGAAATA | cRT-PCR and amplify gRNA |
| gRNA1-F (SEQ ID NO: 31) | GGC AAGATGTCGTAGAGCAGGTAC | Quantitative RT-PCR |
| gRNA2-F (SEQ ID NO: 32) | GTCTACATCGCCACGGAGCTCA | Quantitative RT-PCR |

TABLE 2.2-continued

Primers used for plasmid construction, cRT-PCR, and genotyping

| Oligo Name | Sequence (5'->3') | Purpose |
| --- | --- | --- |
| gRNA-R (SEQ ID NO: 33) | GCACCGACTCGGTGCCAC | Quantitative RT-PCR |
| UBI-qF (SEQ ID NO: 34) | TGGTCAGTAATCAGCCAGTTTG | Quantitative RT-PCR |
| UBI-qR (SEQ ID NO: 35) | CAAATACTTGACGAACAGAGGC | Quantitative RT-PCR |
| MPK5-qF (SEQ ID NO: 36) | GATCCCGCCGCCGATCCCTC | Quantitative PCR |
| g-tRNA-F (SEQ ID NO: 37) | GCACCGAGTCGGTGC AACAAAGCACCAGTGGTCTAGT<u>GGTAGAATAGTACCCTG</u> | Construct pGTR. Overlapped region is underlined. |
| tRNA-R (SEQ ID NO: 38) | CTGCCATGCACCAGCCGGGAATCGAACCCGGG TCTGTACCGTGG<u>CAGGGTACTATTCTAC</u> | |
| UBI-F (SEQ ID NO: 39) | TGCATGCCTGCAGGTCCACAAATTCGGGTCAAGGCGG | Amplify UBIp to construct pRGE32 and pRGEB32 |
| UBI-R: (SEQ ID NO: 40) | CAAACTTGTTGATAACTATCTGCAAGAAATAATCACCAAAC | |
| UGW-U3-F (SEQ ID NO: 41) | GACCATGATTACGCCAAGCTTAAGGAATCTTTAAACATACG | Construct pRGE32 |
| UGW-gRNA-R (SEQ ID NO: 42) | GGACCTGCAGGCATGCACGCGCTAAAAACGGACTAGC | |
| MPKI-F (SEQ ID NO: 43) | GGGTCGGCACAGCATCTC | Genotyping of MPK1 |
| MPK1-R2 (SEQ ID NO: 44) | TGCGCCTAAAAATCGAGGGT | |
| MPK2-F (SEQ ID NO: 45) | TTTGGGAAGCATGTATGAAGC | Genotyping of MPK2 |
| MPK2-R2 (SEQ ID NO: 46) | TATGCCAGCCAATGAGCCAA | |
| MPK5-F256 (SEQ ID NO: 47) | GCCACCTTCCTTCCTCATCCG | Genotyping of MPK5 |
| MPK5-R611 (SEQ ID NO: 48) | GTTGCTCGGCTTCAGGTCGC | |
| MPK6-F (SEQ ID NO: 49) | TTGACGCCCCAACATAAATAA | Genotyping of MPK6 |
| MPK6-R (SEQ ID NO: 50) | TGTTGCTGCCGCTTTTCT | |
| PDS-F (SEQ ID NO: 51) | GGTAGAAATGCCATGCGGGA | Genotyping of PDS |
| PDS-R (SEQ ID NO: 52) | ATTCAGCCGAACCTCACCAC | |
| L5AD5-F (SEQ ID NO: 53) | CG GGTCTC A GGCA <u>GGATG GGCAGTCTG GGCA</u> ACAAAGCACCAGTGG | PTG synthesis and cloning A Fok I site (underlined) was |
| L3AD5-R (SEQ ID NO: 54) | TA GGTCTC C AAAC <u>GGATG AGCGACAGC</u> AAAC AAAAAAAAA GCACCGACTCG | used to generate compatible overhangs (labeled with red |
| S5AD5-F (SEQ ID NO: 55) | CG GGTCTC A GGCA <u>GGATG GGCAGTCTG GGCA</u> | color) for cloning into pRGE32 and pRGEB32. |
| S3AD5-R (SEQ ID NO: 56) | TA GGTCTC C AAAC <u>GGATG AGCGACAGC AAAC</u> | |

TABLE 2.3

Oligo nucleotides used to synthesize PTG genes

| gRNA ID (Target) | Spacer/Protospacer (5'->3')[a] | Oligo ID | Sequence (5'->3')[b] |
|---|---|---|---|
| gRNA1 (MPK5) | AGATGTCCTAGAGCAGGTAC | gR1-F (SEQ ID NO: 57) | TA *GGTCTCC* TAGAGCAGGTAC gttttagagctagaa |
| | | gR1-R (SEQ ID NO: 58) | AT *GGTCTCA* TCTACGACATCT tgcaccagccgggaa |
| gRNA2 (MPK5) | TCTACATCGCCACGGAGCTC | gR2-F (SEQ ID NO: 59) | TA *GGTCTCC* CCACGGAGCTCA gttttagagctagaa |
| | | gR2-R (SEQ ID NO: 60) | AT *GGTCTCA* GTGGCGATGTAGA tgcaccagccgggaa |
| gRNA3 (MPK1) | ATCCAGGCGACGCTGAGCC | gR3-F (SEQ ID NO: 70) | TA *GGTCTCC* GACGCTGAGCCA gttttagagctagaa |
| | | gR3-R (SEQ ID NO: 71) | AT *GGTCTCA* CGTCGCCTGGAT tgcaccagccgggaa |
| gRNA4 (MPK1) | TGGCCCACCGGGGTATAAAA | gR4-F (SEQ ID NO: 72) | TA *GGTCTCC* ACCGGGGTATAAAA gttttagagctagaa |
| | | gR4-R (SEQ ID NO: 73) | CG *GGTCTCA* CGGTGGGCCA tgcaccagccggg |
| gRNA5 (MPK2) | GAACCCGGTCGCCTCAAGGA | gR5-F (SEQ ID NO: 74) | TA *GGTCTCC* GTCGCCTCAAGGA gttttagagctagaa |
| | | gR5-R (SEQ ID NO: 75) | CG *GGTCTCA* CGACCGGGTTC tgcaccagccggg |
| gRNA6 (MPK2) | GAATGCGCAGACTCGTCAG | gR6-F (SEQ ID NO: 76) | TA *GGTCTCC* CAGACTCGTCAGG gttttagagctagaa |
| | | gR6-R (SEQ ID NO: 77) | CG *GGTCTCA* TCTGCGCATTC tgcaccagccggg |
| gRNA7 (MPK6) | GTGTCCGCTTGGCATCGATA | gR7-F (SEQ ID NO: 78) | TA *GGTCTC* C TTGGCATCGATA gttttagagctagaa |
| | | gR7-R (SEQ ID NO: 79) | AT *GGTCTCA* CCAAGCGGACAC tgcaccagccgggaa |
| gRNA8 (MPK6) | GCGGGTGCGGGTCAATCAAA | gR8-F (SEQ ID NO: 80) | TA *GGTCTCC* CGGGTCAATCAAA gttttagagctagaa |
| | | gR8-R (SEQ ID NO: 81) | CG *GGTCTCA* CCCGCACCCGC tgcaccagccggg |
| gRNA7 | Linkers for level 2 GG assembly | Ln-gR7-F (SEQ ID NO: 82) | TA *GGTCTC* C TTGGCATCGATA |
| | | Ln-gR7-R (SEQ ID NO: 83) | AT *GGTCTC* A CCAAGCGGACAC |
| gRNA9 (PDS) | ACAAGCCAGGAGAATTCAGC | gR9-F (SEQ ID NO: 84) | TA *GGTCTC* C CAGGAGAATTCAGC gttttagagctagaa |
| | | gR9-R (SEQ ID NO: 85) | CG *GGTCTC* A CCTGGCTTGT tgcaccagccggg |
| gRNA10 (PDS) | CACTGCATGGATAACTCATC | gR10-F (SEQ ID NO: 86) | TA *GGTCTC* C ATGGATAACTCATC gttttagagctagaa |
| | | gR10-R (SEQ ID NO: 87) | CG *GGTCTC* A CCATGCAGTG tgcaccagccggg |

[a] The boxed letters indicate the overhang sequences in Golden Gate assembly.
[b] The first two letters are randomly added nucleotides. Italic bold sequences indicate the BsaI sites (5'-GGTCTCN-3', N indicates any nucleotide), underlined sequences are part of gRNA spacer whereas bold-underlined sequences are overhangs after BsaI digestion. See SI Methods for details about primer design and PTG assembly. Sequences in lower case are specific for gRNA scaffold (5'-gttttagagctagaa-3', in forward primers) or tRNA (5'-tgcaccagccggg-3', in reverse primers).

TABLE 2.4

Determination of chromosomal fragment deletion frequency at the MPK5 locus in rice protoplasts by qPCR

| Sample | Gene | Ct mean | Ct SD | RQ | RQ-Min | RQ-Max | Del efficiency (100%-RQ) |
|---|---|---|---|---|---|---|---|
| PTG6 | MPK5 | 19.70 | 0.12 | 74% | 61% | 89% | 26% |
| PTG7 | MPK5 | 20.51 | 0.06 | 77% | 65% | 92% | 23% |
| PTG9 | MPK5 | 19.70 | 0.05 | 89% | 82% | 97% | 11% |
| CK | MPK5 | 19.61 | 0.18 | 100% | | | |
| PTG6 | UBI | 20.02 | 0.12 | | | | |
| PTG7 | UBI | 20.84 | 0.15 | | | | |
| PTG9 | UBI | 20.30 | 0.04 | | | | |
| CK | UBI | 20.38 | 0.14 | | | | |

The fragment deletion efficiency at the MPK5 locus was estimated with qPCR using genomic DNA as a template and a pair of specific primers that encompass the gRNA2 cut site within MPK5. Because the MPK5 locus with fragment deletion would not be amplified, the deletion (Del.) efficiency could be estimated as 100%-RQ. The same genomic DNAs in FIG. 3B were used and the UBI gene serves as the reference for relative quantification. Ct, threshold cycle; SD, standard deviation; RQ, relative quantity; RQ-Min and RQ-Max indicate the 95% confidential interval of RQ.

Example 3

Polycistronic tRNA and CRISPR Guide-RNA Enables Highly Efficient Multiplexed Genome Engineering in Human Cells During the past three years, the clustered regularly interspaced short palindromic repeat (CRISPR) and CRISPR-associated protein nuclease has emerged as the most powerful tool for genome editing in many organisms (1-4). The most commonly used Cas endonuclease for genome editing is *Streptococcus pyogenes* Cas9 (referred as Cas9 hereafter). The Cas9 protein is guided by an artificial short guide RNA (gRNA) to cleave the DNA whose sequence is complement to the 5'-end of gRNA and preceded with the protospacer-adjacent motif (PAM, 5'-NGG-3') (5-7). This simple RNA guided DNA targeting system fundamentally enhanced our ability to access specific genomic sites for genetic manipulation. The CRISPR-Cas9 system has been engineered for targeted mutagenesis, site-specific integration of DNA fragment, and precise manipulation of chromosomes such as large segment deletion and translocations, etc. The nuclease defective Cas9 (dCas9) and gRNA were also engineered to control expression of targeted genes (8-11) and labeling specific loci of the chromosomes (12) in vivo. These Cas9 based tools greatly facilitate basic research and the practice of biotechnology in various medical and agricultural fields.

The robust and efficient Cas9-mediated genome engineering requires control of the expression of Cas9 and gRNA in vivo. The expression of Cas9 could be readily and precisely controlled using DNA Polymerase II promoter, while the efficient expression of gRNA, which is a small non-coding RNA, remains a bottleneck. Particularly, many Cas9 based applications require simultaneous expression of multiple gRNAs. For example, a pair of gRNAs are needed to edit one site in the Cas9 nickase (13,14) and dCas9-FokI (15,16) mediated genome editing which helps reduce off-targeting risk associated with the original CRISPR-Cas9 system. In dCas9 mediated transcriptional regulation, multiple gRNAs are required for robust gene activation or suppression, or generating sophisticated device of transcriptional circuit (10,17,18). Generally, the gRNA expression is driven by polymerase III promoters such as the widely used snoRNA U3 and U6 gene promoters. However, these Pol III promoters transcribed gRNA from specific nucleotides. For example, U3 promoter transcribed from "A" and U6 promoter starts a transcript with "G". This restrained the targeting spacer of Cas9-gRNA. Therefore, a more robust gRNA expression strategy is needed to boost the capability of CRISPR-Cas9 tools.

Recently, we demonstrated that the endogenous transfer RNA (tRNA) processing system could be engineered to boost Cas9 multiplex targeting capability (19). Multiple gRNAs were expressed in tandem from an artificial polycistronic-tRNA-gRNA (PTG) gene. The endogenous RNases P and Z recognize tRNA and precisely cleave the PTG to release tRNAs and gRNAs. This system not only enables simultaneous expression of many gRNAs but also enhances the Pol III transcription since the tRNA also acts as an internal enhancer or promoter. The PTG system was implemented in plants but we speculated that it would be functional in all organisms because the tRNA processing system is highly conserved in all living organisms. In this study, we adapted the Cas9-PTG technology for human genome editing. The PTG genes was made to simultaneously express 2 to 6 gRNAs for precise genome editing of one to four histone deacetylase (HDAC) genes. Our study demonstrates that the tRNA system could be engineered as a versatile tool for efficient and multiplex genome editing in human and animal systems.

Materials and Methods

Plasmid Vector Construction

To construct pSicoR-sgRNAs-mCherry-Cas9 vector, the puromycin fragment in pSico-EF1-mCh-Puro (Addgene Plasmid 31845) (20) was fused with the NLS-Cas9-NLS fragment from pX260 (Addgene Plasmid 42229). Then the gRNA scaffold with the cloning site containing two BbsI sites was inserted downstream of the U6 promoter. V The schematic of the pSico-sgRNA-mCherry-Cas9 vector is shown in FIG. 18.

Assembly of PTG Genes

To edit HDAC genes (HDAC1/2/3/4/6) in human cells, a pair of target sites separated by 250-500 bp was selected for each gene based on the presence of PAM and protospacer sequence specificity (Table 3.1). A total of seven PTG genes (hPTG1 to hPTG7, Table 3.2) were assembled in vitro using synthesized oligonucleotides (Table 3.3). The in vitro synthesis of hPTG genes was performed as we described previously (19).

Cell Cultures and Transfection

Human Embryonic Kidney 293 (HEK293) cells were cultured in DMEM (Sigma) with 10% fetal bovine serum (Atlanta Biologicals), 10 unit/mL penicillin and 10 μg/mL streptomycin (Gibco). The cultural medium was replaced every 2 days and was sub-cultured when cells reach to 80% to 90% confluency.

For transfection, HEK293 cells were grown in six-well plates at $3 \times 10^5$ cells per well. After reaching 70% confluency, cells were transfected with plasmids and polyethylenimine (PEI). Briefly, cells were fed with fresh culture medium one hour prior to transfection. And then, 3 μg of plasmid DNA and 12 μg of PEI were added to each well. Transfected cells were incubated for 5 hours in a $CO_2$ incubator and cultured for additional 48 hours with fresh culture medium.

cRT-PCR and Quantitative RT-PCR

The total RNAs were extracted from HEK293 cells with Trizol Reagent (Life Technologies) and treated with DNase I (New England Labs). To amplify the gRNA, cRT-PCR was performed as we described previously. Briefly, the total RNA was self-ligated with T4 RNA ligase (New England Labs) and then purified with Trizol Reagent. The ligated total RNA was reverse transcribed using gRNA specific primers and MMLV reverse transcriptase (New England Labs). The cDNA was amplified using specific primers (See Table 3.3 for sequences) and cloned into pGEM-T easy (Promega) for Sanger sequencing.

DNA Extraction and PCR

Transfected cells were washed with phosphate buffered saline and lyzed in Lysis buffer (10 mM Tris pH 8.0, 100 mM NaCl and 10 mM EDTA) and genomic DNA was then precipitated with isopropanol. To detect fragment deletion between two target sites within each gene, PCR primers encompass the targeting sites were designed for each HDAC gene (Table S2). PCR amplifications were performed in reactions containing 800 ng genomic DNA, 0.2 mM dNTP, 0.4 uM primers, 1x PCR buffer and 1 unit DreamTaq DNA polymerase (Thermo Fisher Scientific). PCR product was separated in 1.5% agarose gel containing ethidium bromide to detect chromosomal fragment deletion. The fragment deletion efficiency was estimate with Image J (http://rsb.info.nih.gov/ij/). In addition, the PCR fragment was cloned into pGEM-T easy (Promega) for Sanger sequencing.

RESULTS AND DISCUSSION

PTG Enables Efficient Production of Multiple gRNAs in Human Cells

We demonstrated previously that a PTG with tandem-arrayed tRNA-gRNAs not only allowed precise processing and efficient production of multiple gRNAs, but also enabled Cas9 to simultaneously target multiple genomic sites in plants. We speculated that the PTG genes should also boost CRISPR/Cas9 targeting efficiency in animals because tRNA and its processing system is highly conserved in all living organism. To demonstrate the utility of PTG for genome editing in the animal system, we first examined the gRNA excision accuracy from hPTG1 and hPTG2 transgenes in human cells. Each of the artificial PTG genes encodes two gRNAs. Whereas hPTG1 expresses HDAC1-sg1 and HDAC2-sg2, hPTG2 expresses HDAC2-sg1 and HDAC2-sg2 (Table 3.2).

After transfection of hPTG1 and hPTG2 constructs into HEK293 cells, the cRT-PCR was performed to map the 5' and 3' end of mature gRNAs. Predicted cDNA products with expected size of single gRNA (~96nt) were detected in cRT-PCR, despite the presence of some nonspecifically amplified products. (FIG. 19A). As shown in FIGS. 19A and 19C DNA sequencing of these cDNA products indicated that mature gRNAs were precisely processed from hPTG genes with desired 5'-end which contains targeting guide sequences. As we observed previously in plants, the gRNA derived from PTG has two additional nucleotides (5'-AA-3') at 3'-ends if it proceeds tRNA or have two additional T if it precedes a Pol III terminator. We also detected a putative polyadenylation at the 3'-end of mature HDAC2-sg2). These results suggest that PTG genes could be processed by the human tRNA processing system to produce multiple gRNAs.

Cas9-PTG Enables Multiplex Genome Editing in Human Cells

To examine the efficiency of PTG method for multiplex genome editing, we transfected human cells with seven plasmid constructs expressing different hPTG genes and Cas9. These hPTG genes encode multiple gRNAs targeting five HDAC genes located in different chromosomes. hPTG1 to hPTG 5 was used to target two genomic sites for each gene within HDAC1, 2, 3, 4, and 6; and the hPTG6 and hPTG7 were designed to simultaneously target HDAC3 and 2, respectively (Table 3.2). Because we used two gRNAs to edit one gene, the efficiency of Cas9-PTG could be estimated by measuring the chromosomal fragment deletion frequency within each targeting gene. As predicted, truncated PCR amplicons were detected in all samples (FIG. 20). DNA sequence analysis further confirmed these chromosomal deletions were introduced by Cas9-PTGs in transfected cells (FIG. 21). The deletion frequencies between two gRNA targeting sites were 40-50% based on the calculation of DNA band intensity. Interestingly, the efficiency of different hPTG genes with variable number of targets were comparable. For example, hPTG2 (2 gRNAs) and hPTG6 (6 gRNAs) resulted a fragment deletion from HDAC2 locus at ~40% frequency despite their difference in gRNA numbers. Our results demonstrate that the PTG method can be used to efficiently express multiple gRNAs and simultaneous editing of multiple sites not only in plants, but also in human cells. Because the PTG strategy does not use multiple promoters and terminators, it drastically reduces the size of gRNA construct. As a result, it is more suitable and effective for various genome editing purposes such as the virus-mediated delivery of multiple gRNAs for human gene therapy.

REFERENCES

1. Doudna, J. A. and Charpentier, E. (2014) Genome editing. The new frontier of genome engineering with CRISPR-Cas9. Science, 346, 1258096.
2. Hsu, P. D., Lander, E. S. and Zhang, F. (2014) Development and applications of CRISPR-Cas9 for genome engineering. Cell, 157, 1262-1278.
3. Sander, J. D. and Joung, J. K. (2014) CRISPR-Cas systems for editing, regulating and targeting genomes. Nat. Biotechnol., 32, 347-355.
4. Mali, P., Esvelt, K. M. and Church, G. M. (2013) Cas9 as a versatile tool for engineering biology. Nat. Methods, 10, 957-963.
5. Jinek, M., Chylinski, K., Fonfara, I., Hauer, M., Doudna, J. A. and Charpentier, E. (2012) A programmable dual-RNA-guided DNA endonuclease in adaptive bacterial immunity. Science, 337, 816-821.
6. Mali, P., Yang, L., Esvelt, K. M., Aach, J., Guell, M., DiCarlo, J. E., Norville, J. E. and Church, G. M. (2013) RNA-guided human genome engineering via Cas9. Science, 339, 823-826.
7. Cong, L., Ran, F. A., Cox, D., Lin, S., Barretto, R., Habib, N., Hsu, P. D., Wu, X., Jiang, W., Marraffini, L. A. et al. (2013) Multiplex genome engineering using CRISPR/Cas systems. Science, 339, 819-823.
8. Gilbert, L. A., Larson, M. H., Morsut, L., Liu, Z., Brar, G. A., Torres, S. E., Stern-Ginossar, N., Brandman, O., Whitehead, E.H., Doudna, J. A. et al. (2013) CRISPR-mediated modular RNA-guided regulation of transcription in eukaryotes. Cell, 154, 442-451.
9. Qi, L. S., Larson, M. H., Gilbert, L. A., Doudna, J. A., Weissman, J. S., Arkin, A. P. and Lim, W. A. (2013) Repurposing CRISPR as an RNA-Guided platform for sequence-specific control of gene expression. Cell, 152, 1173-1183.
10. Cheng, A. W., Wang, H., Yang, H., Shi, L., Katz, Y, Theunissen, T. W., Rangarajan, S., Shivalila, C. S., Dadon, D. B. and Jaenisch, R. (2013) Multiplexed activation of endogenous genes by CRISPR-on, an RNA-guided transcriptional activator system. *Cell Res.*, 23, 1163-1171.
11. Mali, P., Aach, J., Stranges, P. B., Esvelt, K. M., Moosburner, M., Kosuri, S., Yang, L. and Church, G. M. (2013) CAS9 transcriptional activators for target specificity screening and paired nickases for cooperative genome engineering. *Nat. Biotechnol.*, 31, 833-838.
12. Chen, B., Gilbert, L. A., Cimini, B. A., Schnitzbauer, J., Zhang, W., Li, G. W., Park, J., Blackburn, E. H., Weissman, J. S., Qi, L. S. et al. (2013) Dynamic imaging of genomic loci in living human cells by an optimized CRISPR/Cas system. *Cell*, 155, 1479-1491.
13. Ran, F. A., Hsu, P. D., Lin, C. Y., Gootenberg, J. S., Konermann, S., Trevino, A. E., Scott, D. A., Inoue, A., Matoba, S., Zhang, Y. et al. (2013) Double nicking by RNA-Guided CRISPR Cas9 for enhanced genome editing specificity. *Cell*, 154, 1380-1389.
14. Shen, B., Zhang, W., Zhang, J., Zhou, J., Wang, J., Chen, L., Wang, L., Hodgkins, A., Iyer, V., Huang, X. et al. (2014) Efficient genome modification by CRISPR-Cas9 nickase with minimal off-target effects. *Nat. Methods*, 11, 399-402.
15. Tsai, S. Q., Wyvekens, N., Khayter, C., Foden, J. A., Thapar, V., Reyon, D., Goodwin, M. J., Aryee, M. J. and Joung, J. K. (2014) Dimeric CRISPR RNA-guided FokI nucleases for highly specific genome editing. *Nat. Biotechnol.*, 32, 569-576.
16. Guilinger, J. P., Thompson, D. B. and Liu, D. R. (2014) Fusion of catalytically inactive Cas9 to FokI nuclease improves the specificity of genome modification. *Nat. Biotechnol.*, 32, 577-582.
17. Maeder, M. L., Linder, S. J., Cascio, V. M., Fu, Y, Ho, Q. H. and Joung, J. K. (2013) CRISPR RNA-guided activation of endogenous human genes. *Nat. Methods*, 10, 977-979.
18. Perez-Pinera, P., Kocak, D. D., Vockley, C. M., Adler, A. F., Kabadi, A. M., Polstein, L. R., Thakore, P. I., Glass, K. A., Ousterout, D. G., Leong, K. W. et al. (2013) RNA-guided gene activation by CRISPR-Cas9-based transcription factors. *Nat. Methods*, 10, 973-976.
19. Xie, K., Minkenberg, B. and Yang, Y (2015) Boosting CRISPR/Cas9 multiplex editing capability with the endogenous tRNA-processing system. *PNAS*, 112, 3570-3575.
20. Salomonis, N., Schlieve, C. R., Pereira, L., Wahlquist, C., Colas, A., Zambon, A. C., Vranizan, K., Spindler, M. J., Pico, A. R., Cline, M. S. et al. (2010) Alternative splicing regulates mouse embryonic stem cell pluripotency and differentiation. *PNAS*, 107, 10514-10519.

Tables and Figure Legends

TABLE 3.1

Target Sequences for genome editing

| sgRNA | | Guide sequence (5'->3') | Targets | Deletion |
|---|---|---|---|---|
| HDAC1-sg1 | (SEQ ID NO: 164) | GTAAGACCACCGCACTAGGC | HDAC1 | 298 bp |
| HDAC1-sg2 | (SEQ ID NO: 165) | GCCCTGCAGCTATTACCATT | | |
| HDAC2-sg1 | (SEQ ID NO: 166) | GTATTTTAGGATATTGGTGC | HDAC2 | 269 bp |
| HDAC2-sg2 | (SEQ ID NO: 167) | TGTTTCAATCTAACAGTCAA | | |
| HDAC3-sg1 | (SEQ ID NO: 168) | GAGCAGAACTCAAAGAGCCC | HDAC3 | 437 bp |
| HDAC3-sg2 | (SEQ ID NO: 169) | GCTCAAGTAAGTAGCCCAGG | | |
| HDAC4-sg1 | (SEQ ID NO: 170) | GAGCTCCTGAATACGTCGCA | HDAC4 | 275 bp |
| HDAC4-sg2 | (SEQ ID NO: 171) | GCTCCTTTGCCGTCCCCGAG | | |
| HDAC6-sg1 | (SEQ ID NO: 172) | CGACTGGCAGCAGGACGTGC | HDAC6 | 331 bp |
| HDAC6-sg2 | (SEQ ID NO: 173) | CAAGCTGATCCTGTCTCTGG | | |

TABLE 3.2

Structure of hPTG genes

| Gene Name | Target Genes | # of gRNAs | Encoding gRNAs |
|---|---|---|---|
| hPTG1 | HDAC1 | 2 | HDAC1-sg1, HDAC1-sg2 |
| hPTG2 | HDAC2 | 2 | HDAC2-sg1, HDAC2-sg2 |
| hPTG3 | HDAC3 | 2 | HDAC2-sg1, HDAC2-sg2 |
| hPTG4 | HDAC5 | 2 | HDAC4-sg1, HDAC4-sg2 |
| hPTG5 | HDAC6 | 2 | HDAC6-sg1, HDAC6-sg2 |
| hPTG6 | HDAC1, HDAC2, HDAC3 | 6 | HDAC1-sg1, HDAC1-sg2, HDAC2-sg1, HDAC2-sg2, HDAC2-sg1, HDAC2-sg2 |
| hPTG7 | HDAC4, HDAC6 | 4 | HDAC1-sg1, HDAC1-sg2, HDAC6-sg1, HDAC6-sg2 |

TABLE 3.3A

Primers used for the synthesis of hPTG

| Oligo Name | Sequence (5' -> 3') |
|---|---|
| HDAC1-sg1-tR | CG GGTCTC A cggtggtcttac tgcaccagccggg |
| HDAC1-sg1-gF | TA GGTCTC C accgcactaggc gttttagagctagaa |
| HDAC1-sg2-tR | CG GGTCTC A tagctgcagggc tgcaccagccggg |
| HDAC1-sg2-gF | TA GGTCTC C gctattaccatt gttttagagctagaa |
| HDAC2-sg1-tR | CG GGTCTC A atcctaaaatac tgcaccagccggg |
| HDAC2-sg1-gF | TA GGTCTC C ggatattggtgc gttttagagctagaa |
| HDAC2-sg2-tR | CG GGTCTC A tagattgaaaca tgcaccagccggg |
| HDAC2-sg2-gF | TA GGTCTC C tctaacagtcaa gttttagagctagaa |

TABLE 3.3A-continued

Primers used for the synthesis of hPTG

| Oligo Name | Sequence (5' -> 3') |
|---|---|
| HDAC3-sg1-tR | CG GGTCTC A tgagttctgctc tgcaccagccggg |
| HDAC3-sg1-gF | TA GGTCTC C ctcaaagagccc gttttagagctagaa |
| HDAC3-sg2-tR | CG GGTCTC A acttacttgagc tgcaccagccggg |
| HDAC3-sg2-gF | TA GGTCTC C aagtagcccagg gttttagagctagaa |
| HDAC4-sg1-tR | CG GGTCTC A attcaggagctc tgcaccagccggg |
| HDAC4-sg1-gF | TA GGTCTC C gaatacgtcgca gttttagagctagaa |
| HDAC4-sg2-tR | CG GGTCTC A cggcaaaggagc tgcaccagccggg |
| HDAC4-sg2-gF | TA GGTCTC C gccgtcccgag gttttagagctagaa |
| HDAC6-sg1-tR | CG GGTCTC A tgctgccagtcg tgcaccagccggg |
| HDAC6-sg1-gF | TA GGTCTC C agcaggacgtgc gttttagagctag |
| HDAC6-sg2-tR | CG GGTCTC A aggatcagcttg tgcaccagccggg |
| HDAC6-sg2-gF | TA GGTCTC C tcctgtctctgg gttttagagctagaa |
| HDAC3-sg2-lnF | TA GGTCTC C ctcaaagagccc |
| HDAC3-sg2-lnR | CG GGTCTC A acttacttgagc |
| hL5AD6-F | CG GGTCTC A TGTT GGATG GGCAGTCTG TGTT acaaagcaccagtgg |
| hS5AD6-F | CG GGTCTC A TGTT GGATG GGCAGTCTG TGTT |

TABLE 3.3B

Primer sequences for genotyping

| Primer Name | Sequence (5'->3') | Gene | Amplicon size |
|---|---|---|---|
| hHDAC1-del-gPCR-F | gagagggaggccattctagg | HDAC1 | 505 bp |
| hHDAC1-del-gPCR-R | gtccagaccaaaagcaggag | | |
| hHDAC2-del-gPCR-F | tttgattgttccggtctcaac | HDAC2 | 531 bp |
| hHDAC2-del-gPCR-R | agtatgttgtgggcaaaatgg | | |
| hHDAC3-del-gPCR-F | tagcccacgtgtgtaggagag | HDAC3 | 559 bp |
| hHDAC3-del-gPCR-R | catggtggatgtcaatgtcaa | | |
| hHDAC4-del-gPCR-F | gtgggtgtacgtgtgtctct | HDAC4 | 547 bp |
| hHDAC4-del-gPCR-R | cacacgcaaagtagatgtgga | | |

TABLE 3.3B-continued

Primer sequences for genotyping

| Primer Name | Sequence (5'->3') | Gene | Amplicon size |
|---|---|---|---|
| hHDAC6-del-gPCR-F | ctctaactggtccaccacagg | HDAC6 | 493 bp |
| hHDAC6-del-gPCR-R | tcaggaaaggaccagacatga | | |

Example 4

Characterization of Heritable Mutations on Multiple Closely Related Rice Genes Created by the PTG/Cas9 Mediated Genome Editing In this study we showed that PTG/Cas9 is a powerful tool to mutate closely related genes by creating one to eight mutations at different combinations of four rice MITOGEN-ASSOCIATED PROTEIN KINASE (MPK) genes with efficiencies of 66 to 100%. PTG/Cas9 was removed by self-pollination and the transgene-free $T_1$ and $T_2$ plants carried all eight mutations or chromosomal deletions. The induced mutations resulted from multiple base pairs of deletion or insertion and sometimes chromosomal deletions. We Demonstrated that PTG/Cas9 reliably produces multiple mutations which could be stably transmitted to the subsequent generations.

New genome editing tools recently promise to mutate almost any gene in a given genome. Mutation of genes is achieved by inducing a double strand break (DSB) at the target site that is be repaired by the cell. The imperfect non-homologous end-joining (NHEJ) pathway is the prevalent DSB repair pathway and its erroneous nature leads to insertions or deletions (indels) of nucleotides during the repair. These indels can cause a gene knock-out if the mutations prevent or alter the gene's transcription or translation. A more precise repair via homologous recombination is theoretically possible if a donor template with sufficient homology to the DSB site is present, but higher plants possess a low intrinsic homology recombination rate (Voytas, 2013). The primary tools to achieve site-directed DSBs in a genome are Zinc Finger Nucleases (ZFNs), Transcription Activator-Like Nucleases (TALENs), and most recently the bacterial type II clustered regularly interspaced short palindromic repeat (CRISPR) and CRISPR-associated protein 9 nuclease (Cas9) system. The targeting ability of ZFNs and TALENs relies on protein:DNA interaction and therefore new binding domains need to be designed to change the target site of the nucleases (Voytas, 2013). The CRISPR/Cas9 system is much easier to program because the Cas9 endonuclease can be recycled to cut a different target site based on RNA:DNA interactions of the so-called single guide RNA (gRNA; Jinek et al., 2012). The 20 bases at the 5'-end of the gRNA (gRNA spacer) are complementary to the genomic target DNA sequence (protospacer) next to the protospacer adjacent motif (PAM, 5'-NGG-3' in case of the *Streptococcus pyogenes* Cas9; Jinek et al., 2012; Cong et al., 2013; Mali et al., 2013). The CRISPR/Cas9 system has been successfully used in genome editing of *Arabidopsis*, tobacco, *N. benthiama*, potato, tomato, soybean, sweet orange, liverwort, maize, sorghum, wheat, and rice to knock-out genes (Brooks et al., 2014; Cai et al., 2015; Jia and Wang, 2014; Jiang et al., 2013; Li et al., 2013; Miao et al., 2013; Shan et al., 2013; Sugano et al., 2014; Xie and Yang, 2013). In addition to its easy design, the CRISPR/Cas9 system can be used to target almost any gene. When using SpCas9, 97.1% of all transcription units in *Arabidopsis* and 89.6% of the transcription units in rice can be targeted with highly specific gRNA spacers (Xie et al., 2014a). The remaining genes could still be targeted by Cas9 variants with different PAM-requirements for specific gRNAs.

One of the CRISPR/Cas9 system's biggest advantages might be its ability for multiplexed genome editing. The Cas9 endonuclease can theoretically target multiple targets simultaneously if several gRNAs are co-expressed. This enables researchers to target multiple genes for knock-out and to create double, triple, or even decuple mutants in a single step. However, most multiplex editing vectors use several gRNA expression cassettes that drive each gRNA with its own Pol III promoter and terminator (Li et al., 2013; Lowder et al., 2015; Ma et al., 2015a). Each single gRNA expression cassette has a typical length of 500 to 820 bp and leave multiplex genome editing in plants still a challenge because the number of simultaneous expressible gRNAs is limited by vector capacity and cloning efficiency. Even if more than six of these expression cassettes can be stacked, the assembly is inefficient and frequently fails (Lowder et al., 2015). Common plant transformation techniques typically deliver the genome-editing device as plasmids via protoplast transfection or particle bombardment, or as T-DNA via *Agrobacterium*. Expressing multiple gRNAs from a single transcript instead of multiple individual cassettes is a promising alternative to overcome this limitation.

We previously enhanced the multiplexing capability of CRISPR/Cas9 genome-editing by introducing a polycistronic tRNA-gRNA gene (PTG) that produces multiple gRNAs from a single artificial gene (FIG. 1; Xie et al., 2015). This gene consists of tandemly arrayed tRNA-gRNA sequences preceded by a Pol III promoter and followed by a Pol III terminator. The tRNA sequence used, rice glycine pretRNA as disclosed in Examples 1 and 2 has been used successfully in in various organisms, including *C. elegans*, fruit fly and mammalian cells for multiplex genome editing. Every tandem repeat is less than 180 bp long, compared to at least 500 bp needed for an individual cassette. Each gRNA can contain a unique spacer that recognizes a different target, enabling simultaneous targeting of multiple genomic sites in one transformation (FIG. 22). The endogenous RNase P and RNase Z recognize the tRNA's secondary structure (Barbezier et al., 2009; Canino et al., 2009; Gutmann et al., 2012; Phizicky and Hopper, 2010; Schiffer et al., 2002) and cut the tRNAs at specific sites to release the mature gRNAs that direct Cas9 endonuclease to multiple specific targets (FIG. 22). In addition, expression of gRNAs with a PTG is up to 30 times higher than expression with a simple Pol III promoter, probably because the A- and B-box of the tRNA can enhance transcription of the PTG primary transcript (Xie et al., 2015). The ability to simultaneously mutate several genes is especially useful to analyze closely related genes, which tend to have similar or overlapping functions. Researchers currently need to find reliable mutant lines and cross them to obtain double or higher order mutants. The PTG/Cas9 technology may significantly improve analysis of closely related genes because a high number of multiple genes can be efficiently targeted in a single transformation.

In this study, we tested the ability of PTG/Cas9 to create mutant resources for studying closely related genes by successfully mutating four members of the rice TEY-type MITOGEN-ASSOCIATED PROTEIN KINASE (MPK) gene family in single, double, and quadruple mutant combinations with up to eight co-expressed gRNAs. MPKs are important signal transducers that are known to have partly overlapping functions in *Arabidopsis* (Beckers et al., 2009; Pitzschke et al., 2009). We furthermore show that the induced mutations have a high variety and that mutations and chromosomal deletions are reliable inherited into transgene-free future generations. We discovered on the example of MPK1 that essential genes are harder to knock out as the mutations tend to preserve the existing open reading frame. This study demonstrates that closely related genes could be simultaneously edited and mutated with the multiplexed PTG/Cas9 technology and transgene-free, multiple gene mutants could be obtained via stable inheritance for studying complex gene families and gene networks.

Results and Discussion

Highly Efficient Targeting of Four Closely Related Rice MPK Genes with PTG/Cas9

We designed gene constructs for *Agrobacterium*-mediated transformation to mutate single and combinations of stress-responsive MPKs in rice and to explore if PTGs can reliably produce stable mutations to dissect the function of closely related genes and gene families (Table 1). The orthologous MPK genes in *Arabidopsis* overlap in their function and partly compensate for each other in single mutants (Asai et al., 2002; Beckers et al., 2009). The PTG/Cas9 carrying gene constructs were designed to target single MPK genes or combinations of them in double and quadruple mutants (Table 4.1). PTGb3, PTGb4, PTGb5, and PTGb6 carried Cas9 driven by a rice ubiquitin promoter (UBIp: Cas9) and PTGs driven by a rice U3 promoter (U3p:PTG) to target MPK1, MPK2, MPK6, and MPK5, respectively, for creation of single mutants (Table 4.1). PTGs for single mutants encoded two gRNAs targeting one gene. An additional construct, PTGb2, targeted MPK5 with only one gRNA at protospacer 2 (PS2; FIG. 17). PTGb7 and PTGb8 contained PTGs with each four gRNAs targeting MPK5/MPK1 and MPK6/MPK2 to create double mutants (Table 4.1). We chose these pairs of MPK genes based on their close phylogenetic relationship in the rice MPK family (Reyna and Yang, 2006). Creating double mutants of rice MPK genes might help to uncover similar redundant functionality as previously observed in *Arabidopsis*. PTGb9 included a PTG of eight gRNAs to mutate all four closely related rice MPK genes in a single transformation event.

Our previous study confirmed the functionality of all gRNAs used in rice protoplasts and determined the mutation efficiency (86-100%) of PTGb6 (MPK5), PTGb7 (MPK5/1), and PTGb9 (MPK5/1/6/2) in transgenic rice plants produced via the *Agrobacterium*-mediated transformation (Xie et al., 2015). In this study, we targeted MPK1, MPK2, MPK6 and MPK6/2 to investigate if we could mutate these single and combination of MPK genes with a similar high percentage of genome-edited plants. Transformation with PTGb3 (MPK 1), PTGb4 (MPK2), and PTGb5 (MPK6) each yielded a 100% genome-editing efficiency for the tested lines (Table 4.1; FIGS. 28 and 29). However, the efficiencies were lower when targeting MPK6 and MPK2 simultaneously (PTGb8) with 83% for the MPK6 and 66% for the MPK2 locus (FIG. 30). We tested the transformation efficiency at only one of the two target sites per gene because only one protospacer provided a convenient restriction enzyme (RE) site for PCR-RE assay (FIG. 27). Therefore, the actual editing efficiency for PTGb8 could be higher than the measured 83% and 66% if all four target sites would be considered. The main objective of the PTGb8 transformation was to obtain mpk6/mpk2 double mutants. A high percentage of 66% showed genome editing at both genes, which yielded putative double mutants (FIG. 30). Out of these putative double mutant lines, 75% had biallelic mutations on MPK6 and MPK1 simultaneously.

While transformation with PTGb4, PTGb6, PTGb2, PTGb7, PTGb8 and PTGb9 produced an abundance of hygromicin-resistant and putative edited callus cells, efforts to mutate only MPK1 with PTGb3 or MPK6 with PTGb5 were less successful. We could only recover four hygromicin-resistant calli for PTGb3 and two resistant calli for PTGb5 out of a total of 600 transformed calli for each construct (three independent repeats of 200 calli for each vector). Nevertheless, we showed that the small percentage of recovered lines was mutated with an efficiency of 100% (Table 4.1; FIG. 28). Therefore, PTG/Cas9 can be designed to induce gene specific mutations at closely related genes and combinations of those with efficiencies of 66-100%. One critical objective to study phenotypes that might be masked by redundant gene is to successfully obtain multiple mutated genes in a single line. The analysis of PTGb8 showed that 50% of all obtained lines carried biallelic mutations at both targeted genes. Our previous study achieved an even higher efficiency when editing four genes simultaneously with 86% of all lines carrying biallelic mutations at all four targeted genes (Xie et al., 2015). This high frequency of biallelic mutations on all targets should minimize the time and effort to screen multiple knock-out events. Our results indicate that PTG/Cas9 technology is a feasible tool to investigate the function of gene families or redundant genes by multiple gene knock-out.

Transgene-Free $T_1$ Rice Plants Inherited all Eight Simultaneously Induced Mutation from their Parents After we previously showed that PTG/Cas9 can simultaneously induce mutations at eight genomic sites using only a single transformation event (Xie et al., 2015), we now investigated if these mutations could be inherited into the next generation when the genome-editing device was removed. We chose to analyze the seeds of self-pollinated $T_0$ PTGb9 plants that previously showed biallelic mutations. The $T_1$ generation of these biallelic mutants is easy to genotype because five of the eight targeted genomic sites encompass RE sites that were destroyed at both alleles by the introduced mutations (FIG. 23; FIG. 27). Self-pollination could also remove the genome-editing device through the genetic segregation of the T-DNA fragment. Any mutations detected in these transgene-free plants should be the result of inheritance because the genome-editing device is no longer present to induce new mutations. We analyzed one $T_1$ generation plant of four different PTGb9 lines with three plants being transgene-free. The functional PTG/Cas9 system consists of a multiple gRNA encoding PTG and the Cas9 protein. A transgene-free plant should not contain any DNA encoding either the PTG or the Cas9 protein. PCRs with primers amplifying the U3:PTG cassette and a 1 kb fragment of the Cas9 gene confirmed that plants 2-1, 3-2 and 4-2 lack the genome-editing device (FIG. 31, blue arrows). In contrast, the transgenic parent plants ($T_0$) of all four $T_1$ lines showed the presence of U3:PTG and Cas9 DNA in their genomic DNAs (FIG. 31). Primers amplifying an endogenous rice gene confirmed that the DNA in all samples was of good quality because the PCR product could be readily amplified from genomic DNAs extracted from transgenic and transgene-free plants (FIG. 30, control).

To genotype the mutation of the $T_1$ generation lines, we then amplified pieces of the four genes that encompass the targeted eight protospacers for a PCR-RE assay. The $T_1$ progeny of biallelic $T_0$ PTGb9 lines should produce completely indigestible PCR product during the PCR-RE assay if both mutated alleles are inherited as expected. Indeed, the PCR-RE assay found that the mutation carried at the protospacers PS3, PS5, PS2, PS1, and PS7 (FIG. 27) were normally transmitted to the $T_1$ generation (FIG. 23A, 23B). While the appropriate RE digested the PCR product from wildtype DNA, the treatment did not affect the PCR product from any of the tested progeny of biallelic TO plants, indicating mutations that destroy the RE site (FIG. 23A, red arrows). We further tested if mutations could also be found at the remaining three targeted sites. Because it is not possible to detect mutation at PS4, PS6, and PS8 (FIG. 22) with a PCR-RE assay and a T7 Endonucelase I assay is not suitable to detect homozygous mutations (Xie et al., 2014b), we decided to directly sequence the PCR products. The results from direct sequencing of PCR products can also inform about the zygosity of the $T_1$ mutant plants. The sequencing result consists of distinct single peaks if both alleles carry the same mutation and are homozygous. If the gene carries a different mutation on each allele and is heterozygous, the result will consist of ambiguous double peaks, usually starting from Cas9 targeting site. Double peaks from heterozygous mutations could be deciphered with degenerate sequence decoding (Ma et al., 2015b). Sequencing the PCR products revealed mutations at all eight genomic target sites of the four MPK genes in $T_1$ generation plants of PTGb9 and confirmed that eight mutations are faithfully inherited into future generations (FIG. 23B). However, each plant had a different degree of heterozygosity. The plant 2-1 carried eight homozygous mutations at all four genes. Plant 3-2 was homozygous for mpk2, mpk5, and mpk6 but heterozygous for PS4 on mpk1. Plant 1-2 was homozygous for mpk2 and mpk5, but heterozygous on all four PS regions of mpk1 and mpk6. The plant 4-2 carried homozygous mutations for mpk1 and mpk5, but is heterozygous for PS6 of mpk2 and PS7 of mpk6 (FIG. 18b). In addition to carrying eight mutations, three of the examined $T_1$ generation plants were also transgene-free as seen by the lack of detectable U3:PTG and Cas9 fragments from genomic DNA (FIG. 31).

We showed that PTG/Cas9 technology is a highly efficient tool to mutate several members of a gene family simultaneously and with efficiencies of up to 100% (Table 4.1) and that the transgene-free $T_1$ generation carries mutations at all targeted sites (FIG. 23; FIG. 30). Recently, Lowder at al. (2015) showed that their module system based on individual expression cassettes for only one gRNA (each cassette is up to 820 bp long) can be stacked to eight cassettes, but the assembly of six or more cassettes often failed and was inefficient. In addition, the work only analyzed constructs expressing up to three gRNAs simultaneously and it is unknown if expression of more gRNAs with individual cassettes results in satisfying genome-editing efficacy (Lowder et al., 2015). Our PTGs, on the contrary, express multiple gRNAs from a single expression cassette and hijack the robust endogenous tRNA processing machinery to convert the primary transcript into multiple functional gRNAs (FIG. 22). Even when eight gRNAs were simultaneously expressed from one PTG, an editing efficiency of 86% was achieved in all eight target sites in the stable transgenic lines (Table 1; Xie et al., 2015). Therefore, PTG/Cas9 is a highly efficient genome-editing device that enables rapid and reliable mutagenesis of multiple genes.

PTG/Cas9 Produces a Variety of Mutations

Most of the previous studies using the CRISPR/Cas9 system in *Arabidopsis* and rice reported a strong tendency to 1 bp indel mutations in the targeted genes of stably transformed $T_0$ plants (Endo et al., 2014; Feng et al., 2014; Hyun et al., 2014; Mikami et al., 2015; Zhang et al., 2014). In contrast, other studies identified longer deletions (≥3 bp) as main mutational type (Xu et al., 2015; Zhou et al., 2014). We analyzed all available sequencing results (n=54) from PTG/Cas9-mutated $T_0$ lines to investigate if our multiplex genome-editing system produces mainly 1 bp indels or a higher variety of mutations. PTG/Cas9-induced mutations in a total of 54 independent sites were slightly biased towards 1 bp insertions (29.6%; FIG. 24), but to a much lower degree than previous reports (37-54%; Feng et al., 2014; Zhang et al., 2014). A recent study found TALENs (transcription activator-like effector nucleases) to produce 69.9% deletions with 81.1% affecting multiple basepairs (Zhang et al., 2015). However, the overall mutation efficiency TALENs reached only 25% even though the scaffolds were optimized for targeting rice (Zhang et al., 2015). In our PTG/Cas9 system deletions accounted for 64.8% of the detected mutations (FIG. 24) with 59.3% of all detected mutations affecting multiple base pairs. This mutation rate shows that PTG/Cas9 enriches the variety of mutations similar to TALENs (FIG. 24), but advantageously exhibits a much higher targeting efficiency on even multiple genomic sites with 66-100% (Table 4.1). Deletions displayed the highest variety in mutation types with up to 74 bp affected (Table 4.2). In contrast, insertions and conversions were only observed for up to 4 or 3 bp, respectively. The variety in mutations was greater for the MPK5 and MPK6 locus (74 to 1 and 48 to 1 bp) compared to MPK1 and MPK2 (15 to 1 bp and 11 to 1 bp), suggesting that the target region at least partially influences the mutational variety (Table 4.2).

Zhang et al. (2015) claimed that the difference in mutation types between TALENs and CRISPR/Cas9 is due to the nature of the DSB. TALENs produce two spaced-out single strand breaks to induce the DSB, while the Cas9 protein cuts both strands at the same position. However, it seems possible to shift the mutational pattern of CRISPR/Cas9 by boosting its editing efficiency (Table 4.2; FIG. 24). Early results of CRISPR/Cas9 in protoplasts, where expression of the components is assumed to be high, showed a great variety of mutational patterns (Li et al., 2013; Shan et al., 2013; Xie and Yang, 2013). The PTG system drastically increases the amount of gRNAs inside the cell compared to the conventional method (Xie et al., 2015). We hypothesize that the high titer of gRNAs causes the observed high efficiency and enrichment for multiple base pair mutations. The PTG/Cas9 system is a preferable tool to TALENs, even when it is necessary to mutate multiple base pairs, because it provides an easy-to-use multiplex genome-editing device with high efficiencies and a variety of mutations. Furthermore, it is possible to program the PTG/Cas9 system to delete several smaller or larger chromosomal fragments. This enables researchers to remove whole genes or regulatory elements from the genome.

PTG-Induced Chromosomal Deletions of Rice MPK Genes are Faithfully Inherited into T1 and T2 Generations PTGs provide a convenient and efficient way to express multiple gRNAs simultaneously. Targeting a chromosomal region with two gRNAs can result in the deletion of the fragment between both sites. Our previous research showed that PTG/Cas9 can induce chromosomal deletion in transiently transformed protoplasts and in stably transformed rice callus (Xie et al., 2015). But so far it was unknown if next generations would inherit these PTG-induced deletions, and if the inheritance follows mendelian genetics. We analyzed the $T_1$ progeny of PTGb9 lines that were heterozygous for a fragment deletion in MPK5 to address this question. We assumed a full length allele if the PCR product of primers flanking both target sites was the same size as predicted from the wildtype sequence. On the other hand, a 727 bp smaller PCR product would indicate a chromosomal deletion. Simultaneous occurrence of both bands was interpreted as heterozygosity. The $T_0$ PTGb9 lines 4, 5, and 6 carried a full sized MPK5 gene on one allele and a copy with a 727 bp deletion on the other allele, as confirmed by sequencing (FIG. 25A; FIG. 32). The deletion occurred as exact joining of the predicated PS1 and PS2 breaking sites three bp upstream of the protospacer-adjecent motifs (FIG. 32). Line 3 was selected as control and is homozygous for the full length gene (FIG. 25A). Genotyping of two $T_1$ plants from each line already revealed that the chromosomal deletion were faithfully inherited (FIG. 25B). $T_1$ plants 4-2 and 6-1 were homozygous for either the full length allele or the allele with deletion, respectively, showing that each allele can be fixed in the genome by selfpollination.

To investigate if the full length and deletion allele would be inherited by $T_1$ plants in a Mendelian fashion, we further analyzed the progeny of the lines 4, 5, and 6. The expected ratio for heterozygous $T_0$ plants in $T_1$ progeny would be 1:2:1 for D:H:F (D: deletion, homozygous; H: heterozygous; F: full length, homozygous). We tested a subset of eight $T_1$ plants from line 4, ten $T_1$ plants from line 5, and nine $T_1$ plants from line 6. Line 4 and line 6 displayed ratios approximately fitting the expectation with 0.8:2:0.4 (D:H:F) and 1.5:2:1 (D:H:F), respectively, while progeny of line 5 was slightly enriched in heterozygous plants with a ratio of 0.25:2:0.25 (D:H:F; FIG. 33). The slight off-ratio in line 5 could be a result of the small number of tested progeny. But even though the subset was small, we detected from all tested lines at least one $T_1$ plant that was either homozygous for the deletion or homozygous for the full length allele (FIG. 33). Additionally, the $T_1$ plant 6-1, which was homozygous for the deletion, produced a $T_2$ progeny only showing the smaller size fragment with the deletion (FIG. 25C). This result further demonstrates that 6-1 is indeed a plant carrying a homozygous deletion in the MPK5 gene, and that these deletions can be inherited to the $T_2$ generation.

We hereby showed that targeting a single gene with two PTG encoded gRNAs can cause chromosomal deletions in the $T_0$ generation that can be inherited into future generations in a Mendelian manner. If a $T_0$ plant is heterozygous for the deletion, its self-pollination can produce progeny with homozygous deletion and subsequent generations will stay homozygous, as shown by the progeny of plant 6-1. One previous report on similar chromosomal deletions in tobacco only showed deletions in protoplast transfections (Gao et al., 2015). Another report showed larger deletions in $T_0$ generation rice plants but did not demonstrate inheritance of the deletion to future generations (Zhou et al., 2014). In addition, both studies used systems that express each gRNA with their own promoter and terminator, which limited the number of gRNAs that could be coexpressed simultaneously to two gRNAs in the tobacco and four gRNAs in the rice study (Gao et al., 2015; Zhou et al., 2014). The new PTG/Cas9 system used in this study enables expression of a much higher number of gRNAs and also increases the titer of gRNAs inside the cells (Xie et al., 2015). Theoretically, our system could allow four chromosomal deletions when eight gRNAs are simultaneously co-expressed and two deletions when four gRNAs are co-expressed. In PTGb7 $T_0$ lines (four gRNAs in one PTG), however, we previously only detected one line that simultaneously carried a monoallelic deletion in MPK1 and biallelic deletion in MPK5 (Xie et al., 2015). PTGb9 $T_0$ lines (eight gRNAs in one PTG) showed a similar trend with a fragment deletion in MPK5 but not the other three targeted MPK genes (Xie et al., 2015). It is likely that a large number of genome-edited plants may be needed to identify a line with simultaneous deletion of two or four genes. In addition, factors other than gene-targeting efficiency may also affect the formation of chromosomal deletion. That deletions were mainly detected in MPK5 suggests a potential positional effect on fragment deletion efficiency. It is also possible that chromosomal deletions in two or more closely related MPK genes might lead to drastic or detrimental phenotypes considering the importance of MPKs in plant development and stress response. Such lethal phenotypes might prevent the formation of multiple deletions in a single regenerated plant.

Mutations that Might Preserve Protein Function are Favored for MPK1 and MPK6

In conformity with the previous speculation that mutations or deletions in some rice MPK genes are unfavorable, we detected an enrichment of mutations in MPK1 and MPK6 that can be divided by three without remainder in the four analyzed $T_1$ plants of PTGb9 lines (FIG. 26). Such mutations are likely to preserve the open reading frame of the coding sequence because three bases constitute the coding unit for one amino acid. In contrast, all detected mutations in MPK2 and MPK5 were indels that are likely to interrupt the open reading frame of the sequence. 67% of the MPK1 mutations affected three or a multiples of three base pairs (FIG. 26A), and mutations in MPK6 had an even higher tendency of this mutation type with 75% (FIG. 25A). However, when only considering mutations in exons, 100% of the mutations in MPK1 preserve the open reading frame but only 66.7% in MPK6 (FIG. 26B). This result suggests that keeping a functional protein might be more important for the MPK1 gene than the MPK6 gene in rice plants To predict the effect of the mutations in MPK1, we translated the coding sequence of the mutants into a protein sequence and compared the first 60 amino acids with the wildtype sequence (FIG. 26C). Plant 1-2 possessed two different mutant alleles of which one translated into a protein shortened by five amino acids (QATLS; 1-2a) and another into a protein shortened by one amino acid (S; 1-2b). Plants 2-1, 3-2, and 4-2 carry a different nucleotide mutation from 1-2b, but translate into the same protein sequence that is shortened by a serine on position 45 (FIG. 26C). An analysis with InterProScan revealed that the mutations of all three protein sequences leave the predicted protein kinase domains intact, which start at amino acid 67 in the wildtype protein. In contrast to the results from mpk1 alleles, all mpk5 alleles detected in the PTGb9 lines resulted in premature stops of the mpk5 proteins before the predicted protein kinase domains of the wildtype protein starting from amino acid 35 (FIG. 26D).

The results indicate that MPK1 plays an important role in rice and mutations in the MPK1 gene produce a detrimental or lethal phenotype. Indeed, we encoutered problems when we tried to mutate callus with PTGb3 (two gRNAs targeting MPK1). While PTGb3 line 1 (PTGb3-1) and PTGb3-2 produced normal plantlets on regeneration medium, callus of lines PTGb3-3 and PTGb3-4 turned black on the medium and mostly died. PTGb3-3 was not able to regenerate plantlets. Interestingly, even though callus of line PTGb3-4 carried a homozygous deletion on the MPK1 gene (FIG. 28A), we were able to recover two plantlets from the regeneration medium (FIG. 26E). However, the recovered plantlets stayed severely dwarfed and only produced one sterile panicle, supporting the hypothesis that knock-out of MPK1 causes detrimental or lethal effects (FIG. 26E). We did not observe any negative effects for the lines of PTGb7 and PTGb9, which also target MPK1. But as shown for PTGb9, all analyzed $T_1$ mutant plants did carry mpk1 alleles with mutations that preserve the existing open reading frame (FIG. 26C). These other lines might carry a mutated but still functional mpk1 protein that protects the plantlets from the observed detrimental phenotypes of lines PTGb3-3 and PTGb3-4. Previous reports of other groups used an mpk1 knock-out mutant cell line in their research that was induced by insertion of the retroposon Tos17 (Kishi-Kaboshi et al., 2010; Kurusu et al., 2005). It is likely that MPK1 may play a so far undiscovered and essential role in tissue differentiation or plant development.

One difference of nuclease induced mutations compared to insertional mutation via T-DNA or Tos1 7 is that nucleases like CRISPR/Cas9 merely cut the DNA but the mutation that causes the knock-out is dependent on the cell's repair mechanism. We found that in case of MPK1 the mutations on viable $T_1$ generations always preserve the existing open reading frame (FIG. 26B) and that a chromosomal deletion of MPK1 caused callus to die early or yield severely dwarfed and sterile plants (FIG. 26E). While knock-out of a truly essential gene is by definition impossible because of lethality, it seems that CRISPR/Cas9 also fails in reliably producing knock-outs for important but not truly essential genes. This might cause problems for analyzing gene families or redundant genes when knocking out several members may cause a drastic phenotype but the transformation and mutation system selects for open reading frame preserving mutations in one or more of the targeted genes. Even though the researcher wishes to discover this drastic phenotype, it might stay undetected because the mutations are unable to knock-out all genes. Shi et al. (2015) made similar observations in an attempt to identify essential genes in cancer cells by negative selection. When they targeted previously known essential genes in the 5' coding exons with CRISPR/Cas9, the induced mutations often preserved the existing open reading frame and the variants remained functional (Shi et al., 2015). They overcame this limitation by directly targeting protein domains instead of the 5' exon and achieved more severe negative selection phenotypes with this strategy. Therefore, it is suggested to target key protein domains with PTG/Cas9 to increase the chance of generating true knock-out mutants when studying gene families or redundant genes. Alternatively, mono-allelic mutation or heterozygous mutant lines may be generated and used to study essential or lethal genes.

Material and Methods

Plant Materials and Growth Conditions

Rice cultivar Kitaake (*Oryza sativa* spp. *japonica*) was used in this study. Seeds were dried for 36-48 h at 45° C. in a food dehydrator to break dormancy before germination in 37° C. warm water for two days. The germinated seeds were planted into METROMIX 360 Soil (SUNGRO HORTICULTURE, Agawam, Mass.) and grown in a greenhouse with 12 h supplemental light per day at 28° C. day/23° C. night temperature. The plants were fertilized with 0.25% urea and 0.1% Sprint iron solution after the first week and fertilized with 0.25% urea in subsequent weeks until flowering.

PTG/Cas9 Gene Constructs

The PTG constructs PTGb6, PTGb7, and PTGb9 were previously described (Xie et al., 2015). PTGb3, PTGb4, PTGb5, PTGb2, and PTGb8 were constructed by inserting the previously described and assembled PTGs PTG3, PTG4, PTG5, PTG2, and PTG8 (Xie et al., 2015) into the BsaI-digested pRGEB32 binary vector (Addgene Plasmid #63142).

*Agrobacterium*-Mediated Rice Transformation

Binary vectors were transformed via electroporation into the *Agrobacterium tumefaciens* strain EHA105. Rice calli derived from mature seeds of the cultivar Kitaake were transformed with the *Agrobacterium*-mediated method according to the previously described protocol (Hiei and Komari, 2008).

Genomic DNA Extraction

Genomic DNA was extracted from 100-200 µl volume of N2-ground leaf material by adding 0.9 ml of prewarmed CTAB buffer (140 mM sorbitol, 220 mM Tris-HCl pH 8.0, 22 mM EDTA, 800 mM NaCl, 34 mM sarkosyl, and 22 mM CTAB) and incubation at 65° C. for 1 h in a 1.5 ml reaction tube. The sample was vortexed after adding 400 µl of chloroform:isoamylalcohol (24:1) and mixed on a rotator for 20 min at room temperature before centrifugation at 12,000 rpm for 15 min. 2/3 volume of isopropanol was added to the upper aqueous phase before incubation at −20° C. for 30 min to precipitate DNA. The DNA was pelleted by centrifugation at 12,000 rpm for 30 sec to 5 min, and the pellet washed with 70% ethanol before incubation with TE buffer containing 0.1 mg/ml RNase A at 37° C. for 30 min. The DNA was again precipitated by adding 1/10 volume of 3M sodium acetate pH 5.2 and 2-2.5 volumes of absolute ethanol and incubation at −20° C. overnight. The DNA was pelleted and washed with 70% ethanol before dissolving the dried pellet in an appropriate amount of TE buffer. The concentration was measured by a spectrophotometer.

Genotyping of Genome-Edited Progeny

All PCRs were performed with GoTaq DNA Polymerase in GoTaq Reaction Buffer (PROMEGA, Madison, Wis.). PCR products and digestions were analyzed by electrophesis with a 1% agarose gel and stained with ethidium bromide. The primers used for genotyping can be found in supplemental Table 4.1. The presence or absence of the genome-editing device in the progeny was detected by PCR with primers specific for U3p:PTG. Chromosomal deletions were detected by PCR with primers flanking the two target sites of each gene. The product size decreased by a specific number of base pairs if a chromosomal deletion occurred. Indels resulting from genome-editing events on targets sites with RE sites were detected by PCR-RE assay. PCR products encompassing the target sites were digested with the appropriate RE for 2-3 h. Mutated DNA could not be digested by the REs. Selected PCR products were sequenced to determine the specific mutation. Double peaks produced by different mutations in each allele were dissolved using degenerate sequence decoding (Ma et al., 2015b). If the double peaks could not be decoded, the PCR product was cloned into PGEM-T EASY vector (PROMEGA, Madison, Wis.) by TA cloning for sequencing of single alleles.

Alignment of Protein Sequences and Prediction of Functional Domains

The predicted protein sequences of the mpk1 and mpk5 mutant alleles were aligned with their corresponding wild-type sequence (MSU RGAP Release 7) by the Clustal Omega multiple sequence alignment tool (Li et al., 2015). The functional protein domains of the sequences were predicted with the web-based InterProScan tool (Jones et al., 2014).

Gene Accession Numbers

The GenBank RefSeq accession numbers of the targeted genes are Os06g0154500 (MPK1), Os08g0157000 (MPK2), Os03g0285800 (MPK5), and Os10g0533600 (MPK6).

Tables

TABLE 4.1

Design and efficiency of PTG/Cas9 gene constructs to target four closely related MPK genes.

| Binary vector | # of gRNAs | Target genes | Efficiency[2] |
|---|---|---|---|
| PTGb3 | 2 | MPK1 | 100% (4) |
| PTGb4 | 2 | MPK2 | 100% (13) |
| PTGb5 | 2 | MPK6 | 100% (2) |
| PTGb6[1] | 2 | MPK5 | 86% (17) |
| PTGb2 | 1 | MPK5 | 100% (9) |
| PTGb7[1] | 4 | MPK5/1 | 100%/89% (17) |
| PTGb8 | 4 | MPK6/2 | 83%/66% (12) |
| PTGb9[1] | 8 | MPK5/1/6/2 | 86%/86%/86%/86% (14) |

[1]Previously described in Xie et al., PNAS 2015
[2]Percentage of genome-edited T0 lines over total number of tested T0 lines, Number of total tested lines in parentheses.

TABLE 4.2

Summary of PTG/Cas9 induced mutations types observed in all sequenced PCR products from the mutant plants..

| Target gene | x bp insertion | x bp deletion | x bp conversion |
|---|---|---|---|
| MPK1 | 4, 1 | 15, 3, 1 | 1 |
| MPK2 | 2, 1 | 11, 2, 1 | — |
| MPK5 | 1 | 74, 9, 8, 5, 4, 3, 1 | 3, 2, 1 |
| MPK6 | 2, 1 | 48, 21, 9, 6, 4, 3, 1 | 1 |

—: not detected.

TABLE 4.3

Oligonucleotides used in the study and their purposes.

| Oligo name | Sequence (5'-3') | Purpose |
|---|---|---|
| MPK1-F2 | CCTCGTGTTTGGTGTTGCTG | Genotyping of MPK1 |
| MPK1-R2 | TGCGCCTAAAAATCGAGGGT | |
| MPK2-nbF | TTTGGGAAGCATGTATGAAGC | Genotyping of MPK2 |
| MPK2-R2 | TATGCCAGCCAATGAGCCAA | |
| MPK5-F256 | GCCACCTTCCTTCCTCATCCG | Genotyping of MPK5 |
| MPK5-nbR | ACTCCGTCATCATGTCGCTC | |
| MPK6-F | TTGACGCCCAACATAAATAA | Genotyping of MPK6 |
| MPK6-R | TGTTGCTGCCGCTTTTCT | |
| UGW-U3-F | GACCATGATTACGCCAAGCTTAAGG AATCTTTAAACATACG | Detection of U3:PTG |
| UGW-gRNA-R | GGACCTGCAGGCATGCACGCGCTAA AAACGGACTAGC | |
| gtCas9-F | GCTTGTGCGTTTCGATTTGA | Detection of Cas9 |
| gtCas9-R | CCGCTCGTGCTTCTTATCCT | |
| control-F | CGCTGCCACTCTCCACTGA | Control for DNA quality |
| control-R | AGCTGCTTCCACTCGTTCCA | |

MPK1-F2 (SEQ ID NO:174); MPK1-R2 (SEQ ID:175); MPK2-nbF (SEQ ID NO:176); MPK2-R2 (SEQ ID NO:177); MPK5-F256 (SEQ ID NO:178); MPK5-nbR (SEQ ID NO:179); MPK6-F (SEQ ID NO:180); MPK6-R (SEQ ID NO:181); UGW-U3-F (SEQ ID NO:182); UGW-gRNA-R (SEQ ID NO:183); gtCas9-F (SEQ ID NO:184); gtCas9-R (SEQ ID NO:185); control-F (SEQ ID NO:186); control-R (SEQ ID NO:187).

LITERATURE CITED

Asai, T., Tena, G., Plotnikova, J., Willmann, M. R., Chiu, W.-L., Gomez-Gomez, L., Boller, T., Ausubel, F. M., and Sheen, J. (2002). MAP kinase signalling cascade in *Arabidopsis* innate immunity. Nature 415, 977-983.

Barbezier, N., Canino, G., Rodor, J., Jobet, E., Saez-Vasquez, J., Marchfelder, A., and Echeverria, M. (2009). Processing of a dicistronic tRNA-snoRNA precursor: combined analysis in vitro and in vivo reveals alternate pathways and coupling to assembly of snoRNP. Plant Physiol. 150, 1598-1610.

Beckers, G. J. M., Jaskiewicz, M., Liu, Y., Underwood, W. R., He, S. Y., Zhang, S., and Conrath, U. (2009). Mitogen-activated protein kinases 3 and 6 are required for full priming of stress responses in *Arabidopsis thaliana*. Plant Cell 21, 944-953.

Brooks, C., Nekrasov, V., Lippman, Z. B., and Eck, J. Van (2014). Efficient Gene Editing in Tomato in the First Generation Using the Clustered Regularly Interspaced Short Palindromic Repeats/CRISPR-Associated9 System 1. 166, 1292-1297.

Cai, Y., Chen, L., Liu, X., Sun, S., Wu, C., Jiang, B., Han, T., and Hou, W. (2015). CRISPR/Cas9-Mediated Genome Editing in Soybean Hairy Roots. PLoS One 10, e0136064.

Canino, G., Bocian, E., Barbezier, N., Echeverria, M., Forner, J., Binder, S., and Marchfelder, A. (2009). *Arabidopsis* encodes four tRNase Z enzymes. Plant Physiol. 150, 1494-1502.

Cong, L., Ran, F. A., Cox, D., Lin, S., Barretto, R., Habib, N., Hsu, P. D., Wu, X., Jiang, W., Marraffini, L. A., et al. (2013). Multiplex Genome Engineering Using CRISPR/Cas Systems. Science (80-.). 339, 819-824.

Endo, M., Mikami, M., and Toki, S. (2014). Multigene Knockout Utilizing Off-Target Mutations of the CRISPR/Cas9 System in Rice. Plant Cell Physiol. 56, 41-47.

Feng, Z., Mao, Y., Xu, N., Zhang, B., Wei, P., Yang, D.-L., Wang, Z., Zhang, Z., Zheng, R., Yang, L., et al. (2014). Multigeneration analysis reveals the inheritance, specificity, and patterns of CRISPR/Cas-induced gene modifications in *Arabidopsis*. Proc. Natl. Acad. Sci. U.S.A 111, 4632-4637.

Gao, J., Wang, G., Ma, S., Xie, X., Wu, X., Zhang, X., Wu, Y., Zhao, P., and Xia, Q. (2015). CRISPR/Cas9-mediated targeted mutagenesis in *Nicotiana tabacum*. Plant Mol. Biol. 87, 99-110.

Gutmann, B., Gobert, A., and Giegé, P. (2012). PRORP proteins support RNase P activity in both organelles and the nucleus in *Arabidopsis*. Genes Dev. 26, 1022-1027.

Hiei, Y., and Komari, T. (2008). *Agrobacterium*-mediated transformation of rice using immature embryos or calli induced from mature seed. Nat. Protoc. 3, 824-834.

Hyun, Y., Kim, J.-S. J., Cho, S. W., Choi, Y., Kim, J.-S. J., and Coupland, G. (2014). Site-directed mutagenesis in *Arabidopsis thaliana* using dividing tissue-targeted RGEN of the CRISPR/Cas system to generate heritable null alleles. Planta 241, 271-284.

Jia, H., and Wang, N. (2014). Targeted genome editing of sweet orange using Cas9/sgRNA. PLoS One 9, e93806.

Jiang, W., Zhou, H., Bi, H., Fromm, M., Yang, B., and Weeks, D. P. (2013). Demonstration of CRISPR/Cas9/sgRNA-mediated targeted gene modification in *Arabidopsis*, tobacco, sorghum and rice. Nucleic Acids Res. 41, e188.

Jinek, M., Chylinski, K., Fonfara, I., Hauer, M., Doudna, J. a, and Charpentier, E. (2012). A programmable dual-RNA-guided DNA endonuclease in adaptive bacterial immunity. Science 337, 816-821.

Jones, P., Binns, D., Chang, H. Y., Fraser, M., Li, W., McAnulla, C., McWilliam, H., Maslen, J., Mitchell, A., Nuka, G., et al. (2014). InterProScan 5: Genome-scale protein function classification. Bioinformatics 30, 1236-1240.

Kishi-Kaboshi, M., Okada, K., Kurimoto, L., Murakami, S., Umezawa, T., Shibuya, N., Yamane, H., Miyao, A., Takatsuji, H., Takahashi, A., et al. (2010). A rice fungal MAMP-responsive MAPK cascade regulates metabolic flow to antimicrobial metabolite synthesis. Plant J. 63, 599-612.

Kurusu, T., Yagala, T., Miyao, A., Hirochika, H., and Kuchitsu, K. (2005). Identification of a putative voltage-gated Ca2+ channel as a key regulator of elicitor-induced hypersensitive cell death and mitogen-activated protein kinase activation in rice. Plant J. 42, 798-809.

Li, J.-F., Norville, J. E., Aach, J., McCormack, M., Zhang, D., Bush, J., Church, G. M., and Sheen, J. (2013). Multiplex and homologous recombination-mediated genome editing in *Arabidopsis* and *Nicotiana bethamiana* using guide RNA and Cas9. Nat. Biotechnol. 31, 688-691.

Li, W., Cowley, a., Uludag, M., Gur, T., McWilliam, H., Squizzato, S., Park, Y. M., Buso, N., and Lopez, R. (2015). The EMBL-EBI bioinformatics web and programmatic tools framework. Nucleic Acids Res. 43, 580-584.

Lowder, L. G., Paul, J. W., Baltes, N.J., Voytas, D. F., Zhang, Y., Zhang, D., Tang, X., Zheng, X., Hsieh, T.-F., and Qi, Y. (2015). A CRISPR/Cas9 toolbox for multiplexed plant genome editing and transcriptional regulation. Plant Physiol. doi:10.1104/pp. 15.00636.

Ma, X., Zhang, Q., Zhu, Q., Liu, W., Chen, Y., Qiu, R., Wang, B., Yang, Z., Li, H., Lin, Y., et al. (2015a). A Robust CRISPR/Cas9 System for Convenient, High-Efficiency Multiplex Genome Editing in Monocot and Dicot Plants. Mol. Plant 8, 1274-1284.

Ma, X., Chen, L., Zhu, Q., Chen, Y., and Liu, Y.-G. (2015b). Rapid Decoding of Sequence-Specific Nuclease-Induced Heterozygous and Biallelic Mutations by Direct Sequencing of PCR Products. Mol. Plant 8, 1285-1287.

Mali, P., Yang, L., Esvelt, K. M., Aach, J., Guell, M., DiCarlo, J. E., Norville, J. E., and Church, G. M. (2013). RNA-Guided Human Genome Engineering via Cas9. Science (80-.). 339, 823-827.

Miao, J., Guo, D., Zhang, J., Huang, Q., Qin, G., Zhang, X., Wan, J., Gu, H., and Qu, L.-J. (2013). Targeted mutagenesis in rice using CRISPR-Cas system. Cell Res. 23, 1233-1236.

Mikami, M., Toki, S., and Endo, M. (2015). Parameters affecting frequency of CRISPR/Cas9 mediated targeted mutagenesis in rice. Plant Cell Rep. 34, 1807-1815.

Phizicky, E. M., and Hopper, A. K. (2010). tRNA biology charges to the front. Genes Dev. 24, 1832-1860.

Pitzschke, A., Schikora, A., and Hirt, H. (2009). MAPK cascade signalling networks in plant defence. Curr. Opin. Plant Biol. 12, 421-426.

Reyna, N. S., and Yang, Y. (2006). Molecular analysis of the rice MAP kinase gene family in relation to *Magnaporthe grisea* infection. Mol. Plant. Microbe. Interact. 19, 530-540.

Schiffer, S., Rosch, S., and Marchfelder, A. (2002). Assigning a function to a conserved group of proteins: The tRNA 3'-processing enzymes. EMBO J. 21, 2769-2777.

Shan, Q., Wang, Y., Li, J., Zhang, Y., Chen, K., Liang, Z., Zhang, K., Liu, J., Xi, J. J., Qiu, J.-L., et al. (2013).

Targeted genome modification of crop plants using a CRISPR-Cas system. Nat. Biotechnol. 31, 686-688.

Shi, J., Wang, E., Milazzo, J. P., Wang, Z., Kinney, J. B., and Vakoc, C. R. (2015). Discovery of cancer drug targets by CRISPR-Cas9 screening of protein domains. Nat. Biotechnol. 33, 661-667.

Sugano, S. S., Shirakawa, M., Takagi, J., Matsuda, Y., Shimada, T., Hara-Nishimura, I., and Kohchi, T. (2014). CRISPR/Cas9-mediated targeted mutagenesis in the liverwort Marchantia polymorpha L. Plant Cell Physiol. 55, 475-481.

Voytas, D. F. (2013). Plant genome engineering with sequence-specific nucleases. Annu. Rev. Plant Biol. 64, 327-350.

Xie, K., and Yang, Y. (2013). RNA-Guided Genome Editing in Plants Using a CRISPR-Cas System. Mol. Plant 6, 1975-1983.

Xie, K., Zhang, J., and Yang, Y. (2014a). Genome-Wide Prediction of Highly Specific Guide RNA Spacers for the CRISPR-Cas9-Mediated Genome Editing in Model Plants and Major Crops. Mol. Plant 7, 923-926.

Xie, K., Minkenberg, B., and Yang, Y. (2014b). Targeted Gene Mutation in Rice Using a CRISPR-Cas9 System. Bio-Protocol 4, e1225.

Xie, K., Minkenberg, B., and Yang, Y. (2015). Boosting CRISPR/Cas9 multiplex editing capability with the endogenous tRNA-processing system. Proc. Natl. Acad. Sci. 112, 3570-3575.

Xu, R.-F., Li, H., Qin, R.-Y., Li, J., Qiu, C.-H., Yang, Y.-C., Ma, H., Li, L., Wei, P.-C., and Yang, J.-B. (2015). Generation of inheritable and "transgene clean" targeted genome-modified rice in later generations using the CRISPR/Cas9 system. Sci. Rep. 5, 11491 doi: 10.1038/srep11491.

Zhang, H., Gou, F., Zhang, J., Liu, W., Li, Q., Mao, Y., Botella, J. R., and Zhu, J.-K. (2015). TALEN-mediated targeted mutagenesis produces a large variety of heritable mutations in rice. Plant Biotechnol. J. doi: 10.1111/pbi.12372.

Zhang, H. H., Zhang, J., Wei, P., Zhang, B., Gou, F., Feng, Z., Mao, Y., Yang, L., Zhang, H. H., Xu, N., et al. (2014). The CRISPR/Cas9 system produces specific and homozygous targeted gene editing in rice in one generation. Plant Biotechnol. J. 12, 797-807.

Zhou, H., Liu, B., Weeks, D. P., Spalding, M. H., and Yang, B. (2014). Large chromosomal deletions and heritable small genetic changes induced by CRISPR/Cas9 in rice. Nucleic Acids Res. 42, 10903-10914.

TABLE OF SEQUENCES

| SEQ | TYPE | DESCRIPTION |
|---|---|---|
| SEQ ID NO: 1 | DNA | sgRNA1 |
| SEQ ID NO: 2 | DNA | sgRNA2 |
| SEQ ID NO: 3 | DNA | gRNA1 |
| SEQ ID NO: 4 | DNA | gRNA2 |
| SEQ ID NO: 5 | DNA | gRNA3 |
| SEQ ID NO: 6 | DNA | gRNA4 |
| SEQ ID NO: 7 | DNA | gRNA5 |
| SEQ ID NO: 8 | DNA | gRNA6 |
| SEQ ID NO: 9 | DNA | gRNA7 |
| SEQ ID NO: 10 | DNA | gRNA8 |
| SEQ ID NO: 11 | DNA | gRNA9 |
| SEQ ID NO: 12 | DNA | gRNA10 |
| SEQ ID NO: 13 | DNA | pre-tRNA |
| SEQ ID NO: 14 | DNA | Last 10 bp of U3p |
| SEQ ID NO: 15 | DNA | gRNA-tRNA in pGTR plasmid |
| SEQ ID NO: 16 | DNA | PTG1 |

TABLE OF SEQUENCES -continued

| SEQ | TYPE | DESCRIPTION |
|---|---|---|
| SEQ ID NO: 17 | DNA | PTG2 |
| SEQ ID NO: 18 | DNA | PTG1.1 |
| SEQ ID NO: 19 | DNA | PTG2.1 |
| SEQ ID NO: 20 | DNA | PTG3 |
| SEQ ID NO: 21 | DNA | PTG4 |
| SEQ ID NO: 22 | DNA | PTG5 |
| SEQ ID NO: 23 | DNA | PTG6 |
| SEQ ID NO: 24 | DNA | PTG7 |
| SEQ ID NO: 25 | DNA | PTG8 |
| SEQ ID NO: 26 | DNA | PTG9 |
| SEQ ID NO: 27 | DNA | PTG10 |
| SEQ ID NO: 28 | DNA | Primer gRNA1-R |
| SEQ ID NO: 29 | DNA | Primer gRNA2-R |
| SEQ ID NO: 30 | DNA | Primer Bsa-gRNA-F |
| SEQ ID NO: 31 | DNA | Primer gRNA1-F |
| SEQ ID NO: 32 | DNA | Primer gRNA2-F |
| SEQ ID NO: 33 | DNA | Primer gRNA-R |
| SEQ ID NO: 34 | DNA | Primer UBI-qF |
| SEQ ID NO: 35 | DNA | Primer UBI-qR |
| SEQ ID NO: 36 | DNA | Primer MPK5-qF |
| SEQ ID NO: 37 | DNA | Primer g-tRNA-F |
| SEQ ID NO: 38 | DNA | Primer tRNA-R |
| SEQ ID NO: 39 | DNA | Primer UBI-F |
| SEQ ID NO: 40 | DNA | Primer UBI-R |
| SEQ ID NO: 41 | DNA | Primer UGW-U3-F |
| SEQ ID NO: 42 | DNA | Primer UGW-gRNA-R |
| SEQ ID NO: 43 | DNA | Primer MPK1-F |
| SEQ ID NO: 44 | DNA | Primer MPK1-R2 |
| SEQ ID NO: 45 | DNA | Primer MPK2-F |
| SEQ ID NO: 46 | DNA | Primer MPK2-R2 |
| SEQ ID NO: 47 | DNA | Primer MPK5-F256 |
| SEQ ID NO: 48 | DNA | Primer MPK5-R611 |
| SEQ ID NO: 49 | DNA | Primer MPK6-F |
| SEQ ID NO: 50 | DNA | Primer MPK6-R |
| SEQ ID NO: 51 | DNA | Primer PDS-F |
| SEQ ID NO: 52 | DNA | Primer PDS-R |
| SEQ ID NO: 53 | DNA | Primer L5AD5-F |
| SEQ ID NO: 54 | DNA | Primer L3AD5-R |
| SEQ ID NO: 55 | DNA | Primer S5AD5-F |
| SEQ ID NO: 56 | DNA | Primer S3AD5-R |
| SEQ ID NO: 57 | DNA | Primer gR1-F |
| SEQ ID NO: 58 | DNA | Primer gR1-R |
| SEQ ID NO: 59 | DNA | Primer gR2-F |
| SEQ ID NO: 60 | DNA | Primer gR2-R |
| SEQ ID NO: 61 | DNA | Primer gR3-F |
| SEQ ID NO: 62 | DNA | Primer gR3-R |
| SEQ ID NO: 63 | DNA | Primer gR4-F |
| SEQ ID NO: 64 | DNA | Primer gR4-R |
| SEQ ID NO: 65 | DNA | Primer gR5-F |
| SEQ ID NO: 66 | DNA | Primer gR5-R |
| SEQ ID NO: 67 | DNA | Primer gR6-F |
| SEQ ID NO: 68 | DNA | Primer gR6-R |
| SEQ ID NO: 69 | DNA | Primer gR7-F |
| SEQ ID NO: 70 | DNA | Primer gR7-R |
| SEQ ID NO: 71 | DNA | Primer gR8-F |
| SEQ ID NO: 72 | DNA | Primer gR8-R |
| SEQ ID NO: 73 | DNA | Primer Ln-gR7-F |
| SEQ ID NO: 74 | DNA | Primer Ln-gR7-R |
| SEQ ID NO: 75 | DNA | Primer gR9-F |
| SEQ ID NO: 76 | DNA | Primer gR9-R |
| SEQ ID NO: 77 | DNA | Primer gR10-F |
| SEQ ID NO: 78 | DNA | Primer gR10-R |
| SEQ ID NO: 79 | DNA | Wild type MPK1 |
| SEQ ID NO: 80 | PRT | Wild type MPK1 |
| SEQ ID NO: 81 | DNA | Wild type MPK2 |
| SEQ ID NO: 82 | DNA | Wild type MPK5 |
| SEQ ID NO: 83 | PRT | Wild type MPK5 |
| SEQ ID NO: 84 | DNA | Wild type MPK6 |
| SEQ ID NO: 85 | DNA | WT UBI |
| SEQ ID NO: 86 | DNA | WT PSD3 |
| SEQ ID NO: 87 | RNA | tRNA-gRNA-tRNA scheme FIG. 2B |
| SEQ ID NO: 88 | RNA | gRNA from PTG gene FIG. 2C |
| SEQ ID NO: 89 | RNA | gRNA from sgRNA gene FIG. 2H |
| SEQ ID NO: 90 | DNA | MPK1 #1 indel FIG. 3C |
| SEQ ID NO: 91 | DNA | MPK1 #2 indel FIG. 3C |

TABLE OF SEQUENCES

| SEQ | TYPE | DESCRIPTION |
|---|---|---|
| SEQ ID NO: 92 | DNA | MPK2 #1 indel FIG. 3C |
| SEQ ID NO: 93 | DNA | MPK2 #2 indel FIG. 3C |
| SEQ ID NO: 94 | DNA | MPK2 #3 indel FIG. 3C |
| SEQ ID NO: 95 | DNA | MPK5 #1 indel FIG. 3C |
| SEQ ID NO: 96 | DNA | MPK5 #2 indel FIG. 3C |
| SEQ ID NO: 97 | DNA | MPK6 #1 indel FIG. 3C |
| SEQ ID NO: 98 | DNA | MPK6 #2 indel FIG. 3C |
| SEQ ID NO: 99 | DNA | MPK6 #3 indel FIG. 3C |
| SEQ ID NO: 100 | DNA | MPK5 indel FIG. 4B |
| SEQ ID NO: 101 | DNA | MPK1 indel FIG. 4B |
| SEQ ID NO: 102 | DNA | MPK5 target sense strand FIG. 5A |
| SEQ ID NO: 103 | DNA | MPK5 target antisense strand FIG. 5A |
| SEQ ID NO: 104 | DNA | MPK1 target sense strand FIG. 5B |
| SEQ ID NO: 105 | DNA | MPK1 target antisense strand FIG. 5B |
| SEQ ID NO: 106 | DNA | MPK2 target sense strand FIG. 5C |
| SEQ ID NO: 107 | DNA | MPK2 target antisense strand FIG. 5C |
| SEQ ID NO: 108 | DNA | MPK6 target sense strand FIG. 5D |
| SEQ ID NO: 109 | DNA | MPK6 target antisens strand FIG. 5D |
| SEQ ID NO: 110 | DNA | Multiple cloning site sense FIG. 6C |
| SEQ ID NO: 111 | DNA | Multiple cloning site antisense FIG. 6C |
| SEQ ID NO: 112 | DNA | sgRNA1 #1 indel FIG. 8 |
| SEQ ID NO: 113 | DNA | sgRNA1 #2 indel FIG. 8 |
| SEQ ID NO: 114 | DNA | sgRNA1 #3 indel FIG. 8 |
| SEQ ID NO: 115 | DNA | PTG1 indel FIG. 8 |
| SEQ ID NO: 116 | DNA | sgRNA2 indel FIG. 8 |
| SEQ ID NO: 117 | DNA | PTG2 indel FIG. 8 |
| SEQ ID NO: 118 | DNA | PTG1.1 indel FIG. 9A |
| SEQ ID NO: 119 | DNA | PTG2.1 indel FIG. 9B |
| SEQ ID NO: 120 | DNA | MPK1 #1 indel FIG. 16 |
| SEQ ID NO: 121 | DNA | MPK1 #10 indel FIG. 16 |
| SEQ ID NO: 122 | DNA | MPK1 #11 indel FIG. 16 |
| SEQ ID NO: 123 | DNA | MPK2 #1 indel FIG. 16 |
| SEQ ID NO: 124 | DNA | MPK2 #10 indel FIG. 16 |
| SEQ ID NO: 125 | DNA | MPK2 #11 indel FIG. 16 |
| SEQ ID NO: 126 | DNA | MPK5 #1 indel FIG. 16 |
| SEQ ID NO: 127 | DNA | MPK5 #10 indel FIG. 16 |
| SEQ ID NO: 128 | DNA | MPK5 #11 indel FIG. 16 |
| SEQ ID NO: 129 | DNA | MPK6 #1 indel FIG. 16 |
| SEQ ID NO: 130 | DNA | MPK6 #10 indel FIG. 16 |
| SEQ ID NO: 131 | DNA | MPK6 #11 indel FIG. 16 |
| SEQ ID NO: 132 | DNA | PDS target sense strand FIG. 17B |
| SEQ ID NO: 133 | DNA | PDS indel 1 FIG. 17E |
| SEQ ID NO: 134 | DNA | PDS indel 2 FIG. 17E |
| SEQ ID NO: 135 | DNA | MPK1 1-2a FIG. 19B |
| SEQ ID NO: 136 | DNA | MPK1 1-2b FIG. 19B |
| SEQ ID NO: 137 | DNA | MPK1 2-1 FIG. 19B |
| SEQ ID NO: 138 | DNA | MPK1 3-2a FIG. 19B |
| SEQ ID NO: 139 | DNA | MPK1 3-2b FIG. 19B |
| SEQ ID NO: 140 | DNA | MPK1 4-2 FIG. 19B |
| SEQ ID NO: 141 | DNA | MPK2 1-2 FIG. 19B |
| SEQ ID NO: 142 | DNA | MPK2 2-1 FIG. 19B |
| SEQ ID NO: 143 | DNA | MPK2 3-1 FIG. 19B |
| SEQ ID NO: 144 | DNA | MPK2 4-2a FIG. 19B |
| SEQ ID NO: 145 | DNA | MPK2 4-2b FIG. 19B |
| SEQ ID NO: 146 | DNA | MPK5 1-2 FIG. 19B |
| SEQ ID NO: 147 | DNA | MPK5 2-1 FIG. 19B |
| SEQ ID NO: 148 | DNA | MPK5 3-2 FIG. 19B |
| SEQ ID NO: 149 | DNA | MPK5 4-2 FIG. 19B |
| SEQ ID NO: 150 | DNA | MPK6 1-2a FIG. 19B |
| SEQ ID NO: 151 | DNA | MPK6 1-2b FIG. 19B |
| SEQ ID NO: 152 | DNA | MPK6 2-1 FIG. 19B |
| SEQ ID NO: 153 | DNA | MPK6 3-2 FIG. 19B |
| SEQ ID NO: 154 | DNA | MPK6 4-2a FIG. 19B |
| SEQ ID NO: 155 | DNA | MPK6 4-2b FIG. 19B |
| SEQ ID NO: 156 | PRT | MPK1 1-2a FIG. 22C |
| SEQ ID NO: 157 | PRT | MPK1 2-1/3-2/4-2 FIG. 22C |
| SEQ ID NO: 158 | PRT | MPK1 1-2b FIG. 22C |
| SEQ ID NO: 159 | PRT | MPK5 1-2 FIG. 22D |
| SEQ ID NO: 160 | PRT | MPK5 4-2 FIG. 22D |
| SEQ ID NO: 161 | PRT | MPK5 3-2 FIG. 22D |
| SEQ ID NO: 162 | PRT | MPK5 2-1 FIG. 22D |
| SEQ ID NO: 163 | DNA | MPK5 4Δ FIG. 28 |
| SEQ ID NO: 164 | DNA | HDAC1-sg1 |
| SEQ ID NO: 165 | DNA | HDAC1-sg2 |
| SEQ ID NO: 166 | DNA | HDAC2-sg1 |
| SEQ ID NO: 167 | DNA | HDAC2-sg2 |
| SEQ ID NO: 168 | DNA | HDAC3-sg1 |
| SEQ ID NO: 169 | DNA | HDAC3-sg2 |
| SEQ ID NO: 170 | DNA | HDAC4-sg1 |
| SEQ ID NO: 171 | DNA | HDAC4-sg2 |
| SEQ ID NO: 172 | DNA | HDAC6-sg1 |
| SEQ ID NO: 173 | DNA | HDAC6-sg2 |
| SEQ ID NO: 174 | DNA | MPK1-F2 |
| SEQ ID NO: 175 | DNA | MPK1-R2 |
| SEQ ID NO: 176 | DNA | MPK2-nbF |
| SEQ ID NO: 177 | DNA | MPK2-R2 |
| SEQ ID NO: 178 | DNA | MPK5-F256 |
| SEQ ID NO: 179 | DNA | MPK5-nbR |
| SEQ ID NO: 180 | DNA | MPK6-F |
| SEQ ID NO: 181 | DNA | MPK6-R |
| SEQ ID NO: 182 | DNA | UGW-U3-F |
| SEQ ID NO: 183 | DNA | UGW-gRNA-R |
| SEQ ID NO: 184 | DNA | gtCas9-F |
| SEQ ID NO: 185 | DNA | gtCas9-R |
| SEQ ID NO: 186 | DNA | control-F |
| SEQ ID NO: 187 | DNA | control-R |
| SEQ ID NO: 188 | DNA | pretRNA sequence form PTG7 |
| SEQ ID NO: 189 | DNA | pretRNA sequence form PTG10 |

What is claimed is:

1. A method of processing an RNA molecule for RNA mediated genetic manipulation in a recipient cell comprising:
introducing to said cell a nucleic acid construct comprising a polynucleotide encoding an RNA molecule comprising two or more RNA mediated genetic manipulation sequences in tandem array with one or more tRNA cleavage sequences, wherein the tRNA processing system of the recipient cell cleaves the RNA molecule at the tRNA cleavage sequences.

2. The method of claim 1 wherein said RNA mediated genetic manipulation sequences target multiple sites within a single gene in said recipient cell.

3. The method of claim 1 wherein said RNA mediated genetic manipulation sequences target multiple different genes in said recipient cell.

4. The method of claim 1 wherein said RNA mediated genetic manipulation is RNA guided genome editing.

5. The method of claim 4 wherein said RNA guided genome editing includes CRISPR-associated nucleases.

6. The method of claim 1 wherein said RNA genetic manipulation includes RNA interference.

7. The method of claim 6 wherein said RNA interference is microRNA and/or small RNA mediated RNA interference.

8. The method of claim 1 wherein said tRNA cleavage sequence includes a pretRNA acceptor stem, a D-loop arm and a TΨC-loop arm.

9. The method of claim 1 wherein said tRNA cleavage sequence includes an active site for one or more of RNase P and/or RNase Z and/or RNase E.

10. The method of claim 1 wherein said tRNA cleavage sequence is SEQ ID NO: 13, 188 or 189.

11. The method of claim 1 wherein said RNA molecule includes a tRNA-guideRNA-in tandem alignment.

12. The method of claim 11 wherein said guideRNA includes a spacer RNA and a scaffold RNA sequence.

13. The method of claim 1 wherein said RNA molecule includes a tRNA-guideRNA-tRNA.

14. The method of claim 1 wherein said recipient cell is a plant cell.

15. The method of claim 1 wherein said recipient cell is an animal cell.

16. The method of claim 1 wherein said cell is a microbial cell.

17. The method of claim 1 wherein said cell is a human cell.

18. The method of claim 1, wherein the nucleic acid construct is introduced to said cell by particle bombardment, protoplast transfection or *Agrobacterium* transformation.

19. The method of claim 1, wherein the nucleic acid construct comprises a promoter sequence operably linked to the polynucleotide encoding the RNA molecule.

20. The method of claim 19 wherein the promoter sequence is a Pol III promoter or a Pol II promoter.

21. A nucleic acid construct comprising a polynucleotide encoding an RNA molecule for RNA mediated genetic manipulation, wherein the RNA molecule comprises two or more RNA mediated genetic manipulation sequences and s-one or more tRNA cleavage sequences.

22. The nucleic acid construct of claim 21 wherein said two or more RNA mediated genetic manipulation sequences target multiple sites within a single gene.

23. The nucleic acid construct of claim 21 wherein said RNA mediated genetic manipulation sequences target multiple different genes or DNA elements.

24. The nucleic acid construct of claim 21 wherein said RNA mediated genetic manipulation sequence is an interfering RNA sequence.

25. The nucleic acid construct of claim 24 wherein said RNA interference sequence is microRNA and/or small RNA mediated RNA interference.

26. The nucleic acid construct of claim 21 wherein said tRNA cleavage sequence includes a pretRNA acceptor stem, a D-loop arm and a PIT-loop arm.

27. The nucleic acid construct of claim 21 wherein said tRNA cleavage sequence includes an active site for one or more of RNase P and/or RNase Z and/or RNase E.

28. The nucleic acid construct of claim 21 wherein said tRNA cleavage sequence is SEQ ID NO: 13, 188 or 189.

29. The nucleic acid construct of claim 21 wherein said RNA molecule includes a tRNA-guideRNA arrayed in tandem.

30. The nucleic acid construct of claim 29 wherein said guideRNA includes a spacer RNA and a scaffold RNA sequence.

31. The nucleic acid construct of claim 29 wherein said RNA molecule includes a tRNA-guideRNA-tRNA.

32. The nucleic acid construct of claim 21 further comprising a regulatory element for expression of the polynucleotide encoding the RNA molecule in a recipient cell.

33. The nucleic acid construct of claim 32 wherein said nucleic acid construct comprises a promoter sequence operably linked to the polynucleotide encoding the RNA molecule.

34. The nucleic acid construct of claim 33 wherein said promoter sequence is a Pol III promoter.

35. The nucleic acid construct of claim 33 wherein the promoter sequence is a Pol II promoter.

36. The nucleic acid construct of claim 21 further comprising a terminator sequence.

37. The nucleic acid construct of claim 36 wherein said terminator sequence is a Pol III terminator.

38. An expression cassette comprising the nucleic acid construct of claim 21.

39. A vector comprising the expression cassette of claim 38.

40. A recipient cell comprising the nucleic acid construct of claim 21.

41. A tissue comprising the recipient cell of claim 40.

42. A plant or animal comprising the recipient cell of claim 40.

43. The cell of claim 40 wherein said cell is a plant cell.

44. The cell of claim 40 wherein said cell is an animal cell.

45. The cell of claim 40 wherein said cell is a microbial cell.

46. The cell of claim 40 wherein said cell is a human cell.

* * * * *

SEQUENCE LISTING

<160> NUMBER OF SEQ ID NOS: 202

<210> SEQ ID NO 1
<211> LENGTH: 113
<212> TYPE: DNA
<213> ORGANISM: Artificial Sequence
<220> FEATURE:
<223> OTHER INFORMATION: sgRNA1 target MPK5

<400> SEQUENCE: 1
gatccgtggc aagatgtcgt agagcaggta cgttttagag ctagaaatag caagttaaaa     60
taaggctagt ccgttatcaa cttgaaaaag tggcaccgag tcggtgcttt ttt            113

<210> SEQ ID NO 2
<211> LENGTH: 115
<212> TYPE: DNA

<213> ORGANISM: Artificial Sequence
<220> FEATURE:
<223> OTHER INFORMATION: sgRNA2 target MPK5

<400> SEQUENCE: 2

```
gatccgtggc agtctacatc gccacggagc tcagttttag agctagaaat agcaagttaa      60
aataaggcta gtccgttatc aacttgaaaa agtggcaccg agtcggtgct ttttt          115
```

<210> SEQ ID NO 3
<211> LENGTH: 96
<212> TYPE: DNA
<213> ORGANISM: Artificial Sequence
<220> FEATURE:
<223> OTHER INFORMATION: gRNA1 scaffold target MPK5

<400> SEQUENCE: 3

```
agatgtcgta gagcaggtac gttttagagc tagaaatagc aagttaaaat aaggctagtc      60
cgttatcaac ttgaaaaagt ggcaccgagt cggtgc                                96
```

<210> SEQ ID NO 4
<211> LENGTH: 97
<212> TYPE: DNA
<213> ORGANISM: Artificial Sequence
<220> FEATURE:
<223> OTHER INFORMATION: gRNA2 scaffold target MPK5

<400> SEQUENCE: 4

```
tctacatcgc cacggagctc agttttagag ctagaaatag caagttaaaa taaggctagt      60
ccgttatcaa cttgaaaaag tggcaccgag tcggtgc                               97
```

<210> SEQ ID NO 5
<211> LENGTH: 96
<212> TYPE: DNA
<213> ORGANISM: Artificial Sequence
<220> FEATURE:
<223> OTHER INFORMATION: gRNA3 scaffold. Target MPK1

<400> SEQUENCE: 5

```
atccaggcga cgctgagcca gttttagagc tagaaatagc aagttaaaat aaggctagtc      60
cgttatcaac ttgaaaaagt ggcaccgagt cggtgc                                96
```

<210> SEQ ID NO 6
<211> LENGTH: 96
<212> TYPE: DNA
<213> ORGANISM: Artificial Sequence
<220> FEATURE:
<223> OTHER INFORMATION: gRNA4 scaffold. Target MPK1

<400> SEQUENCE: 6

```
tggcccaccg gggtataaaa gttttagagc tagaaatagc aagttaaaat aaggctagtc      60
cgttatcaac ttgaaaaagt ggcaccgagt cggtgc                                96
```

<210> SEQ ID NO 7
<211> LENGTH: 96
<212> TYPE: DNA
<213> ORGANISM: Artificial Sequence
<220> FEATURE:
<223> OTHER INFORMATION: gRNA5 scaffold. Target MPK2

<400> SEQUENCE: 7

```
gaacccggtc gcctcaagga gttttagagc tagaaatagc aagttaaaat aaggctagtc      60
cgttatcaac ttgaaaaagt ggcaccgagt cggtgc                                96
```

<210> SEQ ID NO 8
<211> LENGTH: 96
<212> TYPE: DNA
<213> ORGANISM: Artificial Sequence
<220> FEATURE:
<223> OTHER INFORMATION: gRNA6 scaffold. Target MPK2

<400> SEQUENCE: 8
gaatgcgcag actcgtcagg gttttagagc tagaaatagc aagttaaaat aaggctagtc    60
cgttatcaac ttgaaaaagt ggcaccgagt cggtgc    96

<210> SEQ ID NO 9
<211> LENGTH: 96
<212> TYPE: DNA
<213> ORGANISM: Artificial Sequence
<220> FEATURE:
<223> OTHER INFORMATION: gRNA7 scaffold. Target MPK6

<400> SEQUENCE: 9
gtgtccgctt ggcatcgata gttttagagc tagaaatagc aagttaaaat aaggctagtc    60
cgttatcaac ttgaaaaagt ggcaccgagt cggtgc    96

<210> SEQ ID NO 10
<211> LENGTH: 96
<212> TYPE: DNA
<213> ORGANISM: Artificial Sequence
<220> FEATURE:
<223> OTHER INFORMATION: gRNA8 scaffold. Target MPK6

<400> SEQUENCE: 10
gcgggtgcgg gtcaatcaaa gttttagagc tagaaatagc aagttaaaat aaggctagtc    60
cgttatcaac ttgaaaaagt ggcaccgagt cggtgc    96

<210> SEQ ID NO 11
<211> LENGTH: 96
<212> TYPE: DNA
<213> ORGANISM: Artificial Sequence
<220> FEATURE:
<223> OTHER INFORMATION: gRNA9 scaffold. Target PDS

<400> SEQUENCE: 11
acaagccagg agaattcagc gttttagagc tagaaatagc aagttaaaat aaggctagtc    60
cgttatcaac ttgaaaaagt ggcaccgagt cggtgc    96

<210> SEQ ID NO 12
<211> LENGTH: 96
<212> TYPE: DNA
<213> ORGANISM: Artificial Sequence
<220> FEATURE:
<223> OTHER INFORMATION: gRNA10 scaffold. Target PDS

<400> SEQUENCE: 12
cactgcatgg ataactcatc gttttagagc tagaaatagc aagttaaaat aaggctagtc    60
cgttatcaac ttgaaaaagt ggcaccgagt cggtgc    96

<210> SEQ ID NO 13
<211> LENGTH: 77
<212> TYPE: DNA
<213> ORGANISM: Artificial Sequence
<220> FEATURE:
<223> OTHER INFORMATION: pre-tRNA sequence

```
<400> SEQUENCE: 13
aacaaagcac cagtggtcta gtggtggaat agtaccctgc cacggtacag acccgggttc    60
gattcccggc tggtgca                                                   77

<210> SEQ ID NO 14
<211> LENGTH: 10
<212> TYPE: DNA
<213> ORGANISM: Artificial Sequence
<220> FEATURE:
<223> OTHER INFORMATION: Last 10bp of U3 promoter

<400> SEQUENCE: 14
gatccgtggc                                                           10

<210> SEQ ID NO 15
<211> LENGTH: 153
<212> TYPE: DNA
<213> ORGANISM: Artificial Sequence
<220> FEATURE:
<223> OTHER INFORMATION: gRNA-tRNA in pGTR plasmid

<400> SEQUENCE: 15
gttttagagc tagaaatagc aagttaaaat aaggctagtc cgttatcaac ttgaaaaagt    60
ggcaccgagt cggtgcaaca aagcaccagt ggtctagtgg tagaatagta ccctgccacg   120
gtacagaccc gggttcgatt cccggctggt gca                                153

<210> SEQ ID NO 16
<211> LENGTH: 193
<212> TYPE: DNA
<213> ORGANISM: Artificial Sequence
<220> FEATURE:
<223> OTHER INFORMATION: tRNA-gRNA1

<400> SEQUENCE: 16
gatccgtggc aacaaagcac cagtggtcta gtggtagaat agtaccctgc cacggtacag    60
acccgggttc gattcccggc tggtgcaaga tgtcgtagag caggtacgtt ttagagctag   120
aaatagcaag ttaaaataag gctagtccgt tatcaacttg aaaaagtggc accgagtcgg   180 tgctttttt ttt                                                       193

<210> SEQ ID NO 17
<211> LENGTH: 194
<212> TYPE: DNA
<213> ORGANISM: Artificial Sequence
<220> FEATURE:
<223> OTHER INFORMATION: tRNA-gRNA2

<400> SEQUENCE: 17
gatccgtggc aacaaagcac cagtggtcta gtggtagaat agtaccctgc cacggtacag    60
acccgggttc gattcccggc tggtgcatct acatcgccac ggagctcagt tttagagcta   120
gaaatagcaa gttaaaataa ggctagtccg ttatcaactt gaaaaagtgg caccgagtcg   180 gtgcttttt tttt                                                      194

<210> SEQ ID NO 18
<211> LENGTH: 270
<212> TYPE: DNA
<213> ORGANISM: Artificial Sequence
<220> FEATURE:
<223> OTHER INFORMATION: tRNA-gRNA1-tRNA

<400> SEQUENCE: 18
```

```
gatccgtggc aacaaagcac cagtggtcta gtggtagaat agtaccctgc cacggtacag    60
acccgggttc gattcccggc tggtgcaaga tgtcgtagag caggtacgtt ttagagctag   120
aaatagcaag ttaaaataag gctagtccgt tatcaacttg aaaaagtggc accgagtcgg   180
tgcaacaaag caccagtggt ctagtggtag aatagtaccc tgccacggta cagacccggg   240
ttcgattccc ggctggtgca tttttttttt                                    270
```

<210> SEQ ID NO 19
<211> LENGTH: 271
<212> TYPE: DNA
<213> ORGANISM: Artificial Sequence
<220> FEATURE:
<223> OTHER INFORMATION: tRNA-gRNA2-tRNA

<400> SEQUENCE: 19

```
gatccgtggc aacaaagcac cagtggtcta gtggtagaat agtaccctgc cacggtacag    60
acccgggttc gattcccggc tggtgcatct acatcgccac ggagctcagt tttagagcta   120
gaaatagcaa gttaaaataa ggctagtccg ttatcaactt gaaaaagtgg caccgagtcg   180
gtgcaacaaa gcaccagtgg tctagtggta gaatagtacc ctgccacggt acagacccgg   240
gttcgattcc cggctggtgc atttttttttt t                                271
```

<210> SEQ ID NO 20
<211> LENGTH: 365
<212> TYPE: DNA
<213> ORGANISM: Artificial Sequence
<220> FEATURE:
<223> OTHER INFORMATION: tRNA-gRNA3-tRNA-gRNA4

<400> SEQUENCE: 20

```
gatccgtggc aacaaagcac cagtggtcta gtggtagaat agtaccctgc cacggtacag    60
acccgggttc gattcccggc tggtgcaatc caggcgacgc tgagccagtt ttagagctag   120
aaatagcaag ttaaaataag gctagtccgt tatcaacttg aaaaagtggc accgagtcgg   180
tgcaacaaag caccagtggt ctagtggtag aatagtaccc tgccacggta cagacccggg   240
ttcgattccc ggctggtgca tggcccaccg gggtataaaa gttttagagc tagaaatagc   300
aagttaaaat aaggctagtc cgttatcaac ttgaaaaagt ggcaccgagt cggtgctttt   360
ttttt                                                              365
```

<210> SEQ ID NO 21
<211> LENGTH: 366
<212> TYPE: DNA
<213> ORGANISM: Artificial Sequence
<220> FEATURE:
<223> OTHER INFORMATION: tRNA-gRNA5-tRNA-gRNA6

<400> SEQUENCE: 21

```
gatccgtggc aacaaagcac cagtggtcta gtggtagaat agtaccctgc cacggtacag    60
acccgggttc gattcccggc tggtgcagaa cccggtcgcc tcaaggagtt ttagagctag   120
aaatagcaag ttaaaataag gctagtccgt tatcaacttg aaaaagtggc accgagtcgg   180
tgcaacaaag caccagtggt ctagtggtag aatagtaccc tgccacggta cagacccggg   240
ttcgattccc ggctggtgca gaatgcgcag actcgtcagg ttttagagc tagaaatagc   300 aagttaaaat aaggctagtc cgttatcaac ttgaaaaagt ggcaccgagt cggtgctttt   360
tttttt                                                             366
```

<210> SEQ ID NO 22
<211> LENGTH: 366
<212> TYPE: DNA
<213> ORGANISM: Artificial Sequence
<220> FEATURE:
<223> OTHER INFORMATION: tRNA-gRNA7-tRNA-gRNA8

<400> SEQUENCE: 22

```
gatgatccgt ggcaacaaag caccagtggt ctagtggtag aatagtaccc tgccacggta    60
cagacccggg ttcgattccc ggctggtgca gtgtccgctt ggcatcgata gttttagagc   120
tagaaatagc aagttaaaat aaggctagtc cgttatcaac ttgaaaaagt ggcaccgagt   180
cggtgcaaca aagcaccagt ggtctagtgg tagaatagta ccctgccacg gtacagaccc   240
gggttcgatt cccggctggt gcagcggtg cgggtcaatc aaagttttag agctagaaat   300
agcaagttaa aataaggcta gtccgttatc aacttgaaaa agtggcaccg agtcggtgct   360
tttttt                                                             366
```

<210> SEQ ID NO 23
<211> LENGTH: 367
<212> TYPE: DNA
<213> ORGANISM: Artificial Sequence
<220> FEATURE:
<223> OTHER INFORMATION: tRNA-gRNA1-tRNA-gRNA2

<400> SEQUENCE: 23

```
gatccgtggc aacaaagcac cagtggtcta gtggtagaat agtaccctgc cacggtacag    60
acccgggttc gattcccggc tggtgcaaga tgtcgtagag caggtacgtt ttagagctag   120
aaatagcaag ttaaaataag gctagtccgt tatcaacttg aaaaagtggc accgagtcgg   180
tgcaacaaag caccagtggt ctagtggtag aatagtaccc tgccacggta cagacccggg   240
ttcgattccc ggctggtgca tctacatcgc cacggagctc agttttagag ctagaaatag   300
caagttaaaa taaggctagt ccgttatcaa cttgaaaaag tggcaccgag tcggtgcttt   360
tttttt                                                             367
```

<210> SEQ ID NO 24
<211> LENGTH: 713
<212> TYPE: DNA
<213> ORGANISM: Artificial Sequence
<220> FEATURE:
<223> OTHER INFORMATION: tRNA-gRNA1-tRNA-gRNA2-tRNA-gRNA3-tRNA-gRNA4

<400> SEQUENCE: 24

```
gatccgtggc aataaagcac cagtggtcta gtggtagaat agtaccctgc cacggtacag    60
acccgggttc gattcccggc tggtgcaaga tgtcgtagag caggtacgtt ttagagctag   120
aaatagcaag ttaaaataag gctagtccgt tatcaacttg aaaaagtggc accgagtcgg   180
tgcaacaaag caccagtggt ctagtggtag aatagtaccc tgccacggta cagacccggg   240
ttcgattccc ggctggtgca tctacatcgc cacggagctc agttttagag ctagaaatag   300
caagttaaaa taaggctagt ccgttatcaa cttgaaaaag tggcaccgag tcggtgcaac   360
aaagcaccag tggtctagtg gtagaatagt accctgccac ggtacagacc cgggttcgat   420
tcccggctgg tgcaatccag cgacgctga gccagtttta gagctagaaa tagcaagtta   480
aaataaggct agtccgttat caacttgaaa agtggcacc gagtcggtgc aacaaagcac   540
cagtggtcta gtggtagaat agtaccctgc cacggtacag acccgggttc gattcccggc   600
tggtgcatgg cccaccgggg tataaaagtt ttagagctag aaatagcaag ttaaaataag   660
```

```
gctagtccgt tatcaacttg aaaaagtggc accgagtcgg tgcttttttt ttt          713
```

```
<210> SEQ ID NO 25
<211> LENGTH: 711
<212> TYPE: DNA
<213> ORGANISM: Artificial Sequence
<220> FEATURE:
<223> OTHER INFORMATION: tRNA-gRNA7-tRNA-gRNA8-tRNA-gRNA5-tRNA-gRNA6

<400> SEQUENCE: 25
gatccgtggc aacaaagcac cagtggtcta gtggtagaat agtaccctgc cacggtacag    60
acccgggttc gattcccggc tggtgcagtg tccgcttggc atcgatagtt ttagagctag   120
aaatagcaag ttaaaataag gctagtccgt tatcaacttg aaaaagtggc accgagtcgg   180
tgcaacaaag caccagtggt ctagtggtag aatagtaccc tgccacggta cagacccggg   240
ttcgattccc ggctggtgca gcgggtgcgg tcaatcaaa gttttagagc tagaaatagc   300
aagttaaaat aaggctagtc cgttatcaac ttgaaaaagt ggcaccgagt cggtgcaaca   360
aagcaccagt ggtctagtgg tagaatagta ccctgccacg gtacagaccc gggttcgatt   420
cccggctggt gcagaacccg tcgcctcaa ggagttttag agctagaaat agcaagttaa   480
aataaggcta gtccgttatc aacttgaaaa agtggcaccg agtcggtgca acaaagcacc   540
agtggtctag tggtagaata gtaccctgcc acggtacaga cccgggttcg attcccggct   600
ggtgcagaat gcgcagactc gtcagggttt tagagctaga aatagcaagt taaaataagg   660
ctagtccgtt atcaacttga aaagtggca ccgagtcggt gcttttttttt t           711
```

```
<210> SEQ ID NO 26
<211> LENGTH: 1404
<212> TYPE: DNA
<213> ORGANISM: Artificial Sequence
<220> FEATURE:
<223> OTHER INFORMATION: tRNA-gRNA1-tRNA-gRNA2-tRNA-gRNA3-tRNA-gRNA4-
      tRNA-gRNA7-tRNA-gRNA8-tRNA-gRNA5-tRNA-gRNA6

<400> SEQUENCE: 26
gatccgtggc aacaaagcac cagtggtcta gtggtagaat agtaccctgc cacggtacag    60
acccgggttc gattcccggc tggtgcaaga tgtcgtagag caggtacgtt ttagagctag   120
aaatagcaag ttaaaataag gctagtccgt tatcaacttg aaaaagtggc accgagtcgg   180
tgcaacaaag caccagtggt ctagtggtag aatagtaccc tgccacggta cagacccggg   240
ttcgattccc ggctggtgca tctacatcgc cacggagctc agttttagag ctagaaatag   300
caagttaaaa taaggctagt ccgttatcaa cttgaaaaag tggcaccgag tcggtgcaac   360
aaagcaccag tggtctagtg gtagaatagt accctgccac ggtacagacc cgggttcgat   420
tcccggctgg tgcaatccag gcgacgctga gccagtttta gagctagaaa tagcaagtta   480
aaataaggct agtccgttat caacttgaaa agtggcacc gagtcggtgc aacaaagcac   540
cagtggtcta gtggtagaat agtaccctgc cacggtacag acccgggttc gattcccggc   600
tggtgcatgg cccaccgggg tataaaagtt ttagagctag aaatagcaag ttaaaataag   660
gctagtccgt tatcaacttg aaaaagtggc accgagtcgg tgcaacaaag caccagtggt   720
ctagtggtag aatagtaccc tgccacggta cagacccggg ttcgattccc ggctggtgca   780
gtgtccgctt ggcatcgata gttttagagc tagaaatagc aagttaaaat aaggctagtc   840
cgttatcaac ttgaaaaagt ggcaccgagt cggtgcaaca aagcaccagt ggtctagtgg   900
tagaatagta ccctgccacg gtacagaccc gggttcgatt cccggctggt gcagcgggtg   960
```

```
cgggtcaatc aaagttttag agctagaaat agcaagttaa aataaggcta gtccgttatc    1020
aacttgaaaa agcggcaccg agtcggtgca acaaagcacc agtggtctag tggtagaata    1080
gtaccctgcc acgtacaga cccgggttcg attcccggct ggtgcagaac ccggtcgcct     1140
caaggagttt tagagctaga aatagcaagt taaaataagg ctagtccgtt atcaacttga    1200
aaaagtggca ccgagtcggt gcaacaaagc accagtggtc tagtggtaga atagtaccct   1260
gccacggtac agacccgggt tcgattcccg gctggtgcag aatgcgcaga ctcgtcaggg    1320
ttttagagct agaaatagca agttaaaata aggctagtcc gttatcaact tgaaaaagtg    1380
gcaccgagtc ggtgcttttt tttt                                           1404

<210> SEQ ID NO 27
<211> LENGTH: 367
<212> TYPE: DNA
<213> ORGANISM: Artificial Sequence
<220> FEATURE:
<223> OTHER INFORMATION: tRNA-gRNA9-tRNA-gRNA10

<400> SEQUENCE: 27
gatccgtggc aacaaagcac cagtggtcta gtggtggaat agtaccctgc cacggtacag     60 acccggttc gattcccggc tggtgcaaca agccaggaga attcagcgtt ttagagctag     120
aaatagcaag ttaaataag gctagtccgt tatcaacttg aaaaagtggc accgagtcgg    180
tgcaacaaag caccagtggt ctagtggtag aatagtaccc tgccacggta cagacccggg    240
tccgattccc ggctggtgca cactgcatgg ataactcatc gttttagagc tagaaatagc    300
aagttaaaat aaggctagtc cgttatcaac ttgaaaaagt ggcaccgagt cggtgctttt    360
tttttt                                                               367

<210> SEQ ID NO 28
<211> LENGTH: 20
<212> TYPE: DNA
<213> ORGANISM: Artificial Sequence
<220> FEATURE:
<223> OTHER INFORMATION: Primer gRNA1-R for cRT-PCR of gRNA1

<400> SEQUENCE: 28
aaacgtacct gctctacgac                                                 20

<210> SEQ ID NO 29
<211> LENGTH: 20
<212> TYPE: DNA
<213> ORGANISM: Artificial Sequence
<220> FEATURE:
<223> OTHER INFORMATION: Primer gRNA2-R for cRT-PCR of gRNA2

<400> SEQUENCE: 29
aaactgagct ccgtggcgat                                                 20

<210> SEQ ID NO 30
<211> LENGTH: 34
<212> TYPE: DNA
<213> ORGANISM: Artificial Sequence
<220> FEATURE:
<223> OTHER INFORMATION: Primer Bsa-gRNA-F for cRT-PCR and amplify gRNA

<400> SEQUENCE: 30
ggagaccgag gtctcggttt tagagctaga aata                                 34

<210> SEQ ID NO 31
```

```
<211> LENGTH: 24
<212> TYPE: DNA
<213> ORGANISM: Artificial Sequence
<220> FEATURE:
<223> OTHER INFORMATION: Primer gRNA1-F for qRT-PCR

<400> SEQUENCE: 31
ggcaagatgt cgtagagcag gtac                                            24

<210> SEQ ID NO 32
<211> LENGTH: 22
<212> TYPE: DNA
<213> ORGANISM: Artificial Sequence
<220> FEATURE:
<223> OTHER INFORMATION: Primer gRNA2-F for qRT-PCR

<400> SEQUENCE: 32
gtctacatcg ccacggagct ca                                              22

<210> SEQ ID NO 33
<211> LENGTH: 18
<212> TYPE: DNA
<213> ORGANISM: Artificial Sequence
<220> FEATURE:
<223> OTHER INFORMATION: Primer gRNA-R for qRT-PCR

<400> SEQUENCE: 33
gcaccgactc ggtgccac                                                   18

<210> SEQ ID NO 34
<211> LENGTH: 22
<212> TYPE: DNA
<213> ORGANISM: Artificial Sequence
<220> FEATURE:
<223> OTHER INFORMATION: Primer UBI-qF for qRT-PCR

<400> SEQUENCE: 34
tggtcagtaa tcagccagtt tg                                              22

<210> SEQ ID NO 35
<211> LENGTH: 22
<212> TYPE: DNA
<213> ORGANISM: Artificial Sequence
<220> FEATURE:
<223> OTHER INFORMATION: Primer UBI-qR for qRT-PCR

<400> SEQUENCE: 35
caaatacttg acgaacagag gc                                              22

<210> SEQ ID NO 36
<211> LENGTH: 20
<212> TYPE: DNA
<213> ORGANISM: Artificial Sequence
<220> FEATURE:
<223> OTHER INFORMATION: Primer MPK5-qF for qPCR

<400> SEQUENCE: 36
gatcccgccg ccgatccctc                                                 20

<210> SEQ ID NO 37
<211> LENGTH: 54
<212> TYPE: DNA
<213> ORGANISM: Artificial Sequence
<220> FEATURE:
<223> OTHER INFORMATION: Primer g-tRNA-F for construct pGTR

<400> SEQUENCE: 37
```
gcaccgagtc ggtgcaacaa agcaccagtg gtctagtggt agaatagtac cctg         54

<210> SEQ ID NO 38
<211> LENGTH: 60
<212> TYPE: DNA
<213> ORGANISM: Artificial Sequence
<220> FEATURE:
<223> OTHER INFORMATION: Primer tRNA-R for construct pGTR

<400> SEQUENCE: 38
ctgccatgca ccagccggga atcgaacccg ggtctgtacc gtggcagggt actattctac    60

<210> SEQ ID NO 39
<211> LENGTH: 37
<212> TYPE: DNA
<213> ORGANISM: Artificial Sequence
<220> FEATURE:
<223> OTHER INFORMATION: Primer UBI-F for amplifying UBIp

<400> SEQUENCE: 39
tgcatgcctg caggtccaca aattcgggtc aaggcgg                             37

<210> SEQ ID NO 40
<211> LENGTH: 41
<212> TYPE: DNA
<213> ORGANISM: Artificial Sequence
<220> FEATURE:
<223> OTHER INFORMATION: Primer UBI-R to amplify UBIp

<400> SEQUENCE: 40
caaacttgtt gataactatc tgcaagaaat aatcaccaaa c                        41

<210> SEQ ID NO 41
<211> LENGTH: 41
<212> TYPE: DNA
<213> ORGANISM: Artificial Sequence
<220> FEATURE:
<223> OTHER INFORMATION: Primer UGW-U3-F for construct pRGE32

<400> SEQUENCE: 41
gaccatgatt acgccaagct taaggaatct ttaaacatac g                        41

<210> SEQ ID NO 42
<211> LENGTH: 37
<212> TYPE: DNA
<213> ORGANISM: Artificial Sequence
<220> FEATURE:
<223> OTHER INFORMATION: Primer UGW-gRNA-R for construct pRGE32

<400> SEQUENCE: 42
ggacctgcag gcatgcacgc gctaaaaacg gactagc                             37

<210> SEQ ID NO 43
<211> LENGTH: 18
<212> TYPE: DNA
<213> ORGANISM: Artificial Sequence
<220> FEATURE:
<223> OTHER INFORMATION: Primer MPK1-F for Genotyping of MPK1

<400> SEQUENCE: 43
gggtcggcac agcatctc                                                  18

<210> SEQ ID NO 44
<211> LENGTH: 20
<212> TYPE: DNA

```
<213> ORGANISM: Artificial Sequence
<220> FEATURE:
<223> OTHER INFORMATION: Primer MPK1-R2 for genotyping of MPK1

<400> SEQUENCE: 44
tgcgcctaaa aatcgagggt                                               20

<210> SEQ ID NO 45
<211> LENGTH: 21
<212> TYPE: DNA
<213> ORGANISM: Artificial Sequence
<220> FEATURE:
<223> OTHER INFORMATION: Primer  MPK2-F for genotyping of MPK2

<400> SEQUENCE: 45
tttgggaagc atgtatgaag c                                             21

<210> SEQ ID NO 46
<211> LENGTH: 20
<212> TYPE: DNA
<213> ORGANISM: Artificial Sequence
<220> FEATURE:
<223> OTHER INFORMATION: Primer MPK2-R2 for genotyping of MPK2

<400> SEQUENCE: 46
tatgccagcc aatgagccaa                                               20

<210> SEQ ID NO 47
<211> LENGTH: 21
<212> TYPE: DNA
<213> ORGANISM: Artificial Sequence
<220> FEATURE:
<223> OTHER INFORMATION: Primer MPK5-F256 for genotyping of MPK5

<400> SEQUENCE: 47
gccaccttcc ttcctcatcc g                                             21

<210> SEQ ID NO 48
<211> LENGTH: 20
<212> TYPE: DNA
<213> ORGANISM: Artificial Sequence
<220> FEATURE:
<223> OTHER INFORMATION: Primer MPK5-R611 for genotyping of MPK5

<400> SEQUENCE: 48
gttgctcggc ttcaggtcgc                                               20

<210> SEQ ID NO 49
<211> LENGTH: 21
<212> TYPE: DNA
<213> ORGANISM: Artificial Sequence
<220> FEATURE:
<223> OTHER INFORMATION: Primer MPK6-F for genotyping of MPK6

<400> SEQUENCE: 49
ttgacgcccc aacataaata a                                             21

<210> SEQ ID NO 50
<211> LENGTH: 18
<212> TYPE: DNA
<213> ORGANISM: Artificial Sequence
<220> FEATURE:
<223> OTHER INFORMATION: Primer MPK6-R for genotyping of MPK6

<400> SEQUENCE: 50
tgttgctgcc gcttttct                                                 18
```

<210> SEQ ID NO 51
<211> LENGTH: 20
<212> TYPE: DNA
<213> ORGANISM: Artificial Sequence
<220> FEATURE:
<223> OTHER INFORMATION: Primer PDS-F for genotyping of PDS

<400> SEQUENCE: 51
ggtagaaatg ccatgcggga                                        20

<210> SEQ ID NO 52
<211> LENGTH: 20
<212> TYPE: DNA
<213> ORGANISM: Artificial Sequence
<220> FEATURE:
<223> OTHER INFORMATION: Primer PDS-R for genotyping of PDS

<400> SEQUENCE: 52
attcagccga acctcaccac                                        20

<210> SEQ ID NO 53
<211> LENGTH: 46
<212> TYPE: DNA
<213> ORGANISM: Artificial Sequence
<220> FEATURE:
<223> OTHER INFORMATION: Primer  L5AD5-F for PTG synthesis and cloning

<400> SEQUENCE: 53
cgggtctcag gcaggatggg cagtctgggc aacaaagcac cagtgg           46

<210> SEQ ID NO 54
<211> LENGTH: 52
<212> TYPE: DNA
<213> ORGANISM: Artificial Sequence
<220> FEATURE:
<223> OTHER INFORMATION: Primer L3AD5-R for PTG synthesis and cloning

<400> SEQUENCE: 54
taggtctcca aacggatgag cgacagcaaa caaaaaaaaa agcaccgact cg    52

<210> SEQ ID NO 55
<211> LENGTH: 31
<212> TYPE: DNA
<213> ORGANISM: Artificial Sequence
<220> FEATURE:
<223> OTHER INFORMATION: Primer S5AD5-F for PTG synthesis and cloning

<400> SEQUENCE: 55
cgggtctcag gcaggatggg cagtctgggc a                           31

<210> SEQ ID NO 56
<211> LENGTH: 31
<212> TYPE: DNA
<213> ORGANISM: Artificial Sequence
<220> FEATURE:
<223> OTHER INFORMATION: Primer S3AD5-R for PTG synthesis and cloning

<400> SEQUENCE: 56
taggtctcca aacggatgag cgacagcaaa c                           31

<210> SEQ ID NO 57
<211> LENGTH: 36
<212> TYPE: DNA
<213> ORGANISM: Artificial Sequence
<220> FEATURE:

<223> OTHER INFORMATION: Primer gR1-F for synthesis of PTG

<400> SEQUENCE: 57
taggtctcct agagcaggta cgttttagag ctagaa                    36

<210> SEQ ID NO 58
<211> LENGTH: 36
<212> TYPE: DNA
<213> ORGANISM: Artificial Sequence
<220> FEATURE:
<223> OTHER INFORMATION: Primer gR1-R for synthesis of PTG

<400> SEQUENCE: 58
atggtctcat ctacgacatc ttgcaccagc cgggaa                    36

<210> SEQ ID NO 59
<211> LENGTH: 36
<212> TYPE: DNA
<213> ORGANISM: Artificial Sequence
<220> FEATURE:
<223> OTHER INFORMATION: Primer gR2-F for synthesis of PTG

<400> SEQUENCE: 59
taggtctccc cacggagctc agttttagag ctagaa                    36

<210> SEQ ID NO 60
<211> LENGTH: 37
<212> TYPE: DNA
<213> ORGANISM: Artificial Sequence
<220> FEATURE:
<223> OTHER INFORMATION: Primer gR2-R for synthesis of PTG

<400> SEQUENCE: 60
atggtctcag tggcgatgta gatgcaccag ccgggaa                   37

<210> SEQ ID NO 61
<211> LENGTH: 36
<212> TYPE: DNA
<213> ORGANISM: Artificial Sequence
<220> FEATURE:
<223> OTHER INFORMATION: Primer gR3-F for synthesis of PTG

<400> SEQUENCE: 61
taggtctccg acgctgagcc agttttagag ctagaa                    36

<210> SEQ ID NO 62
<211> LENGTH: 36
<212> TYPE: DNA
<213> ORGANISM: Artificial Sequence
<220> FEATURE:
<223> OTHER INFORMATION: Primer gR3-R for synthesis of PTG

<400> SEQUENCE: 62
atggtctcac gtcgcctgga ttgcaccagc cgggaa                    36

<210> SEQ ID NO 63
<211> LENGTH: 38
<212> TYPE: DNA
<213> ORGANISM: Artificial Sequence
<220> FEATURE:
<223> OTHER INFORMATION: Primer gR4-F for synthesis of PTG

<400> SEQUENCE: 63
taggtctcca ccggggtata aaagttttag agctagaa                  38

<210> SEQ ID NO 64
<211> LENGTH: 32
<212> TYPE: DNA
<213> ORGANISM: Artificial Sequence
<220> FEATURE:
<223> OTHER INFORMATION: Primer gR4-R  for synthesis of PTG

<400> SEQUENCE: 64
cgggtctcac ggtgggccat gcaccagccg gg                          32

<210> SEQ ID NO 65
<211> LENGTH: 37
<212> TYPE: DNA
<213> ORGANISM: Artificial Sequence
<220> FEATURE:
<223> OTHER INFORMATION: Primer gR5-F for synthesis of PTG

<400> SEQUENCE: 65
taggtctccg tcgcctcaag gagtttttaga gctagaa                    37

<210> SEQ ID NO 66
<211> LENGTH: 33
<212> TYPE: DNA
<213> ORGANISM: Artificial Sequence
<220> FEATURE:
<223> OTHER INFORMATION: Primer gR5-R for synthesis of PTG

<400> SEQUENCE: 66
cgggtctcac gaccgggttc tgcaccagcc ggg                         33

<210> SEQ ID NO 67
<211> LENGTH: 37
<212> TYPE: DNA
<213> ORGANISM: Artificial Sequence
<220> FEATURE:
<223> OTHER INFORMATION: Primer gR6-F for synthesis of PTG

<400> SEQUENCE: 67
taggtctccc agactcgtca gggttttaga gctagaa                     37

<210> SEQ ID NO 68
<211> LENGTH: 33
<212> TYPE: DNA
<213> ORGANISM: Artificial Sequence
<220> FEATURE:
<223> OTHER INFORMATION: Primer gR6-R for synthesis of PTG

<400> SEQUENCE: 68
cgggtctcat ctgcgcattc tgcaccagcc ggg                         33

<210> SEQ ID NO 69
<211> LENGTH: 36
<212> TYPE: DNA
<213> ORGANISM: Artificial Sequence
<220> FEATURE:
<223> OTHER INFORMATION: Primer gR7-F for synthesis of PTG

<400> SEQUENCE: 69
taggtctcct tggcatcgat agtttttagag ctagaa                     36

<210> SEQ ID NO 70
<211> LENGTH: 36
<212> TYPE: DNA
<213> ORGANISM: Artificial Sequence
<220> FEATURE:
<223> OTHER INFORMATION: Primer  gR7-R for synthesis of PTG

```
<400> SEQUENCE: 70
atggtctcac caagcggaca ctgcaccagc cgggaa                                    36

<210> SEQ ID NO 71
<211> LENGTH: 37
<212> TYPE: DNA
<213> ORGANISM: Artificial Sequence
<220> FEATURE:
<223> OTHER INFORMATION: Primer gR8-F for synthesis of PTG

<400> SEQUENCE: 71
taggtctccc gggtcaatca aagtttaga gctagaa                                    37

<210> SEQ ID NO 72
<211> LENGTH: 33
<212> TYPE: DNA
<213> ORGANISM: Artificial Sequence
<220> FEATURE:
<223> OTHER INFORMATION: Primer gR8-R for synthesis of PTG

<400> SEQUENCE: 72
cgggtctcac ccgcacccgc tgcaccagcc ggg                                       33

<210> SEQ ID NO 73
<211> LENGTH: 21
<212> TYPE: DNA
<213> ORGANISM: Artificial Sequence
<220> FEATURE:
<223> OTHER INFORMATION: Primer Ln-gR7-F for synthesis of PTG

<400> SEQUENCE: 73
taggtctcct tggcatcgat a                                                    21

<210> SEQ ID NO 74
<211> LENGTH: 21
<212> TYPE: DNA
<213> ORGANISM: Artificial Sequence
<220> FEATURE:
<223> OTHER INFORMATION: Primer Ln-gR7-R for synthesis of PTG

<400> SEQUENCE: 74
atggtctcac caagcggaca c                                                    21

<210> SEQ ID NO 75
<211> LENGTH: 38
<212> TYPE: DNA
<213> ORGANISM: Artificial Sequence
<220> FEATURE:
<223> OTHER INFORMATION: Primer gR9-F for synthesis of PTG

<400> SEQUENCE: 75
taggtctccc aggagaattc agcgttttag agctagaa                                  38

<210> SEQ ID NO 76
<211> LENGTH: 32
<212> TYPE: DNA
<213> ORGANISM: Artificial Sequence
<220> FEATURE:
<223> OTHER INFORMATION: Primer gR9-R for synthesis of PTG

<400> SEQUENCE: 76
cgggtctcac ctggcttgtt gcaccagccg gg                                        32

<210> SEQ ID NO 77
<211> LENGTH: 38
```

```
<212> TYPE: DNA
<213> ORGANISM: Artificial Sequence
<220> FEATURE:
<223> OTHER INFORMATION: Primer gR10-F Artificial synthesis of PTG

<400> SEQUENCE: 77
taggtctcca tggataactc atcgttttag agctagaa                              38

<210> SEQ ID NO 78
<211> LENGTH: 32
<212> TYPE: DNA
<213> ORGANISM: Artificial Sequence
<220> FEATURE:
<223> OTHER INFORMATION: Primer gR10-R for synthesis of PTG

<400> SEQUENCE: 78
cgggtctcac catgcagtgt gcaccagccg gg                                    32

<210> SEQ ID NO 79
<211> LENGTH: 1720
<212> TYPE: DNA
<213> ORGANISM: Oryza sativa

<400> SEQUENCE: 79
attccgcctc cactttccct tcccttcctc ctccacctcc acctcctcgt cgcgatccaa      60
atccgaatcc ggccatggac gccggggcgc agccgccgga cacggagatg gcggaggccg     120
gcggcgggca gcagccgcct gctgcggctg cggcggcggg ggcgggggca ggggcgggga     180
tgatggagaa catccaggcg acgctgagcc atggcgggag gttcatccag tacaacatct     240
tcgggaacgt gttcgaggtc accgccaagt acaagccccc catcctcccc atcggcaagg     300
gcgcctacgg catcgtctgc tcggcgctca actcggagac gggggagcag gtggcgatca     360
agaagatcgc caacgcgttc gacaacaaga tcgacgccaa gcgcacgctc agggagatca     420
agctgctccg ccacatggac cacgagaata ttgttgccat aagggatatc atacctcctc     480
cacaaaggaa ttcattcaat gacgtttata ttgcatatga attgatggat actgatctgc     540
atcaaattat tcgctcaaat caagcattgt cagaggagca ctgccagtat ttcctttatc     600
agattctccg tggcttgaag tatatacatt cagcaaatgt ccttcaccga gacttgaagc     660
ccagcaacct acttttgaat gcaaattgtg acctcaaaat ttgtgatttt ggacttgctc     720
gtaccacctc agaaaccgat tttatgactg agtatgttgt cacaagatgg tatagggcac     780
cggaacttct gttgaattcc tctgaatata ctgcagcaat tgatgtgtgg tctgtgggct     840 gtattttat ggaactcatg gatcgtaaac ctttgttttc tggaagagat catgtccatc      900
aattacgtct actaatggag ctcatcggaa cgccaaatga ggctgatctg gattttgtaa     960
atgaaaatgc aagaagatac attcgccaac ttcctagaca tgcaaggcag tccttcctg     1020 aaaaatttcc acatgttcat cctttagcaa ttgatctggt tgaaaagatg ctgacatttg    1080
atccTagaca gagaataaca gttgaaggtg cccttgcaca tccttacctg gcatcactgc    1140
atgacataag tgatgagcca gtctgctcat caccccttcag ctttgacttc gagcagcatg    1200
cattgtccga ggaacaaatg aaggatctaa tctaccaaga aggccttgcg ttcaaccctg    1260
attaccagta gctggtgttc tatttcagcc ttggattgat tctattcata tggagttttt    1320
tcctcctgcg ccacaaaagg tcgccgacag tgatcactag ttgtaaataa ttgcctcacc    1380
tgaaaaatcc tccctggttc aaagctgaag gtgttgttct aagagtagaa atgtactttg    1440
tgatcaagtt cctgggtagc tgctatgcca ttccttatgct tatgtatgtt gtttaatgtg    1500
```

```
ggattttttt ccatcttaaa tgttttagt ccctttgta agaagagtta gttcatgaac   1560
gatgacggcc taaattctgc ggttatcatc aaattcccca ttttcttgtc gattcatgga   1620
tttctcatgg ttttacttaa tgctccatgt tgtaagacgt ggtcaatgga agaggatata   1680
ttgactcttg attcagtggt ggcagttggg agttgatcgt                         1720
```

<210> SEQ ID NO 80
<211> LENGTH: 398
<212> TYPE: PRT
<213> ORGANISM: Oryza sativa

<400> SEQUENCE: 80

```
Met Asp Ala Gly Ala Gln Pro Pro Asp Thr Glu Met Ala Glu Ala Gly
1               5                   10                  15

Gly Gly Gln Gln Pro Pro Ala Ala Ala Ala Ala Gly Ala Gly Ala
                20                  25                  30

Gly Ala Gly Met Met Glu Asn Ile Gln Ala Thr Leu Ser His Gly Gly
            35                  40                  45

Arg Phe Ile Gln Tyr Asn Ile Phe Gly Asn Val Phe Glu Val Thr Ala
    50                  55                  60

Lys Tyr Lys Pro Pro Ile Leu Pro Ile Gly Lys Gly Ala Tyr Gly Ile
65                  70                  75                  80

Val Cys Ser Ala Leu Asn Ser Glu Thr Gly Glu Gln Val Ala Ile Lys
                85                  90                  95

Lys Ile Ala Asn Ala Phe Asp Asn Lys Ile Asp Ala Lys Arg Thr Leu
            100                 105                 110

Arg Glu Ile Lys Leu Leu Arg His Met Asp His Glu Asn Ile Val Ala
        115                 120                 125

Ile Arg Asp Ile Ile Pro Pro Pro Gln Arg Asn Ser Phe Asn Asp Val
130                 135                 140

Tyr Ile Ala Tyr Glu Leu Met Asp Thr Asp Leu His Gln Ile Ile Arg
145                 150                 155                 160

Ser Asn Gln Ala Leu Ser Glu Glu His Cys Gln Tyr Phe Leu Tyr Gln
                165                 170                 175

Ile Leu Arg Gly Leu Lys Tyr Ile His Ser Ala Asn Val Leu His Arg
            180                 185                 190

Asp Leu Lys Pro Ser Asn Leu Leu Asn Ala Asn Cys Asp Leu Lys
        195                 200                 205

Ile Cys Asp Phe Gly Leu Ala Arg Thr Thr Ser Glu Thr Asp Phe Met
210                 215                 220

Thr Glu Tyr Val Val Thr Arg Trp Tyr Arg Ala Pro Glu Leu Leu Leu
225                 230                 235                 240

Asn Ser Ser Glu Tyr Thr Ala Ala Ile Asp Val Trp Ser Val Gly Cys
                245                 250                 255

Ile Phe Met Glu Leu Met Asp Arg Lys Pro Leu Phe Pro Gly Arg Asp
            260                 265                 270

His Val His Gln Leu Arg Leu Leu Met Glu Leu Ile Gly Thr Pro Asn
        275                 280                 285

Glu Ala Asp Leu Asp Phe Val Asn Glu Asn Ala Arg Arg Tyr Ile Arg
    290                 295                 300

Gln Leu Pro Arg His Ala Arg Gln Ser Phe Pro Glu Lys Phe Pro His
305                 310                 315                 320

Val His Pro Leu Ala Ile Asp Leu Val Glu Lys Met Leu Thr Phe Asp
                325                 330                 335
```

```
Pro Arg Gln Arg Ile Thr Val Glu Gly Ala Leu Ala His Pro Tyr Leu
            340                 345                 350

Ala Ser Leu His Asp Ile Ser Asp Glu Pro Val Cys Ser Ser Pro Phe
        355                 360                 365

Ser Phe Asp Phe Glu Gln His Ala Leu Ser Glu Glu Gln Met Lys Asp
        370                 375                 380

Leu Ile Tyr Gln Glu Gly Leu Ala Phe Asn Pro Asp Tyr Gln
385                 390                 395

<210> SEQ ID NO 81
<211> LENGTH: 1577
<212> TYPE: DNA
<213> ORGANISM: Oryza sativa

<400> SEQUENCE: 81
gggttcgttt cttggctggt tttcttgggc ggcgatcgat cgatgcgcat ggagggcggc      60
ggcggcggcg ccatggcca tcacggcggc ggcggcggtg ccatggcca tcacggtggc     120 atcggaggag gggaggcgca gatcaagggg acgctgacgc acggcgggag gtacgtgcag     180
tacaacgtgt atggtaacct gttcgaggtt tcgtccaagt acgtccctcc catccgcccc     240
gtcggccgcg gcgcctgcgg catcatctgt gcggttgtga atgcgcagac tcgtcaggag     300
gtggcaatca agaagatcgg caacgcgttc gacaaccaga tcgacgccaa gcgcaccctg     360
cgagagatca agctgcttcg gcacatggat catgataatg tcatctcaat aaaggacatc     420
atacggccac caaggaggga gaacttcaat gatgtctaca ttgtctatga gctcatggac     480
actgatcttc accaccttct tcgatcaaac cagccactaa cagatgatca ctgtcagtat     540
tttctctatc aggtactacg aggattgaag tatgtgcatt cagcaaatgt cttgcacaga     600
gacctcaggc caagtaattt gctgctgaat gcgaaatgcg atcttaagat cggagacttt     660
ggattagcaa ggaccacaaa tgaaactgac ttcatgatgg agtatgttgt tactcgatgg     720
tacagggcac ctgaactcct gctaaactgc tcagagtaca ctgcagctat tgatatctgg     780
tcggtaggct gcatccttgg tgagatcgtt acaagggagc ctttgtttcc tggaaaggat     840
tatgtccatc agctgaggct aataactgag ttaataggct cacctgatga ctcgagcctt     900
gggtttcttc gaagcgacaa cgcccgcaga tatgtgaggt cgcttcctca ataccccaag     960
caacaattcc gtgcacggtt ccccactatg tctagtggtg ccatggattt gcttgagagg    1020
atgcttgtgt ttgatcccag caaaaggatt actgttgatg aagctctgtg ccatccatac    1080
ttggcatccc ttcatgagat atatgatgaa ccagtctgcc cagcgccttt cagcttcgat    1140
ttcgagcagc cgtcgctcac cgaagaagat atcaaggaga tcatatggag ggaggcactt    1200
aagttcaacc ctgaaccaat tcactagatg aatttccaat gaagaacgga agcagatcac    1260
actggcagat gatcatccat ccactccttg gggaagacat gagccaacag catgatgtat    1320
agttgatcac cctctcagca tctcatcttg tggcttgtca gcgacaccct gacatcgcaa    1380
attcggacat ttatgaaaac aagaaaagct tgatcaaata atttgtagta cgaaaaaaat    1440
caggagctta actgtatctt cttgttagat ttgtatctat cccatttggt tgtatgctta    1500
agaaacctgg gagcttgtca ctagttatgg aggtacagca atctccagat actcttcagt    1560
catcagttca gttcacc                                                  1577

<210> SEQ ID NO 82
<211> LENGTH: 1489
<212> TYPE: DNA
<213> ORGANISM: Oryza sativa
```

<400> SEQUENCE: 82

```
agcgatcaca aattgtgcca attcacaaac cgccgccccc ttcccttttt aatagctgcc      60
ttcgcctctc gtcccctctc cctcatcgcc ttgctgtctc tgcgaatcga gagagagtca     120
gataaggtcg ttaattaggt ttgtcaattc ggctgcttgc ggcgagagaa gaggaggagg     180
gattagggat ggacggggcg ccggtggcgg agttcaggcc gacgatgacg cacggcggcc     240
ggtacctgct ctacgacatc ttcgggaaca agttcgaggt gacgaacaag taccagccgc     300
ccatcatgcc cattggccgc ggcgcctacg ggatcgtctg ctccgtgatg aactttgaga     360
cgagggagat ggtggcgata aagaagatcg ccaacgcgtt caacaacgac atggacgcca     420
agcgcacgct ccgggagatc aagctcctca ggcacctcga ccacgagaac atcataggca     480
tcagggatgt gatcccgccg ccgatccctc aggcgttcaa cgacgtctac atcgccacgg     540
agctcatgga caccgaccte catcacatca tccgctccaa ccaagaactg tcagaagagc     600
actgccagta tttcctgtac cagatcctgc ggggctcaa gtacatccac tcggcgaacg     660
tgatccaccg cgacctgaag ccgagcaacc tgctgctgaa cgccaactgc gacctcaaga     720
tctgcgactt cgggctggcg cggccgtcgt cggagagcga catgatgacg gagtacgtgg     780
tcacccggtg gtaccgcgcg ccggagctgc tgctcaactc caccgactac tccgccgcca     840
tcgacgtctg gtccgtcggc tgcatcttca tggagctcat caaccgccag ccgctcttcc     900
ccggcaggga ccacatgcac cagatgcgcc tcatcaccga ggtgatcggg acgccgacgg     960
acgacgagct ggggttcata cggaacgagg acgcgaggaa gtacatgagg cacctgccgc    1020
agtacccgcg ccggacgttc gcgagcatgt tcccgcgggt gcagcccgcc gcgctcgacc    1080
tcatcgagag gatgctcacc ttcaacccgc tgcagagaat cacagttgag gaggcgctcg    1140
atcatcctta cctagagaga ttgcacgaca tcgccgatga gcccatctgc ctggagccct    1200
tctccttcga cttcgagcag aaggctctaa acgaggacca aatgaagcag ctgatcttca    1260
acgaagcgat cgagatgaac ccaaacatcc ggtactagat tgaatcacca tggaaatgag    1320
atcccgtcta tacctgcttt gtacatatga tcaagattga gagccgggta gactgaacat    1380
tgcatttgtt tgtttgttga tgttcgaaac ccacattctc tgcaagttgt ggctgctttg    1440
tatgatatat ggtactatgt tcgaataaaa gggtttggaa ctttggatt                1489
```

<210> SEQ ID NO 83
<211> LENGTH: 369
<212> TYPE: PRT
<213> ORGANISM: Oryza sativa

<400> SEQUENCE: 83

```
Met Asp Gly Ala Pro Val Ala Glu Phe Arg Pro Thr Met Thr His Gly
  1               5                  10                  15

Gly Arg Tyr Leu Leu Tyr Asp Ile Phe Gly Asn Lys Phe Glu Val Thr
             20                  25                  30

Asn Lys Tyr Gln Pro Pro Ile Met Pro Ile Gly Arg Gly Ala Tyr Gly
         35                  40                  45

Ile Val Cys Ser Val Met Asn Phe Glu Thr Arg Glu Met Val Ala Ile
     50                  55                  60

Lys Lys Ile Ala Asn Ala Phe Asn Asn Asp Met Asp Ala Lys Arg Thr
 65                  70                  75                  80

Leu Arg Glu Ile Lys Leu Leu Arg His Leu Asp His Glu Asn Ile Ile
                 85                  90                  95
```

```
Gly Ile Arg Asp Val Ile Pro Pro Ile Pro Gln Ala Phe Asn Asp
            100                 105                 110

Val Tyr Ile Ala Thr Glu Leu Met Asp Thr Asp Leu His His Ile Ile
        115                 120                 125

Arg Ser Asn Gln Glu Leu Ser Glu Glu His Cys Gln Tyr Phe Leu Tyr
    130                 135                 140

Gln Ile Leu Arg Gly Leu Lys Tyr Ile His Ser Ala Asn Val Ile His
145                 150                 155                 160

Arg Asp Leu Lys Pro Ser Asn Leu Leu Asn Ala Asn Cys Asp Leu
                165                 170                 175

Lys Ile Cys Asp Phe Gly Leu Ala Arg Pro Ser Ser Glu Ser Asp Met
            180                 185                 190

Met Thr Glu Tyr Val Val Thr Arg Trp Tyr Arg Ala Pro Glu Leu Leu
        195                 200                 205

Leu Asn Ser Thr Asp Tyr Ser Ala Ala Ile Asp Val Trp Ser Val Gly
    210                 215                 220

Cys Ile Phe Met Glu Leu Ile Asn Arg Gln Pro Leu Phe Pro Gly Arg
225                 230                 235                 240

Asp His Met His Gln Met Arg Leu Ile Thr Glu Val Ile Gly Thr Pro
                245                 250                 255

Thr Asp Asp Glu Leu Gly Phe Ile Arg Asn Glu Asp Ala Arg Lys Tyr
            260                 265                 270

Met Arg His Leu Pro Gln Tyr Pro Arg Arg Thr Phe Ala Ser Met Phe
        275                 280                 285

Pro Arg Val Gln Pro Ala Ala Leu Asp Leu Ile Glu Arg Met Leu Thr
    290                 295                 300

Phe Asn Pro Leu Gln Arg Ile Thr Val Glu Glu Ala Leu Asp His Pro
305                 310                 315                 320

Tyr Leu Glu Arg Leu His Asp Ile Ala Asp Glu Pro Ile Cys Leu Glu
                325                 330                 335

Pro Phe Ser Phe Asp Phe Glu Gln Lys Ala Leu Asn Glu Asp Gln Met
            340                 345                 350

Lys Gln Leu Ile Phe Asn Glu Ala Ile Glu Met Asn Pro Asn Ile Arg
        355                 360                 365

Tyr

<210> SEQ ID NO 84
<211> LENGTH: 1560
<212> TYPE: DNA
<213> ORGANISM: Oryza sativa

<400> SEQUENCE: 84
attccgcggt cgccgcccga gtcaaaaaga gggggaagct tctcccacca tagtcctcct      60
cctcctcctc ctactcccat caacgactag tcgcggcgac caagagccaa accctacgcc     120
tcctcccctc cccctccacc tcgtcctccc cgcgagcggc ggcggccatg gattcctcct     180
ccggcggcgc gggcggcggc ggcggcgcgc agatcaaggg gatggggacg cacggggcc     240 gctacgtgct gtacaacgtg tacgggaact tcttcgaggt ctcctccaag tacgcccctc     300
ccatccgccc catcggccgg ggcgcctacg gcattgtctg cgcggctgtt aactcggaga     360
acggcgagga agttgccatc aagaagattg caatgcatt cgacaaccat atcgatgcca     420
agcggacact gagagaaatc aagctgcttc gccacatgga ccacgagaat attattgcca     480
taaaggacat aattcgcccc caagaagag acaactttaa tgatgtttac attgtttctg     540
```

```
agttgatgga tactgatctc catcagatca tacgctcaaa tcaaccattg actgatgacc    600
actgccagta cttcctgtac cagttgctac gagggctaaa atatgtgcac tcggcaaatg    660
tcttgcaccg tgatctgaag ccaagcaatt tgttccttaa tgcaaattgt gatctcaaga    720
ttgctgattt tgggcttgca agaaccacta cggagactga cctcatgaca gagtatgtgg    780
tcactcgttg gtatcgagca ccagagctgc tgttgaactg ctcgcagtat actgctgcta    840
ttgatgtctg gtcagttgga tgcatacttg gtgaaattgt gactcgtcaa cccctgtttc    900
ctggaaggga ttacattcag caactaaaat tgatcactga gctgataggg tcgccagatg    960
actcaagcct agggtttctt cggagtgata atgcaagaag atacatgaaa cagctaccac   1020
agtacccaag gcaggacttc cgcttgcgct tccgcaacat gtctgctggt gcagtcgatc   1080
tgttagagaa aatgctggtg tttgacccaa gcagacggat aactgttgat gaggctcttc   1140
atcacccata cttggcttct cttcatgaca tcaatgaaga acccacctgc ccagcacctt   1200
tcagctttga ttttgagcaa ccatcccttta ctgaagaaca tataaaagaa ctcatctgga   1260
gggaatcctt ggcatttaat ccggatcctc cctactaaga gctcagagca atttatcaat   1320
gctggcatct gaagatcggt agctctagaa aagccaaatc cccttgcttt gtgcatctat   1380
taattttatg cccacttgtt gggcgaatga gcatggatta ttgttatagt gacaatttt     1440
cttaaggcct gtctaaagaa acaacatttg tattccttat cagatagcct gaacttgggc   1500
ctgtattata ccggttgatt gcataactgt tcttatgtat ctaagcctgt aattgtcttc   1560
```

<210> SEQ ID NO 85
<211> LENGTH: 1641
<212> TYPE: DNA
<213> ORGANISM: Oryza sativa

<400> SEQUENCE: 85

```
gcatcagctc caccccccgaa aaatttctcc ccaatctcgc gaggctctcg tcgtcgaatc     60
gaatcctctc gcgtcctcaa gatgcagatc tttgtgaaga cattgaccgg caagactatc    120
accctcgagg tggagtcctc tgacaccatc gataatgtca aggctaagat ccaagataag    180
gagggcatcc ccccggacca gcagcgtctc atcttcgctg gcaagcagct ggaggatggc    240
aggacccttg ctgactacaa catccagaag gagtcgaccc ttcaccttgt cctccgcctc    300
cgtggtggca tgcagatctt tgtcaagact ctgaccggca agactatcac ccttgaggtg    360
gagtcttctg acaccatcga caacgtcaag gccaagatcc aggacaaaga gggcatcccc    420
ccagaccagc agcgtctcat cttcgccggc aagcagctgg aggatggcag gacccttgct    480
gactacaaca tccagaagga gtccacccctc caccttgtcc tccgcctccg tggtggcatg    540
cagatctttg tcaagacact gaccggcaag accatcaccc tcgaggtgga atcttctgac    600
accatcgaca acgtcaaggc caagatccag gacaaggagg gcattccccc ggaccagcag    660
cgtctcatct tgccggcaa gcagcttgag gacggcagga cccttgctga ctacaacatc    720
cagaaggagt caacgcttca ccttgtcctc cgtctcaggg gaggcatgca aatcttcgtg    780
aagactctga ccggcaagac catcaccctc gaggtggagt cttctgatac catcgacaat    840
gtcaaggcca agatccagga caaggagggc attccccgg accagcagcg cctcatcttt    900
gctggcaagc agctggagga tgcaggacc cttgctgact acaacatcca gaaggagtcc    960
accctccacc ttgtgctccg ccttcgtggt ggtatgcaga tctttgtcaa gaccctcaca   1020
ggcaagacca tccctggaa ggttgagagc tcggacacca tcgacaacgt caaggccaag   1080
atccaggaca aggagggcat cccccagac cagcagcgtc tcatcttcgc cggcaagcag   1140
```

| | |
|---|---|
| ctcgaggatg gccgcaccct cgccgactac aacatccaga aggagtctac cctccacctg | 1200 |
| gtgcttcgtc tccgtggtgg tatgcagatc ttcgtgaaga ccttgactgg gaagaccatc | 1260 |
| actttggagg ttgagagctc cgacaccatt gataatgtga aggccaagat ccaggacaag | 1320 |
| gaggggattc ccccagacca gcagcgtctg atcttcgctg gcaagcagct ggaggatgga | 1380 |
| cgcaccctcg ccgactacaa catccagaag gagtccaccc tccacctggt gctccgcctc | 1440 |
| cgtggtggtc agtaatcagc cagtttggtg gagctgccga tgtgcctggt cgtcccgagc | 1500 |
| ctctgttcgt caagtatttg tggtgctgat gtctacttgt gtctggttta atggaccatc | 1560 |
| gagtccgtat gatatgttag ttttatgaaa cagtttcctg tgggacagca gtatgcttta | 1620 |
| tgaataagtt ggatttgaac c | 1641 |

<210> SEQ ID NO 86
<211> LENGTH: 1971
<212> TYPE: DNA
<213> ORGANISM: Oryza sativa

<400> SEQUENCE: 86

| | |
|---|---|
| ggacaacttc ctactcatag gtgcttcgca agtagcagca tccaagcact gaaaagtagt | 60 |
| cagcatgtga gctttggagt gaaatctctt gtcttaagga ataaaggaaa aagattccgt | 120 |
| cggaggctcg gtgctctaca ggttgtttgc caggactttc caagacctcc actagaaaac | 180 |
| acaataaact ttttggaagc tggacaacta tcttcatttt tcagaaacag tgaacaaccc | 240 |
| actaaaccat tacaggtcgt gattgctgga gcaggattag ctggtttatc aacggcaaaa | 300 |
| tatctggcag atgctggtca taaacccata ttgcttgagg caagggatgt tttgggtgga | 360 |
| aagatagctg cttggaagga tgaagatgga gattggtatg aaactgggct tcatatctt | 420 |
| tttggagctt atcccaacat acagaacttg tttggcgagc ttggtattaa tgatcggttg | 480 |
| caatggaagg aacactccat gatatttgcc atgccaaaca agccaggaga attcagccgg | 540 |
| tttgattttc ctgaaacatt gcctgcaccc ttaaatggaa tatgggccat actaagaaac | 600 |
| aatgaaatgc taacttggcc agagaaggtg aagtttgctc ttggacttt gccagcaatg | 660 |
| gttggtggcc aagcttatgt tgaagctcaa gatggtttta ctgtttctga gtggatgaaa | 720 |
| aagcagggtg ttcctgatcg agtgaacgat gaggttttca ttgcaatgtc aaaggcactt | 780 |
| aatttcataa atcctgatga gttatccatg cagtgcattc tgattgcttt aaaccgattt | 840 |
| cttcaggaga agcatggttc taagatggca ttcttggatg gtaatcctcc tgaaaggtta | 900 |
| tgcatgccta tgttgaccca tgttcgctct tgggtggtg aggttcggct gaattctcgt | 960 |
| attcagaaaa tagaacttaa tcctgatgga acagtgaaac actttgcact tactgatgga | 1020 |
| actcaaataa ctgagatgc ttatgttttt gcaacaccag ttgatatctt gaagcttctt | 1080 |
| gtacctcaag agtggaaaga aatatcttat ttcaagaagc tggagaagtt ggtgggagtt | 1140 |
| cctgttataa atgttcatat atggtttgat agaaaactga gaacacata tgaccacctt | 1200 |
| cttttcagca ggagttcact tttaagtgtt tatgcggaca tgtcagtaac ttgcaaggaa | 1260 |
| tactatgatc caaaccgttc aatgctggag ttggtctttg ctcctgcaga ggaatgggtt | 1320 |
| ggacggagtg acactgaaat catcgaagca actatgcaag agctagccaa gctatttcct | 1380 |
| gatgaaattg ctgctgatca gagtaaagca aagattctga gtatcatgt tgtgaagaca | 1440 |
| ccaagatctg tttacaagac tatcccggac tgtgaacctt gccgacctct gcaaagatca | 1500 |
| ccgattgaag ggttctatct agctggtgac tacacaaagc agaaatattt ggcttcgatg | 1560 |

```
gagggtgcag ttctatctgg gaagctttgt gctcagtctg tagtggagga ttataaaatg    1620
ctatctcgta ggagcctgaa aagtctgcag tctgaagttc ctgttgcctc ctagttgtag    1680
tcaggactat tcccaatggt gtgtgtgtca tcatcccta gtcagttttt ttctatttag     1740
tgggtgccca actctccacc aatttacaca tgatggaact tgaaagatgc ctattttggt    1800
cttatcatat ttctgtaaag ttgatttgtg actgagagct gatgccgata tgccatgctg    1860
gagaaaaaga acattatgta aaacgacctg catagtaatt cttagacttt tgcaaaaggc    1920
aaaaggggta aagcgacctt ttttttctat gtgaagggat taagagacct t            1971
```

```
<210> SEQ ID NO 87
<211> LENGTH: 250
<212> TYPE: RNA
<213> ORGANISM: Artificial Sequence
<220> FEATURE:
<223> OTHER INFORMATION: tRNA-gRNA-tRNA scheme
<220> FEATURE:
<221> NAME/KEY: misc_feature
<222> LOCATION: (78)..(97)
<223> OTHER INFORMATION: n is a, c, g, or u

<400> SEQUENCE: 87
```

```
aacaaagcac cagggucua guggguagaau aguacccugc cacgguacag acccggguuc    60
gauucccggc uggugcannn nnnnnnnnnn nnnnnnnguu uuagagcuag aaauagcaag    120
uuaaaauaag gcuaguccgu uaucaacuug aaaaaguggc accgaucgg ugcaacaaag    180 caccaguggu cuaguggguag aauaguaccc ugccacgguua cagacccggg uucgauuccc    240
ggcuggugca                                                          250
```

```
<210> SEQ ID NO 88
<211> LENGTH: 100
<212> TYPE: RNA
<213> ORGANISM: Artificial Sequence
<220> FEATURE:
<223> OTHER INFORMATION: gRNA from PTG gene
<220> FEATURE:
<221> NAME/KEY: misc_feature
<222> LOCATION: (1)..(20)
<223> OTHER INFORMATION: n is a, c, g, or u

<400> SEQUENCE: 88
```

```
nnnnnnnnnn nnnnnnnnnn guuuuagagc uagaaauagc aaguuaaaau aaggcuaguc    60
cguuaucaac uugaaaaagu ggcaccgagu cggugcaaca                          100
```

```
<210> SEQ ID NO 89
<211> LENGTH: 100
<212> TYPE: RNA
<213> ORGANISM: Artificial Sequence
<220> FEATURE:
<223> OTHER INFORMATION: gRNA from sgRNA gene
<220> FEATURE:
<221> NAME/KEY: misc_feature
<222> LOCATION: (2)..(20)
<223> OTHER INFORMATION: n is a, c, g, or u

<400> SEQUENCE: 89
```

```
annnnnnnnn nnnnnnnnnn guuuuagagc uagaaauagc aaguuaaaau aaggcuaguc    60
cguuaucaac uugaaaaagu ggcaccgagu cggugcuuuu                          100
```

```
<210> SEQ ID NO 90
<211> LENGTH: 27
<212> TYPE: DNA
<213> ORGANISM: Oryza sativa
```

```
<400> SEQUENCE: 90
ccaaccattt tccatggcgg gaggttc                                        27

<210> SEQ ID NO 91
<211> LENGTH: 26
<212> TYPE: DNA
<213> ORGANISM: Oryza sativa

<400> SEQUENCE: 91
ccaaccattt ccatggcggg aggttc                                         26

<210> SEQ ID NO 92
<211> LENGTH: 26
<212> TYPE: DNA
<213> ORGANISM: Oryza sativa

<400> SEQUENCE: 92
ttctccctcc aggaggtggc aatcaa                                         26

<210> SEQ ID NO 93
<211> LENGTH: 61
<212> TYPE: DNA
<213> ORGANISM: Oryza sativa

<400> SEQUENCE: 93
ttctccctcc taatctggac caaagtgctg tccgcctaca acaagaggag gtggcaatca    60
a                                                                    61

<210> SEQ ID NO 94
<211> LENGTH: 29
<212> TYPE: DNA
<213> ORGANISM: Oryza sativa

<400> SEQUENCE: 94
ttctcccctc ctcaggaggt ggcaatcaa                                      29

<210> SEQ ID NO 95
<211> LENGTH: 27
<212> TYPE: DNA
<213> ORGANISM: Oryza sativa

<400> SEQUENCE: 95
gcggccggta ctcatggaca ccgacct                                        27

<210> SEQ ID NO 96
<211> LENGTH: 26
<212> TYPE: DNA
<213> ORGANISM: Oryza sativa

<400> SEQUENCE: 96
gcggccggta tcatggacac cgacct                                         26

<210> SEQ ID NO 97
<211> LENGTH: 24
<212> TYPE: DNA
<213> ORGANISM: Oryza sativa

<400> SEQUENCE: 97
atcacccttt ggccaagcgg acac                                           24

<210> SEQ ID NO 98
```

```
<211> LENGTH: 23
<212> TYPE: DNA
<213> ORGANISM: Oryza sativa

<400> SEQUENCE: 98
atcacccttt gccaagcgga cac                                             23

<210> SEQ ID NO 99
<211> LENGTH: 27
<212> TYPE: DNA
<213> ORGANISM: Oryza sativa

<400> SEQUENCE: 99
atcacccttt cgatgccaag cggacac                                         27

<210> SEQ ID NO 100
<211> LENGTH: 31
<212> TYPE: DNA
<213> ORGANISM: Oryza sativa

<400> SEQUENCE: 100
gcacggcggc cggtatcatg gacaccgacc t                                    31

<210> SEQ ID NO 101
<211> LENGTH: 32
<212> TYPE: DNA
<213> ORGANISM: Oryza sativa

<400> SEQUENCE: 101
cgcgtgccaa ccatttgcca tggcgggagg tt                                   32

<210> SEQ ID NO 102
<211> LENGTH: 85
<212> TYPE: DNA
<213> ORGANISM: Oryza sativa

<400> SEQUENCE: 102
cgcacggcgc cggtacctgc tctacgacat cttcgggaac aagttcaacg acgtctacat     60
cgccacggag ctcatggaca ccgac                                           85

<210> SEQ ID NO 103
<211> LENGTH: 87
<212> TYPE: DNA
<213> ORGANISM: Oryza sativa

<400> SEQUENCE: 103
gtcggtgtcc atgagctccg tggcgatgta gacgtcgttg aaacttgttc ccgaagatgt     60
cgtagagcag gtaccggccg ccgtgcg                                         87

<210> SEQ ID NO 104
<211> LENGTH: 78
<212> TYPE: DNA
<213> ORGANISM: Oryza sativa

<400> SEQUENCE: 104
gccaaccatt ttatccccg gtgggccacc accccacct atggagaaca tccaggcgac       60
gctgagccat ggcgggag                                                   78

<210> SEQ ID NO 105
<211> LENGTH: 78
<212> TYPE: DNA
<213> ORGANISM: Oryza sativa
```

<400> SEQUENCE: 105
ctcccgccat ggctcagcgt cgcctccatg ttctccatag gtgggggtgg tggcccaccg    60
gggtataaaa tggttggc                                                 78

<210> SEQ ID NO 106
<211> LENGTH: 92
<212> TYPE: DNA
<213> ORGANISM: Oryza sativa

<400> SEQUENCE: 106
cctccttctc cctccttgag gcgaccgggt tcgtttcttg gctgtgcggt tgtgaatgcg    60
cagactcgtc aggaggtggc aatcaagaag at                                 92

<210> SEQ ID NO 107
<211> LENGTH: 92
<212> TYPE: DNA
<213> ORGANISM: Oryza sativa

<400> SEQUENCE: 107
atcttcttga ttgccacctc ctgacgagtc tgcgcattca caaccgcaca gccaagaaac    60
gaacccggtc gcctcaagga gggagaagga gg                                 92

<210> SEQ ID NO 108
<211> LENGTH: 86
<212> TYPE: DNA
<213> ORGANISM: Oryza sativa

<400> SEQUENCE: 108
tgatcaaccc tttgattgac ccgcacccgc atccctttcc ccattcgaca accatatcga    60
tgccaagcgg acactgagag aaatca                                        86

<210> SEQ ID NO 109
<211> LENGTH: 83
<212> TYPE: DNA
<213> ORGANISM: Oryza sativa

<400> SEQUENCE: 109
tgatttctca gtgtccgctt ggcatcgata tggttgtcga atggggaaag ggatgcgggt    60
gcgggtcaat caaagggtga tca                                           83

<210> SEQ ID NO 110
<211> LENGTH: 100
<212> TYPE: DNA
<213> ORGANISM: Artificial Sequence
<220> FEATURE:
<223> OTHER INFORMATION: Vector

<400> SEQUENCE: 110
aaggaatctt taaacatgat ttaaaagagt tgtgcagatg atccgtggca ggagaccgag    60
gtctcggttt tagagctaga aaccgagtcg gtgcttttt                          100

<210> SEQ ID NO 111
<211> LENGTH: 100
<212> TYPE: DNA
<213> ORGANISM: Artificial Sequence
<220> FEATURE:
<223> OTHER INFORMATION: Vector

<400> SEQUENCE: 111

-continued

```
aaaaaagcac cgactcggtt tctagctcta aaaccgagac ctcggtctcc tgccacggat    60
catctgcaca actcttttaa atcatgttta aagattcctt                         100
```

<210> SEQ ID NO 112
<211> LENGTH: 44
<212> TYPE: DNA
<213> ORGANISM: Oryza sativa

<400> SEQUENCE: 112

```
agtggcaccg agtcggtgct ttaagatgtc gtagagcagg tacg                     44
```

<210> SEQ ID NO 113
<211> LENGTH: 42
<212> TYPE: DNA
<213> ORGANISM: Oryza sativa

<400> SEQUENCE: 113

```
agtggcaccg agtcggtgct aagatgtcgt agagcaggta cg                       42
```

<210> SEQ ID NO 114
<211> LENGTH: 43
<212> TYPE: DNA
<213> ORGANISM: Oryza sativa

<400> SEQUENCE: 114

```
agtggcaccg agtcggtgct taagatgtcg tagagcaggt acg                      43
```

<210> SEQ ID NO 115
<211> LENGTH: 46
<212> TYPE: DNA
<213> ORGANISM: Oryza sativa

<400> SEQUENCE: 115

```
gtggcaccga gtcggtgctt tttttagatg tcgtagagca ggtacg                   46
```

<210> SEQ ID NO 116
<211> LENGTH: 37
<212> TYPE: DNA
<213> ORGANISM: Oryza sativa

<400> SEQUENCE: 116

```
ggcaccgagt cggtgcttta catcgccacg gagctca                             37
```

<210> SEQ ID NO 117
<211> LENGTH: 44
<212> TYPE: DNA
<213> ORGANISM: Oryza sativa

<400> SEQUENCE: 117

```
aagtggcacc gagtcggtgc tttctacatc gccacggagc tcag                     44
```

<210> SEQ ID NO 118
<211> LENGTH: 46
<212> TYPE: DNA
<213> ORGANISM: Oryza sativa

<400> SEQUENCE: 118

```
agtggcaccg agtcggtgca aagatgtcgt agagcaggta caatcg                   46
```

<210> SEQ ID NO 119
<211> LENGTH: 47
<212> TYPE: DNA
<213> ORGANISM: Oryza sativa

```
<400> SEQUENCE: 119
aaaagtggca ccgagtcggt gcaatctaca tcgccacgga gctcagt            47

<210> SEQ ID NO 120
<211> LENGTH: 67
<212> TYPE: DNA
<213> ORGANISM: Oryza sativa

<400> SEQUENCE: 120
cgcgtgccaa ccatttatac cccggtgggc cacatccagg cgacgctgaa accatggcgg  60
gaggttc                                                             67

<210> SEQ ID NO 121
<211> LENGTH: 63
<212> TYPE: DNA
<213> ORGANISM: Oryza sativa

<400> SEQUENCE: 121
cgcgtgccaa ccatttatac cccggtgggc cacatccagg cgacgctcca tggcgggagg  60
ttc                                                                 63

<210> SEQ ID NO 122
<211> LENGTH: 65
<212> TYPE: DNA
<213> ORGANISM: Oryza sativa

<400> SEQUENCE: 122
cgcgtgccaa ccatttatac cccggtgggc cacatccagg cgacgctgac catggcggga  60
ggttc                                                               65

<210> SEQ ID NO 123
<211> LENGTH: 39
<212> TYPE: DNA
<213> ORGANISM: Oryza sativa

<400> SEQUENCE: 123
tcctccttct ccctcctgag gcgaccgggt tcgaatgcg                          39

<210> SEQ ID NO 124
<211> LENGTH: 68
<212> TYPE: DNA
<213> ORGANISM: Oryza sativa

<400> SEQUENCE: 124
tcctccttct ccctcctttg aggcgaccgg gttcgaatgc gcagactcgt ctaggaggtg  60
gcaatcaa                                                            68

<210> SEQ ID NO 125
<211> LENGTH: 56
<212> TYPE: DNA
<213> ORGANISM: Oryza sativa

<400> SEQUENCE: 125
tcctccttag gcgaccgggt tcgaatgcgc agactcgtct aggaggtggc aatcaa       56

<210> SEQ ID NO 126
<211> LENGTH: 61
<212> TYPE: DNA
<213> ORGANISM: Oryza sativa
```

<400> SEQUENCE: 126
cgcacggcgg ccggtatacg acatcttcta catcgccacg gagcatcatg gacaccgacc     60
t                                                                     61

<210> SEQ ID NO 127
<211> LENGTH: 52
<212> TYPE: DNA
<213> ORGANISM: Oryza sativa

<400> SEQUENCE: 127
cgcacggcgg ccggtattct acatcgccac ggagcttcat ggacaccgac ct            52

<210> SEQ ID NO 128
<211> LENGTH: 32
<212> TYPE: DNA
<213> ORGANISM: Oryza sativa

<400> SEQUENCE: 128
cgcacggcgg ccggtatcat ggacaccgac ct                                  32

<210> SEQ ID NO 129
<211> LENGTH: 59
<212> TYPE: DNA
<213> ORGANISM: Oryza sativa

<400> SEQUENCE: 129
ggtgtgatca ccctttacc cgcacccgcc attcgacaac catattgcca agcggacac       59

<210> SEQ ID NO 130
<211> LENGTH: 58
<212> TYPE: DNA
<213> ORGANISM: Oryza sativa

<400> SEQUENCE: 130
ggtgtgatca cccttatga cccgcacccg ccattcgaca accataccaa gcggacac        58

<210> SEQ ID NO 131
<211> LENGTH: 64
<212> TYPE: DNA
<213> ORGANISM: Oryza sativa

<400> SEQUENCE: 131
ggtgtgatca ccctttagac ccgcacccgc cattcgacaa ccatatacga tgccaagcgg    60
acac                                                                 64

<210> SEQ ID NO 132
<211> LENGTH: 76
<212> TYPE: DNA
<213> ORGANISM: Oryza sativa

<400> SEQUENCE: 132
gccatgccaa acaagccagg agaattcagc cggtttgaaa atcctgatga gttatccatg    60
cagtgcattc tgattg                                                    76

<210> SEQ ID NO 133
<211> LENGTH: 26
<212> TYPE: DNA
<213> ORGANISM: Oryza sativa

<400> SEQUENCE: 133
ccatgccaaa caagccagcc ggttga                                         26

<210> SEQ ID NO 134
<211> LENGTH: 31
<212> TYPE: DNA
<213> ORGANISM: Oryza sativa

<400> SEQUENCE: 134
aaatcctgat atccatgcag tgcattctga t                              31

<210> SEQ ID NO 135
<211> LENGTH: 50
<212> TYPE: DNA
<213> ORGANISM: Oryza sativa

<400> SEQUENCE: 135
cgcgtgccaa ccatttatac cccggtggcc acatccatgg cgggaggttc          50

<210> SEQ ID NO 136
<211> LENGTH: 62
<212> TYPE: DNA
<213> ORGANISM: Oryza sativa

<400> SEQUENCE: 136
cgcgtgccaa ccaggggacc ccggtgggcc acatccaggc gacgctgaat ggcgggaggt    60
tc                                                              62

<210> SEQ ID NO 137
<211> LENGTH: 68
<212> TYPE: DNA
<213> ORGANISM: Oryza sativa

<400> SEQUENCE: 137
cgcgtgccaa ccaaccattt tatacccccgg tgggccacat ccaggcgacg ctccatggcg    60
ggaggttc                                                        68

<210> SEQ ID NO 138
<211> LENGTH: 65
<212> TYPE: DNA
<213> ORGANISM: Oryza sativa

<400> SEQUENCE: 138
cgcgtgccaa ccatttatat accccggtgg gccacatcca ggcgacgctc catggcggga    60
ggttc                                                           65

<210> SEQ ID NO 139
<211> LENGTH: 64
<212> TYPE: DNA
<213> ORGANISM: Oryza sativa

<400> SEQUENCE: 139
cgcgtgccaa ccattttata tcccggtggg ccacatccag gcgacgctcc atggcgggag    60
gttc                                                            64

<210> SEQ ID NO 140
<211> LENGTH: 63
<212> TYPE: DNA
<213> ORGANISM: Oryza sativa

<400> SEQUENCE: 140
cgcgtgccaa ccatttgtgc cccggtgggc cacatccagg cgacgctcca tggcgggagg    60

```
ttc                                                               63

<210> SEQ ID NO 141
<211> LENGTH: 66
<212> TYPE: DNA
<213> ORGANISM: Oryza sativa

<400> SEQUENCE: 141
tcctccttct ccctccgagg cgaccgggtt cgaatgcgca gactcgtcaa aggaggtggc    60
aatcaa                                                            66

<210> SEQ ID NO 142
<211> LENGTH: 68
<212> TYPE: DNA
<213> ORGANISM: Oryza sativa

<400> SEQUENCE: 142
tcctccttct ccctcctttg aggcgaccgg gttcgaatgc gcagactcgt ctaggaggtg    60
gcaatcaa                                                          68

<210> SEQ ID NO 143
<211> LENGTH: 68
<212> TYPE: DNA
<213> ORGANISM: Oryza sativa

<400> SEQUENCE: 143
tcctccttct ccctcctttg aggcgaccgg gttcgaatgc gcagactcgt ccaggaggtg    60
gcaatcaa                                                          68

<210> SEQ ID NO 144
<211> LENGTH: 54
<212> TYPE: DNA
<213> ORGANISM: Oryza sativa

<400> SEQUENCE: 144
tcctccttag gcgaccgggt tcgaatgcgc agactcgtcg gaggtggcaa tcaa         54

<210> SEQ ID NO 145
<211> LENGTH: 54
<212> TYPE: DNA
<213> ORGANISM: Oryza sativa

<400> SEQUENCE: 145
tcctccttag gcgaccgggt tcgaatgcgc agactcgtcg gaggtggcaa tcaa         54

<210> SEQ ID NO 146
<211> LENGTH: 71
<212> TYPE: DNA
<213> ORGANISM: Oryza sativa

<400> SEQUENCE: 146
cgcacggcgg ccggtatcct gctctacgac atcttctcta catcgccacg gagcctcatg    60
gacaccgacc t                                                      71

<210> SEQ ID NO 147
<211> LENGTH: 57
<212> TYPE: DNA
<213> ORGANISM: Oryza sativa

<400> SEQUENCE: 147
cgcacggcgg ccgcttctct acgacatctt ctctacatcg ctcatggaca ccgacct       57
```

```
<210> SEQ ID NO 148
<211> LENGTH: 56
<212> TYPE: DNA
<213> ORGANISM: Oryza sativa

<400> SEQUENCE: 148
cgcacggcgg ccgctatcta cgacatcttc tctacatcgc tcatggacac cgacct        56

<210> SEQ ID NO 149
<211> LENGTH: 65
<212> TYPE: DNA
<213> ORGANISM: Oryza sativa

<400> SEQUENCE: 149
cgcacggcgg ccgctatcta cgacatcttc tctacatcgc cacggagctt catggacacc    60
gacct                                                                 65

<210> SEQ ID NO 150
<211> LENGTH: 58
<212> TYPE: DNA
<213> ORGANISM: Oryza sativa

<400> SEQUENCE: 150
ggtgtgatca ccttgacccg cagggcgatt cgacaaccat ccgatgccaa gcggacac      58

<210> SEQ ID NO 151
<211> LENGTH: 26
<212> TYPE: DNA
<213> ORGANISM: Oryza sativa

<400> SEQUENCE: 151
acccgcaccc gctgccaagc ggacac                                          26

<210> SEQ ID NO 152
<211> LENGTH: 58
<212> TYPE: DNA
<213> ORGANISM: Oryza sativa

<400> SEQUENCE: 152
ggtgtgatca ccctttaacc cgcacccgca ttcgacaacc atattgccaa gcggacac      58

<210> SEQ ID NO 153
<211> LENGTH: 53
<212> TYPE: DNA
<213> ORGANISM: Oryza sativa

<400> SEQUENCE: 153
ggtgtgatca ccctttacac ccgcattcga caaccatatt gccaagcgga cac           53

<210> SEQ ID NO 154
<211> LENGTH: 53
<212> TYPE: DNA
<213> ORGANISM: Oryza sativa

<400> SEQUENCE: 154
ggtgtgatca ccctttacac ccgcattcga caaccatatt gccaagcgga cac           53

<210> SEQ ID NO 155
<211> LENGTH: 57
<212> TYPE: DNA
<213> ORGANISM: Oryza sativa
```

-continued

```
<400> SEQUENCE: 155
ggtgtgatca cccttttacac ccgcattcga caaccatata cgatgccaag cggacac     57
```

```
<210> SEQ ID NO 156
<211> LENGTH: 55
<212> TYPE: PRT
<213> ORGANISM: Oryza sativa

<400> SEQUENCE: 156
```

Met Asp Ala Gly Ala Gln Pro Pro Asp Thr Glu Met Ala Glu Ala Gly
1               5                   10                  15

Gly Gly Gln Gln Pro Pro Ala Ala Ala Ala Ala Gly Ala Gly Ala
            20                  25                  30

Gly Ala Gly Met Met Glu Asn Ile His Gly Gly Arg Phe Ile Gln Tyr
        35                  40                  45

Asn Ile Phe Gly Asn Val Phe
        50              55

```
<210> SEQ ID NO 157
<211> LENGTH: 59
<212> TYPE: PRT
<213> ORGANISM: Oryza sativa

<400> SEQUENCE: 157
```

Met Asp Ala Gly Ala Gln Pro Pro Asp Thr Glu Met Ala Glu Ala Gly
1               5                   10                  15

Gly Gly Gln Gln Pro Pro Ala Ala Ala Ala Ala Gly Ala Gly Ala
            20                  25                  30

Gly Ala Gly Met Met Glu Asn Ile Gln Ala Thr Leu His Gly Gly Arg
        35                  40                  45

Phe Ile Gln Tyr Asn Ile Phe Gly Asn Val Phe
        50                  55

```
<210> SEQ ID NO 158
<211> LENGTH: 59
<212> TYPE: PRT
<213> ORGANISM: Oryza sativa

<400> SEQUENCE: 158
```

Met Asp Ala Gly Ala Gln Pro Pro Asp Thr Glu Met Ala Glu Ala Gly
1               5                   10                  15

Gly Gly Gln Gln Pro Pro Ala Ala Ala Ala Ala Gly Ala Gly Ala
            20                  25                  30

Gly Ala Gly Met Met Glu Asn Ile Gln Ala Thr Leu Asn Gly Gly Arg
        35                  40                  45

Phe Ile Gln Tyr Asn Ile Phe Gly Asn Val Phe
        50                  55

```
<210> SEQ ID NO 159
<211> LENGTH: 21
<212> TYPE: PRT
<213> ORGANISM: Oryza sativa

<400> SEQUENCE: 159
```

Met Asp Gly Ala Pro Val Ala Glu Phe Arg Pro Thr Met Thr His Gly
1               5                   10                  15

Gly Arg Tyr Pro Ala
            20

```
<210> SEQ ID NO 160
<211> LENGTH: 19
<212> TYPE: PRT
<213> ORGANISM: Oryza sativa

<400> SEQUENCE: 160

Met Asp Gly Ala Pro Val Ala Glu Phe Arg Pro Thr Met Thr His Gly
1               5                   10                  15

Gly Arg Tyr

<210> SEQ ID NO 161
<211> LENGTH: 19
<212> TYPE: PRT
<213> ORGANISM: Oryza sativa

<400> SEQUENCE: 161

Met Asp Gly Ala Pro Val Ala Glu Phe Arg Pro Thr Met Thr His Gly
1               5                   10                  15

Gly Arg Tyr

<210> SEQ ID NO 162
<211> LENGTH: 19
<212> TYPE: PRT
<213> ORGANISM: Oryza sativa

<400> SEQUENCE: 162

Met Asp Gly Ala Pro Val Ala Glu Phe Arg Pro Thr Met Thr His Gly
1               5                   10                  15

Gly Arg Phe

<210> SEQ ID NO 163
<211> LENGTH: 31
<212> TYPE: PRT
<213> ORGANISM: Oryza sativa

<400> SEQUENCE: 163

Gly Cys Ala Cys Gly Gly Cys Gly Gly Cys Cys Gly Gly Thr Ala Thr
1               5                   10                  15

Cys Ala Thr Gly Gly Ala Cys Ala Cys Cys Gly Ala Cys Cys Thr
            20                  25                  30

<210> SEQ ID NO 164
<211> LENGTH: 20
<212> TYPE: DNA
<213> ORGANISM: Artificial Sequence
<220> FEATURE:
<223> OTHER INFORMATION: sg1 target Human HDAC1

<400> SEQUENCE: 164
gtaagaccac cgcactaggc                                             20

<210> SEQ ID NO 165
<211> LENGTH: 20
<212> TYPE: DNA
<213> ORGANISM: Artificial Sequence
<220> FEATURE:
<223> OTHER INFORMATION: sg2 target Human HDAC1

<400> SEQUENCE: 165
gccctgcagc tattaccatt                                             20

<210> SEQ ID NO 166
<211> LENGTH: 20
```

```
<212> TYPE: DNA
<213> ORGANISM: Artificial Sequence
<220> FEATURE:
<223> OTHER INFORMATION: sg1 target Human HDAC2

<400> SEQUENCE: 166 gtatttagg atattggtgc                                              20

<210> SEQ ID NO 167
<211> LENGTH: 20
<212> TYPE: DNA
<213> ORGANISM: Artificial Sequence
<220> FEATURE:
<223> OTHER INFORMATION: sg2 target Human HDAC2

<400> SEQUENCE: 167
tgtttcaatc taacagtcaa                                             20

<210> SEQ ID NO 168
<211> LENGTH: 20
<212> TYPE: DNA
<213> ORGANISM: Artificial Sequence
<220> FEATURE:
<223> OTHER INFORMATION: sg1 target human HDAC3

<400> SEQUENCE: 168
gagcagaact caaagagccc                                             20

<210> SEQ ID NO 169
<211> LENGTH: 20
<212> TYPE: DNA
<213> ORGANISM: Artificial Sequence
<220> FEATURE:
<223> OTHER INFORMATION: sg2 target human HDAC3

<400> SEQUENCE: 169
gctcaagtaa gtagcccagg                                             20

<210> SEQ ID NO 170
<211> LENGTH: 20
<212> TYPE: DNA
<213> ORGANISM: Artificial Sequence
<220> FEATURE:
<223> OTHER INFORMATION: sg1 target human HDAC4

<400> SEQUENCE: 170
gagctcctga atacgtcgca                                             20

<210> SEQ ID NO 171
<211> LENGTH: 20
<212> TYPE: DNA
<213> ORGANISM: Artificial Sequence
<220> FEATURE:
<223> OTHER INFORMATION: sg2 target human HDAC4

<400> SEQUENCE: 171
gctcctttgc cgtccccgag                                             20

<210> SEQ ID NO 172
<211> LENGTH: 20
<212> TYPE: DNA
<213> ORGANISM: Artificial Sequence
<220> FEATURE:
<223> OTHER INFORMATION: sg1 target human HDAC6

<400> SEQUENCE: 172
```

-continued cgactggcag caggacgtgc                                               20

<210> SEQ ID NO 173
<211> LENGTH: 20
<212> TYPE: DNA
<213> ORGANISM: Artificial Sequence
<220> FEATURE:
<223> OTHER INFORMATION: sg2 target human HDAC6

<400> SEQUENCE: 173
caagctgatc ctgtctctgg                                               20

<210> SEQ ID NO 174
<211> LENGTH: 20
<212> TYPE: DNA
<213> ORGANISM: Artificial Sequence
<220> FEATURE:
<223> OTHER INFORMATION: Primer: Genotyping of MPK1

<400> SEQUENCE: 174
cctcgtgttt ggtgttgctg                                               20

<210> SEQ ID NO 175
<211> LENGTH: 20
<212> TYPE: DNA
<213> ORGANISM: Artificial Sequence
<220> FEATURE:
<223> OTHER INFORMATION: Primer: Genotyping of MPK2

<400> SEQUENCE: 175
tgcgcctaaa aatcgagggt                                               20

<210> SEQ ID NO 176
<211> LENGTH: 21
<212> TYPE: DNA
<213> ORGANISM: Artificial Sequence
<220> FEATURE:
<223> OTHER INFORMATION: Primer: Genotyping MPK2

<400> SEQUENCE: 176
tttgggaagc atgtatgaag c                                             21

<210> SEQ ID NO 177
<211> LENGTH: 20
<212> TYPE: DNA
<213> ORGANISM: Artificial Sequence
<220> FEATURE:
<223> OTHER INFORMATION: Primer: Gentoyping MPK2

<400> SEQUENCE: 177
tatgccagcc aatgagccaa                                               20

<210> SEQ ID NO 178
<211> LENGTH: 21
<212> TYPE: DNA
<213> ORGANISM: Artificial Sequence
<220> FEATURE:
<223> OTHER INFORMATION: Genotyping of MPK5

<400> SEQUENCE: 178
gccaccttcc ttcctcatcc g                                             21

<210> SEQ ID NO 179
<211> LENGTH: 20
<212> TYPE: DNA
<213> ORGANISM: Artificial Sequence

```
<220> FEATURE:
<223> OTHER INFORMATION: Genotyping of MPK5

<400> SEQUENCE: 179
actccgtcat catgtcgctc                                                    20

<210> SEQ ID NO 180
<211> LENGTH: 21
<212> TYPE: DNA
<213> ORGANISM: Artificial Sequence
<220> FEATURE:
<223> OTHER INFORMATION: Genotyping of MPK6

<400> SEQUENCE: 180
ttgacgcccc aacataaata a                                                  21

<210> SEQ ID NO 181
<211> LENGTH: 18
<212> TYPE: DNA
<213> ORGANISM: Artificial Sequence
<220> FEATURE:
<223> OTHER INFORMATION: Genotyping of MPK6

<400> SEQUENCE: 181
tgttgctgcc gcttttct                                                      18

<210> SEQ ID NO 182
<211> LENGTH: 41
<212> TYPE: DNA
<213> ORGANISM: Artificial Sequence
<220> FEATURE:
<223> OTHER INFORMATION: Detection of U3:PTG

<400> SEQUENCE: 182
gaccatgatt acgccaagct taaggaatct ttaaacatac g                            41

<210> SEQ ID NO 183
<211> LENGTH: 37
<212> TYPE: DNA
<213> ORGANISM: Artificial Sequence
<220> FEATURE:
<223> OTHER INFORMATION: Detection of U3:PTG

<400> SEQUENCE: 183
ggacctgcag gcatgcacgc gctaaaaacg gactagc                                 37

<210> SEQ ID NO 184
<211> LENGTH: 20
<212> TYPE: DNA
<213> ORGANISM: Artificial Sequence
<220> FEATURE:
<223> OTHER INFORMATION: Detection of Cas9

<400> SEQUENCE: 184
gcttgtgcgt ttcgatttga                                                    20

<210> SEQ ID NO 185
<211> LENGTH: 20
<212> TYPE: DNA
<213> ORGANISM: Artificial Sequence
<220> FEATURE:
<223> OTHER INFORMATION: Detection of Cas9

<400> SEQUENCE: 185
ccgctcgtgc ttcttatcct                                                    20
```

<210> SEQ ID NO 186
<211> LENGTH: 19
<212> TYPE: DNA
<213> ORGANISM: Artificial Sequence
<220> FEATURE:
<223> OTHER INFORMATION: Control for DNA quality

<400> SEQUENCE: 186
cgctgccact ctccactga                                                    19

<210> SEQ ID NO 187
<211> LENGTH: 20
<212> TYPE: DNA
<213> ORGANISM: Artificial Sequence
<220> FEATURE:
<223> OTHER INFORMATION: Control for DNA quality

<400> SEQUENCE: 187
agctgcttcc actcgttcca                                                   20

<210> SEQ ID NO 188
<211> LENGTH: 77
<212> TYPE: DNA
<213> ORGANISM: Artificial Sequence
<220> FEATURE:
<223> OTHER INFORMATION: tRNA1 for PTG7

<400> SEQUENCE: 188
aataaagcac cagtggtcta gtggtagaat agtaccctgc cacggtacag acccgggttc       60
gattcccggc tggtgca                                                      77

<210> SEQ ID NO 189
<211> LENGTH: 77
<212> TYPE: DNA
<213> ORGANISM: Artificial Sequence
<220> FEATURE:
<223> OTHER INFORMATION: tRNA used for PTG10

<400> SEQUENCE: 189
aacaaagcac cagtggtcta gtggtggaat agtaccctgc cacggtacag acccgggttc       60
gattcccggc tggtgca                                                      77

<210> SEQ ID NO 190
<211> LENGTH: 38
<212> TYPE: DNA
<213> ORGANISM: Artificial Sequence
<220> FEATURE:
<223> OTHER INFORMATION: PSicoR-sgRNAs-EF1a-mCherry-T2A-Cas9 Cloning
      Site

<400> SEQUENCE: 190
gccttgtttg agacgagcgt ctcagtttta gagctaga                               38

<210> SEQ ID NO 191
<211> LENGTH: 38
<212> TYPE: DNA
<213> ORGANISM: Artificial Sequence
<220> FEATURE:
<223> OTHER INFORMATION: PSicoR-sgRNAs-EF1a-mCherry-T2A-Cas9 Cloning
      Site

<400> SEQUENCE: 191
cggaacaaac tctgctcgca gagtcaaaat ctcgatct                               38

<210> SEQ ID NO 192
<211> LENGTH: 41
<212> TYPE: DNA
<213> ORGANISM: Artificial Sequence
<220> FEATURE:
<223> OTHER INFORMATION: HDAC1-sg1

<400> SEQUENCE: 192
agtggcaccg agtcggtgca agtaagacca ccgcactagg c        41

<210> SEQ ID NO 193
<211> LENGTH: 41
<212> TYPE: DNA
<213> ORGANISM: Artificial Sequence
<220> FEATURE:
<223> OTHER INFORMATION: HDAC1-sg2

<400> SEQUENCE: 193
agtggcaccg agtcggtgct tgccctgcag ctattaccat t        41

<210> SEQ ID NO 194
<211> LENGTH: 41
<212> TYPE: DNA
<213> ORGANISM: Artificial Sequence
<220> FEATURE:
<223> OTHER INFORMATION: HDAC2-sg1

<400> SEQUENCE: 194
agtggcaccg agtcggtgca agtattttag gatattggtg c        41

<210> SEQ ID NO 195
<211> LENGTH: 43
<212> TYPE: DNA
<213> ORGANISM: Artificial Sequence
<220> FEATURE:
<223> OTHER INFORMATION: HDAC2-sg2

<400> SEQUENCE: 195
agtggcaccg agtcggtgct taatgtttca atctaacagt caa      43

<210> SEQ ID NO 196
<211> LENGTH: 354
<212> TYPE: DNA
<213> ORGANISM: Artificial Sequence
<220> FEATURE:
<223> OTHER INFORMATION: hPTG1

<400> SEQUENCE: 196
aacaaagcac cagtggtcta gtggtagaat agtaccctgc cacggtacag acccgggttc        60
gattcccggc tggtgcgtaa gaccaccgca ctaggcgttt tagagctaga aatagcaagt       120
taaaataagg ctagtccgtt atcaacttga aaaagtggca ccgagtcggt gcaacaaagc       180
accagtggtc tagtggtaga atagtaccct gccacggtac agacccgggt tcgattcccg       240
gctggtgcgc cctgcagcta ttaccattgt tttagagcta gaaatagcaa gttaaaataa       300
ggctagtccg ttatcaactt gaaaaagtgg caccgagtcg gtgcttttttt tttt           354

<210> SEQ ID NO 197
<211> LENGTH: 354
<212> TYPE: DNA
<213> ORGANISM: Artificial Sequence
<220> FEATURE:
<223> OTHER INFORMATION: hPTG2

<400> SEQUENCE: 197

-continued

```
aacaaagcac cagtggtcta gtggtagaat agtaccctgc cacggtacag acccgggttc      60
gattcccggc tggtgcgtat tttaggatat tggtgcgttt tagagctaga aatagcaagt     120
taaaataagg ctagtccgtt atcaacttga aaaagtggca ccgagtcggt gcaacaaagc     180
accagtggtc tagtggtaga atagtaccct gccacggtac agacccgggt tcgattcccg     240
gctggtgctg tttcaatcta acagtcaagt tttagagcta gaaatagcaa gttaaaataa     300
ggctagtccg ttatcaactt gaaaaagtgg caccgagtcg gtgcttttt tttt            354
```

<210> SEQ ID NO 198
<211> LENGTH: 30
<212> TYPE: DNA
<213> ORGANISM: Artificial Sequence
<220> FEATURE:
<223> OTHER INFORMATION: HDAC1 deletion

<400> SEQUENCE: 198

```
cctgcagcta ttaccggctg gaacatctcc                                        30
```

<210> SEQ ID NO 199
<211> LENGTH: 30
<212> TYPE: DNA
<213> ORGANISM: Artificial Sequence
<220> FEATURE:
<223> OTHER INFORMATION: HDAC2 deletion

<400> SEQUENCE: 199

```
aattgcttac ctttgacaat atcctaaaat                                        30
```

<210> SEQ ID NO 200
<211> LENGTH: 30
<212> TYPE: DNA
<213> ORGANISM: Artificial Sequence
<220> FEATURE:
<223> OTHER INFORMATION: HDAC3 deletion

<400> SEQUENCE: 200

```
cagtgtttcc cgggaggagg agatgggggc                                        30
```

<210> SEQ ID NO 201
<211> LENGTH: 30
<212> TYPE: DNA
<213> ORGANISM: Artificial Sequence
<220> FEATURE:
<223> OTHER INFORMATION: HDAC4 deletion

<400> SEQUENCE: 201

```
gagggttccc tgcgcgagcg gacagcagcg                                        30
```

<210> SEQ ID NO 202
<211> LENGTH: 30
<212> TYPE: DNA
<213> ORGANISM: Artificial Sequence
<220> FEATURE:
<223> OTHER INFORMATION: HDAC6 deletion

<400> SEQUENCE: 202

```
tgctgctttc ctgcatggag gtgagtgact                                        30
```